United States Patent
Coschigano (12)

(10) Patent No.: US 6,395,539 B1
(45) Date of Patent: May 28, 2002

(54) COMPOSITION AND METHODS FOR BIOREMEDIATION

(75) Inventor: Peter W. Coschigano, The Plains, OH (US)

(73) Assignee: Ohio University, Athens, OH (US)

( * ) Notice: Subject to any disclaimer, the term of this patent is extended or adjusted under 35 U.S.C. 154(b) by 0 days.

(21) Appl. No.: 09/323,872

(22) Filed: Jun. 1, 1999

Related U.S. Application Data

(63) Continuation-in-part of application No. 09/072,433, filed on May 4, 1998.
(60) Provisional application No. 60/046,845, filed on May 5, 1997.

(51) Int. Cl.$^7$ .................. C12N 15/63; C12N 15/54; C12N 9/10

(52) U.S. Cl. ............. 435/320.1; 435/193; 536/23.2

(58) Field of Search ................ 536/23.2; 435/193, 435/320.1

(56) References Cited

U.S. PATENT DOCUMENTS

| | | | |
|---|---|---|---|
| 4,283,390 A | 8/1981 | Koch et al. | 424/122 |
| 4,683,195 A | 7/1987 | Mullis et al. | 435/6 |
| 4,683,202 A | 7/1987 | Mullis | 435/91 |
| 4,919,813 A | 4/1990 | Weaver | 210/603 |
| 4,996,153 A | 2/1991 | Cadmus et al. | 435/209 |
| 5,017,495 A | 5/1991 | Yen et al. | 435/320.1 |
| 5,037,551 A | 8/1991 | Barkley et al. | 210/603 |
| 5,057,221 A | 10/1991 | Bryant et al. | 210/610 |
| 5,139,945 A | 8/1992 | Liu | 435/232 |
| 5,171,684 A | 12/1992 | Yen et al. | 435/252.3 |
| 5,182,199 A | 1/1993 | Hartley | 435/162 |
| 5,232,596 A | 8/1993 | Castaldi | 210/603 |
| 5,277,815 A | 1/1994 | Beeman | 210/605 |
| 5,342,769 A | 8/1994 | Hunter et al. | 435/166 |
| 5,369,031 A | 11/1994 | Middletich et al. | 435/284 |
| 5,482,630 A | 1/1996 | Lee et al. | 210/605 |
| 5,512,479 A | 4/1996 | Steffan | 435/262.5 |
| 5,519,134 A | 5/1996 | Acevedeo et al. | 544/243 |
| 5,543,317 A | 8/1996 | Shields et al. | 435/240.2 |
| 5,554,520 A | 9/1996 | Fowler et al. | 435/165 |
| 5,556,536 A | 9/1996 | Turk | 210/150 |
| 5,560,737 A | 10/1996 | Schuring et al. | 405/128 |
| 5,571,705 A | 11/1996 | Pierce | 435/174 |
| 5,585,272 A | 12/1996 | Pierce et al. | 435/262.5 |
| 5,610,061 A | 3/1997 | Pierce | 435/252.1 |
| 5,610,065 A | 3/1997 | Kelley et al. | 435/264 |
| 5,849,566 A | 12/1998 | Dale et al. | 435/262 |

OTHER PUBLICATIONS

Bioremediation of Mixed Harardous Wastes, YES Technologies.

Blattner, et al. Analysis of the *Escherichia coli* genome. IV. DNA sequence of the region from 89.2 to 92.8 minutes. *Nucleic Acids Res.* 21:5408 (1993).

Blattner, et al, The complete genome sequence of *Escherichia coli* K–12. *Science* (Wash. D.C.). 277:1453 (1997.

Bertoni, et al. "Cloning of the genes for and characterization of the early stages of toluene and o–xylene catabolism in *Pseudomonas stutzeri* OX1", *Applied Envir Microbiol* 62:3704–3711 (1996).

Boshart et al., "A Very Strong Enhancer Is Located Upstream of an Immediate Early Gene of Human Cytomegalovirus," *Cell* 41:521–530 (1985).

Coschigano et al., "Identification and sequence analysis of two regulatory genes involved in anaerobic toluene metabolism by strain T1," *Appl. Environ. Microbiol.* 63:652–660 (1997).

Coschigano et al., "Identification and Analysis of Genes Involved in Anaerobic Toluene Metabolism by Strain T1: Putative Role of a Glycine Free Radical," *Appl Environ Microbiol.* 64:1650–1656 (1998).

Coshigano and Young, ASM Abstract Q–406 (1994).

Coshigano and Young, ASM Abstract Q–183 (1995).

Dijkema et al., "Cloning and Expression of The Chromosomal Immune Interferon Gene of The Rat," *EMBO J.* 4:761–767 (1985).

Ditta et al., "Plasmids Related to The Broad Host Range Vector, pRK290, Useful for Gene Cloning and ofr Monitoring Gene Expression," *Plasmid* 13:149–153 (1985).

Doty et al., "Strand Separation and Specific Recombination in Deoxyribonucleic Acids: Physical Chemical Studies," *Proc. Natl. Acad. Sci. USA* 46:461–476 (1960).

Evans, et al., "Metabolites formed during anaerobic transformation of toluene and o–xylene and their proposed relationship to the initial steps of toluene mineralization" *Appl. Environ. Microbiol.* 58:496–501 (1992).

Franklin, et al. "Molecular and functional analysis of the TOL plasmid pWWO form *Pseudomonas putida* and cloning of genes for the entire regulated aromatic ring meta cleavage pathway" *Proc Natl Acad Sci, U.S.A.* 78:7458–7462 (1981).

Frazer et al., "Toluene Metabolism Under Anaerobic Conditions: A Review," *Anaerobe* 1:293–303 (1995).

Frey et al. (1994) "Adenosylmethionine–dependent Synthesis of the Glycyl Radical in Pyruvate Formate–lyase by Abstraction of the Glycine C–2 pro–S Hydrogen Atom," *J. Biol. Chem.* 269:12432–12437.

Fries et al., "Isolation, characterization and distribution of denitrifying toluene degraders from a variety of habitats," *Appl. Environ. Microbiol.* 60:2802–2810 (1994).

Furukawa, et al. "SAL–TOL in vivo recombinant plasmid pKF439" *J Bact* 162:1325–1328 (1985).

(List continued on next page.)

Primary Examiner—Rebecca E. Prouty
Assistant Examiner—David J Steadmann
(74) Attorney, Agent, or Firm—Medlen & Carroll, LLP

(57) ABSTRACT

Compositions and methods for the degradation of compounds contained in a liquid or solid waste stream are described. Genes encoding toluene-degrading enzymes are described. The enzymes have homology to the *E. coli* pyruvate formate lyase and pyruvate formate lyase activator.

3 Claims, 78 Drawing Sheets

OTHER PUBLICATIONS

Ghosal, et al. "Nucleotide sequence and expression of gene nahH of plasmid NAH7 and housing with gene xylE of TOL pWWO" *Gene* 55:19–28 (1987).

Gorman et al., "The Rouse Sarcoma Virus Long Terminal Repeat is a Strong Promoter When Introduced Into a Variety of Eukaryotic Cells By DNA–mediated Transfection," *Proc. Natl. Acad. Sci. USA* 79:6777–6781 (1982).

Harayama, et al. "Characterization of five genes in the upper–pathway operon of TOL plasmid pWWO from *Pseudomonas putida* and identification of the gene products" *J Bact* 171:5048–5055 (1989).

Harayama, et al. "Gene order or the TOL catabolic plasmid upper pathway operon and oxidation of both toluene and benzyl alcohol by the xylA product" *J Bact* 167:455–461 (1986).

Hirose, et al. "Construction of hybrid biphenyl (bph) and toluene (tod) genes for functional analysis of aromatic ring dioxygenases" *Gene* 138:27–33 (1994).

Horn, et al. "DNA sequence determination of the TOL plasmid (pWWO) xylGFJ genes of *Pseudomonas putida*: implications for the evolution of aromatic catabolism" *Mol. Microbiology* 5:2459–2474 (1991).

Inouye, et al. "Molecular cloning of regulatory gene xylR and operator–promoter regions of the xylABC and xylDEGF operons of the TOL plasmid" *J Bact* 155:1192–1199 (1983).

Inouye, et al. "Molecular cloning of TOL genes xylB and xylE in *Escherichia coli*" *J Bact* 145:1137–1143 (1981).

Inouye, et al. "Overproduction of the xylS gene product and activation of the xylDLEGF operon on the TOL plasmid" *J Bact* 169:3587–3592 (1987).

Johnson and Olsen "Nucleotide sequence analysis of genes encoding a toluene/benzene–2–monooxygenase from Pseudomonas sp. strain JS150" *Applied Envir Microbiol* 61:3336–3346 (1995).

Keen et al. (1988) "Improved broad–host–range plasmids for DNA cloning in Gram–negative bacteria," *Gene* 70:191–197.

Keil et al., "Molecular analysis of regulatory and structural xyl genes of the TOL plasmid pWW53–4" *J General Microbiology* 133: 1149–1158 (1987).

Kim et al., "Use of The Human Elongation Factor 1 α Promoter as a Versatile and Efficient Expression System," *Gene* 91:217–223 (1990).

Maniatis et al., "Regulation of Inducible and Tissue–Specific Gene Expression," *Science* 236:1237–1244 (1987).

Marmur and Lane, "Strand Separation and Specific Recombination in Deoxyribonucleic Acids: Biological Studies," *Proc. Natl. Acad. Sci. USA* 46:453–461 (1960).

Mizushima and Nagata, "pEF–BOS, a Powerful Mammalian Expression Vector," *Nuc. Acids. Res.*, 18:5322 (1990).

Ogiwara et al. "Construction and analysis of a profile library characterizing groups of structurally known proteins," *Protein Sci.* 5:1991 (1996) abstract.

Olsen, et al. "A novel toluene–3–monooxygenase pathway cloned from *Pseudomonas pickettii* PKO1" *J Bact* 176;3749–3756 (1994).

Pérez–Martin and Lorenzo "VTR expression cassettes for engineering conditional phenotypes in Pseudomonas: activity on the Pu promoter of the TOL plasmid under limiting concentrations of the XylR activator protein" *Gene* 172:81–86 (1996).

Plaga et al., "Catalytic–site mapping of pyruvate formate lyase," *Eur. J. Biochem.* 178:445–450 (1988).

Rabus et al., "Complete oxidation of toluene under strictly anoxic conditions by a new sulfate–reducing bacterium," *Appl. Environ. Microbiol.* 59:1444–1451 (1993).

Ramos, et al. "Altered effector specificities in regulators of gene expression: TOL plasmid xylS mutants and their use to engineer expansion of the range of aromatics degraded by bacteria" *Proc Natl Acad Sci, U.S.A.* 83:8467–8471 (1986).

Rödel et al., "Primary structure of *Escherichia coli* pyruvate formate–lyase and pyruvate format–lyase activating enzyme deduced from the DNA nucleotide sequences," *Eur. J. Biochem.* 177:153–158 (1988).

Sayler, et al. "Application of DNA–DNA colony hybridization to the detection of catabolic genotypes in environmental samples" *Applied Envir Microbiol* 49:1295–1303 (1985).

Shields, et al. "TOM, a new aromatic degradative plasmid from *Burkholderia* (*Pseudomonas*( *cepacia* G4" *Applied Envir Microbiol* 61;1352–1356 (1995).

Toluene Fact Sheet, Agency for Toxic Substances and Disease Registry (1995).

Uetsuki et al., "Isolation and Characterization of the Human Chromosomal Gene for Polypeptide Chain Elongation Factor–1α," *J. Biol. Chem.*, 264:5791–5798 (1989).

Voss et al., "The Role of Enhancers in the Regulation of Cell–Type–Specific Transcriptional Control," *Trends Biochem. Sci.* 11:287–289 (1986).

Wagner et al., "The free radical in pyruvate formate–lyase is located on glycine–734," *Proc. Natl. Acad. Sci. U.S.A.* 89, 996–1000 (1992).

Wright and Olsen "Self–mobilization and organization of the genes encoding the toluene metabolic pathway of *Pseudmonoas mendocina* KRI" *Applied Envir Microbiol* 60:235–242 (1994).

Yen and Karl "Identification of a new gene, tmoF, in the *Pseudomonas mendocina* KR1 gene cluster encoding toluene–4–monooxygenase" *J Bact* 174:7253–7261 (1992).

Zylstra and Gibson "Toluene degradation by *Pseudomonas putida* F1" *J. Biol. Chem.* 264:14940–14946 (1989).

FIG. 2A

```
                                                                                                   1900
        P  A  F  M  E  A  E  V  D  V  E  K  Y  E  R  I  V  L  N  L  L  S  N  A  F  K  F  S  P  D  G  G  R
1801  ATTCGCTGTTCGTTGAGTGCCGAACTGGTACCGGAAGAATCTTGCTCAGTATTCAGGACAGTGGTCCTGAATTCCAGCTGATCAACAGAGTGAAATTTCG
                                                                                                   2000
        I  R  C  S  L  S  A  T  G  T  G  R  I  L  L  S  I  Q  D  S  G  P  I  P  A  D  Q  S  E  I  F  G
1901  GCCGGTTTCGGCAAGGTGGGGATATCAAGTCCCGGCAGTTTGGCGGTACGGCAGTTTGACTATTGTGAAGGATTTTGTCTGCCTGCATGGGGGGGT
                                                                                                   2100
        R  F  R  Q  G  G  D  I  K  S  R  Q  F  G  G  T  G  L  G  L  T  I  V  K  D  F  V  C  L  H  G  G  V
2001  TGTGGTCCGTTTCAGACGCGTCCCGGGAGGGGGCTTTATTTCAGATCGAAATCGCCTTCTGGGGTGTATGTAAATGCGGTTGCAAAGGCT
                                                                                                   2200
        V  V  S  D  A  P  G  G  G  A  L  F  Q  I  E  L  P  R  N  A  P  S  G  V  Y  V  N  A  K  A
2101  GGTGAATTAAGCCCTACATCTTTTGATATCAGCGCATGGGGCCTGAGGGGCCGAGTGAATGCGACAAGCCCAGTGAATGGAGCCCAGTGATCGTCCTCGGATCC
                                                                                                   2300
        G  E  L  S  P  T  S  F  D  I  S  A  W  G  L  E  G  R  S  E  W  T  S  A  E  G  A  S  D  R  P  R  I  L
2201  TGATTGTCGAAGATAACGTCGATATGCGCTGTTTTATAGGAGGGTGCTCATTGACGATCAGTTGCCGCTGACAGTGTTGCCGCTGACGAGCAGCACTGGA
                                                                                                   2400
        I  V  E  D  N  V  D  M  R  C  F  I  G  R  V  L  I  D  E  Y  Q  I  S  V  A  A  D  G  E  Q  A  L  E
2301  GCTTATTACCTCACTCCATCCCCCTCCGGATCCTGTCTGTAACGGATCCAAGGTCTCAGCTTCTGTCAAAGAGATGCGCTCGAGAGGGAC
                                                                                                   2500
        L  I  T  S  S  P  P  D  L  V  I  T  D  L  M  M  P  K  V  S  G  Q  L  L  V  K  E  M  R  S  R  G  D
2401  CTAGCCAATGTTCCTATACTCGTGCTTTCGGCCAAGGCGGATGATGGTTGAGAATAAAATTGCTGGCCGAGTCGGTTCAAGATATGTTGTCAAGCCAT
                                                                                                   2600
        L  A  N  V  P  I  L  V  L  S  A  K  A  D  D  G  L  R  I  K  L  L  A  E  S  V  Q  D  Y  V  V  K  P  F
2501  TCTCGGCTACGGAGTTGCGAGCGCGAGTTCGAATCTTGTTACCATGAAGCGGAAGCGCTTGCAGGAGAATCGACTTGAGTCCCGCTGGCGCCCAGTCTATGAG
                                                                                                   2700
        S  A  T  E  L  R  A  R  V  R  N  L  V  T  M  K  R  A  R  D  A  L  Q  R  A  L  D  S  Q  S  D  D  L
2601  ATCGCCAATTGACTCGGCAGATCATCGACAATCGCCAGGAGTTGCAGCCATGAAGCGAGCAAGCTTTGCAGGAATCATTCAAAAATGGTTGGCTATGCCGAGGATGAGTTGC
                                                                                                   2800
        S  Q  L  T  R  Q  I  I  D  N  R  Q  E  L  Q  R  S  H  D  A  L  Q  E  S  E  S  R  W  R  A  V  Y  E
2701  AATTCTGCTGCAGATATTGTTGATCAAATTTGACAAATTTGACAAATTTCAAATTCAAGCATTTCAAAAAATGGTTGGCTATGCCGAGGATGAGTTGC
                                                                                                   2900
        N  S  A  A  G  I  V  L  T  N  L  D  G  L  I  L  S  A  N  Q  A  F  Q  K  M  V  G  Y  A  E  D  E  L  R
2801  GGGTGAATTGAAATATCGGATCTCGTCCCCGACATGATCGCGAACATGATCGCGAAAAATCCGGTCGCCGTTTCAAATCTGACAGTGACGACTATCAAGT
                                                                                                   3000
        V  I  E  I  S  D  L  V  P  E  H  D  R  E  K  I  R  S  V  S  N  L  I  S  G  R  V  D  D  Y  Q  V
2901  GCAAAGGCAATGCCGACGAAAGGACGGCCGAATGATGTGGGCAAATGCGAGCATCGCGAGCCTCATACCTGGCTGGCCAATCAGTCTCCGATGGTTGTGAGA
                                                                                                   3100
        Q  R  Q  C  R  R  K  D  G  R  M  M  W  A  N  V  R  A  S  L  I  P  G  L  A  N  Q  S  P  M  V  V  R
3001  GCAAAGGCAATGCCGACGAAAGATTCAGACTGAAGCTGAACTGGCAAGAGCAAGGGAAAAGTTGACCAGAGTCATGCGTTACCGCAATGGGAGAAT
```

FIG. 2B

```
      I  F  D  D  I  T  E  K  I  Q  T  E  A  E  L  A  R  A  R  E  K  L  T  R  V  M  R  V  T  A  M  G  E  L
3101  TGGCGGCATCGATTGCTGATGAGTTGGCCCGCGCCATTGCTGTTACCAGCGCTCATGATGGTCATCATTACGCGTCGTGGCTGGCCTTGTAATCT  3200
      A  A  S  I  A  H  E  L  N  Q  P  L  A  A  I  V  T  N  G  H  A  S  L  R  W  L  G  S  E  P  C  N  L
3201  ATTGGAAGCCGTCGAAGCAGTGCGAAGAATCATCCATGATGCTAATCGCGCAGTGAAATAATCAAACGGATCGCGTGGCTTTCTTCAGCGGGGAGGGG  3300
      L  E  A  V  E  A  V  R  R  I  I  H  D  A  N  R  A  S  E  I  I  K  R  I  R  G  F  L  Q  R  G  E  G
3301  AGGCGCTCGGCACTGGATATTTTTCAGGTCGTTGCCGTAGTCGGCCTCGCCAGTTGTCAGCGACATATGCGCGAGTTCATTGATATGCGTTATCAAGCAG  3400
      R  R  S  A  V  D  I  F  Q  V  V  A  D  V  A  A  I  V  S  D  M  A  R  S  H  C  I  D  M  R  Y  Q  A  V
3401  TCGGTCAATTGTCGCTAGTGATTGCGGATAAGGTCCAGTTGCAACAGGTTATTCTGAATTTGTGCATCAACAGAATCCATTGTTGCCGGAAACTC  3500
      G  Q  L  S  L  V  I  A  D  K  V  Q  L  Q  Q  V  I  L  N  L  C  I  N  G  I  E  S  I  V  G  G  N  S
3501  CGAACGAGGCGAACTTTCAATTACCGTGTTACCCAGTCCAGTCAGCGTGAGGTCCAGTCGCATCATGATTCTTGACCGTCAGCGTACATCGGCCCGGCCTTGCACTGGCGGAGGCG  3600
      E  R  G  E  L  S  I  T  V  T  Q  S  D  K  R  F  L  T  V  S  V  H  D  S  G  P  G  L  A  P  G  E  A
3601  GAAACGTGTTGATCGTTCTATACGAGCAAGGTGGAGGGCTTGCCATGGTGCTCGCCATCAGTCGCTCTATCATTGAGGGCATGGTGGGCGCCTTG  3700
      E  N  V  F  D  A  F  Y  T  S  K  V  E  G  L  G  M  G  L  A  I  S  R  S  I  I  E  A  H  G  G  R  L  D
3701  ATGTTCGTCCCCTTCCACGGAGGGGATGCACGTTCGTGTTTCACGGTTGCCTACGGAGGAGATGGCTAGCCCATGCCCCACAATAGATGCATCGACT  3800
      V  L  S  P  S  T  E  G  G  C  T  F  C  F  F  T  L  P  T  E  E  M  A  S  P  C  A  P  Q  *
                                                                        M  C  P  T  I  D  A  S  T
3801  GTTTATCTGGCTGGACGGACCATCGCTCAGCGGTGACGCAGCTTGGTTCCGACGCAATTTCCAGCTCGGTCGGAGACATTTGCGTCTCAAGTGAGT  3900
      V  Y  L  V  D  D  D  R  S  M  R  D  A  I  S  S  L  V  R  S  V  G  L  N  V  E  T  F  A  S  A  S  E  F
3901  TCTTGGAGCACGCTCGTTCGGAAGCCATGTGCCCTGCTTGGTTCTTGATGTTCGGATGCGACGCCATGAGCGCGGTTTTGATCTTCAGCATGCGTTAAGCAAAAA  4000
      L  E  H  A  R  S  E  A  C  L  V  L  D  V  R  M  P  R  M  S  G  F  D  L  Q  H  A  L  S  K  N
4001  TGGTGTCGATATTCCAATCATCTTTATTACCGGCACGCCATGGTGATATCCCATGGTGTCGCGCCATCAAGTCGGGTGCCCTAGAATTCTTCCAAAGCCT  4100
      G  V  D  I  P  I  F  I  F  I  T  G  H  G  D  I  P  M  A  V  R  A  I  K  S  G  A  L  E  F  L  P  K  P
4101  TTTCGTGCTGCTGAAGAACTGCTCCGAAGCAATCAACAGGGCTCGAATATCGATCAGGAGCTCGGAGTACAAGCAGTAGATATTGAAGAAAT  4200
      F  R  A  E  E  L  L  E  A  I  N  R  A  L  N  I  D  Q  E  A  R  E  Y  K  A  E  L  D  K  I  L  K  K  Y
4201  ATGAGGGCTTACAGATCCGAGAAAAGGAGGTATTTCCCTTATTGCCCAGGGCTTGTTGAACAAGCAGATTGCCGGATATCCGGAATTACTGAGGTCAC  4300
      E  G  L  T  D  R  E  K  E  V  F  P  L  I  A  Q  G  L  L  N  K  Q  I  A  G  Y  L  G  I  T  E  V  T
4301  CATAAAGGTTCATCGTCATAATATTACGAGAAAAATGGGGGTCCGGACACTGGCTAATCTGGTGCGACTTTAAGGAAGTTAAAGAATGCTGGCTGATC  4400
```

FIG. 2C

```
          I  K  V  H  R  H  N  I  T  R  K  M  G  V  R  T  L  A  N  L  V  R  L  Y  E  K  L  K  N  A  G  L  I
4401 GAAAAAAGAACGGAAATCTATCGGCATAGAGTTCAAAGCGATGAAGAGCCGCGACTGGAACCCTTCAGCTCTTGGCGGCCACGCTGTAGGAACGCTACCTGCCTACCTGCCGAAT  4500
     E  K  N  G  N  L  S  G  *
4501 GTCTAAACTCACTGAAACGCCGCATAGAGTTCAAAGCGATGAAGAGCCGCGACTGGAACCCTTCAGCTCTTGGCGGCCACGCTGTAGGAACGCTACCTGCCTACCTGCCGAAT  4600
```

```
              EcoR I                                BspLU11 I
              |                                     |
              GAATTCATCGTCGGCTACCACGCCGAAGATCCCAACATGTTCCCGCTGTATCCCGAACTGTCCCACATGG
              ├┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┤ 70
              CTTAAGTAGCAGCCGATGGTGCGGCTTCTAGGGTTGTACAAGGGCGACATAGGGCTTGACAGGGTGTACC
```

Glu Phe Ile Val Gly Tyr His Ala Glu Asp Pro Asn Met Phe Pro Leu Tyr Pro Glu Leu Ser His Met
    Asn Ser Ser Ser Ala Thr Thr Pro Lys Ile Pro Thr Cys Ser Arg Cys Ile Pro Asn Cys Pro Thr Trp
    Arg Ile His Arg Arg Leu Pro Arg Arg Arg Ser Gln His Val Pro Ala Val Ser Arg Thr Val Pro His Gly
```
              ├┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┤
```
  Ser Asn Met Thr Pro • Trp Ala Ser Ser Gly Leu Met Asn Gly Ser Tyr Gly Ser Ser Asp Trp Met Ala
    Phe Glu Asp Asp Ala Val Val Gly Phe Ile Gly Val His Glu Arg Gln Ile Gly Phe Gln Gly Val His
       Ile • Arg Arg Ser Gly Arg Arg Leu Asp Trp Cys Thr Gly Ala Thr Asp Arg Val Thr Gly Cys Pro

```
                                              NgoM I
                                              Eag I
                          BspM I              Eco52 I
                          |    Bsg I          Nae I    Bgl I
                RleA I    |    |              |        |
                |         |    |              |        |
                CCGTGCAGGACTACCTGCGGAGCGACTACTCGCCGCAGCCGGCCGACGAGGCGGCGGCGATCAATGAATA
                ├┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┤ 140
                GGCACGTCCTGATGGACGCCTCGCTGATGAGCGGCGTCGGCCGGCTGCTCCGCCGCCGCTAGTTACTTAT
```

Ala Val Gln Asp Tyr Leu Arg Ser Asp Tyr Ser Pro Gln Pro Ala Asp Glu Ala Ala Ala Ile Asn Glu Tyr
    Pro Cys Arg Thr Thr Cys Gly Ala Thr Thr Arg Arg Ser Arg Pro Thr Arg Arg Arg Ser Met Asn
      Arg Ala Gly Leu Pro Ala Glu Arg Leu Leu Ala Ala Ala Gly Arg Arg Gly Gly Gly Asp Gln • Ile
```
                ├┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┤
```
    Thr Cys Ser • Arg Arg Leu Ser • Glu Gly Cys Gly Ala Ser Ser Ala Ala Ala Ile Leu Ser Tyr
    Gly His Leu Val Val Gln Pro Ala Val Val Arg Arg Leu Arg Gly Val Leu Arg Arg Arg Asp Ile Phe Val
    Arg Ala Pro Ser Gly Ala Ser Arg Ser Ser Ala Ala Ala Pro Arg Arg Pro Pro Pro Ser • His Ile

```
                          ApaB I                                              Eag I
                          |   Pst I                                           |Eco52 I
                          |   |                                               ||
                CTGGAAGCCGCATAGCCTGCAGAGCAAGTGTCAGCCCTATTTCGATCCGGCAGACCTCGGCCGCATGTAT
                ├┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┤ 210
                GACCTTCGGCGTATCGGACGTCTCGTTCACAGTCGGGATAAAGCTAGGCCGTCTGGAGCCGGCGTACATA
```

Trp Lys Pro His Ser Leu Gln Ser Lys Cys Gln Pro Tyr Phe Asp Pro Ala Asp Leu Gly Arg Met Tyr
    Thr Gly Ser Arg Ile Ala Cys Arg Ala Ser Val Ser Pro Ile Ser Ile Arg Gln Thr Ser Ala Ala Cys Ile
    Leu Glu Ala Ala • Pro Ala Glu Gln Val Ser Ala Leu Phe Arg Ser Gly Arg Pro Arg Pro His Val
```
                ├┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┤
```
    Gln Phe Gly Cys Leu Arg Cys Leu Leu His • Gly • Lys Ser Gly Ala Ser Arg Pro Arg Met Tyr
      Pro Leu Arg Met Ala Gln Leu Ala Leu Thr Leu Gly Ile Glu Ile Arg Cys Val Glu Ala Ala His Ile
    Ser Ser Ala Ala Tyr Gly Ala Ser Cys Thr Asp Ala Arg Asn Arg Asp Pro Leu Gly Arg Gly Cys Thr Asp

FIG. 5A

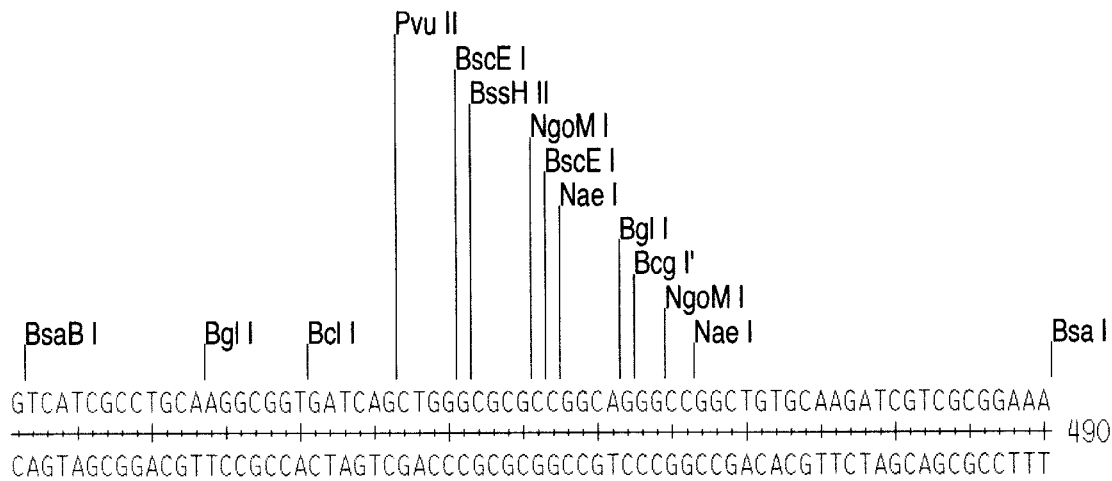
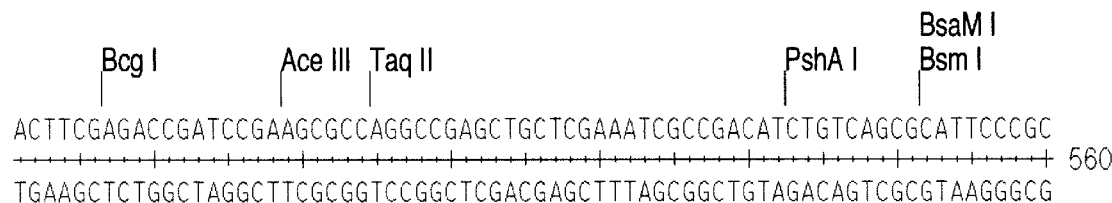
FIG. 5C

```
            Bce83 I                                                                    Pvu I
CGAGCCCTGCAAGGGCCTCAAGGACGCGATGCAGGCGAAATTCTTTACCTTCCTGATCTGTCACGCGATC
++++++++++++++++++++++++++++++++++++++++++++++++++++++++++++++++++++++ 630
GCTCGGGACGTTCCCGGAGTTCCTGCGCTACGTCCGCTTTAAGAAATGGAAGGACTAGACAGTGCGCTAG
```

Glu Pro Cys Lys Gly Leu Lys Asp Ala Met Gln Ala Lys Phe Phe Thr Phe Leu Ile Cys His Ala Ile
Pro Ser Pro Ala Arg Ala Ser Arg Thr Arg Cys Arg Arg Asn Ser Leu Pro Ser  •  Ser Val Thr Arg Ser
   Arg Ala Leu Gln Gly Pro Gln Gly Arg Asp Ala Gly Glu Ile Leu Tyr Leu Pro Asp Leu Ser Arg Asp
Ser Gly Gln Leu Pro Arg Leu Ser Ala Ile Cys Ala Phe Asn Lys Val Lys Arg Ile Gln  •  Ala Ile
   Leu Gly Ala Leu Ala Glu Leu Val Arg His Leu Arg Phe Glu Lys Gly Glu Gln Asp Thr Val Arg Asp
Arg Ala Arg Cys Pro Gly  •  Pro Arg Ser Ala Pro Ser Ile Arg  •  Arg Gly Ser Arg Asp Arg Ser Arg

```
                    EcoP15 I
         Eco47 III  BsrB I                     Bbs I                    BsaX I Stu I      Sal I
GAGCGCTACGCGAGCGGCTACGCCCAGAAGGAAGACACCCTGCTGTGGCCGTACTACAAGGCCTCCGTCG
++++++++++++++++++++++++++++++++++++++++++++++++++++++++++++++++++++++ 700
CTCGCGATGCGCTCGCCGATGCGGGTCTTCCTTCTGTGGGACGACACCGGCATGATGTTCCGGAGGCAGC
```

Glu Arg Tyr Ala Ser Gly Tyr Ala Gln Lys Glu Asp Thr Leu Leu Trp Pro Tyr Tyr Lys Ala Ser Val
   Ser Ala Thr Arg Ala Ala Thr Pro Arg Arg Lys Thr Pro Cys Cys Gly Arg Thr Thr Arg Pro Pro Ser
Arg Ala Leu Arg Glu Arg Leu Arg Pro Glu Gly Arg His Pro Ala Val Ala Val Leu Gln Gly Leu Arg Arg
Ser Arg  •  Ala Leu Pro  •  Ala Trp Phe Ser Ser Val Arg Ser His Gly Tyr  •  Leu Ala Glu Thr Thr
   Leu Ala Val Arg Ala Ala Val Gly Leu Leu Phe Val Gly Gln Gln Pro Arg Val Val Leu Gly Gly Asp
   Ala Ser Arg Ser Arg Ser Arg Gly Ser Pro Leu Cys Gly Ala Thr Ala Thr Ser Cys Pro Arg Arg Arg

```
                                                           Psp1406 I
TCGACAAGAAATTCCAGCCGATGAGCCACATGGATGCGGTGGAACTCGTCGAGATGGAACGTTTGAAGAT
++++++++++++++++++++++++++++++++++++++++++++++++++++++++++++++++++++++ 770
AGCTGTTCTTTAAGGTCGGCTACTCGGTGTACCTACGCCACCTTGAGCAGCTCTACCTTGCAAACTTCTA
```

Val Asp Lys Lys Phe Gln Pro Met Ser His Met Asp Ala Val Glu Leu Val Glu Met Glu Arg Leu Lys Ile
   Ser Thr Arg Asn Ser Ser Arg  •  Ala Thr Trp Met Arg Trp Asn Ser Ser Arg Trp Asn Val  •  Arg
    Arg Gln Glu Ile Pro Ala Asp Glu Pro His Gly Cys Gly Gly Thr Arg Arg Asp Gly Thr Phe Glu Asp
   Ser Leu Phe Asn Trp Gly Ile Leu Trp Met Ser Ala Thr Ser Ser Thr Ser Ile Ser Arg Lys Phe Ile
Asp Val Leu Phe Glu Leu Arg His Ala Val His Ile Arg His Phe Glu Asp Leu His Phe Thr Gln Leu Asn
  Arg Cys Ser Ile Gly Ala Ser Ser Gly Cys Pro His Pro Pro Val Arg Arg Ser Pro Val Asn Ser Ser

FIG. 5D

```
                    Eag I
        BamH I      Eco52 I      Bbs I
CAGCCAAGCGGATCCGCACGGCCGAGCCCTCCATCGTCTTCCGCTATTCCAAGAAGAACCGCGAGAAGAC
+----+----+----+----+----+----+----+----+----+----+----+----+----+----+ 980
GTCGGTTCGCCTAGGCGTGCCGGCTCGGGAGGTAGCAGAAGGCGATAAGGTTCTTCTTGGCGCTCTTCTG
```

Ala Ala Lys Arg Ile Arg Thr Ala Glu Pro Ser Ile Val Phe Arg Tyr Ser Lys Lys Asn Arg Glu Lys Thr
 Gln Pro Ser Gly Ser Ala Arg Pro Ser Pro Pro Ser Ser Ser Ala Ile Pro Arg Arg Thr Ala Arg Arg
  Ser Gln Ala Asp Pro His Gly Arg Ala Leu His Arg Leu Pro Leu Phe Gln Glu Glu Pro Arg Glu Asp

Ala Leu Arg Ile Arg Val Ala Ser Gly Glu Met Thr Lys Arg • Glu Leu Phe Phe Arg Ser Phe Val
 Cys Gly Leu Pro Asp Ala Arg Gly Leu Gly Gly Asp Asp Glu Ala Ile Gly Leu Leu Val Ala Leu Leu Arg
  Leu Trp Ala Ser Gly Cys Pro Arg Ala Arg Trp Arg Arg Gly Ser Asn Trp Ser Ser Gly Arg Ser Ser

```
        Bbs I
GCTGCGCTGGGTTTTCGAGTGCATCCGCGACGGACTCGGCTATCCGTCGATCAAGCACGACGAGATCGGC
+----+----+----+----+----+----+----+----+----+----+----+----+----+----+ 1050
CGACGCGACCCAAAAGCTCACGTAGGCGCTGCCTGAGCCGATAGGCAGCTAGTTCGTGCTGCTCTAGCCG
```

Leu Arg Trp Val Phe Glu Cys Ile Arg Asp Gly Leu Gly Tyr Pro Ser Ile Lys His Asp Glu Ile Gly
Arg Cys Ala Gly Phe Ser Ser Ala Ser Ala Thr Asp Ser Ala Ile Arg Arg Ser Ser Thr Thr Arg Ser Ala
  Ala Ala Leu Gly Phe Arg Val His Pro Arg Arg Thr Arg Leu Ser Val Asp Gln Ala Arg Arg Asp Arg

Ser Arg Gln Thr Lys Ser His Met Arg Ser Pro Ser Pro • Gly Asp Ile Leu Cys Ser Ser Ile Pro
   Gln Ala Pro Asn Glu Leu Ala Asp Ala Val Ser Glu Ala Ile Arg Arg Asp Leu Val Val Leu Asp Ala
    Ala Ala Ser Pro Lys Arg Thr Cys Gly Arg Arg Val Arg Ser Asp Thr Ser • Ala Arg Arg Ser Arg Cys

```
                                                  Kas I
                                                  Nar I
                                                  Ehe I
                                      Bgl I       Bbe I
ACGGAGCAGATGAAGGAATACGCCAAGTTCAGCCTCAACGGCAACGGCGCCACCGACGAGGAAGCCCACA
+----+----+----+----+----+----+----+----+----+----+----+----+----+----+ 1120
TGCCTCGTCTACTTCCTTATGCGGTTCAAGTCGGAGTTGCCGTTGCCGCGGTGGCTGCTCCTTCGGGTGT
```

Thr Glu Gln Met Lys Glu Tyr Ala Lys Phe Ser Leu Asn Gly Asn Gly Ala Thr Asp Glu Glu Ala His
   Arg Ser Arg • Arg Asn Thr Pro Ser Ser Ala Ser Thr Ala Thr Ala Pro Pro Thr Arg Lys Pro Thr
    His Gly Ala Asp Glu Gly Ile Arg Gln Val Gln Pro Gln Arg Gln Arg Arg His Arg Arg Gly Ser Pro Gln

Val Ser Cys Ile Phe Ser Tyr Ala Leu Asn Leu Arg Leu Pro Leu Pro Ala Val Ser Ser Ser Ala Trp Leu
 Arg Leu Leu His Leu Phe Val Gly Leu Glu Ala Glu Val Ala Val Ala Gly Gly Val Leu Phe Gly Val
   Pro Ala Ser Ser Pro Ile Arg Trp Thr • Gly • Arg Cys Arg Arg Trp Arg Arg Pro Leu Gly Cys

FIG. 5F

```
                    RleA I
                    |
ACTGGGTCAACGTGCTGTGCATGTCGCCCGGCATCCACGGTCGCCGCAAGACGCAAAAAACCCGTTCGGA
++++++++++++++++++++++++++++++++++++++++++++++++++++++++++++++++++++ 1190
TGACCCAGTTGCACGACACGTACAGCGGGCCGTAGGTGCCAGCGGCGTTCTGCGTTTTTTGGGCAAGCCT
```

Asn Trp Val Asn Val Leu Cys Met Ser Pro Gly Ile His Gly Arg Arg Lys Thr Gln Lys Thr Arg Ser Glu
 Thr Gly Ser Thr Cys Cys Ala Cys Arg Pro Ala Ser Thr Val Ala Ala Arg Arg Lys Lys Pro Val Arg
  Leu Gly Gln Arg Ala Val His Val Ala Arg His Pro Arg Ser Pro Gln Asp Ala Lys Asn Pro Phe Gly
++++++++++++++++++++++++++++++++++++++++++++++++++++++++++++++++++++
  Gln Thr Leu Thr Ser His Met Asp Gly Pro Met Trp Pro Arg Arg Leu Val Cys Phe Val Arg Glu Ser
 Val Pro Asp Val His Gln Ala His Arg Gly Ala Asp Val Thr Ala Ala Leu Arg Leu Phe Gly Thr Arg Phe
Ser Pro • Arg Ala Thr Cys Thr Ala Arg Cys Gly Arg Asp Gly Cys Ser Ala Phe Phe Gly Asn Pro

```
EcoP15 I                          BstX I                              BsiW I
|                                 |                                   |
AGGTGGCGGCTCAATCTTCCCGGCCAAGCTGCTGGAAATCTCGCTCAATGACGGCTACGACTGGTCGTAC
++++++++++++++++++++++++++++++++++++++++++++++++++++++++++++++++++++ 1260
TCCACCGCCGAGTTAGAAGGGCCGGTTCGACGACCTTTAGAGCGAGTTACTGCCGATGCTGACCAGCATG
```

Gly Gly Gly Ser Ile Phe Pro Ala Lys Leu Leu Glu Ile Ser Leu Asn Asp Gly Tyr Asp Trp Ser Tyr
Lys Val Ala Ala Gln Ser Ser Arg Pro Ser Cys Trp Lys Ser Arg Ser Met Thr Ala Thr Thr Gly Arg Thr
  Arg Trp Arg Leu Asn Leu Pro Gly Gln Ala Ala Gly Asn Leu Ala Gln • Arg Leu Arg Leu Val Val
++++++++++++++++++++++++++++++++++++++++++++++++++++++++++++++++++++
  Pro Pro Pro Glu Ile Lys Gly Ala Leu Ser Ser Ser Ile Glu Ser Leu Ser Pro • Ser Gln Asp Tyr
    Thr Ala Ala • Asp Glu Arg Gly Leu Gln Gln Phe Asp Arg Glu Ile Val Ala Val Val Pro Arg Val
 Leu His Arg Ser Leu Arg Gly Pro Trp Ala Ala Pro Phe Arg Ala • His Arg Ser Arg Ser Thr Thr Arg

FIG. 5G

```
                    Age I
                         Bbs I                    Xmn I            Eco57 I
GCCGACATGCAACTCGGCCCGAAGACCGGTGATCTCTCGTCGCTGAAGTCCTTCGAGGATGTTTGGGAGG
+----+----+----+----+----+----+----+----+----+----+----+----+----+----+  1330
CGGCTGTACGTTGAGCCGGGCTTCTGGCCACTAGAGAGCAGCGACTTCAGGAAGCTCCTACAAACCCTCC
```

Ala Asp Met Gln Leu Gly Pro Lys Thr Gly Asp Leu Ser Ser Leu Lys Ser Phe Glu Asp Val Trp Glu
  Pro Thr Cys Asn Ser Ala Arg Arg Pro Val Ile Ser Arg Arg • Ser Pro Ser Arg Met Phe Gly Arg
Arg Arg His Ala Thr Arg Pro Glu Asp Arg • Ser Leu Val Ala Glu Val Leu Arg Gly Cys Leu Gly Gly

Ala Ser Met Cys Ser Pro Gly Phe Val Pro Ser Arg Glu Asp Ser Phe Asp Lys Ser Ser Thr Gln Ser Ala
  Gly Val His Leu Glu Ala Arg Leu Gly Thr Ile Glu Arg Arg Gln Leu Gly Glu Leu Ile Asn Pro Leu
Arg Cys Ala Val Arg Gly Ser Ser Arg His Asp Arg Thr Ala Ser Thr Arg Arg Pro His Lys Pro Pro

```
CTTTCCGCAAGCAGTATCAATATGCGATCAACCTCTGTATCAGCACCAAGGACGTGTCGCGCTACTTCGA
+----+----+----+----+----+----+----+----+----+----+----+----+----+----+  1400
GAAAGGCGTTCGTCATAGTTATACGCTAGTTGGAGACATAGTCGTGGTTCCTGCACAGCGCGATGAAGCT
```

Ala Phe Arg Lys Gln Tyr Gln Tyr Ala Ile Asn Leu Cys Ile Ser Thr Lys Asp Val Ser Arg Tyr Phe Glu
  Leu Ser Ala Ser Ser Ile Asn Met Arg Ser Thr Ser Val Ser Ala Pro Arg Thr Cys Arg Ala Thr Ser
   Phe Pro Gln Ala Val Ser Ile Cys Asp Gln Pro Leu Tyr Gln His Gln Gly Arg Val Ala Leu Leu Arg

Lys Arg Leu Cys Tyr • Tyr Ala Ile Leu Arg Gln Ile Leu Val Leu Ser Thr Asp Arg • Lys Ser
Ser Glu Ala Leu Leu Ile Leu Ile Arg Asp Val Glu Thr Asp Ala Gly Leu Val His Arg Ala Val Glu Leu
  Lys Gly Cys Ala Thr Asp Ile His Ser • Gly Arg Tyr • Cys Trp Pro Arg Thr Ala Ser Ser Arg

```
    Eco47 III   Pst I                        Bcg I'
GCAGCGCTTCCTGCAGATGCCTTTCGTGTCCGCAATCGACGACGGCTGCATGGAACTCGGGATGGACGCC
+----+----+----+----+----+----+----+----+----+----+----+----+----+----+→ 1470
CGTCGCGAAGGACGTCTACGGAAAGCACAGGCGTTAGCTGCTGCCGACGTACCTTGAGCCCTACCTGCGG
```

Gln Arg Phe Leu Gln Met Pro Phe Val Ser Ala Ile Asp Asp Gly Cys Met Glu Leu Gly Met Asp Ala
Ser Ser Ala Ser Cys Arg Cys Leu Ser Cys Pro Gln Ser Thr Thr Ala Ala Trp Asn Ser Gly Trp Thr Pro
  Ala Ala Leu Pro Ala Asp Ala Phe Arg Val Arg Asn Arg Arg Leu His Gly Thr Arg Asp Gly Arg

Cys Arg Lys Arg Cys Ile Gly Lys Thr Asp Ala Ile Ser Ser Pro Gln Met Ser Ser Pro Ile Ser Ala
  Leu Ala Glu Gln Leu His Arg Glu His Gly Cys Asp Val Val Ala His Phe Glu Pro His Val Gly
Ala Ala Ser Gly Ala Ser Ala Lys Arg Thr Arg Leu Arg Arg Arg Ser Cys Pro Val Arg Ser Pro Arg Arg

FIG. 5H

```
   Beg I                                           PshA I              BssS I
   |                    Van91 I                    |Pvu I              |Msp20 I
   |                    |                          ||                  ||
   TGCGCCCTGTCCGAGCAGCCCAATGGCTGGCACAACCCGATCACGACGATCGTCGCGGCGAACTCCCTCG
   +----+----+----+----+----+----+----+----+----+----+----+----+----+----+ 1540
   ACGCGGGACAGGCTCGTCGGGTTACCGACCGTGTTGGGCTAGTGCTGCTAGCAGCGCCGCTTGAGGGAGC
```

Cys Ala Leu Ser Glu Gln Pro Asn Gly Trp His Asn Pro Ile Thr Thr Ile Val Ala Ala Asn Ser Leu
  Ala Pro Cys Pro Ser Ser Pro Met Ala Gly Thr Thr Arg Ser Arg Arg Ser Ser Arg Arg Thr Pro Ser
Leu Arg Pro Val Arg Ala Ala Gln Trp Leu Ala Gln Pro Asp His Asp Asp Arg Arg Gly Glu Leu Pro Arg

Gln Ala Arg Asp Ser Cys Gly Leu Pro Gln Cys Leu Gly Ile Val Val Ile Thr Ala Ala Phe Glu Arg Thr
 Ala Gly Gln Gly Leu Leu Gly Ile Ala Pro Val Val Arg Asp Arg Arg Asp Asp Arg Arg Val Gly Glu
   Arg Gly Thr Arg Ala Ala Trp His Ser Ala Cys Gly Ser  •  Ser Ser Arg Arg Pro Ser Ser Gly Arg

```
         Msc I                                BseR I
         |Msp20 I                             |Xho I
         ||   Xcm I                           ||Sci I
         ||   |                               |||
         TGGCCATCAAGAAACTGGTATTCGAGGAGAAGAAATACACCCTCGAGCAACTCAGCCAAGCGTTGAAGGC
         +----+----+----+----+----+----+----+----+----+----+----+----+----+----+ 1610
         ACCGGTAGTTCTTTGACCATAAGCTCCTCTTCTTTATGTGGGAGCTCGTTGAGTCGGTTCGCAACTTCCG
```

Val Ala Ile Lys Lys Leu Val Phe Glu Glu Lys Lys Tyr Thr Leu Glu Gln Leu Ser Gln Ala Leu Lys Ala
 Trp Pro Ser Arg Asn Trp Tyr Ser Arg Arg Asn Thr Pro Ser Ser Asn Ser Ala Lys Arg  •  Arg
  Gly His Gln Glu Thr Gly Ile Arg Gly Glu Glu Ile His Pro Arg Ala Thr Gln Pro Ser Val Glu Gly

Ala Met Leu Phe Ser Thr Asn Ser Ser Phe Phe Tyr Val Arg Ser Cys Ser Leu Trp Ala Asn Phe Ala
His Gly Asp Leu Phe Gln Tyr Glu Leu Leu Leu Phe Val Gly Glu Leu Leu Glu Ala Leu Arg Gln Leu Arg
   Pro Trp  •  Ser Val Pro Ile Arg Pro Ser Ser Ile Cys Gly Arg Ala Val  •  Gly Leu Thr Ser Pro

```
                                                     Kas I
                                                     |Nar I
                                                     ||Ehe I
                                    Sal I            |||Bbe I
                                    |                ||||
                                    GAACTGGGAAGGTTTCGAGGAAATGCGCGTCGACTTCAAGCGGGCGCCGAAGTGGGGCAACGACGATGAT
                                    +----+----+----+----+----+----+----+----+----+----+----+----+----+----+ 1680
                                    CTTGACCCTTCCAAAGCTCCTTTACGCGCAGCTGAAGTTCGCCCGCGGCTTCACCCCGTTGCTGCTACTA
```

Asn Trp Glu Gly Phe Glu Glu Met Arg Val Asp Phe Lys Arg Ala Pro Lys Trp Gly Asn Asp Asp
Arg Thr Gly Lys Val Ser Arg Lys Cys Ala Ser Thr Ser Ser Gly Arg Arg Ser Gly Ala Thr Thr Met Ile
  Glu Leu Gly Arg Phe Arg Gly Asn Ala Arg Arg Leu Gln Ala Gly Ala Glu Val Gly Gln Arg Arg  •

Phe Gln Ser Pro Lys Ser Ser Ile Arg Thr Ser Lys Leu Arg Ala Gly Phe His Pro Leu Ser Ser Ser
   Val Pro Phe Thr Glu Leu Phe His Ala Asp Val Glu Leu Pro Arg Arg Leu Pro Ala Val Val Ile Ile
Ser Ser Pro Leu Asn Arg Pro Phe Ala Arg Arg Ser  •  Ala Pro Ala Ser Thr Pro Cys Arg Arg His Asn

FIG. 5I

```
                                                        Fsp I
         TACGCCGACGGTATCATCACCCGCTTCTACGAGGAAATCATCGGCGGCGAAATGCGCAAGATCACCAACT
         ┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼  1750
         ATGCGGCTGCCATAGTAGTGGGCGAAGATGCTCCTTTAGTAGCCGCCGCTTTACGCGTTCTAGTGGTTGA
```

Tyr Ala Asp Gly Ile Ile Thr Arg Phe Tyr Glu Glu Ile Ile Gly Gly Glu Met Arg Lys Ile Thr Asn
 Thr Pro Thr Val Ser Ser Pro Ala Ser Thr Arg Lys Ser Ser Ala Ala Lys Cys Ala Arg Ser Pro Thr
  Leu Arg Arg Arg Tyr His His Pro Leu Leu Arg Gly Asn His Arg Arg Arg Asn Ala Gln Asp His Gln Leu
  ┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼
   • Ala Ser Pro Ile Met Val Arg Lys  • Ser Ser Ile Met Pro Pro Ser Ile Arg Leu Ile Val Leu •
    Val Gly Val Thr Asp Asp Gly Ala Glu Val Leu Phe Asp Asp Ala Ala Phe His Ala Leu Asp Gly Val
     Arg Arg Arg Tyr  •    •  Gly Ser Arg Arg Pro Phe  •  Arg Arg Arg Phe Ala Cys Ser  •  Trp Ser

BsrG I                              Bsp120 I
         ACTCTGGTGGTCCGGTCATGCCGACTGGTCAGGCTGTCGGCCTGTACATGGAAGTCGGTTCGCGCACGGG
         ┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼  1820
         TGAGACCACCAGGCCAGTACGGCTGACCAGTCCGACAGCCGGACATGTACCTTCAGCCAAGCGCGTGCCC

Tyr Ser Gly Gly Pro Val Met Pro Thr Gly Gln Ala Val Gly Leu Tyr Met Glu Val Gly Ser Arg Thr Gly
 Thr Leu Val Val Arg Ser Cys Arg Leu Val Arg Leu Ser Ala Cys Thr Trp Lys Ser Val Arg Ala Arg
  Leu Trp Trp Ser Gly His Ala Asp Trp Ser Gly Cys Arg Pro Val His Gly Ser Arg Phe Ala His Gly
  ┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼
   Glu Pro Pro Gly Thr Met Gly Val Pro  •  Ala Thr Pro Arg Tyr Met Ser Thr Pro Glu Arg Val Pro
    Val Arg Thr Thr Arg Asp His Arg Ser Thr Leu Ser Asp Ala Gln Val His Phe Asp Thr Arg Ala Arg Ala
     Ser Gln His Asp Pro  •  Ala Ser Gln Asp Pro Gln Arg Gly Thr Cys Pro Leu Arg Asn Ala Cys Pro

Apa I   Bgl I
         CCCCACGCCGGACGGGCGCTTCGGGGGTGAAGCGGCAGACGACGGCGGCATTTCTCCCTACATGGGAACC
         ┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼  1890
         GGGGTGCGGCCTGCCCGCGAAGCCCCCACTTCGCCGTCTGCTGCCGCCGTAAAGAGGGATGTACCCTTGG

Pro Thr Pro Asp Gly Arg Phe Gly Gly Glu Ala Ala Asp Asp Gly Gly Ile Ser Pro Tyr Met Gly Thr
   Ala Pro Arg Arg Thr Gly Ala Ser Gly Val Lys Arg Gln Thr Thr Ala Ala Phe Leu Pro Thr Trp Glu Pro
    Pro His Ala Gly Arg Ala Leu Arg Gly  • Ser Gly Arg Arg Arg His Phe Ser Leu His Gly Asn
    ┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼
     Gly Val Gly Ser Pro Arg Lys Pro Pro Ser Ala Ala Ser Ser Pro Pro Met Glu Gly  • Met Pro Val
      Gly Arg Arg Val Pro Ala Glu Pro Thr Phe Arg Cys Val Val Ala Ala Asn Arg Gly Val His Ser Gly
       Gly Trp Ala Pro Arg Ala Ser Arg Pro His Leu Pro Leu Arg Arg Arg Cys Lys Glu Arg Cys Pro Phe Arg

FIG. 5J

```
                                                                    Bsg I
                                              EcoP15 I              Bsp24 I
GACAAGAAGGGGCCGACGGCGGTGTTGCGCTCGGTGTCCAAGGTGCAGAAGAACCAGAAGGGCAACCTGC
++++++++++|++++++++++|++++++++++|++++++++++|++++++++++|++++++++++|++++ 1960
CTGTTCTTCCCCGGCTGCCGCCACAACGCGAGCCACAGGTTCCACGTCTTCTTGGTCTTCCCGTTGGACG
```

Asp Lys Lys Gly Pro Thr Ala Val Leu Arg Ser Val Ser Lys Val Gln Lys Asn Gln Lys Gly Asn Leu
 Thr Arg Arg Gly Arg Arg Arg Cys Cys Ala Arg Cys Pro Arg Cys Arg Arg Thr Arg Arg Ala Thr Cys
Arg Gln Glu Gly Ala Asp Gly Gly Val Ala Leu Gly Val Gln Gly Ala Glu Glu Pro Glu Gly Gln Pro Ala

Ser Leu Phe Pro Gly Val Ala Thr Asn Arg Glu Thr Asp Leu Thr Cys Phe Phe Trp Phe Pro Leu Arg Ser
 Val Leu Leu Pro Arg Arg Arg His Gln Ala Arg His Gly Leu His Leu Leu Val Leu Leu Ala Val Gln
  Cys Ser Pro Ala Ser Pro Pro Thr Ala Ser Pro Thr Trp Pro Ala Ser Ser Gly Ser Pro Cys Gly Ala

```
   BspM I                                       BstB I
    Eco47 III                 Bsp24 I'          Csp45 I
TGAACCAGCGCTTGTCGGTGCCGATCATGCGCTCCAAGCATGGCTTCGAAATCTGGAACTCGTACATGAA
++++++++++|++++++++++|++++++++++|++++++++++|++++++++++|++++++++++|++++ 2030
ACTTGGTCGCGAACAGCCACGGCTAGTACGCGAGGTTCGTACCGAAGCTTTAGACCTTGAGCATGTACTT
```

Leu Asn Gln Arg Leu Ser Val Pro Ile Met Arg Ser Lys His Gly Phe Glu Ile Trp Asn Ser Tyr Met Lys
 • Thr Ser Ala Cys Arg Cys Arg Ser Cys Ala Pro Ser Met Ala Ser Lys Ser Gly Thr Arg Thr •
  Glu Pro Ala Leu Val Gly Ala Asp His Ala Leu Gln Ala Trp Leu Arg Asn Leu Glu Leu Val His Glu

Phe Trp Arg Lys Asp Thr Gly Ile Met Arg Glu Leu Cys Pro Lys Ser Ile Gln Phe Glu Tyr Met Phe
Gln Val Leu Ala Gln Arg His Arg Asp His Ala Gly Leu Met Ala Glu Phe Asp Pro Val Arg Val His Leu
 Ser Gly Ala Ser Thr Pro Ala Ser • Ala Ser Trp Ala His Ser Arg Phe Arg Ser Ser Thr Cys Ser

```
                                                        BscE I
                                                        BssH II
                        BspD I                           |  BscE I
          Bbs I          Cla I                           |  |  Fsp I
GACTTGGCACGATCTGAATATCGATCATGTTCAGTTCAATGTCGTCAGCACGGATGAAATGCGCGCTGCG
++++++++++|++++++++++|++++++++++|++++++++++|++++++++++|++++++++++|++++ 2100
CTGAACCGTGCTAGACTTATAGCTAGTACAAGTCAAGTTACAGCAGTCGTGCCTACTTTACGCGCGACGC
```

Thr Trp His Asp Leu Asn Ile Asp His Val Gln Phe Asn Val Val Ser Thr Asp Glu Met Arg Ala Ala
Arg Leu Gly Thr Ile • Ile Ser Ile Met Phe Ser Ser Met Ser Ser Ala Arg Met Lys Cys Ala Leu Arg
 Asp Leu Ala Arg Ser Glu Tyr Arg Ser Cys Ser Val Gln Cys Arg Gln His Gly • Asn Ala Arg Cys

Val Gln Cys Ser Arg Phe Ile Ser • Thr • Asn Leu Thr Thr Leu Val Ser Ser Ile Arg Ala Ala
 Ser Pro Val Ile Gln Ile Asp Ile Met Asn Leu Glu Ile Asp Asp Ala Arg Ile Phe His Ala Ser Arg
Ser Lys Ala Arg Asp Ser Tyr Arg Asp His Glu Thr • His Arg • Cys Pro His Phe Ala Arg Gln Ala

FIG. 5K

```
                                                        Eco47 III
                                                        |
CAGCGCGAACCCGAGAAGCACCATGATCTTATCGTGCGCGTTTCCGGCTACAGCGCTCGGTTCGTAGACA
++++++++++++++++++++++++++++++++++++++++++++++++++++++++++++++++++++ 2170
GTCGCGCTTGGGCTCTTCGTGGTACTAGAATAGCACGCGCAAAGGCCGATGTCGCGAGCCAAGCATCTGT
```

Gln Arg Glu Pro Glu Lys His His Asp Leu Ile Val Arg Val Ser Gly Tyr Ser Ala Arg Phe Val Asp
  Ser Ala Asn Pro Arg Ser Thr Met Ile Leu Ser Cys Ala Phe Pro Ala Thr Ala Leu Gly Ser • Thr
    A l a Ala Arg Thr Arg Glu Ala Pro • Ser Tyr Arg Ala Arg Phe Arg Leu Gln Arg Ser Val Arg Arg His

Cys Arg Ser Gly Ser Phe Cys Trp Ser Arg Ile Thr Arg Thr Glu Pro • Leu Ala Arg Asn Thr Ser Met
  Leu Ala Phe Gly Leu Leu Val Met Ile Lys Asp His Ala Asn Gly Ala Val Ala Ser Pro Glu Tyr Val
    Ala Arg Val Arg Ser Ala Gly His Asp • Arg Ala Arg Lys Arg Ser Cys Arg Glu Thr Arg Leu Cys

```
                                                              Xho I
                                                              | Sci I
                                                              |  |
TTCCGACCTATGGGCAGAACACCATCATCGCCCGTCAGGAACAGGATTTCAGCGCATCCGATCTCGAGTT
++++++++++++++++++++++++++++++++++++++++++++++++++++++++++++++++++++ 2240
AAGGCTGGATACCCGTCTTGTGGTAGTAGCGGGCAGTCCTTGTCCTAAAGTCGCGTAGGCTAGAGCTCAA
```

Ile Pro Thr Tyr Gly Gln Asn Thr Ile Ile Ala Arg Gln Glu Gln Asp Phe Ser Ala Ser Asp Leu Glu Phe
  Phe Arg Pro Met Gly Arg Thr Pro Ser Ser Pro Val Arg Asn Arg Ile Ser Ala His Pro Ile Ser Ser
    Ser Asp Leu Trp Ala Glu His His His Arg Pro Ser Gly Thr Gly Phe Gln Arg Ile Arg Ser Arg Val

Gly Val • Pro Cys Phe Val Met Met Ala Arg • Ser Cys Ser Lys Leu Ala Asp Ser Arg Ser Asn
Asn Arg Gly Ile Pro Leu Val Gly Asp Asp Gly Thr Leu Phe Leu Ile Glu Ala Cys Gly Ile Glu Leu Glu
  Glu Ser Arg His Ala Ser Cys Trp • Arg Gly Asp Pro Val Pro Asn • Arg Met Arg Asp Arg Thr

```
        Bce83 I
        |
CCTAAACGTCGAAATCTAGGACAAGCCACTCAAGGGGGGCAGCATCCCGTCCCCCTTTACCTTACGGTTG
++++++++++++++++++++++++++++++++++++++++++++++++++++++++++++++++++++ 2310
GGATTTGCAGCTTTAGATCCTGTTCGGTGAGTTCCCCCCGTCGTAGGGCAGGGGGAAATGGAATGCCAAC
```

Leu Asn Val Glu Ile • Asp Lys Pro Leu Lys Gly Gly Ser Ile Pro Ser Pro Phe Thr Leu Arg Leu
Ser • Thr Ser Lys Ser Arg Thr Ser His Ser Arg Gly Ala Ala Ser Arg Pro Pro Leu Pro Tyr Gly Cys
  Pro Lys Arg Arg Asn Leu Gly Gln Ala Thr Gln Gly Gly Gln His Pro Val Pro Leu Tyr Leu Thr Val

Arg Phe Thr Ser Ile • Ser Leu Gly Ser Leu Pro Pro Leu Met Gly Asp Gly Lys Val Lys Arg Asn
    • Val Asp Phe Asp Leu Val Leu Trp Glu Leu Pro Ala Ala Asp Arg Gly Gly Lys Gly • Pro Gln
Gly Leu Arg Arg Phe Arg Pro Cys Ala Val • Pro Pro Cys Cys Gly Thr Gly Arg • Arg Val Thr Ala

FIG. 5L

```
CACGAAAAAACATGGAGGGCAGCAACATGGAAACAGGACAGAATTTGCAAAACCAGCCGCATACCGAGGT
----+----+----+----+----+----+----+----+----+----+----+----+----+----+ 2380
GTGCTTTTTTGTACCTCCCGTCGTTGTACCTTTGTCCTGTCTTAAACGTTTTGGTCGGCGTATGGCTCCA
```

His Glu Lys Thr Trp Arg Ala Ala Thr Trp Lys Gln Asp Arg Ile Cys Lys Thr Ser Arg Ile Pro Arg
 Thr Lys Lys His Gly Gly Gln Gln His Gly Asn Arg Thr Glu Phe Ala Lys Pro Ala Ala Tyr Arg Gly
Ala Arg Lys Asn Met Glu Gly Ser Asn Met Glu Thr Gly Gln Asn Leu Gln Asn Gln Pro His Thr Glu Val

Cys Ser Phe Val His Leu Ala Ala Val His Phe Cys Ser Leu Ile Gln Leu Val Leu Arg Met Gly Leu His
 Val Phe Phe Cys Pro Pro Cys Cys Pro Phe Leu Val Ser Asn Ala Phe Gly Ala Ala Tyr Arg Pro
 Arg Phe Phe Met Ser Pro Leu Leu Met Ser Val Pro Cys Phe Lys Cys Phe Trp Gly Cys Val Ser Thr

```
GGGTACGGCGAGGCCGTGCCGGAGTTGCAAATGGCAAACCCCCGACCCCACCGATCCGCACCGTGGGCAA
----+----+----+----+----+----+----+----+----+----+----+----+----+----+ 2450
CCCATGCCGCTCCGGCACGGCCTCAACGTTTACCGTTTGGGGGCTGGGGTGGCTAGGCGTGGCACCCGTT
```

Trp Val Arg Arg Gly Arg Ala Gly Val Ala Asn Gly Lys Pro Pro Thr Pro Pro Ile Arg Thr Val Gly Asn
 Gly Tyr Gly Glu Ala Val Pro Glu Leu Gln Met Ala Asn Pro Arg Pro His Arg Ser Ala Pro Trp Ala
 Gly Thr Ala Arg Pro Cys Arg Ser Cys Lys Trp Gln Thr Pro Asp Pro Thr Asp Pro His Arg Gly Gln

Thr Arg Arg Pro Arg Ala Pro Thr Ala Phe Pro Leu Gly Gly Val Gly Gly Ile Arg Val Thr Pro Leu
Pro Tyr Pro Ser Ala Thr Gly Ser Asn Cys Ile Ala Phe Gly Arg Gly Trp Arg Asp Ala Gly His Ala Ile
 Pro Val Ala Leu Gly His Arg Leu Gln Leu His Cys Val Gly Ser Gly Val Ser Gly Cys Arg Pro Cys

```
       BsrD I    Taq II'  Nco I                    Bpu10 I       Bpm I
TGCACCGCCAACCGGCACGCCATGGGTGGCGTCTGGAAACGCTGGCTTAGGGACGTTGAAAACACGACCT
----+----+----+----+----+----+----+----+----+----+----+----+----+----+ 2520
ACGTGGCGGTTGGCCGTGCGGTACCCACCGCAGACCTTTGCGACCGAATCCCTGCAACTTTTGTGCTGGA
```

Ala Pro Pro Thr Gly Thr Pro Trp Val Ala Ser Gly Asn Ala Gly Leu Gly Thr Leu Lys Thr Arg Pro
Met His Arg Gln Pro Ala Arg His Gly Trp Arg Leu Glu Thr Leu Ala • Gly Arg • Lys His Asp Leu
 Cys Thr Ala Asn Arg His Ala Met Gly Gly Val Trp Lys Arg Trp Leu Arg Asp Val Glu Asn Thr Thr

Ala Gly Gly Val Pro Val Gly His Thr Ala Asp Pro Phe Ala Pro Lys Pro Val Asn Phe Val Arg Gly
 Cys Arg Trp Gly Ala Arg Trp Pro His Arg Arg Ser Val Ser Ala • Pro Arg Gln Phe Cys Ser Arg
His Val Ala Leu Arg Cys Ala Met Pro Pro Thr Gln Phe Arg Gln Ser Leu Ser Thr Ser Phe Val Val Gln

FIG. 5M

```
         EcoN I
          BspM I
            BssS I                              Tth111 I              Bpm I
GCTCCAGGCACGAGGAAGGCAAACTAAGTTTCCGCGACCACGTCTGAACACCGGACAGACGTGGTTCACC
++++++++++|++++++++++|++++++++++|++++++++++|++++++++++|++++++++++|++++ 2590
CGAGGTCCGTGCTCCTTCCGTTTGATTCAAAGGCGCTGGTGCAGACTTGTGGCCTGTCTGCACCAAGTGG
```

Ala Pro Gly Thr Arg Lys Ala Asn • Val Ser Ala Thr Thr Ser Glu His Arg Thr Asp Val Val His
  Leu Gln Ala Arg Gly Arg Gln Thr Lys Phe Pro Arg Pro Arg Leu Asn Thr Gly Gln Thr Trp Phe Thr
 Cys Ser Arg His Glu Glu Gly Lys Leu Ser Phe Arg Asp His Val • Thr Pro Asp Arg Arg Gly Ser Pro
++++++++++|++++++++++|++++++++++|++++++++++|++++++++++|++++++++++|++++
 Ala Gly Pro Val Leu Phe Ala Phe • Thr Glu Ala Val Val Asp Ser Cys Arg Val Ser Thr Thr • Arg
  Ser Trp Ala Arg Pro Leu Cys Val Leu Asn Gly Arg Gly Arg Arg Phe Val Pro Cys Val His Asn Val
   Glu Leu Cys Ser Ser Pro Leu Ser Leu Lys Arg Ser Trp Thr Gln Val Gly Ser Leu Arg Pro Glu Gly

```
                   Bpm I
                     BspH I
TCCAGACCACTGTAGTGATAGATCATGAAAACCTACTCCAGCGCAAATGGCCTGTTCGTCCCGGAAGTCG
++++++++++|++++++++++|++++++++++|++++++++++|++++++++++|++++++++++|++++ 2660
AGGTCTGGTGACATCACTATCTAGTACTTTTGGATGAGGTCGCGTTTACCGGACAAGCAGGGCCTTCAGC
```

Leu Gln Thr Thr Val Val Ile Asp His Glu Asn Leu Leu Gln Arg Lys Trp Pro Val Arg Pro Gly Ser Arg
 Ser Arg Pro Leu • • • Ile Met Lys Thr Tyr Ser Ser Ala Asn Gly Leu Phe Val Pro Glu Val
   Pro Asp His Cys Ser Asp Arg Ser • Lys Pro Thr Pro Ala Gln Met Ala Cys Ser Ser Arg Lys Ser
++++++++++|++++++++++|++++++++++|++++++++++|++++++++++|++++++++++|++++
  Trp Val Val Thr Thr Ile Ser • Ser Phe Arg Ser Trp Arg Leu His Gly Thr Arg Gly Pro Leu Arg
 Glu Leu Gly Ser Tyr His Tyr Ile Met Phe Val • Glu Leu Ala Phe Pro Arg Asn Thr Gly Ser Thr Ser
   Gly Ser Trp Gln Leu Ser Leu Asp His Phe Gly Val Gly Ala Cys Ile Ala Gln Glu Asp Arg Phe Asp

```
                                Bcg I      Bcg I'                EcoR V Bcg I'
ATCCCTACTACTATGTAAGTACGGAAAACCAGAGCTTCCTCGATAAATTTGCAAAGATATCGAAAAAGCA
++++++++++|++++++++++|++++++++++|++++++++++|++++++++++|++++++++++|++++ 2730
TAGGGATGATGATACATTCATGCCTTTTGGTCTCGAAGGAGCTATTTAAACGTTTCTATAGCTTTTTCGT
```

Ser Leu Leu Leu Cys Lys Tyr Gly Lys Pro Glu Leu Pro Arg • Ile Cys Lys Asp Ile Glu Lys Ala
Asp Pro Tyr Tyr Tyr Val Ser Thr Glu Asn Gln Ser Phe Leu Asp Lys Phe Ala Lys Ile Ser Lys Lys His
  Ile Pro Thr Thr Met • Val Arg Lys Thr Arg Ala Ser Ser Ile Asn Leu Gln Arg Tyr Arg Lys Ser
++++++++++|++++++++++|++++++++++|++++++++++|++++++++++|++++++++++|++++
  Asp Arg Ser Ser His Leu Tyr Pro Phe Gly Ser Ser Gly Arg Tyr Ile Gln Leu Ser Ile Ser Phe Ala
    Gly • • • Thr Leu Val Ser Phe Trp Leu Lys Arg Ser Leu Asn Ala Phe Ile Asp Phe Phe Cys
   Ile Gly Val Val Ile Tyr Thr Arg Phe Val Leu Ala Glu Glu Ile Phe Lys Cys Leu Tyr Arg Phe Leu Met

FIG. 5N

```
                Bcg I                              Bbs I
                 |                                  |
     TCCCGTCAATGTACTGGTGGTCGGCAAACAAGGCTGCGGCAAGTCTTCCCTAGTGCGGCAATACGCCGCC
     +---+---+---+---+---+---+---+---+---+---+---+---+---+---+---+---+---+---+  2800
     AGGGCAGTTACATGACCACCAGCCGTTTGTTCCGACGCCGTTCAGAAGGGATCACGCCGTTATGCGGCGG
```

Ser Arg Gln Cys Thr Gly Gly Arg Gln Thr Arg Leu Arg Gln Val Phe Pro Ser Ala Ala Ile Arg Arg
  Pro Val Asn Val Leu Val Val Gly Lys Gln Gly Cys Gly Lys Ser Ser Leu Val Arg Gln Tyr Ala Ala
  Ile Pro Ser Met Tyr Trp Trp Ser Ala Asn Lys Ala Ala Ala Ser Leu Pro • Cys Gly Asn Thr Pro Pro

Asp Arg • His Val Pro Pro Arg Cys Val Leu Ser Arg Cys Thr Lys Gly Leu Ala Ala Ile Arg Arg Arg
  Gly Thr Leu Thr Ser Thr Thr Pro Leu Cys Pro Gln Pro Leu Asp Glu Arg Thr Arg Cys Tyr Ala Ala
  Gly Asp Ile Tyr Gln His Asp Ala Phe Leu Ala Ala Ala Leu Arg Gly • His Pro Leu Val Gly Gly

```
                                         BsaB I
                                           |
     GTCAACAGGCTACCCTTGGCGACCTTCCAGATCGGCATCCTGTCGGAGCCGGGGCAACTGTTTGGTGAAT
     +---+---+---+---+---+---+---+---+---+---+---+---+---+---+---+---+---+---+  2870
     CAGTTGTCCGATGGGAACCGCTGGAAGGTCTAGCCGTAGGACAGCCTCGGCCCCGTTGACAAACCACTTA
```

Arg Gln Gln Ala Thr Leu Gly Asp Leu Pro Asp Arg His Pro Val Gly Ala Gly Ala Thr Val Trp • Ile
  Val Asn Arg Leu Pro Leu Ala Thr Phe Gln Ile Gly Ile Leu Ser Glu Pro Gly Gln Leu Phe Gly Glu
  Ser Thr Gly Tyr Pro Trp Arg Pro Ser Arg Ser Ala Ser Cys Arg Ser Arg Gly Asn Cys Leu Val Asn

• Cys Ala Val Arg Pro Ser Arg Gly Ser Arg Cys Gly Thr Pro Ala Pro Ala Val Thr Gln His Ile
Thr Leu Leu Ser Gly Lys Ala Val Lys Trp Ile Pro Met Arg Asp Ser Gly Pro Cys Ser Asn Pro Ser Tyr
  Asp Val Pro • Gly Gln Arg Gly Glu Leu Asp Ala Asp Gln Arg Leu Arg Pro Leu Gln Lys Thr Phe

```
                                                                      Mfe I
         Bsa I              Bpm I              Ear I                  Mun I
          |                  |                  |                      |
     ACGCGCTGGAGAACGGGGAGACCCGTTACAAGCAGTTCCTCTTCCCCCAGGCCATCCAGACACCCAATTG
     +---+---+---+---+---+---+---+---+---+---+---+---+---+---+---+---+---+---+  2940
     TGCGCGACCTCTTGCCCCTCTGGGCAATGTTCGTCAAGGAGAAGGGGGTCCGGTAGGTCTGTGGGTTAAC
```

Arg Ala Gly Glu Arg Gly Asp Pro Leu Gln Ala Val Pro Leu Pro Pro Gly His Pro Asp Thr Gln Leu
Tyr Ala Leu Glu Asn Gly Glu Thr Arg Tyr Lys Gln Phe Leu Phe Pro Gln Ala Ile Gln Thr Pro Asn Cys
  Thr Arg Trp Arg Thr Gly Arg Pro Val Thr Ser Ser Ser Ser Pro Arg Pro Ser Arg His Pro Ile

Arg Ala Pro Ser Arg Pro Ser Gly Asn Cys Ala Thr Gly Arg Gly Gly Pro Trp Gly Ser Val Trp Asn
  Ala Ser Ser Phe Pro Ser Val Arg • Leu Cys Asn Arg Lys Gly Trp Ala Met Trp Val Gly Leu Gln
Val Arg Gln Leu Val Pro Leu Gly Thr Val Leu Leu Glu Glu Glu Gly Leu Gly Asp Leu Cys Gly Ile Ala

FIG. 5O

```
              Taq II'
                Ear I                                           BspLU11 I
CGTCATCCACCTTGAAGAGATCAATCGCCCCGAGCATCCGAAGGCGTTGAACATGTTGTTCTCCATTCTC
++++-+----+----+----+----+----+----+----+----+----+----+----+----+---+  3010
GCAGTAGGTGGAACTTCTCTAGTTAGCGGGGCTCGTAGGCTTCCGCAACTTGTACAACAAGAGGTAAGAG
```

Arg His Pro Pro • Arg Asp Gln Ser Pro Arg Ala Ser Glu Gly Val Glu His Val Val Leu His Ser
  Val Ile His Leu Glu Glu Ile Asn Arg Pro Glu His Pro Lys Ala Leu Asn Met Leu Phe Ser Ile Leu
Ala Ser Ser Thr Leu Lys Arg Ser Ile Ala Pro Ser Ile Arg Arg Arg • Thr Cys Cys Ser Pro Phe Ser

Arg • Gly Gly Gln Leu Ser • Asp Gly Arg Ala Asp Ser Pro Thr Ser Cys Thr Thr Arg Trp Glu Arg
  Thr Met Trp Arg Ser Ser Ile Leu Arg Gly Ser Cys Gly Phe Ala Asn Phe Met Asn Asn Glu Met Arg
Asp Asp Val Lys Phe Leu Asp Ile Ala Gly Leu Met Arg Leu Arg Gln Val His Gln Glu Gly Asn Glu

```
                                       EcolCR I
             EcoP15 I                    Sac I
TCCGATGACCGTCAGGTATGGATGGACGAGCTCGGACTGCTGCAAGTAGCGCCCGGAGTCGTTTTCTTCG
++++-+----+----+----+----+----+----+----+----+----+----+----+----+---+  3080
AGGCTACTGGCAGTCCATACCTACCTGCTCGAGCCTGACGACGTTCATCGCGGGCCTCAGCAAAAGAAGC
```

Leu Arg • Pro Ser Gly Met Asp Gly Arg Ala Arg Thr Ala Ala Ser Ser Ala Arg Ser Arg Phe Leu Arg
  Ser Asp Asp Arg Gln Val Trp Met Asp Glu Leu Gly Leu Leu Gln Val Ala Pro Gly Val Val Phe Phe
    Pro Met Thr Val Arg Tyr Gly Trp Thr Ser Ser Asp Cys Cys Lys • Arg Pro Glu Ser Phe Ser Ser

Arg His Gly Asp Pro Ile Ser Pro Arg Ala Arg Val Ala Ala Leu Leu Ala Arg Leu Arg Lys Arg Arg
Glu Ser Ser Arg • Thr His Ile Ser Ser Ser Pro Ser Ser Cys Thr Ala Gly Pro Thr Thr Lys Lys Ala
  Gly Ile Val Thr Leu Tyr Pro His Val Leu Glu Ser Gln Gln Leu Tyr Arg Gly Ser Asp Asn Glu Glu

```
                          EcoR I
CAACGCTCAACGAAGGGTCCGAATTC
++++-+----+----+----+----+→  3106
GTTGCGAGTTGCTTCCCAGGCTTAAG
```

Asn Ala Gln Arg Arg Val Arg Ile
Ala Thr Leu Asn Glu Gly Ser Glu Phe
 Gln Arg Ser Thr Lys Gly Pro Asn Ser

Leu Ala • Arg Leu Thr Arg Ile Gly
 Val Ser Leu Ser Pro Asp Ser Asn
Cys Arg Glu Val Phe Pro Gly Phe Glu

FIG. 5P

```
                ApoB I
                 Sph I
                  Mfe I                           AflII
                   Mun I  ApoB I    ApoB I       Bst98 I          BspM I
ATACGGCGACGCAGCGCATGCAATTGATGCACTTGCTGCGGTCGAGCTTAAGCACCTGCTTGCGCCCGGT
├──┼──┼──┼──┼──┼──┼──┼──┼──┼──┼──┼──┼──┼──┼──┼──┼──┼──┼──┼──┼──┤ 70
TATGCCGCTGCGTCGCGTACGTTAACTACGTGAACGACGCCAGCTCGAATTCGTGGACGAACGCGGGCCA

Ile Arg Arg Arg Ser Ala Cys Asn  •  Cys Thr Cys Cys Gly Arg Ala  •  Ala Pro Ala Cys Ala Arg
  Tyr Gly Asp Ala Ala His Ala Ile Asp Ala Leu Ala Ala Val Glu Leu Lys His Leu Leu Ala Pro Gly
 Asn Thr Ala Thr Gln Arg Met Gln Leu Met His Leu Leu Arg Ser Ser Leu Ser Thr Cys Leu Arg Pro Val
├──┼──┼──┼──┼──┼──┼──┼──┼──┼──┼──┼──┼──┼──┼──┼──┼──┼──┼──┼──┼──┤
 Ile Arg Arg Arg Leu Ala His Leu Gln His Val Gln Gln Pro Arg Ala  •  Ala Gly Ala Gln Ala Arg Asp
  Tyr Pro Ser Ala Ala Cys Ala Ile Ser Ala Ser Ala Ala Thr Ser Ser Leu Cys Arg Ser Ala Gly Pro
   Val Ala Val Cys Arg Met Cys Asn Ile Cys Lys Ser Arg Asp Leu Lys Leu Val Gln Lys Arg Gly Thr

Age I                                              Ace III
CCATCAAGAAGCTGCGATGCACCGGTTGGGCAGACCGTTGCACACCGTCCGCAGCTCACGCAACGATCAC
├──┼──┼──┼──┼──┼──┼──┼──┼──┼──┼──┼──┼──┼──┼──┼──┼──┼──┼──┼──┼──┤ 140
GGTAGTTCTTCGACGCTACGTGGCCAACCCGTCTGGCAACGTGTGGCAGGCGTCGAGTGCGTTGCTAGTG

Ser Ile Lys Lys Leu Arg Cys Thr Gly Trp Ala Asp Arg Cys Thr Pro Ser Ala Ala His Ala Thr Ile Thr
 Pro Ser Arg Ser Cys Asp Ala Pro Val Gly Gln Thr Val Ala His Arg Pro Gln Leu Thr Gln Arg Ser
   His Gln Glu Ala Ala Met His Arg Leu Gly Arg Pro Leu His Thr Val Arg Ser Ser Arg Asn Asp His
├──┼──┼──┼──┼──┼──┼──┼──┼──┼──┼──┼──┼──┼──┼──┼──┼──┼──┼──┼──┼──┤
 Met Leu Phe Ser Arg His Val Pro Gln Ala Ser Arg Gln Val Gly Asp Ala Ala  •  Ala Val Ile Val
Gly Asp Leu Leu Gln Ser Ala Gly Thr Pro Cys Val Thr Ala Cys Arg Gly Cys Ser Val Cys Arg Asp Arg
  Trp  •  Ser Ala Ala Ile Cys Arg Asn Pro Leu Gly Asn Cys Val Thr Arg Leu Glu Arg Leu Ser  •

Van91 I
GGTTGTAATAGTATTCCTTGCCCACCTTTTGGGTTTCAGGGTTGTGGCACCACGGACATCTCAATGGGCA
├──┼──┼──┼──┼──┼──┼──┼──┼──┼──┼──┼──┼──┼──┼──┼──┼──┼──┼──┼──┼──┤ 210
CCAACATTATCATAAGGAACGGGTGGAAAACCCAAAGTCCCAACACCGTGGTGCCTGTAGAGTTACCCGT

Val Val Ile Val Phe Leu Ala His Leu Leu Gly Phe Arg Val Val Ala Pro Arg Thr Ser Gln Trp Ala
Arg Leu  •   •  Tyr Ser Leu Pro Thr Phe Trp Val Ser Gly Leu Trp His His Gly His Leu Asn Gly Gln
   Gly Cys Asn Ser Ile Pro Cys Pro Pro Phe Gly Phe Gln Gly Cys Gly Thr Thr Asp Ile Ser Met Gly
├──┼──┼──┼──┼──┼──┼──┼──┼──┼──┼──┼──┼──┼──┼──┼──┼──┼──┼──┼──┼──┤
  Thr Thr Ile Thr Asn Arg Ala Trp Arg Lys Pro Lys Leu Thr Thr Ala Gly Arg Val Asp  •  His Ala
   Asn Tyr Tyr Tyr Glu Lys Gly Val Lys Gln Thr Glu Pro Asn His Cys Trp Pro Cys Arg Leu Pro Cys
Pro Gln Leu Leu Ile Gly Gln Gly Gly Lys Pro Asn  •  Pro Gln Pro Val Val Ser Met Glu Ile Pro Leu
```

FIG. 6A

```
         ACCCTTCAAGAACACCGTCGTCCGNAATCCAGGACCGTCTTGCAGGCTAAAACGCTGTATTTCGGTGACT
      ┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼ 280
         TGGGAAGTTCTTGTGGCAGCAGGCNTTAGGTCCTGGCAGAACGTCCGATTTTGCGACATAAAGCCACTGA
```

Thr Leu Gln Glu His Arg Arg Pro ??? Ser Arg Thr Val Leu Gln Ala Lys Thr Leu Tyr Phe Gly Asp
     Pro Phe Lys Asn Thr Val Val Arg Asn Pro Gly Pro Ser Cys Arg Leu Lys Arg Cys Ile Ser Val Thr
   Asn Pro Ser Arg Thr Pro Ser Ser ??? Ile Gln Asp Arg Leu Ala Gly • Asn Ala Val Phe Arg • Leu
      ┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼
   Val Arg • Ser Cys Arg Arg Gly ??? Asp Leu Val Thr Lys Cys Ala Leu Val Ser Tyr Lys Pro Ser •
     Gly Lys Leu Phe Val Thr Thr Arg ??? Gly Pro Gly Asp Gln Leu Ser Phe Arg Gln Ile Glu Thr Val
       Gly Glu Leu Val Gly Asp Asp ??? Ile Trp Ser Arg Arg Ala Pro • Phe Ala Thr Asn Arg His Ser

Bcg I'
                                                                            |
```
         AATGGAATTTTCACGTCAGCCCCAGAATCGCATGTTGGAAACGTCATCCGTCCGGTATCAATCGGCTCGC
      ┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼ 350
         TTACCTTAAAAGTGCAGTCGGGGTCTTAGCGTACAACCTTTGCAGTAGGCAGGCCATAGTTAGCCGAGCG
```

• Trp Asn Phe His Val Ser Pro Arg Ile Ala Cys Trp Lys Arg His Pro Ser Gly Ile Asn Arg Leu Ala
     Asn Gly Ile Phe Thr Ser Ala Pro Glu Ser His Val Gly Asn Val Ile Arg Pro Val Ser Ile Gly Ser
       Met Glu Phe Ser Arg Gln Pro Gln Asn Arg Met Leu Glu Thr Ser Ser Val Arg Tyr Gln Ser Ala Arg
      ┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼
     His Phe Lys • Thr Leu Gly Leu Ile Ala His Gln Phe Arg • Gly Asp Pro Ile Leu Arg Ser Ala
   Leu Pro Ile Lys Val Asp Ala Gly Ser Asp Cys Thr Pro Phe Thr Met Arg Gly Thr Asp Ile Pro Glu Ser
       Ile Ser Asn Glu Arg • Gly Trp Phe Arg Met Asn Ser Val Asp Asp Thr Arg Tyr • Asp Ala Arg

BsaM I    BstB I
             Bsm I     Csp45 I           Bcg I
             |         |                 |
```
         TGTGCGAGCATTCATTTCGAACGATTACGCCTCCGCCCAAATCCGGCGGCGGAGGCCGATCCACCACGAC
      ┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼ 420
         ACACGCTCGTAAGTAAAGCTTGCTAATGCGGAGGCGGGTTTAGGCCGCCGCCTCCGGCTAGGTGGTGCTG
```

Val Arg Ala Phe Ile Ser Asn Asp Tyr Ala Ser Ala Gln Ile Arg Arg Arg Arg Pro Ile His His Asp
   Leu Cys Glu His Ser Phe Arg Thr Ile Thr Pro Pro Pro Lys Ser Gly Gly Gly Gly Arg Ser Thr Thr Thr
       Cys Ala Ser Ile His Phe Glu Arg Leu Arg Leu Arg Pro Asn Pro Ala Ala Glu Ala Asp Pro Pro Arg
      ┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼
     Thr Arg Ala Asn Met Glu Phe Ser • Ala Glu Ala Trp Ile Arg Arg Arg Leu Gly Ile Trp Trp Ser
       His Ser Cys Glu Asn Arg Val Ile Val Gly Gly Gly Leu Asp Pro Pro Pro Arg Asp Val Val Val
   Gln Ala Leu Met • Lys Ser Arg Asn Arg Arg Arg Gly Phe Gly Ala Ala Ser Ala Ser Gly Gly Arg Gly

FIG. 6B

```
              EcoP15 I                          Bgl I
CATAGAAGTGAATCTTGTAAGGGTTCATTGAACTTCCGCCCTGCTGGCGGCGTCAATAAGTGCGATCACC
                                                                       490
GTATCTTCACTTAGAACATTCCCAAGTAACTTGAAGGCGGGACGACCGCCGCAGTTATTCACGCTAGTGG

His Arg Ser Glu Ser Cys Lys Gly Ser Leu Asn Phe Arg Pro Ala Gly Gly Val Asn Lys Cys Asp His
  Ile Glu Val Asn Leu Val Arg Val His  •  Thr Ser Ala Leu Leu Ala Ala Ser Ile Ser Ala Ile Thr
Pro  •  Lys  •  Ile Leu  •  Gly Phe Ile Glu Leu Pro Pro Cys Trp Arg Arg Gln  •  Val Arg Ser Pro

Trp Leu Leu Ser Asp Gln Leu Pro Glu Asn Phe Lys Arg Gly Ala Pro Pro Thr Leu Leu His Ser  •  Trp
  Met Ser Thr Phe Arg Thr Leu Thr  •  Gln Val Glu Ala Arg Ser Ala Ala Asp Ile Leu Ala Ile Val
Tyr Phe His Ile Lys Tyr Pro Asn Met Ser Ser Gly Gly Gln Gln Arg Arg  •  Tyr Thr Arg Asp Gly

Mlu113 I
                                  Sac II
                                   Uba1221 I
                                              Uba1221 I
AGTCGGTGTGGTGATTTCCCTCATGTATTCGTTTGTCACCGCGGCTCAGCTAAAATATGCAAATAAA
                                                                     557
TCAGCCACACCACTAAAGGGAGTACATAAGCAAACAGTGGCGCCGAGTCGATTTTATACGTTTATTT

Gln Ser Val Trp  •  Phe Pro Ser Cys Ile Arg Leu Ser Pro Arg Leu Ser  •  Asn Met Gln Ile Lys
  Ser Arg Cys Gly Asp Phe Pro His Val Phe Val Cys His Arg Gly Ser Ala Lys Ile Cys Lys  •
  Val Gly Val Val Ile Ser Leu Met Tyr Ser Phe Val Thr Ala Ala Gln Leu Lys Tyr Ala Asn Lys

Asp Thr His His Asn Gly Glu His Ile Arg Lys Asp Gly Arg Ser Leu  •  Phe Ile Cys Ile Phe
Leu Arg His Pro Ser Lys Gly  •  Thr Asn Thr Gln  •  Arg Pro Glu Ala Leu Ile His Leu Tyr Phe
Thr Pro Thr Thr Ile Glu Arg Met Tyr Glu Asn Thr Val Ala Ala  •  Ser Phe Tyr Ala Phe Leu
```

FIG. 6C

```
TutD.T1      MF--------PLYPELSHMAVQDYLRSDYSPQPADEAAAI  32
PflD.coli    MTNRISRLKTALFANTREISLERALLYTASHRQTEGEPVI  40
Pfl.Clostrid MFKQWEGFQDGEWTN--DVNVRDFIQKNY--KEYTGDKSF  36

TutD.T1      ------------------NEYW------------------  37
PflD.coli    LR---------RAKATAYILEHVEISI--RDEELIAGNRT  69
Pfl.Clostrid LKGPTEKTKKVWDKAVSLILEELKKGILDVDTETISGINS  76

TutD.T1      -KPHS--LQSKCQP---YFDPADLGRM---YQVSSMEAPS  67
PflD.coli    VKPRAGIMSPEMDP---YWLLKELD-----QFPTRPQDR  100
Pfl.Clostrid FKP--GYLDKDNEVIVGFQTDAPLKRITNPFGGIRMAEQS 114

TutD.T1      -----FASG------YNSIVPPY------ETVLEDGLLAR  90
PflD.coli    -----FAISEEDKRIYREELFPYWEKRSMKDFINGQMTDE 135
Pfl.Clostrid LKEYGFKISDEMHNIFTN----YRKTHNQGVF--DAYSEE 148

TutD.T1      IK-------LAEKHIAEAQADMST-FPWNGTKGLDN-IAK 121
PflD.coli    VKAATNTQIFSINQTDKGQGHIIIDYPRLLNHGLGELVAQ 175
Pfl.Clostrid TRIARSAGVLTGLPDAYGRGRIIGDYRRVALYGIDFLI-- 187

TutD.T1      IDN----------WKAMVIACKAVISWARRQGRLCKIVAE 151
PflD.coli    MQQHCQQQPENHFYQAALLLLEASQKHILRYAELAETMAA 215
Pfl.Clostrid ------QEKKKDLSNLKGDMLDELI-------RLREEVSE 213

TutD.T1      NFET-DPKRQAELLEIADICQRIPAEPCKGLKDAMQAKFF 190
PflD.coli    NC-T-DAQRREELLTIAEISRHNAQHKPQTFWQACQ--LF 251
Pfl.Clostrid QIRALDEIKKMALSYGVDISRPAVNAK-----EAAQFLYF 248

TutD.T1      TFLICHAIERYASGYAQ----KEDTLLWPYYKASVVDKKF 226
PflD.coli    WYM--NIILQYESNASSLSLGRFDQYMLPFYQTSLTQG-- 288
Pfl.Clostrid GYLAGVK----ENNGAAMSLGRTSTFLDIYIERDLEQGLI 284
```

FIG. 7A

```
TutD.T1      QPMSHMDAVELVEMERLKISEHGAGKSRAYREIFPGSNDL  266
PflD.coli    EDAAFLK--ELLESLWVKCNDIVLLRSTSSARYFAGFPTG   325
Pfl.Clostrid TED---EAQEVIDQFIIKLRLVRHLRTPEYNELFAGDPTW   321

TutD.T1      FILTVGGTNAKGEDACNDMTDAILEAAKRI-RTAEPSIVF   305
PflD.coli    YTALLGGLTENGRSAVNVLSFLCLDAYQSV-QLPQPNLGV   364
Pfl.Clostrid VTESIAGVGIDGRSLVTKNSFRYLHTLINLGSAPEPNMTV   361

TutD.T1      RYSKKNREKTLRWVFECIRDGLGYPSIKHDEIGTEQMKEY   345
PflD.coli    RTNALIDTPFLMKTAETIRFGTGIPQIFNDEVVVP-----  400
Pfl.Clostrid LWSENLPESFKKFCAE-MSILTDSIQYENDDIMRPI---Y 397

TutD.T1      AKFSLNGNGATDEEAHNWVNVLCMSPGIHGRRKTQKTRSE   385
PflD.coli    ---AFLNRGVSLEDARDYSVVGCVELSIPGR-----TYGL  431
Pfl.Clostrid GD--------------DYAIACVSAMRVGK---------  415

TutD.T1      GGGSIF----PA-KLLEISLNDGYDWSYADMQLGPKTGDL   420
PflD.coli    HDIAMF----NLLKVMEICLHE--------------NEGN  453
Pfl.Clostrid -DMQFFGARCNLAKCLLLAINGGVD-EKKGIKVVPDIEPI  452

TutD.T1      SS-LKSFEDVWEAFRKQYQYAINLCISTKDVSRYFEQRFL   459
PflD.coli    AA-L-TYEGLLEQIRAKISHYITLMVEGSNICDIGHRDWA   491
Pfl.Clostrid TDEVLDYEKVKENYFKVLEYMAGLYVNTMNIIHFMHDKY-  492

TutD.T1      QMPFVSAIDDGCMELGMDACALSEQPNGWH----NPITTI  495
PflD.coli    PVPLLSSFISDCLEKGRD---ITDGGARYNFSGVQGIGIA  528
Pfl.Clostrid ------AYEASQMAL---------------HDTKVGRLMAFGIA 514

TutD.T1      VAANSLVAIKKLVFEEKKYTLEQLSQALKANWEGFEEMRV   535
PflD.coli    NLSDSLHALKGMVFEQQRLSFDELLSVLKANFATPEGEKV   568
Pfl.Clostrid GFSVAADSLSAIRYAKVKPIREN---GITVDFVKEGD--- 549
```

FIG. 7B

```
TutD.T1      D - - - F K R A P K W G N D D D Y A D G I I T R F Y E E I I G G E M R K I T N Y   572
PflD.coli    R A R L I N R F E K Y G N D I D E V D N I S A E L L R H Y C K - E V E K Y Q N P   607
Pfl.Clostrid - - - - - - - F P K Y G N D D D R V D S I A V E I V E K F - S D E L K K H P T Y  580

TutD.T1      S G G P V M P T G Q A V G L Y M E V G S R T G P T P D G R F G G E A A D D G G I   612
PflD.coli    R G G Y F T P G S Y T V S A H V P L G S V V G A T P D G R F A G E Q L A D G G L   647
Pfl.Clostrid R N A K H T L S V L T I T S N V M Y G K K T G T T P D G R K V G E P L A P G A -   620

TutD.T1      S P Y M G T D K K G P T A V L R S V S K V Q K N - - Q K G N L L N Q R L S V P I   650
PflD.coli    S P M L G Q D A Q G P T A V L K S V S K L D N T L L S N G T L L N V K F T P A T   687
Pfl.Clostrid N P M H G R D M E G A L A S L N S V A K V P Y V C C E D G V S N T F S I V P D A   659

TutD.T1      M R S K H G F E I - - W N S Y M K T W H D L N I D H V Q F N V V S T D E M R A A   688
PflD.coli    L E G E A G L R K - - L A D F L R A F T Q L K L Q H I Q F N V V N A D T L R E A   725
Pfl.Clostrid L G N D H D V R I N N L V S I M G G Y F G Q G A H H L N V N V L N R E T L I D A   699
                                                *
TutD.T1      Q R E P E K H H D L I V R V S G Y S A R F V D I P T Y G Q N T I I A R Q E Q D F   728
PflD.coli    Q Q R P Q D Y A G L V V R V A G Y S A F F V E L S K E I Q D D I I R R T A H Q L   765
Pfl.Clostrid M N N P D K Y P T L T I R V S G Y A V N F N R L S K D H Q K E V I S R T F H E -   739

TutD.T1      S A S D L E F L N V E I                                                           740
PflD.coli                                                                                     765
Pfl.Clostrid - - - - - - - - - - K L                                                          740
```

FIG. 7C pUC129

ATG ACC ATG ATT ACG CCA AGC TTG CAT GCA TCG GTA CCG GGC CCC
met thr met ile thr pro ser leu his ala ser val pro gly pro /HindIII\/-SphI\    /-KpnI\/-ApaI\
                    /-NsiI-\

/-XhoI\/-SalI-\    /-ClaI-\/HindIII\/EcoRV\/EcoRI\/-PstI-\/SmaI-\/
CCC TCG AGG TCG ACG GTA TCG ATA AGC TTG ATA TCG AAT TCC TGC AGC CCG GGG
pro ser arg ser thr val ser ile ser leu ile ser asn ser cys ser pro gly /---NotI--\
-BamHI\/-SpeI-\/XbaI-\    /-EagI\    /-SacI\    /-SacI-\/EcoRI\
                                    /---BstXI---\
GAT CCA CTA GTT CTA GAG CGG CCG CCA CCG CGG TGG AGC TCG AAT TCA
asp pro leu val leu glu arg pro pro arg trp ser ser asn ser

```
                  Uba1221 I
                  |
                  | Uba1221 I
                  | |
                  | | Mlu113 I
                  | | |
                  | | | Sac II
                  | | | |
TTTATTTGCATATTTTAGCTGAGCCGCGGTGACAAACGAATACATGAGGGAAATCACCACACCGACTGGT
+----+----+----+----+----+----+----+----+----+----+----+----+----+----+ 70
AAATAAACGTATAAAATCGACTCGGCGCCACTGTTTGCTTATGTACTCCCTTTAGTGGTGTGGCTGACCA
```

Phe Ile Cys Ile Phe • Leu Ser Arg Gly Asp Lys Arg Ile His Glu Gly Asn His His Thr Asp Trp
  Leu Phe Ala Tyr Phe Ser • Ala Ala Val Thr Asn Glu Tyr Met Arg Glu Ile Thr Thr Pro Thr Gly
Leu Tyr Leu His Ile Leu Ala Glu Pro Arg • Gln Thr Asn Thr • Gly Lys Ser Pro His Arg Leu Val
+----+----+----+----+----+----+----+----+----+----+----+----+----+----+
Lys Ile Gln Met Asn • Ser Leu Arg Pro Ser Leu Arg Ile Cys Ser Pro Phe • Trp Val Ser Gln His
  Lys Asn Ala Tyr Lys Leu Gln Ala Ala Thr Val Phe Ser Tyr Met Leu Ser Ile Val Val Gly Val Pro
    • Lys Cys Ile Lys Ala Ser Gly Arg His Cys Val Phe Val His Pro Phe Asp Gly Cys Arg Ser Thr

```
                              Bgl I                          EcoP15 I
                              |                              |
GATCGCACTTATTGACGCCGCCAGCAGGGCGGAAGTTCAATGAACCCTTACAAGATTCACTTCTATGGTC
+----+----+----+----+----+----+----+----+----+----+----+----+----+----+ 140
CTAGCGTGAATAACTGCGGCGGTCGTCCCGCCTTCAAGTTACTTGGGAATGTTCTAAGTGAAGATACCAG
```

• Ser His Leu Leu Thr Pro Pro Ala Gly Arg Lys Phe Asn Glu Pro Leu Gln Asp Ser Leu Leu Trp Ser
  Asp Arg Thr Tyr • Arg Arg Gln Gln Gly Gly Ser Ser Met Asn Pro Tyr Lys Ile His Phe Tyr Gly
    Ile Ala Leu Ile Asp Ala Ala Ser Arg Ala Glu Val Gln • Thr Leu Thr Arg Phe Thr Ser Met Val
+----+----+----+----+----+----+----+----+----+----+----+----+----+----+
Asp Cys Lys Asn Val Gly Gly Ala Pro Arg Phe Asn Leu Ser Gly Lys Cys Ser Glu Ser Arg His Asp
  Ser Arg Val • Gln Arg Arg Trp Cys Pro Pro Leu Glu Ile Phe Gly • Leu Ile • Lys • Pro Arg
    Ile Ala Ser Ile Ser Ala Ala Leu Leu Ala Ser Thr • His Val Arg Val Leu Asn Val Glu Ile Thr

```
                                              BstB I         BsaM I
                                        Bcg I  Csp45 I       Bsm I
                                        |      |             |
GTGGTGGATCGGCCTCCGCCGCCGGATTTGGGCGGAGGCGTAATCGTTCGAAATGAATGCTCGCACAGCG
+----+----+----+----+----+----+----+----+----+----+----+----+----+----+ 210
CACCACCTAGCCGGAGGCGGCGGCCTAAACCCGCCTCCGCATTAGCAAGCTTTACTTACGAGCGTGTCGC
```

Trp Trp Ile Gly Leu Arg Arg Arg Ile Trp Ala Glu Ala • Ser Phe Glu Met Asn Ala Arg Thr Ala
  Arg Gly Gly Ser Ala Ser Ala Ala Gly Phe Gly Arg Arg Arg Asn Arg Ser Lys • Met Leu Ala Gln Arg
    Val Val Asp Arg Pro Pro Pro Asp Leu Gly Gly Gly Val Ile Val Arg Asn Glu Cys Ser His Ser
+----+----+----+----+----+----+----+----+----+----+----+----+----+----+
His His Ile Pro Arg Arg Arg Arg Ile Gln Ala Ser Ala Tyr Asp Asn Ser Ile Phe Ala Arg Val Ala
  Pro Pro Asp Ala Glu Ala Ala Pro Asn Pro Arg Leu Arg Leu Arg Glu Phe His Ile Ser Ala Cys Arg
    Thr Thr Ser Arg Gly Gly Gly Gly Ser Lys Pro Pro Pro Thr Ile Thr Arg Phe Ser His Glu Cys Leu Ser

FIG. 12A

Bcg I'

```
AGCCGATTGATACCGGACGGATGACGTTTCCAACATGCGATTCTGGGGCTGACGTGAAAATTCCATTAGT
                                                                      280
TCGGCTAACTATGGCCTGCCTACTGCAAAGGTTGTACGCTAAGACCCCGACTGCACTTTTAAGGTAATCA
```

Ser Arg Leu Ile Pro Asp Gly • Arg Phe Gln His Ala Ile Leu Gly Leu Thr • Lys Phe His •
  Ala Asp • Tyr Arg Thr Asp Asp Val Ser Asn Met Arg Phe Trp Gly • Arg Glu Asn Ser Ile Ser
    Glu Pro Ile Asp Thr Gly Arg Met Thr Phe Pro Thr Cys Asp Ser Gly Ala Asp Val Lys Ile Pro Leu Val

Leu Arg Asn Ile Gly Ser Pro His Arg Lys Trp Cys Ala Ile Arg Pro Ser Val His Phe Asn Trp • Asp
  Ala Ser Gln Tyr Arg Val Ser Ser Thr Glu Leu Met Arg Asn Gln Pro Gln Arg Ser Phe Glu Met Leu
    Gly Ile Ser Val Pro Arg Ile Val Asn Gly Val His Ser Glu Pro Ala Ser Thr Phe Ile Gly Asn Thr

Acc III
BspE I

```
CACCGAAATACAGCGTTTTAGCCTGCAAGACGGTCCTGGATTCCGGACGACGGTGTTCTTGAAGGGTTGC
                                                                      350
GTGGCTTTATGTCGCAAAATCGGACGTTCTGCCAGGACCTAAGGCCTGCTGCCACAAGAACTTCCCAACG
```

Ser Pro Lys Tyr Ser Val Leu Ala Cys Lys Thr Val Leu Asp Ser Gly Arg Arg Cys Ser • Arg Val Ala
  His Arg Asn Thr Ala Phe • Pro Ala Arg Arg Ser Trp Ile Pro Asp Asp Gly Val Leu Glu Gly Leu
    Thr Glu Ile Gln Arg Phe Ser Leu Gln Asp Gly Pro Gly Phe Arg Thr Thr Val Phe Leu Lys Gly Cys

Gly Phe Tyr Leu Thr Lys Ala Gln Leu Val Thr Arg Ser Glu Pro Arg Arg His Glu Gln Leu Thr Ala
• Arg Phe Val Ala Asn • Gly Ala Leu Arg Asp Gln Ile Gly Ser Ser Pro Thr Arg Ser Pro Asn Gly
  Val Ser Ile Cys Arg Lys Leu Arg Cys Ser Pro Gly Pro Asn Arg Val Val Thr Asn Lys Phe Pro Gln

Van91 I                          Ace III

```
CCATTGAGATGTCCGTGGTGCCACAACCCTGAAACCCAAAAGGTGGGCAAGGAATACTATTACAACCGTG
                                                                      420
GGTAACTCTACAGGCACCACGGTGTTGGGACTTTGGGTTTTCCACCCGTTCCTTATGATAATGTTGGCAC
```

His • Asp Val Arg Gly Ala Thr Thr Leu Lys Pro Lys Arg Trp Ala Arg Asn Thr Ile Thr Thr Val
Pro Ile Glu Met Ser Val Val Pro Gln Pro • Asn Pro Lys Gly Gly Gln Gly Ile Leu Leu Gln Pro •
  Pro Leu Arg Cys Pro Trp Cys His Asn Pro Glu Thr Gln Lys Val Gly Lys Glu Tyr Tyr Tyr Asn Arg

Trp Gln Ser Thr Arg Pro Ala Val Val Arg Phe Gly Leu Leu His Ala Leu Phe Val Ile Val Val Thr
  Met Ser Ile Asp Thr Thr Gly Cys Gly Gln Phe Gly Phe Pro Pro Cys Pro Ile Ser Asn Cys Gly His
    Gly Asn Leu His Gly His His Trp Leu Gly Ser Val Trp Phe Thr Pro Leu Ser Tyr • • Leu Arg Ser

FIG. 12B

```
                                          Age I
ATCGTTGCGTGAGCTGCGGACGGTGTGCAACGGTCTGCCCAACCGGTGCATCGCAGCTTCTTGATGGACC
+----+----+----+----+----+----+----+----+----+----+----+----+----+----+ 490
TAGCAACGCACTCGACGCCTGCCACACGTTGCCAGACGGGTTGGCCACGTAGCGTCGAAGAACTACCTGG
```

Ile Val Ala  •  Ala Ala Asp Gly Val Gln Arg Ser Ala Gln Pro Val His Arg Ser Phe Leu Met Asp
  Ser Leu Arg Glu Leu Arg Thr Val Cys Asn Gly Leu Pro Asn Arg Cys Ile Ala Ala Ser  •  Trp Thr
Asp Arg Cys Val Ser Cys Gly Arg Cys Ala Thr Val Cys Pro Thr Gly Ala Ser Gln Leu Leu Asp Gly Pro

Ile Thr Ala His Ala Ala Ser Pro Thr Cys Arg Asp Ala Trp Gly Thr Cys Arg Leu Lys Lys Ile Ser Arg
 Asp Asn Arg Ser Ser Arg Val Thr His Leu Pro Arg Gly Leu Arg His Met Ala Ala Glu Gln His Val
  Arg Gln Thr Leu Gln Pro Arg His Ala Val Thr Gln Gly Val Pro Ala Asp Cys Ser Arg Ser Pro Gly

```
                                    Mfe I
              Afl II                Mun I    Sph I
              Bst98 I       ApaB I  | ApaB I | ApaB I
              |             |       |        |    |
GGGCGCAAGCCAGGTGCTTAAGCTCGACCGCAGCAAGTGCATCAATTGCATGCGCTGCGTCGCCGTATGC
+----+----+----+----+----+----+----+----+----+----+----+----+----+----+ 560
CCCGCGTTCGGTCCACGAATTCGAGCTGGCGTCGTTCACGTAGTTAACGTACGCGACGCAGCGGCATACG
```

Arg Ala Gln Ala Arg Cys Leu Ser Ser Thr Ala Ala Ser Ala Ser Ile Ala Cys Ala Ala Ser Pro Tyr Ala
  Gly Arg Lys Pro Gly Ala  •  Ala Arg Pro Gln Gln Val His Gln Leu His Ala Leu Arg Arg Arg Met
   Gly Ala Ser Gln Val Leu Lys Leu Asp Arg Ser Lys Cys Ile Asn Cys Met Arg Cys Val Ala Val Cys

Ala Cys Ala Leu His Lys Leu Glu Val Ala Ala Leu Ala Asp Ile Ala His Ala Ala Asp Gly Tyr Ala
Pro Arg Leu Gly Pro Ala  •  Ala Arg Gly Cys Cys Thr Cys  •  Asn Cys Ala Ser Arg Arg Arg Ile Gly
 Pro Ala Leu Trp Thr Ser Leu Ser Ser Arg Leu Leu His Met Leu Gln Met Arg Gln Thr Ala Thr His

```
    Age I            Tth111 I
    |                |
CTCACCGGTAGCCGCGACTCTGTCGGGATGGAAATGACACTCGACGAGATTTTGCGCGAGGTCTTGTCCG
+----+----+----+----+----+----+----+----+----+----+----+----+----+----+ 630
GAGTGGCCATCGGCGCTGAGACAGCCCTACCTTTACTGTGAGCTGCTCTAAAACGCGCTCCAGAACAGGC
```

Ser Pro Val Ala Ala Thr Leu Ser Gly Trp Lys  •  His Ser Thr Arg Phe Cys Ala Arg Ser Cys Pro
Pro His Arg  •  Pro Arg Leu Cys Arg Asp Gly Asn Asp Thr Arg Arg Asp Phe Ala Arg Gly Leu Val Arg
  Leu Thr Gly Ser Arg Asp Ser Val Gly Met Glu Met Thr Leu Asp Glu Ile Leu Arg Glu Val Leu Ser

Glu Gly Thr Ala Ala Val Arg Asp Pro His Phe His Cys Glu Val Leu Asn Gln Ala Leu Asp Gln Gly
   •  Arg Tyr Gly Arg Ser Gln Arg Ser Pro Phe Ser Val Arg Arg Ser Lys Ala Arg Pro Arg Thr Arg
Arg Val Pro Leu Arg Ser Glu Thr Pro Ile Ser Ile Val Ser Ser Ser Ile Lys Arg Ser Thr Lys Asp Ser

FIG. 12C

```
                                                                    BsaM I
                                                           Ear I    Bsm I
                                                           |        |
ATGAGCCTTTCTACCGCAATAGCGGGGGCGGAGTGACGATCAGCGGAGGCGATCCTCTCTTCCACCCTGC
++++++++++++++++++++++++++++++++++++++++++++++++++++++++++++++++++++++ 700
TACTCGGAAAGATGGCGTTATCGCCCCCGCCTCACTGCTAGTCGCCTCCGCTAGGAGAGAAGGTGGGACG
```

Met Ser Leu Ser Thr Ala Ile Ala Gly Ala Glu • Arg Ser Ala Glu Ala Ile Leu Ser Ser Thr Leu
 • Ala Phe Leu Pro Gln • Arg Gly Arg Ser Asp Asp Gln Arg Arg Arg Ser Ser Leu Pro Pro Cys
Asp Glu Pro Phe Tyr Arg Asn Ser Gly Gly Gly Val Thr Ile Ser Gly Gly Asp Pro Leu Phe His Pro Ala

Ile Leu Arg Glu Val Ala Ile Ala Pro Ala Ser His Arg Asp Ala Ser Ala Ile Arg Glu Glu Val Arg Cys
  His Ala Lys Arg Gly Cys Tyr Arg Pro Arg Leu Ser Ser • Arg Leu Arg Asp Glu Arg Gly Gly Gln
    Ser Gly Lys • Arg Leu Leu Pro Pro Pro Thr Val Ile Leu Pro Pro Ser Gly Arg Lys Trp Gly Ala

```
             BscE I
             BssH II                               Nru I
             |  BscE I                             |   Pvu I
             ||                                    |   |
ATTCACATTGGAACTAGCGCGCAAGATCAAGGAACGCGGCGTCCATGTCGCGATCGAGACTTCCTGCTTC
++++++++++++++++++++++++++++++++++++++++++++++++++++++++++++++++++++++ 770
TAAGTGTAACCTTGATCGCGCGTTCTAGTTCCTTGCGCCGCAGGTACAGCGCTAGCTCTGAAGGACGAAG
```

His Ser His Trp Asn • Arg Ala Arg Ser Arg Asn Ala Ala Ser Met Ser Arg Ser Arg Leu Pro Ala Ser
  Ile His Ile Gly Thr Ser Ala Gln Asp Gln Gly Thr Arg Arg Pro Cys Arg Asp Arg Asp Phe Leu Leu
    Phe Thr Leu Glu Leu Ala Arg Lys Ile Lys Glu Arg Gly Val His Val Ala Ile Glu Thr Ser Cys Phe

Glu Cys Gln Phe • Arg Ala Leu Asp Leu Phe Ala Ala Asp Met Asp Arg Asp Leu Ser Gly Ala Glu
Met • Met Pro Val Leu Ala Cys Ser • Pro Val Arg Arg Gly His Arg Ser Arg Ser Lys Arg Ser Gly
  Asn Val Asn Ser Ser Ala Arg Leu Ile Leu Ser Arg Pro Thr Trp Thr Ala Ile Ser Val Glu Gln Lys

```
      BstX I                                             Sal I
      |                                                  |
CCAAAAAAATGGGCGACTATCCAGCCGCTACTTAAACTCGTCGATCTTTTCATCGTCGACCTGAAATCGC
++++++++++++++++++++++++++++++++++++++++++++++++++++++++++++++++++++++ 840
GGTTTTTTTACCCGCTGATAGGTCGGCGATGAATTTGAGCAGCTAGAAAAGTAGCAGCTGGACTTTAGCG
```

Gln Lys Asn Gly Arg Leu Ser Ser Arg Tyr Leu Asn Ser Ser Ile Phe Ser Ser Ser Thr • Asn Arg
Pro Lys Lys Met Gly Asp Tyr Pro Ala Ala Thr • Thr Arg Arg Ser Phe His Arg Arg Pro Glu Ile Ala
  Pro Lys Lys Trp Ala Thr Ile Gln Pro Leu Leu Lys Leu Val Asp Leu Phe Ile Val Asp Leu Lys Ser

Trp Phe Phe Pro Arg Ser Asp Leu Arg • Lys Phe Glu Asp Ile Lys Glu Asp Asp Val Gln Phe Arg
   Leu Phe Ile Pro Ser • Gly Ala Ala Val • Val Arg Arg Asp Lys • Arg Arg Gly Ser Ile Ala
Gly Phe Phe His Ala Val Ile Trp Gly Ser Ser Leu Ser Thr Ser Arg Lys Met Thr Ser Arg Phe Asp Ser

FIG. 12D

```
                            Msp20 I
                             |Msc I
                             | |Msp20 I
                             | | |
TGAATCGGAAAAAGCATGAGGAAACTGTTGGCTGGCCACTGCAACCCATACTCGACAATATCGAGCATCT
++++++++++++++++++++++++++++++++++++++++++++++++++++++++++++++++++++++ 910
ACTTAGCCTTTTTCGTACTCCTTTGACAACCGACCGGTGACGTTGGGTATGAGCTGTTATAGCTCGTAGA
```

• Ile Gly Lys Ser Met Arg Lys Leu Leu Ala Gly His Cys Asn Pro Tyr Ser Thr Ile Ser Ser Ile
    Glu Ser Glu Lys Ala  •  Gly Asn Cys Trp Leu Ala Thr Ala Thr His Thr Arg Gln Tyr Arg Ala Ser
 Leu Asn Arg Lys Lys His Glu Glu Thr Val Gly Trp Pro Leu Gln Pro Ile Leu Asp Asn Ile Glu His Leu
 ++++++++++++++++++++++++++++++++++++++++++++++++++++++++++++++++++++++
 Gln Ile Pro Phe Leu Met Leu Phe Ser Asn Ala Pro Trp Gln Leu Gly Tyr Glu Val Ile Asp Leu Met Glu
   Ser Asp Ser Phe Ala His Pro Phe Gln Gln Ser Ala Val Ala Val Trp Val Arg Cys Tyr Arg Ala Asp
     Phe Arg Phe Phe Cys Ser Ser Val Thr Pro Gln Gly Ser Cys Gly Met Ser Ser Leu Ile Ser Cys Arg

```
CATACAAGCCAAGGCCAATATCCGCATACACATTCCTGTAATCCCTGGATTCAACGACTCACCAATGGAT
++++++++++++++++++++++++++++++++++++++++++++++++++++++++++++++++++++++ 980
GTATGTTCGGTTCCGGTTATAGGCGTATGTGTAAGGACATTAGGGACCTAAGTTGCTGAGTGGTTACCTA
```

Ser Tyr Lys Pro Arg Pro Ile Ser Ala Tyr Thr Phe Leu  •  Ser Leu Asp Ser Thr Thr His Gln Trp Ile
   His Thr Ser Gln Gly Gln Tyr Pro His Thr His Ser Cys Asn Pro Trp Ile Gln Arg Leu Thr Asn Gly
     Ile Gln Ala Lys Ala Asn Ile Arg Ile His Ile Pro Val Ile Pro Gly Phe Asn Asp Ser Pro Met Asp
     ++++++++++++++++++++++++++++++++++++++++++++++++++++++++++++++++++++++
     Tyr Leu Gly Leu Gly Ile Asp Ala Tyr Val Asn Arg Tyr Asp Arg Ser Glu Val Val  •  Trp His Ile
   •  Val Leu Trp Pro Trp Tyr Gly Cys Val Cys Glu Gln Leu Gly Gln Ile  •  Arg Ser Val Leu Pro Asn
 Met Cys Ala Leu Ala Leu Ile Arg Met Cys Met Gly Thr Ile Gly Pro Asn Leu Ser Glu Gly Ile Ser

```
                                               Pvu II
                                                 |
TTCGAGGATTACATCGCTTACTTGGGTCGCCATGCCGCGCAGCTGGATGGCGTAGACATTCTAAATTATC
++++++++++++++++++++++++++++++++++++++++++++++++++++++++++++++++++++++ 1050
AAGCTCCTAATGTAGCGAATGAACCCAGCGGTACGGCGCGTCGACCTACCGCATCTGTAAGATTTAATAG
```

Ser Arg Ile Thr Ser Leu Thr Trp Val Ala Met Pro Arg Ser Trp Met Ala  •  Thr Phe  •  Ile Ile
 Phe Arg Gly Leu His Arg Leu Leu Gly Ser Pro Cys Arg Ala Ala Gly Trp Arg Arg His Ser Lys Leu Ser
   Phe Glu Asp Tyr Ile Ala Tyr Leu Gly Arg His Ala Ala Gln Leu Asp Gly Val Asp Ile Leu Asn Tyr
   ++++++++++++++++++++++++++++++++++++++++++++++++++++++++++++++++++++++
   Glu Leu Ile Val Asp Ser Val Gln Thr Ala Met Gly Arg Leu Gln Ile Ala Tyr Val Asn  •  Ile Ile
     Arg Pro Asn Cys Arg Lys Ser Pro Asp Gly His Arg Ala Ala Pro His Arg Leu Cys Glu Leu Asn Asp
 Lys Ser Ser  •  Met Ala  •  Lys Pro Arg Trp Ala Ala Cys Ser Ser Pro Thr Ser Met Arg Phe  •  •

FIG. 12E

```
                                                              BstX I
                       BsrB I                                 Ear I
                       |                                      |
   ACGTCTATGGAGAAGGCAAGTACCGCTCCTTGGGCCGGGAAAATGAATACCAGTATTTTGGCGTGGAAGA
   ++++++++++|++++++++++|++++++++++|++++++++++|++++++++++|++++++++++|+++++++ 1120
   TGCAGATACCTCTTCCGTTCATGGCGAGGAACCCGGCCCTTTTACTTATGGTCATAAAACCGCACCTTCT
```

Thr Ser Met Glu Lys Ala Ser Thr Ala Pro Trp Ala Gly Lys Met Asn Thr Ser Ile Leu Ala Trp Lys
 Arg Leu Trp Arg Arg Gln Val Pro Leu Leu Gly Pro Gly Lys • Ile Pro Val Phe Trp Arg Gly Arg
His Val Tyr Gly Glu Gly Lys Tyr Arg Ser Leu Gly Arg Glu Asn Glu Tyr Gln Tyr Phe Gly Val Glu Glu

Val Asp Ile Ser Phe Ala Leu Val Ala Gly Gln Ala Pro Phe Ile Phe Val Leu Ile Lys Ala His Phe Leu
 Arg Arg His Leu Leu Cys Thr Gly Ser Arg Pro Gly Pro Phe His Ile Gly Thr Asn Gln Arg Pro Leu
   Thr • Pro Ser Pro Leu Tyr Arg Glu Lys Pro Arg Ser Phe Ser Tyr Trp Tyr Lys Pro Thr Ser Ser

```
                                                  NgoM I
                        Nru I                     Nae I   BssS I             Pvu I
                        |                         |       |                  |
   GAACCCACCCGAAAAGGTAGTGCCACTCGCGAAAGGTTTGAAACTCGCCGGCATCACGAGCGTAACGATC
   ++++++++++|++++++++++|++++++++++|++++++++++|++++++++++|++++++++++|+++++++ 1190
   CTTGGGTGGGCTTTTCCATCACGGTGAGCGCTTTCCAAACTTTGAGCGGCCGTAGTGCTCGCATTGCTAG
```

Arg Thr His Pro Lys Arg • Cys His Ser Arg Lys Val • Asn Ser Pro Ala Ser Arg Ala • Arg Ser
  Glu Pro Thr Arg Lys Gly Ser Ala Thr Arg Glu Arg Phe Glu Thr Arg Arg His His Glu Arg Asn Asp
    Asn Pro Pro Glu Lys Val Val Pro Leu Ala Lys Gly Leu Lys Leu Ala Gly Ile Thr Ser Val Thr Ile

Val Trp Gly Phe Leu Tyr His Trp Glu Arg Phe Thr Gln Phe Glu Gly Ala Asp Arg Ala Tyr Arg Asp
Ser Gly Val Arg Phe Pro Leu Ala Val Arg Ser Leu Asn Ser Val Arg Arg Cys • Ser Arg Leu Ser Arg
  Phe Gly Gly Ser Phe Thr Thr Gly Ser Ala Phe Pro Lys Phe Ser Ala Pro Met Val Leu Thr Val Ile

```
                                     Nru I
                                     |  Taq II'
                                     |  |
   GGCGGGTTGGTCGGGATCACAGCGGACAGACACAAGAGTAGTCGCGACGCTGGGACTGGGTGTATTGCAT
   ++++++++++|++++++++++|++++++++++|++++++++++|++++++++++|++++++++++|+++++++ 1260
   CCGCCCAACCAGCCCTAGTGTCGCCTGTCTGTGTTCTCATCAGCGCTGCGACCCTGACCCACATAACGTA
```

Ala Gly Trp Ser Gly Ser Gln Arg Thr Asp Thr Arg Val Val Ala Thr Leu Gly Leu Gly Val Leu His
Arg Arg Val Gly Arg Asp His Ser Gly Gln Thr Gln Glu • Ser Arg Arg Trp Asp Trp Val Tyr Cys Ile
  Gly Gly Leu Val Gly Ile Thr Ala Asp Arg His Lys Ser Ser Arg Asp Ala Gly Thr Gly Cys Ile Ala

Ala Pro Gln Asp Pro Asp Cys Arg Val Ser Val Leu Thr Thr Ala Val Ser Pro Ser Pro Thr Asn Cys
    Arg Thr Pro Arg Ser • Leu Pro Cys Val Cys Ser Tyr Asp Arg Arg Gln Ser Gln Thr Tyr Gln Met
Pro Pro Asn Thr Pro Ile Val Ala Ser Leu Cys Leu Leu Leu Arg Ser Ala Pro Val Pro His Ile Ala Tyr

FIG. 12F

```
           Bsa I                              BstX I
           |                                  |
      GATCAAGGAGACCGCCATGAACGACATCGTAAGCGCCAAGGTTCTGGAATATAAAGGAAAGAAGCTCAAT
      ┤┤┤┤┤┤┤┼┤┤┤┤┤┼┤┤┤┤┤┼┤┤┤┤┤┼┤┤┤┤┤┼┤┤┤┤┤┼┤┤┤┤┤┼┤┤┤┤┤┼┤┤┤┤┤┼┤┤┤┤┤┼┤┤┤┤┤┤┼ 1540
      CTAGTTCCTCTGGCGGTACTTGCTGTAGCATTCGCGGTTCCAAGACCTTATATTTCCTTTCTTCGAGTTA
```

Asp Gln Gly Asp Arg His Glu Arg His Arg Lys Arg Gln Gly Ser Gly Ile • Arg Lys Glu Ala Gln
  Ile Lys Glu Thr Ala Met Asn Asp Ile Val Ser Ala Lys Val Leu Glu Tyr Lys Gly Lys Lys Leu Asn
Arg Ser Arg Arg Pro Pro • Thr Thr Ser • Ala Pro Arg Phe Trp Asn Ile Lys Glu Arg Ser Ser Ile

Ser • Pro Ser Arg Trp Ser Arg Cys Arg Leu Arg Trp Pro Glu Pro Ile Tyr Leu Phe Ser Ala • Asn
 Ile Leu Ser Val Ala Met Phe Ser Met Thr Leu Ala Leu Thr Arg Ser Tyr Leu Pro Phe Phe Ser Leu
  Asp Leu Leu Gly Gly His Val Val Asp Tyr Ala Gly Leu Asn Gln Phe Ile Phe Ser Leu Leu Glu Ile

```
                                      Eag I
                                      Eco52 I
                  Ear I               |    Eco57 I   BssS I
                  |                   |    |         |
      TTCACGCCGGAAGATCCGGCTGAAGAGACAATTCCGGCCGACGAGTTGCACGAGCATCTGCAAAAGCCTT
      ┤┤┤┤┤┤┤┼┤┤┤┤┤┼┤┤┤┤┤┼┤┤┤┤┤┼┤┤┤┤┤┼┤┤┤┤┤┼┤┤┤┤┤┼┤┤┤┤┤┼┤┤┤┤┤┼┤┤┤┤┤┼┤┤┤┤┤┤┼ 1610
      AAGTGCGGCCTTCTAGGCCGACTTCTCTGTTAAGGCCGGCTGCTCAACGTGCTCGTAGACGTTTTCGGAA
```

Phe His Ala Gly Arg Ser Gly • Arg Asp Asn Ser Gly Arg Arg Val Ala Arg Ala Ser Ala Lys Ala Phe
 Phe Thr Pro Glu Asp Pro Ala Glu Glu Thr Ile Pro Ala Asp Glu Leu His Glu His Leu Gln Lys Pro
  Ser Arg Arg Lys Ile Arg Leu Lys Arg Gln Phe Arg Pro Thr Ser Cys Thr Ser Ile Cys Lys Ser Leu

• Ala Pro Leu Asp Pro Gln Leu Ser Leu Glu Pro Arg Arg Thr Ala Arg Ala Asp Ala Phe Ala Lys
Lys Val Gly Ser Ser Gly Ala Ser Ser Val Ile Gly Ala Ser Ser Asn Cys Ser Cys Arg Cys Phe Gly Glu
 Glu Arg Arg Phe Ile Arg Ser Phe Leu Cys Asn Arg Gly Val Leu Gln Val Leu Met Gln Leu Leu Arg

```
                                                            NgoM I
                                                            Nae I
                              Eco57 I                       |    EcoR I
                              |                             |    |
      CGACGGCGAGGACCAAGCGCCTGAAGGAGCGTTGCCGCTGGAAACACGCATCTGCCGGCGAATTCATTGA
      ┤┤┤┤┤┤┤┼┤┤┤┤┤┼┤┤┤┤┤┼┤┤┤┤┤┼┤┤┤┤┤┼┤┤┤┤┤┼┤┤┤┤┤┼┤┤┤┤┤┼┤┤┤┤┤┼┤┤┤┤┤┼┤┤┤┤┤┤┼ 1680
      GCTGCCGCTCCTGGTTCGCGGACTTCCTCGCAACGGCGACCTTTGTGCGTAGACGGCCGCTTAAGTAACT
```

Asp Gly Glu Asp Gln Ala Pro Glu Gly Ala Leu Pro Leu Glu Thr Arg Ile Cys Arg Arg Ile His •
Ser Thr Ala Arg Thr Lys Arg Leu Lys Glu Arg Cys Arg Trp Lys His Ala Ser Ala Gly Glu Phe Ile Glu
 Arg Arg Arg Gly Pro Ser Ala • Arg Ser Val Ala Ala Gly Asn Thr His Leu Pro Ala Asn Ser Leu

Ser Pro Ser Ser Trp Ala Gly Ser Pro Ala Asn Gly Ser Ser Val Arg Met Gln Arg Arg Ile • Gln
  Val Ala Leu Val Leu Arg Arg Phe Ser Arg Gln Arg Gln Phe Cys Ala Asp Ala Pro Ser Asn Met Ser
Arg Arg Arg Pro Gly Leu Ala Gln Leu Leu Thr Ala Ala Pro Phe Val Cys Arg Gly Ala Phe Glu Asn Phe

FIG. 12H

```
          Eag I
          Eco52 I
           NgoM I
            Nae I               Sph I                          Taq II
AAAGAGCGTCACGGCCGGCATCGAGCGCATGCGCTATCTGACCGAAGCACACAAGGCCAGCGAAGGCAAA
++++++++++++++++++++++++++++++++++++++++++++++++++++++++++++++++++++++ 1750
TTTCTCGCAGTGCCGGCCGTAGCTCGCGTACGCGATAGACTGGCTTCGTGTGTTCCGGTCGCTTCCGTTT
```

Lys Glu Arg His Gly Arg His Arg Ala His Ala Leu Ser Asp Arg Ser Thr Gln Gly Gln Arg Arg Gln
  Lys Ser Val Thr Ala Gly Ile Glu Arg Met Arg Tyr Leu Thr Glu Ala His Lys Ala Ser Glu Gly Lys
Lys Arg Ala Ser Arg Pro Ala Ser Ser Ala Cys Ala Ile • Pro Lys His Thr Arg Pro Ala Lys Ala Asn

Phe Ser Arg • Pro Arg Cys Arg Ala Cys Ala Ser Asp Ser Arg Leu Val Cys Pro Trp Arg Leu Cys Val
  Phe Leu Thr Val Ala Pro Met Ser Arg Met Arg • Arg Val Ser Ala Cys Leu Ala Leu Ser Pro Leu
    Leu Ala Asp Arg Gly Ala Asp Leu Ala His Ala Ile Gln Gly Phe Cys Val Leu Gly Ala Phe Ala Phe

```
           BscE I
           BssH II                      Bpm I
            BscE I            Bcg I    Sal I
CCCGAAGCCATCCGTCGCGCGCTGGGCCTGGCGAACGTCCTGAACAAGTCGACCCTGGTGCTCCAGGAGG
++++++++++++++++++++++++++++++++++++++++++++++++++++++++++++++++++++++ 1820
GGGCTTCGGTAGGCAGCGCGCGACCCGGACCGCTTGCAGGACTTGTTCAGCTGGGACCACGAGGTCCTCC
```

Thr Arg Ser His Pro Ser Arg Ala Gly Pro Gly Glu Arg Pro Glu Gln Val Asp Pro Gly Ala Pro Gly Gly
  Pro Glu Ala Ile Arg Arg Ala Leu Gly Leu Ala Asn Val Leu Asn Lys Ser Thr Leu Val Leu Gln Glu
    Pro Lys Pro Ser Val Ala Arg Trp Ala Trp Arg Thr Ser • Thr Ser Arg Pro Trp Cys Ser Arg Arg

Arg Leu Trp Gly Asp Arg Ala Pro Gly Pro Ser Arg Gly Ser Cys Thr Ser Gly Pro Ala Gly Pro Pro
Gly Ser Ala Met Arg Arg Ala Ser Pro Arg Ala Phe Thr Arg Phe Leu Asp Val Arg Thr Ser Trp Ser Ser
  Gly Phe Gly Asp Thr Ala Arg Gln Ala Gln Arg Val Asp Gln Val Leu Arg Gly Gln His Glu Leu Leu

```
    Bcg I'
    EcoR I                        BspLU11 I
ACGAATTCATCGTCGGCTACCACGCCGAAGATCCCAACATGTTCCCGCTGTATCCCGAACTGTCCCACAT
++++++++++++++++++++++++++++++++++++++++++++++++++++++++++++++++++++++ 1890
TGCTTAAGTAGCAGCCGATGGTGCGGCTTCTAGGGTTGTACAAGGGCGACATAGGGCTTGACAGGGTGTA
```

Arg Ile His Arg Arg Leu Pro Arg Arg Arg Ser Gln His Val Pro Ala Val Ser Arg Thr Val Pro His
Asp Glu Phe Ile Val Gly Tyr His Ala Glu Asp Pro Asn Met Phe Pro Leu Tyr Pro Glu Leu Ser His Met
  Thr Asn Ser Ser Ser Ala Thr Thr Pro Lys Ile Pro Thr Cys Ser Arg Cys Ile Pro Asn Cys Pro Thr

Arg Ile • Arg Arg Ser Gly Arg Arg Leu Asp Trp Cys Thr Gly Ala Thr Asp Arg Val Thr Gly Cys
  Ser Asn Met Thr Pro • Trp Ala Ser Ser Gly Leu Met Asn Gly Ser Tyr Gly Ser Ser Asp Trp Met
Val Phe Glu Asp Asp Ala Val Val Gly Phe Ile Gly Val His Glu Arg Gln Ile Gly Phe Gln Gly Val His

FIG. 12I

```
                    BscE I
        Bbs I     BssH II
         Bcg I'      BscE I                              Bcg I              BspLU11 I
CGTCCTGGAAGACGGGCTGCTGGCGCGCATCAAGCTCGCCGAAAAGCATATCGCCGAAGCCCAGGCCGAC
++++++++++++++++++++++++++++++++++++++++++++++++++++++++++++++++++++++ 2170
GCAGGACCTTCTGCCCGACGACCGCGCGTAGTTCGAGCGGCTTTTCGTATAGCGGCTTCGGGTCCGGCTG
```

Arg Pro Gly Arg Arg Ala Ala Gly Ala His Gln Ala Arg Arg Lys Ala Tyr Arg Arg Ser Pro Gly Arg
  Val Leu Glu Asp Gly Leu Leu Ala Arg Ile Lys Leu Ala Glu Lys His Ile Ala Glu Ala Gln Ala Asp
Pro Ser Trp Lys Thr Gly Cys Trp Arg Ala Ser Ser Ser Pro Lys Ser Ile Ser Pro Lys Pro Arg Pro Thr

Arg Gly Pro Leu Arg Ala Ala Pro Ala Cys • Ala Arg Arg Phe Ala Tyr Arg Arg Leu Gly Pro Arg Cys
  Thr Arg Ser Ser Pro Ser Ser Ala Arg Met Leu Ser Ala Ser Phe Cys Ile Ala Ser Ala Trp Ala Ser
    Asp Gln Phe Val Pro Gln Gln Arg Ala Asp Leu Glu Gly Phe Leu Met Asp Gly Phe Gly Leu Gly Val

```
   Sal I                              Bsa I
      |                                |
ATGTCGACCTTCCCCTGGAACGGCACGAAGGGTCTCGACAACATCGCCAAGATCGACAACTGGAAGGCGA
++++++++++++++++++++++++++++++++++++++++++++++++++++++++++++++++++++++ 2240
TACAGCTGGAAGGGGACCTTGCCGTGCTTCCCAGAGCTGTTGTAGCGGTTCTAGCTGTTGACCTTCCGCT
```

His Val Asp Leu Pro Leu Glu Arg His Glu Gly Ser Arg Gln His Arg Gln Asp Arg Gln Leu Glu Gly Asp
  Met Ser Thr Phe Pro Trp Asn Gly Thr Lys Gly Leu Asp Asn Ile Ala Lys Ile Asp Asn Trp Lys Ala
    Cys Arg Pro Ser Pro Gly Thr Ala Arg Arg Val Ser Thr Thr Ser Pro Arg Ser Thr Thr Gly Arg Arg

Thr Ser Arg Gly Arg Ser Arg Cys Ser Pro Asp Arg Cys Cys Arg Trp Ser Arg Cys Ser Ser Pro Ser
Met Asp Val Lys Gly Gln Phe Pro Val Phe Pro Arg Ser Leu Met Ala Leu Ile Ser Leu Gln Phe Ala Ile
  His Arg Gly Glu Gly Pro Val Ala Arg Leu Thr Glu Val Val Asp Gly Leu Asp Val Val Pro Leu Arg

FIG. 12K

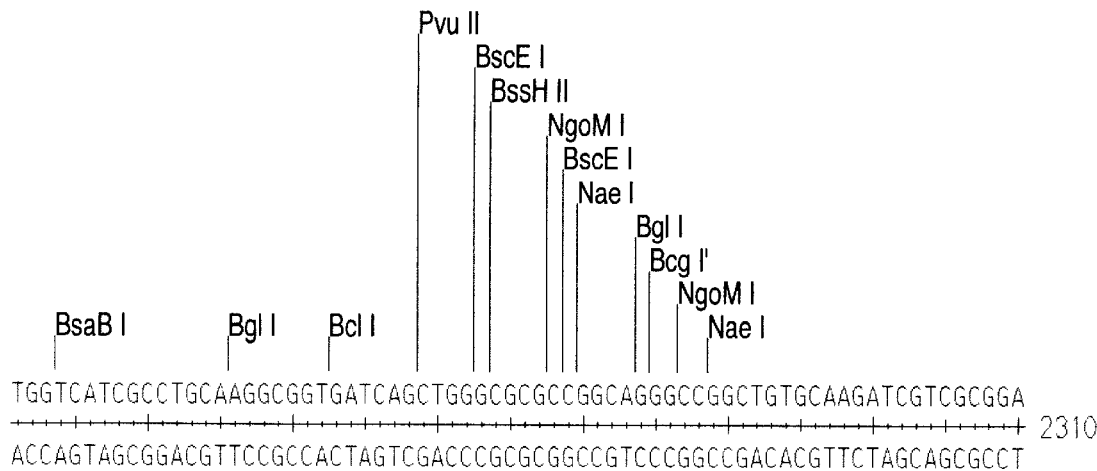
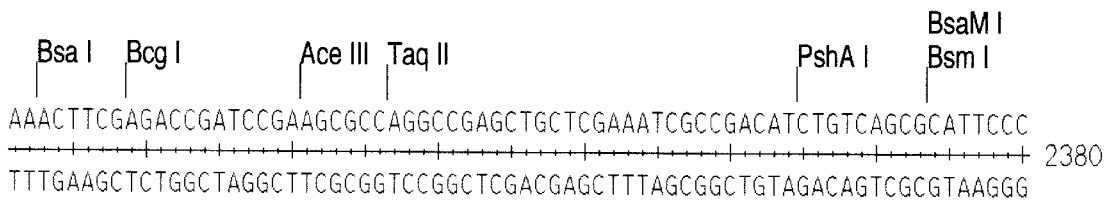
FIG. 12L

```
                   Bce83 I
                   |
         GCCGAGCCCTGCAAGGGCCTCAAGGACGCGATGCAGGCGAAATTCTTTACCTTCCTGATCTGTCACGCGA
         ++++++++++|++++++++++|++++++++++|++++++++++|++++++++++|++++++++++|++++++++++|  2450
         CGGCTCGGGACGTTCCCGGAGTTCCTGCGCTACGTCCGCTTTAAGAAATGGAAGGACTAGACAGTGCGCT
```

Arg Arg Ala Leu Gln Gly Pro Gln Gly Arg Asp Ala Gly Glu Ile Leu Tyr Leu Pro Asp Leu Ser Arg Asp
  Ala Glu Pro Cys Lys Gly Leu Lys Asp Ala Met Gln Ala Lys Phe Phe Thr Phe Leu Ile Cys His Ala
    Pro Ser Pro Ala Arg Ala Ser Arg Thr Arg Cys Arg Arg Asn Ser Leu Pro Ser • Ser Val Thr Arg

Arg Ala Arg Cys Pro Gly • Pro Arg Ser Ala Pro Ser Ile Arg • Arg Gly Ser Arg Asp Arg Ser
  Ala Ser Gly Gln Leu Pro Arg Leu Ser Ala Ile Cys Ala Phe Asn Lys Val Lys Arg Ile Gln • Ala Ile
Gly Leu Gly Ala Leu Ala Glu Leu Val Arg His Leu Arg Phe Glu Lys Gly Glu Gln Asp Thr Val Arg

```
                        EcoP15 I
         Pvu I  Eco47 III  BsrB I                   Bbs I              BsaX I  Stu I
         |      |        | |                        |                  |       |
         TCGAGCGCTACGCGAGCGGCTACGCCCAGAAGGAAGACACCCTGCTGTGGCCGTACTACAAGGCCTCCGT
         ++++++++++|++++++++++|++++++++++|++++++++++|++++++++++|++++++++++|++++++++++|  2520
         AGCTCGCGATGCGCTCGCCGATGCGGGTCTTCCTTCTGTGGGACGACACCGGCATGATGTTCCGGAGGCA
```

Arg Ala Leu Arg Glu Arg Leu Arg Pro Glu Gly Arg His Pro Ala Val Ala Val Leu Gln Gly Leu Arg
Ile Glu Arg Tyr Ala Ser Gly Tyr Ala Gln Lys Glu Asp Thr Leu Leu Trp Pro Tyr Tyr Lys Ala Ser Val
  Ser Ser Ala Thr Arg Ala Ala Thr Pro Arg Arg Lys Thr Pro Cys Cys Gly Arg Thr Thr Arg Pro Pro

Arg Ala Ser Arg Ser Arg Ser Arg Gly Ser Pro Leu Cys Gly Ala Thr Ala Thr Ser Cys Pro Arg Arg
    Ser Arg • Ala Leu Pro • Ala Trp Phe Ser Ser Val Arg Ser His Gly Tyr • Leu Ala Glu Thr
Asp Leu Ala Val Arg Ala Ala Val Gly Leu Leu Phe Val Gly Gln Gln Pro Arg Val Val Leu Gly Gly Asp

```
         Sal I                                                     Psp1406 I
         |                                                         |
         CGTCGACAAGAAATTCCAGCCGATGAGCCACATGGATGCGGTGGAACTCGTCGAGATGGAACGTTTGAAG
         ++++++++++|++++++++++|++++++++++|++++++++++|++++++++++|++++++++++|++++++++++|  2590
         GCAGCTGTTCTTTAAGGTCGGCTACTCGGTGTACCTACGCCACCTTGAGCAGCTCTACCTTGCAAACTTC
```

Arg Arg Gln Glu Ile Pro Ala Asp Glu Pro His Gly Cys Gly Gly Thr Arg Arg Asp Gly Thr Phe Glu
  Val Asp Lys Lys Phe Gln Pro Met Ser His Met Asp Ala Val Glu Leu Val Glu Met Glu Arg Leu Lys
    Ser Ser Thr Arg Asn Ser Ser Arg • Ala Thr Trp Met Arg Trp Asn Ser Ser Arg Trp Asn Val • Arg

Arg Arg Cys Ser Ile Gly Ala Ser Ser Gly Cys Pro His Pro Pro Val Arg Arg Ser Pro Val Asn Ser Ser
    Thr Ser Leu Phe Asn Trp Gly Ile Leu Trp Met Ser Ala Thr Ser Ser Thr Ser Ile Ser Arg Lys Phe
Asp Val Leu Phe Glu Leu Arg His Ala Val His Ile Arg His Phe Glu Asp Leu His Phe Thr Gln Leu

FIG. 12M

```
                    Kas I
                    Nar I
                    Ehe I
                    NgoM I      BscE I
                    Bbe I       BssH II                    Xma I
                    Nae I          BscE I                  Sma I
ATTTCGAGCATGGCGCCGGCAAGTCGCGCGCCTACCGCGAAATCTTCCCGGGGTCGAACGATCTGTTCA
                                                                         2660
TAAAGGCTCGTACCGCGGCCGTTCAGCGCGCGGATGGCGCTTTAGAAGGGCCCCAGCTTGCTAGACAAGT
```

Asp Phe Arg Ala Trp Arg Arg Gln Val Ala Arg Leu Pro Arg Asn Leu Pro Gly Val Glu Arg Ser Val His
  Ile Ser Glu His Gly Ala Gly Lys Ser Arg Ala Tyr Arg Glu Ile Phe Pro Gly Ser Asn Asp Leu Phe
   Phe Pro Ser Met Ala Pro Ala Ser Arg Ala Pro Thr Ala Lys Ser Ser Arg Gly Arg Thr Ile Cys Ser

Lys Arg Ala His Arg Arg Cys Thr Ala Arg Arg Gly Arg Phe Arg Gly Pro Thr Ser Arg Asp Thr •
   Ile Glu Ser Cys Pro Ala Pro Leu Asp Arg Ala • Arg Ser Ile Lys Gly Pro Asp Phe Ser Arg Asn Met
  Asn Gly Leu Met Ala Gly Ala Leu Arg Ala Gly Val Ala Phe Asp Glu Arg Pro Arg Val Ile Gln Glu

```
                                                                       Xho I
                                                                       Sci I
                                                                       Taq II
TCCTCACCGTCGGCGGCACCAACGCCAAGGGCGAGGACGCCTGCAACGACATGACCGACGCCATCCTCGA
                                                                         2730
AGGAGTGGCAGCCGCCGTGGTTGCGGTTCCCGCTCCTGCGGACGTTGCTGTACTGGCTGCGGTAGGAGCT
```

Pro His Arg Arg Arg His Gln Arg Gln Gly Arg Gly Arg Leu Gln Arg His Asp Arg Arg His Pro Arg
  Ile Leu Thr Val Gly Gly Thr Asn Ala Lys Gly Glu Asp Ala Cys Asn Asp Met Thr Asp Ala Ile Leu Glu
   Ser Ser Pro Ser Ala Ala Pro Thr Pro Arg Ala Arg Thr Pro Ala Thr Thr • Pro Thr Pro Ser Ser

Gly • Arg Arg Arg Cys Trp Arg Trp Pro Arg Pro Arg Arg Cys Arg Cys Ser Arg Arg Trp Gly Arg
   Arg Val Thr Pro Pro Val Leu Ala Leu Pro Ser Ser Ala Gln Leu Ser Met Val Ser Ala Met Arg Ser
  Asp Glu Gly Asp Ala Ala Gly Val Gly Leu Ala Leu Val Gly Ala Val Val His Gly Val Gly Asp Glu Leu

```
                  Eag I
         BamH I   Eco52 I      Bbs I
GGCAGCCAAGCGGATCCGCACGGCCGAGCCCTCCATCGTCTTCCGCTATTCCAAGAAGAACCGCGAGAAG
                                                                         2800
CCGTCGGTTCGCCTAGGCGTGCCGGCTCGGGAGGTAGCAGAAGGCGATAAGGTTCTTCTTGGCGCTCTTC
```

Gly Ser Gln Ala Asp Pro His Gly Arg Ala Leu His Arg Leu Pro Leu Phe Gln Glu Glu Pro Arg Glu
   Ala Ala Lys Arg Ile Arg Thr Ala Glu Pro Ser Ile Val Phe Arg Tyr Ser Lys Lys Asn Arg Glu Lys
  Arg Gln Pro Ser Gly Ser Ala Arg Pro Ser Pro Pro Ser Ser Ala Ile Pro Arg Arg Thr Ala Arg Arg

Pro Leu Trp Ala Ser Gly Cys Pro Arg Ala Arg Trp Arg Arg Gly Ser Asn Trp Ser Ser Gly Arg Ser Ser
    Ala Ala Leu Arg Ile Arg Val Ala Ser Gly Glu Met Thr Lys Arg • Glu Leu Phe Phe Arg Ser Phe
      Cys Gly Leu Pro Asp Ala Arg Gly Leu Gly Gly Asp Asp Glu Ala Ile Gly Leu Leu Val Ala Leu Leu

FIG. 12N

```
                    Bbs I
                    |
       ACGCTGCGCTGGGTTTTCGAGTGCATCCGCGACGGACTCGGCTATCCGTCGATCAAGCACGACGAGATCG
       ++++++++++|++++++++++|++++++++++|++++++++++|++++++++++|++++++++++|++++++++++  2870
       TGCGACGCGACCCAAAAGCTCACGTAGGCGCTGCCTGAGCCGATAGGCAGCTAGTTCGTGCTGCTCTAGC

Asp Ala Ala Leu Gly Phe Arg Val His Pro Arg Arg Thr Arg Leu Ser Val Asp Gln Ala Arg Arg Asp Arg
    Thr Leu Arg Trp Val Phe Glu Cys Ile Arg Asp Gly Leu Gly Tyr Pro Ser Ile Lys His Asp Glu Ile
     Arg Cys Ala Gly Phe Ser Ser Ala Ser Ala Thr Asp Ser Ala Ile Arg Arg Ser Ser Thr Thr Arg Ser
    ++++++++++|++++++++++|++++++++++|++++++++++|++++++++++|++++++++++|++++++++++
   Ala Ala Ser Pro Lys Arg Thr Cys Gly Arg Arg Val Arg Ser Asp Thr Ser  •  Ala Arg Arg Ser Arg
   Val Ser Arg Gln Thr Lys Ser His Met Arg Ser Pro Ser Pro  •  Gly Asp Ile Leu Cys Ser Ser Ile Pro
   Arg Gln Ala Pro Asn Glu Leu Ala Asp Ala Val Ser Glu Ala Ile Arg Arg Asp Leu Val Val Leu Asp
```

```
                                                              Kas I
                                                              |Nar I
                                                              ||Ehe I
                                       Bgl I                  |||Bbe I
                                       |                      ||||
       GCACGGAGCAGATGAAGGAATACGCCAAGTTCAGCCTCAACGGCAACGGCGCCACCGACGAGGAAGCCCA
       ++++++++++|++++++++++|++++++++++|++++++++++|++++++++++|++++++++++|++++++++++  2940
       CGTGCCTCGTCTACTTCCTTATGCGGTTCAAGTCGGAGTTGCCGTTGCCGCGGTGGCTGCTCCTTCGGGT

His Gly Ala Asp Glu Gly Ile Arg Gln Val Gln Pro Gln Arg Gln Arg Arg His Arg Arg Gly Ser Pro
   Gly Thr Glu Gln Met Lys Glu Tyr Ala Lys Phe Ser Leu Asn Gly Asn Gly Ala Thr Asp Glu Glu Ala His
    Ala Arg Ser Arg  •  Arg Asn Thr Pro Ser Ser Ala Ser Thr Ala Thr Ala Pro Pro Thr Arg Lys Pro
    ++++++++++|++++++++++|++++++++++|++++++++++|++++++++++|++++++++++|++++++++++
   Cys Pro Ala Ser Ser Pro Ile Arg Trp Thr  •  Gly  •  Arg Cys Arg Arg Trp Arg Arg Pro Leu Gly
     Val Ser Cys Ile Phe Ser Tyr Ala Leu Asn Leu Arg Leu Pro Leu Pro Ala Val Ser Ser Ser Ala Trp
   Ala Arg Leu Leu His Leu Phe Val Gly Leu Glu Ala Glu Val Ala Val Ala Gly Gly Val Leu Phe Gly Val
```

```
                    RleA I
                    |
       CAACTGGGTCAACGTGCTGTGCATGTCGCCCGGCATCCACGGTCGCCGCAAGACGCAAAAAACCCGTTCG
       ++++++++++|++++++++++|++++++++++|++++++++++|++++++++++|++++++++++|++++++++++  3010
       GTTGACCCAGTTGCACGACACGTACAGCGGGCCGTAGGTGCCAGCGGCGTTCTGCGTTTTTTGGGCAAGC

Gln Leu Gly Gln Arg Ala Val His Val Ala Arg His Pro Arg Ser Pro Gln Asp Ala Lys Asn Pro Phe
     Asn Trp Val Asn Val Leu Cys Met Ser Pro Gly Ile His Gly Arg Arg Lys Thr Gln Lys Thr Arg Ser
   Thr Thr Gly Ser Thr Cys Cys Ala Cys Arg Pro Ala Ser Thr Val Ala Ala Arg Lys Lys Pro Val Arg
    ++++++++++|++++++++++|++++++++++|++++++++++|++++++++++|++++++++++|++++++++++
   Cys Ser Pro  •  Arg Ala Thr Cys Thr Ala Arg Cys Gly Arg Asp Gly Cys Ser Ala Phe Phe Gly Asn Pro
    Leu Gln Thr Leu Thr Ser His Met Asp Gly Pro Met Trp Pro Arg Arg Leu Val Cys Phe Val Arg Glu
   Val Pro Asp Val His Gln Ala His Arg Gly Ala Asp Val Thr Ala Ala Leu Arg Leu Phe Gly Thr Arg
```

FIG. 12O

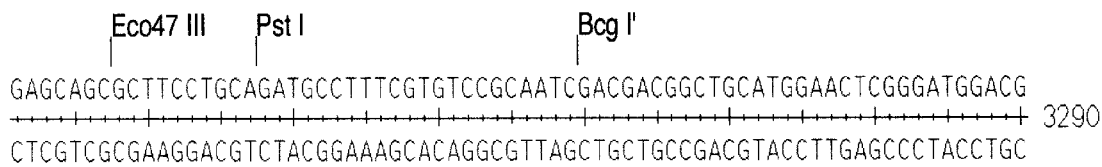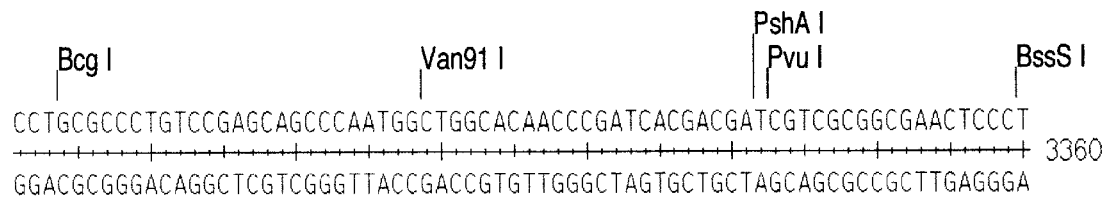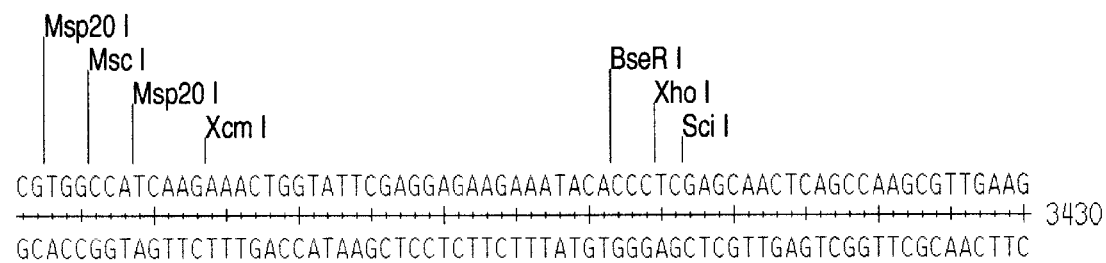
FIG. 12Q

FIG. 12R

```
          Apa I        Bgl I
GGCCCCACGCCGGACGGGCGCTTCGGGGGTGAAGCGGCAGACGACGGCGGCATTTCTCCCTACATGGGAA
++++++++++++++++++++++++++++++++++++++++++++++++++++++++++++++++++++++ 3710
CCGGGGTGCGGCCTGCCCGCGAAGCCCCCACTTCGCCGTCTGCTGCCGCCGTAAAGAGGGATGTACCCTT
```

Gly Pro His Ala Gly Arg Ala Leu Arg Gly • Ser Gly Arg Arg Arg Arg His Phe Ser Leu His Gly Asn
  Gly Pro Thr Pro Asp Gly Arg Phe Gly Gly Glu Ala Ala Asp Asp Gly Gly Ile Ser Pro Tyr Met Gly
    Ala Pro Arg Arg Thr Gly Ala Ser Gly Val Lys Arg Gln Thr Thr Ala Ala Phe Leu Pro Thr Trp Glu

Gly Trp Ala Pro Arg Ala Ser Arg Pro His Leu Pro Leu Arg Arg Arg Cys Lys Glu Arg Cys Pro Phe
Pro Gly Val Gly Ser Pro Arg Lys Pro Pro Ser Ala Ala Ser Ser Pro Pro Met Glu Gly • Met Pro Val
  Ala Gly Arg Arg Val Pro Ala Glu Pro Thr Phe Arg Cys Val Val Ala Ala Asn Arg Gly Val His Ser

Bsg I
                                    EcoP15 I                                Bsp24 I
```
CCGACAAGAAGGGGCCGACGGCGGTGTTGCGCTCGGTGTCCAAGGTGCAGAAGAACCAGAAGGGCAACCT
++++++++++++++++++++++++++++++++++++++++++++++++++++++++++++++++++++++ 3780
GGCTGTTCTTCCCCGGCTGCCGCCACAACGCGAGCCACAGGTTCCACGTCTTCTTGGTCTTCCCGTTGGA
```

Arg Gln Glu Gly Ala Asp Gly Gly Val Ala Leu Gly Val Gln Gly Ala Glu Glu Pro Glu Gly Gln Pro
Thr Asp Lys Lys Gly Pro Thr Ala Val Leu Arg Ser Val Ser Lys Val Gln Lys Asn Gln Lys Gly Asn Leu
  Pro Thr Arg Arg Gly Arg Arg Arg Cys Cys Ala Arg Cys Pro Arg Cys Arg Arg Thr Arg Arg Ala Thr

Arg Cys Ser Pro Ala Ser Pro Pro Thr Ala Ser Pro Thr Trp Pro Ala Ser Ser Gly Ser Pro Cys Gly
  Ser Leu Phe Pro Gly Val Ala Thr Asn Arg Glu Thr Asp Leu Thr Cys Phe Phe Trp Phe Pro Leu Arg
Gly Val Leu Leu Pro Arg Arg His Gln Ala Arg His Gly Leu His Leu Leu Val Leu Leu Ala Val Gln

BspM I
        Eco47 III                                        BstB I
                          Bsp24 I'                       Csp45 I
```
GCTGAACCAGCGCTTGTCGGTGCCGATCATGCGCTCCAAGCATGGCTTCGAAATCTGGAACTCGTACATG
++++++++++++++++++++++++++++++++++++++++++++++++++++++++++++++++++++++ 3850
CGACTTGGTCGCGAACAGCCACGGCTAGTACGCGAGGTTCGTACCGAAGCTTTAGACCTTGAGCATGTAC
```

Ala Glu Pro Ala Leu Val Gly Ala Asp His Ala Leu Gln Ala Trp Leu Arg Asn Leu Glu Leu Val His
    Leu Asn Gln Arg Leu Ser Val Pro Ile Met Arg Ser Lys His Gly Phe Glu Ile Trp Asn Ser Tyr Met
  Cys • Thr Ser Ala Cys Arg Cys Arg Ser Cys Ala Pro Ser Met Ala Ser Lys Ser Gly Thr Arg Thr •

Ala Ser Gly Ala Ser Thr Pro Ala Ser • Ala Ser Trp Ala His Ser Arg Phe Arg Ser Ser Thr Cys Ser
  Ser Phe Trp Arg Lys Asp Thr Gly Ile Met Arg Glu Leu Cys Pro Lys Ser Ile Gln Phe Glu Tyr Met
    Gln Val Leu Ala Gln Arg His Arg Asp His Ala Gly Leu Met Ala Glu Phe Asp Pro Val Arg Val His

FIG. 12S

```
                                                                BscE I
                              BspD I                            BssH II
        Bbs I                 Cla I                             │ BscE I
        │                     │                                 │ │ │
    AAGACTTGGCACGATCTGAATATCGATCATGTTCAGTTCAATGTCGTCAGCACGGATGAAATGCGCGCTG
    ++++++++++++++++++++++++++++++++++++++++++++++++++++++++++++++++++++ 3920
    TTCTGAACCGTGCTAGACTTATAGCTAGTACAAGTCAAGTTACAGCAGTCGTGCCTACTTTACGCGCGAC
```

Glu Asp Leu Ala Arg Ser Glu Tyr Arg Ser Cys Ser Val Gln Cys Arg Gln His Gly • Asn Ala Arg Cys
Lys Thr Trp His Asp Leu Asn Ile Asp His Val Gln Phe Asn Val Val Ser Thr Asp Glu Met Arg Ala
  Arg Leu Gly Thr Ile • Ile Ser Ile Met Phe Ser Ser Met Ser Ser Ala Arg Met Lys Cys Ala Leu

Ser Lys Ala Arg Asp Ser Tyr Arg Asp His Glu Thr • His Arg • Cys Pro His Phe Ala Arg Gln
Phe Val Gln Cys Ser Arg Phe Ile Ser • Thr • Asn Leu Thr Thr Leu Val Ser Ser Ile Arg Ala Ala
 Leu Ser Pro Val Ile Gln Ile Asp Ile Met Asn Leu Glu Ile Asp Asp Ala Arg Ile Phe His Ala Ser

```
        Fsp I                                      Eco47 III
        │                                          │
    CGCAGCGCGAACCCGAGAAGCACCATGATCTTATCGTGCGCGTTTCCGGCTACAGCGCTCGGTTCGTAGA
    ++++++++++++++++++++++++++++++++++++++++++++++++++++++++++++++++++++ 3990
    GCGTCGCGCTTGGGCTCTTCGTGGTACTAGAATAGCACGCGCAAAGGCCGATGTCGCGAGCCAAGCATCT
```

Ala Ala Arg Thr Arg Glu Ala Pro • Ser Tyr Arg Ala Arg Phe Arg Leu Gln Arg Ser Val Arg Arg
Ala Gln Arg Glu Pro Glu Lys His His Asp Leu Ile Val Arg Val Ser Gly Tyr Ser Ala Arg Phe Val Asp
  Arg Ser Ala Asn Pro Arg Ser Thr Met Ile Leu Ser Cys Ala Phe Pro Ala Thr Ala Leu Gly Ser •

Ala Ala Arg Val Arg Ser Ala Gly His Asp • Arg Ala Arg Lys Arg Ser Cys Arg Glu Thr Arg Leu
   Cys Arg Ser Gly Ser Phe Cys Trp Ser Arg Ile Thr Arg Thr Glu Pro • Leu Ala Arg Asn Thr Ser
Arg Leu Ala Phe Gly Leu Leu Val Met Ile Lys Asp His Ala Asn Gly Ala Val Ala Ser Pro Glu Tyr Val

```
                                                                 Xho I
                                                                 │ Sci I
                                                                 │ │
    CATTCCGACCTATGGGCAGAACACCATCATCGCCCGTCAGGAACAGGATTTCAGCGCATCCGATCTCGAG
    ++++++++++++++++++++++++++++++++++++++++++++++++++++++++++++++++++++ 4060
    GTAAGGCTGGATACCCGTCTTGTGGTAGTAGCGGGCAGTCCTTGTCCTAAAGTCGCGTAGGCTAGAGCTC
```

His Ser Asp Leu Trp Ala Glu His His His Arg Pro Ser Gly Thr Gly Phe Gln Arg Ile Arg Ser Arg
   Ile Pro Thr Tyr Gly Gln Asn Thr Ile Ile Ala Arg Gln Glu Gln Asp Phe Ser Ala Ser Asp Leu Glu
Thr Phe Arg Pro Met Gly Arg Thr Pro Ser Ser Pro Val Arg Asn Arg Ile Ser Ala His Pro Ile Ser Ser

Cys Glu Ser Arg His Ala Ser Cys Trp • Arg Gly Asp Pro Val Pro Asn • Arg Met Arg Asp Arg Thr
   Met Gly Val • Pro Cys Phe Val Met Met Ala Arg • Ser Cys Ser Lys Leu Ala Asp Ser Arg Ser
 Asn Arg Gly Ile Pro Leu Val Gly Asp Asp Gly Thr Leu Phe Leu Ile Glu Ala Cys Gly Ile Glu Leu

FIG. 12T

Bce83 I

```
TTCCTAAACGTCGAAATCTAGGACAAGCCACTCAAGGGGGGCAGCATCCCGTCCCCCTTTACCTTACGGT
++++++++++++++++++++++++++++++++++++++++++++++++++++++++++++++++++++++ 4130
AAGGATTTGCAGCTTTAGATCCTGTTCGGTGAGTTCCCCCCGTCGTAGGGCAGGGGGAAATGGAATGCCA
```

Val Pro Lys Arg Arg Asn Leu Gly Gln Ala Thr Gln Gly Gly Gln His Pro Val Pro Leu Tyr Leu Thr Val
 Phe Leu Asn Val Glu Ile • Asp Lys Pro Leu Lys Gly Gly Ser Ile Pro Ser Pro Phe Thr Leu Arg
  Ser • Thr Ser Lys Ser Arg Thr Ser His Ser Arg Gly Ala Ala Ser Arg Pro Pro Leu Pro Tyr Gly

Gly Leu Arg Arg Phe Arg Pro Cys Ala Val • Pro Pro Cys Cys Gly Thr Gly Arg • Arg Val Thr
Asn Arg Phe Thr Ser Ile • Ser Leu Gly Ser Leu Pro Pro Leu Met Gly Asp Gly Lys Val Lys Arg Asn
  Glu • Val Asp Phe Asp Leu Val Leu Trp Glu Leu Pro Ala Ala Asp Arg Gly Gly Lys Gly • Pro

```
TGCACGAAAAAACATGGAGGGCAGCAACATGGAAACAGGACAGAATTTGCAAAACCAGCCGCATACCGAG
++++++++++++++++++++++++++++++++++++++++++++++++++++++++++++++++++++++ 4200
ACGTGCTTTTTTGTACCTCCCGTCGTTGTACCTTTGTCCTGTCTTAAACGTTTTGGTCGGCGTATGGCTC
```

Ala Arg Lys Asn Met Glu Gly Ser Asn Met Glu Thr Gly Gln Asn Leu Gln Asn Gln Pro His Thr Glu
Leu His Glu Lys Thr Trp Arg Ala Ala Thr Trp Lys Gln Asp Arg Ile Cys Lys Thr Ser Arg Ile Pro Arg
 Cys Thr Lys Lys His Gly Gly Gln Gln His Gly Asn Arg Thr Glu Phe Ala Lys Pro Ala Ala Tyr Arg

Ala Arg Phe Phe Met Ser Pro Leu Leu Met Ser Val Pro Cys Phe Lys Cys Phe Trp Gly Cys Val Ser
   Cys Ser Phe Val His Leu Ala Ala Val His Phe Cys Ser Leu Ile Gln Leu Val Leu Arg Met Gly Leu
 Gln Val Phe Cys Pro Pro Cys Cys Cys Pro Phe Leu Val Ser Asn Ala Phe Gly Ala Ala Tyr Arg Pro

```
GTGGGTACGGCGAGGCCGTGCCGGAGTTGCAAATGGCAAACCCCCGACCCCACCGATCCGCACCGTGGGC
++++++++++++++++++++++++++++++++++++++++++++++++++++++++++++++++++++++ 4270
CACCCATGCCGCTCCGGCACGGCCTCAACGTTTACCGTTTGGGGGCTGGGGTGGCTAGGCGTGGCACCCG
```

Val Gly Thr Ala Arg Pro Cys Arg Ser Cys Lys Trp Gln Thr Pro Asp Pro Thr Asp Pro His Arg Gly
   Trp Val Arg Arg Gly Arg Ala Gly Val Ala Asn Gly Lys Pro Pro Thr Pro Pro Ile Arg Thr Val Gly
 Gly Gly Tyr Gly Glu Ala Val Pro Glu Leu Gln Met Ala Asn Pro Arg Pro His Arg Ser Ala Pro Trp Ala

Thr Pro Val Ala Leu Gly His Arg Leu Gln Leu His Cys Val Gly Ser Gly Val Ser Gly Cys Arg Pro Cys
  His Thr Arg Arg Pro Arg Ala Pro Thr Ala Phe Pro Leu Gly Gly Val Gly Gly Ile Arg Val Thr Pro
   Pro Tyr Pro Ser Ala Thr Gly Ser Asn Cys Ile Ala Phe Gly Arg Gly Trp Arg Asp Ala Gly His Ala

FIG. 12U

```
        BsrD I   Taq II'  Nco I                                    Bpu10 I      Bpm I
AATGCACCGCCAACCGGCACGCCATGGGTGGCGTCTGGAAACGCTGGCTTAGGGACGTTGAAAACACGAC
++++++++++++++++++++++++++++++++++++++++++++++++++++++++++++++++++++++ 4340
TTACGTGGCGGTTGGCCGTGCGGTACCCACCGCAGACCTTTGCGACCGAATCCCTGCAACTTTTGTGCTG
```

Gln Cys Thr Ala Asn Arg His Ala Met Gly Gly Val Trp Lys Arg Trp Leu Arg Asp Val Glu Asn Thr Thr
  Asn Ala Pro Pro Thr Gly Thr Pro Trp Val Ala Ser Gly Asn Ala Gly Leu Gly Thr Leu Lys Thr Arg
    Met His Arg Gln Pro Ala Arg His Gly Trp Arg Leu Glu Thr Leu Ala • Gly Arg • Lys His Asp
His Val Ala Leu Arg Cys Ala Met Pro Pro Thr Gln Phe Arg Gln Ser Leu Ser Thr Ser Phe Val Val
Leu Ala Gly Gly Val Pro Val Gly His Thr Ala Asp Pro Phe Ala Pro Lys Pro Val Asn Phe Val Arg Gly
  Ile Cys Arg Trp Gly Ala Arg Trp Pro His Arg Arg Ser Val Ser Ala • Pro Arg Gln Phe Cys Ser

```
    EcoN I
       BspM I
        BssS I                                    Tth111 I        Bpm I
CTGCTCCAGGCACGAGGAAGGCAAACTAAGTTTCCGCGACCACGTCTGAACACCGGACAGACGTGGTTCA
++++++++++++++++++++++++++++++++++++++++++++++++++++++++++++++++++++++ 4410
GACGAGGTCCGTGCTCCTTCCGTTTGATTCAAAGGCGCTGGTGCAGACTTGTGGCCTGTCTGCACCAAGT
```

Cys Ser Arg His Glu Glu Gly Lys Leu Ser Phe Arg Asp His Val • Thr Pro Asp Arg Arg Gly Ser
Pro Ala Pro Gly Thr Arg Lys Ala Asn • Val Ser Ala Thr Thr Ser Glu His Arg Thr Asp Val Val His
  Leu Leu Gln Ala Arg Gly Arg Gln Thr Lys Phe Pro Arg Pro Arg Leu Asn Thr Gly Gln Thr Trp Phe
Gln Glu Leu Cys Ser Ser Pro Leu Ser Leu Lys Arg Ser Trp Thr Gln Val Gly Ser Leu Arg Pro Glu
  Ala Gly Pro Val Leu Phe Ala Phe • Thr Glu Ala Val Val Asp Ser Cys Arg Val Ser Thr Thr •
Arg Ser Trp Ala Arg Pro Leu Cys Val Leu Asn Gly Arg Gly Arg Arg Phe Val Pro Cys Val His Asn Val

```
                    Bpm I
                     BspH I
CCTCCAGACCACTGTAGTGATAGATCATGAAAACCTACTCCAGCGCAAATGGCCTGTTCGTCCCGGAAGT
++++++++++++++++++++++++++++++++++++++++++++++++++++++++++++++++++++++ 4480
GGAGGTCTGGTGACATCACTATCTAGTACTTTTGGATGAGGTCGCGTTTACCGGACAAGCAGGGCCTTCA
```

Pro Pro Asp His Cys Ser Asp Arg Ser • Lys Pro Thr Pro Ala Gln Met Ala Cys Ser Ser Arg Lys
  Leu Gln Thr Thr Val Val Ile Asp His Glu Asn Leu Leu Gln Arg Lys Trp Pro Val Arg Pro Gly Ser
    Thr Ser Arg Pro Leu • • • Ile Met Lys Thr Tyr Ser Ser Ala Asn Gly Leu Phe Val Pro Glu Val
Gly Gly Ser Trp Gln Leu Ser Leu Asp His Phe Gly Val Gly Ala Cys Ile Ala Gln Glu Asp Arg Phe Asp
  Arg Trp Val Val Thr Thr Ile Ser • Ser Phe Arg Ser Trp Arg Leu His Gly Thr Arg Gly Pro Leu
    Glu Leu Gly Ser Tyr His Tyr Ile Met Phe Val • Glu Leu Ala Phe Pro Arg Asn Thr Gly Ser Thr

FIG. 12V

```
                                              EcoR V
                    Bcg I         Bcg I'              Bcg I'
CGATCCCTACTACTATGTAAGTACGGAAAACCAGAGCTTCCTCGATAAATTTGCAAAGATATCGAAAAAG
++++++++++++++++++++++++++++++++++++++++++++++++++++++++++++++++++++++ 4550
GCTAGGGATGATGATACATTCATGCCTTTTGGTCTCGAAGGAGCTATTTAAACGTTTCTATAGCTTTTTC
```

Ser Ile Pro Thr Thr Met  •  Val Arg Lys Thr Arg Ala Ser Ser Ile Asn Leu Gln Arg Tyr Arg Lys Ser
  Arg Ser Leu Leu Leu Cys Lys Tyr Gly Lys Pro Glu Leu Pro Arg  •  Ile Cys Lys Asp Ile Glu Lys
    Asp Pro Tyr Tyr Tyr Val Ser Thr Glu Asn Gln Ser Phe Leu Asp Lys Phe Ala Lys Ile Ser Lys Lys

Ile Gly Val Val Ile Tyr Thr Arg Phe Val Leu Ala Glu Glu Ile Phe Lys Cys Leu Tyr Arg Phe Leu
Arg Asp Arg Ser Ser His Leu Tyr Pro Phe Gly Ser Ser Gly Arg Tyr Ile Gln Leu Ser Ile Ser Phe Ala
  Ser Gly  •   •   •  Thr Leu Val Ser Phe Trp Leu Lys Arg Ser Leu Asn Ala Phe Ile Asp Phe Phe

```
        Bcg I                           Bbs I
CATCCCGTCAATGTACTGGTGGTCGGCAAACAAGGCTGCGGCAAGTCTTCCCTAGTGCGGCAATACGCCG
++++++++++++++++++++++++++++++++++++++++++++++++++++++++++++++++++++++ 4620
GTAGGGCAGTTACATGACCACCAGCCGTTTGTTCCGACGCCGTTCAGAAGGGATCACGCCGTTATGCGGC
```

Ile Pro Ser Met Tyr Trp Trp Ser Ala Asn Lys Ala Ala Ala Ser Leu Pro  •  Cys Gly Asn Thr Pro
Ala Ser Arg Gln Cys Thr Gly Gly Arg Gln Thr Arg Leu Arg Gln Val Phe Pro Ser Ala Ala Ile Arg Arg
  His Pro Val Asn Val Leu Val Val Gly Lys Gln Gly Cys Gly Lys Ser Ser Leu Val Arg Gln Tyr Ala

Met Gly Asp Ile Tyr Gln His Asp Ala Phe Leu Ala Ala Ala Leu Arg Gly  •  His Pro Leu Val Gly
    Asp Arg  •  His Val Pro Pro Arg Cys Val Leu Ser Arg Cys Thr Lys Gly Leu Ala Ala Ile Arg Arg
Cys Gly Thr Leu Thr Ser Thr Thr Pro Leu Cys Pro Gln Pro Leu Asp Glu Arg Thr Arg Cys Tyr Ala Ala

```
                            BsaB I
CCGTCAACAGGCTACCCTTGGCGACCTTCCAGATCGGCATCCTGTCGGAGCCGGGGCAACTGTTTGGTGA
++++++++++++++++++++++++++++++++++++++++++++++++++++++++++++++++++++++ 4690
GGCAGTTGTCCGATGGGAACCGCTGGAAGGTCTAGCCGTAGGACAGCCTCGGCCCCGTTGACAAACCACT
```

Pro Ser Thr Gly Tyr Pro Trp Arg Pro Ser Arg Ser Ala Ser Cys Arg Ser Arg Gly Asn Cys Leu Val
  Arg Gln Gln Ala Thr Leu Gly Asp Leu Pro Asp Arg His Pro Val Gly Ala Gly Ala Thr Val Trp  •
Ala Val Asn Arg Leu Pro Leu Ala Thr Phe Gln Ile Gly Ile Leu Ser Glu Pro Gly Gln Leu Phe Gly Glu

Gly Asp Val Pro  •  Gly Gln Arg Gly Glu Leu Asp Ala Asp Gln Arg Leu Arg Pro Leu Gln Lys Thr Phe
  Arg  •  Cys Ala Val Arg Pro Ser Arg Gly Ser Arg Cys Gly Thr Pro Ala Pro Ala Val Thr Gln His
    Thr Leu Leu Ser Gly Lys Ala Val Lys Trp Ile Pro Met Arg Asp Ser Gly Pro Cys Ser Asn Pro Ser

FIG. 12W

```
                    Bsa I              Bpm I              Ear I              Mfe I
                                                                             Mun I
         ATACGCGCTGGAGAACGGGGAGACCCGTTACAAGCAGTTCCTCTTCCCCCAGGCCATCCAGACACCCAAT
         ++++++++++++++++++++++++++++++++++++++++++++++++++++++++++++++++++++++ 4760
         TATGCGCGACCTCTTGCCCCTCTGGGCAATGTTCGTCAAGGAGAAGGGGGTCCGGTAGGTCTGTGGGTTA
```

Asn Thr Arg Trp Arg Thr Gly Arg Pro Val Thr Ser Ser Ser Ser Ser Pro Arg Pro Ser Arg His Pro Ile
  Ile Arg Ala Gly Glu Arg Gly Asp Pro Leu Gln Ala Val Pro Leu Pro Pro Gly His Pro Asp Thr Gln
    Tyr Ala Leu Glu Asn Gly Glu Thr Arg Tyr Lys Gln Phe Leu Phe Pro Gln Ala Ile Gln Thr Pro Asn

Val Arg Gln Leu Val Pro Leu Gly Thr Val Leu Leu Glu Glu Glu Gly Leu Gly Asp Leu Cys Gly Ile
Ile Arg Ala Pro Ser Arg Pro Ser Gly Asn Cys Ala Thr Gly Arg Gly Gly Pro Trp Gly Ser Val Trp Asn
  Tyr Ala Ser Ser Phe Pro Ser Val Arg  •  Leu Cys Asn Arg Lys Gly Trp Ala Met Trp Val Gly Leu

```
           Taq II'
           | Ear I                                              BspLU11 I
         TGCGTCATCCACCTTGAAGAGATCAATCGCCCCGAGCATCCGAAGGCGTTGAACATGTTGTTCTCCATTC
         ++++++++++++++++++++++++++++++++++++++++++++++++++++++++++++++++++++++ 4830
         ACGCAGTAGGTGGAACTTCTCTAGTTAGCGGGGCTCGTAGGCTTCCGCAACTTGTACAACAAGAGGTAAG
```

Ala Ser Ser Thr Leu Lys Arg Ser Ile Ala Pro Ser Ile Arg Arg Arg  •  Thr Cys Cys Ser Pro Phe
Leu Arg His Pro Pro  •  Arg Asp Gln Ser Pro Arg Ala Ser Glu Gly Val Glu His Val Val Leu His Ser
  Cys Val Ile His Leu Glu Glu Ile Asn Arg Pro Glu His Pro Lys Ala Leu Asn Met Leu Phe Ser Ile

Ala Asp Asp Val Lys Phe Leu Asp Ile Ala Gly Leu Met Arg Leu Arg Gln Val His Gln Glu Gly Asn
    Arg  •  Gly Gly Gln Leu Ser  •  Asp Gly Arg Ala Asp Ser Pro Thr Ser Cys Thr Thr Arg Trp Glu
Gln Thr Met Trp Arg Ser Ser Ile Leu Arg Gly Ser Cys Gly Phe Ala Asn Phe Met Asn Asn Glu Met Arg

```
                                       EcoICR I
              EcoP15 I                  | Sac I
         TCTCCGATGACCGTCAGGTATGGATGGACGAGCTCGGACTGCTGCAAGTAGCGCCCGGAGTCGTTTTCTT
         ++++++++++++++++++++++++++++++++++++++++++++++++++++++++++++++++++++++ 4900
         AGAGGCTACTGGCAGTCCATACCTACCTGCTCGAGCCTGACGACGTTCATCGCGGGCCTCAGCAAAAGAA
```

Ser Pro Met Thr Val Arg Tyr Gly Trp Thr Ser Ser Asp Cys Cys Lys  •  Arg Pro Glu Ser Phe Ser
    Leu Arg  •  Pro Ser Gly Met Asp Gly Arg Ala Arg Thr Ala Ala Ser Ser Ala Arg Ser Arg Phe Leu
Leu Ser Asp Asp Arg Gln Val Trp Met Asp Glu Leu Gly Leu Leu Gln Val Ala Pro Gly Val Val Phe Phe

Glu Gly Ile Val Thr Leu Tyr Pro His Val Leu Glu Ser Gln Gln Leu Tyr Arg Gly Ser Asp Asn Glu Glu
   Arg Arg His Gly Asp Pro Ile Ser Pro Arg Ala Arg Val Ala Ala Leu Leu Ala Arg Leu Arg Lys Arg
     Glu Ser Ser Arg  •  Thr His Ile Ser Ser Ser Pro Ser Ser Cys Thr Ala Gly Pro Thr Thr Lys Lys

FIG. 12X

```
                                          EcoR I
                                          |
CGCAACGCTCAACGAAGGGTCCGAATTC
────┼────┼────┼────┼────┼───▶ 4928
GCGTTGCGAGTTGCTTCCCAGGCTTAAG
```

Ser Gln Arg Ser Thr Lys Gly Pro Asn Ser
 Arg Asn Ala Gln Arg Arg Val Arg Ile
  Ala Thr Leu Asn Glu Gly Ser Glu Phe
────┼────┼────┼────┼────┼───▶
 Cys Arg Glu Val Phe Pro Gly Phe Glu
Arg Leu Ala  •  Arg Leu Thr Arg Ile Arg
 Ala Val Ser Leu Ser Pro Asp Ser Asn

FIG. 12Y

```
tutE.T1    MVVVDRPPPPDLGGGVIVRNECSHSEPIDTGRMTFPTCDSGADVKIPLVTEIQRFSLQDG  60
f308.coli  ML----------E-----------------RNRE----------ATMIFNIQRYSTHDG    22
pf1C.coli  MT---------------SSAGQRISCNVVETRRDD---------------------DG    35
pf1A.coli  MSVIGRIHS----------------------------------VARIFNIQRYSLNDG    18 tutE.T1    PGFRTTVFLKGCPLRCPWCHNPETQKV-GKEYYYNRDRCV-SCGRCATVCPTGASQLLDG  118
f308.coli  PGIRTVVFLKGCSLGCRWCQNPES-RARTQDLLYDARLCLEGCELCAKAAPEVIERALNG  81
pf1C.coli  EGIRTVVFFKGCPHLCPWCANPESISGKKIQTVRREAK-CLH-CAKCLRDADE------  85
pf1A.coli  PGIRFITFFQGCLMRCLYCHNRDTWDTHG------------------------------  47 tutE.T1    PGASQVLKLDRSKCINCMRCVAVCLTGSRDSVGMEMTLDEILREVLSDEPFYRNSGGGVT  178
f308.coli  L--LIHREKLTPEHLTALTDC---CPTQALTVCGEVKSVEEIMTTVLRDKPFYDRSGGGLT  137
pf1C.coli  -------------------CPSGAFERIGRDISLDALEREVMKDDIFFRTSGGGVT    122
pf1A.coli  ------------------------GKEVTVEDLMKEVTYRHFMNASGGGVT    75 tutE.T1    ISGGDPLFHPAFTLELARKKIKERGVHVAIETSCFPKKW-ATIQPLLKLVDLFIVDLKSLN  237
f308.coli  LSGGEPFMQPEMAMALLQASHEAGIHTAVET-CLHVPW-KYIAPSLPYIDLFLADLKHVA  195
pf1C.coli  LSGGEVLMQAEFATRFLQRLRLWGVSCAIET-AGDAPA-SKLLPLAKLCDEVLFFLKIMD  180
pf1A.coli  ASGEAILQAEFVRDWFRACKKEGIHTCLDTNGFVRRYDPVIDELLEVTDLVMLDLKQMN  135
```

FIG. 13A

```
tutE.T1   RKKHEETVGWPLQPILDNIEHLIQAKANIRIHPVIPGFNDSPMDFEDYIAYLGRHAAQL 297
f308.coli DAPFKQWTDGNAARVLDNLKKLAAAGKKIHIRVPLIHQGFNADETSVKAITDFAA-DELHV 254
pflC.coli ATQARDVKMNLPRVLENVSEGVNIPRLPLIHPGFTLSRENMQQALDVLI-P-LNI 238
pflA.coli DEIHQNLVGVSNHRTLEFAKYLANKNVKVWIRYVVVPGWSDDDSAHRLGEF-TRDMGNV 194 tutE.T1   DGVDILNYHVYGEGKKYRSLGRENEYQYFGVEENPPEKVVPLAKGLKLAGITSVTIGGLVG 357
f308.coli GEIHFLPYHTLGINKYHLLNLP----YDAPEKPLDAPELDFAQQYACQKGLTAT-LRG 308
pflC.coli RQIHLLPFHQYGEPKKYRLLGKT---WSMKEVPAPSSADVATMREMAERAGLQVT-VGG 292
pflA.coli EKIELLPYHELG--KHKWVAMGEEYK--LDGVKPPKKETMERVKGILEQYGHKV---- 244 tutE.T1   ITADRHKSSRDAGTGCIA 375
f308.coli ------------------ 308
pflC.coli ------------------ 292
pflA.coli ----------------MF 246
```

FIG. 13B

```
CCATGGGTGGCGTCTGGAAACGCTGGCTTAGGGACGTTGAAAACACGACCTGCTCC
AGGCACGAGGAAGGCAAACTAAGT
TTCCGCGACCACGTCTGAACACCGGACAGACGTGGTTCACCTCCAGACCACTGTAGT
GATAGATCATGAAAACCTACTCC
AGCGCAAATGGCCTGTTCGTCCCGGAAGTCGATCCCTACTACTATGTAAGTACGGAA
AACCAGAGCTTCCTCGATAAATT
TGCAAAGATATCGAAAAGCATCCCGTCAATGTACTGGTGGTCGGCAAACAAGGCT
GCGGCAAGTCTTCCCTAGTGCGGC
AATACGCCGCCGTCAACAGGCTACCCTTGGCGACCTTCCAGATCGGCATCCTGTCGG
AGCCGGGGCAACTGTTTGGTGAA
TACGCGCTGGAGAACGGGGAGACCCGTTACAAGCAGTTCCTCTTCCCCCAGGCCATC
CAGACACCCAATTGCGTCATCCA
CCTTGAAGAGATCAATCGCCCCGAGCATCCGAAGGCGTTGAACATGTTGTTCTCCAT
TCTCTCCGATGACCGTCAGGTAT
GGATGGACGAGCTCGGACTGCTGCAAGTAGCGCCCGGAGTCGTTTTCTTCGCAACGC
TCAACGAAGGGTCCGAATTCGTC
GGTACCGAGTTACTCGACCCGGCCCTGCGCGACCGTTTTTATGTCACTACCATGGAT
TTCCTGCCGAATGAAGTGGAAGT
CGAGGTGCTGGAAAAGAAGACCGGCGTGAAAAATGAGCAGGCGAGGGAAATCATC
GCGGTAGCAAACAGCATCCGCGCCA
ATGCCGACCTCGGCATCGATGTTTCCACACGCAAGATCCTGATGCTCGGCGAGATGA
TTGCCGCCGGCGGAACGTTGCGC
GAAGCCATCGTGACGAGTCTCCAAACCGACAAGAAGACGCTTGAATCGGTTTTGCTG
TCCCTGCACGTCAATCTGGGGAA
GGTGGAAAAAGCAAGACAGAATACGTCCAATACATCGCCGCCTAAGGTCTTCCAT
GG
```

FIG. 18

MKTYSSANGLFVPEVDPYYYVSTENQSFLDKFAKISKKHPVNVLVVGKQGCGKSSLVRQY
AAVNRLPLATFQIGILSEPG
QLFGEYALENGETRYKQFLFPQAIQTPNCVIHLEEINRPEHPKALNMLFSILSDDRQVWMD
ELGLLQVAPGVVFFATLNE
GSEFVGTELLDPALRDRFYVTTMDFLPNEVEVEVLEKKTGVKNEQAREIIAVANSIRANAD
LGIDVSTRKILMLGEMIAA
GGTLREAIVTSLQTDKKTLESVLLSLHVNLGKVEKSKTEYVQYIAA

```
CCATGGCCAAGAACCACGACACCACACTTCGGCTGATGAGCAGCGCTGGAGACGTCAA
GCGTTTCGTCATTCCCGGCGAG
GAGGGCTATTCCGATTTCTGGCGTCGAGACAAGTCGCCGATCGAATCCGTCGAGTTGG
TGAAGCTATTGGTCGCCATTCG
TAAACTCTCGACTTTCATCGGACGCAACGTCGGCGAAATCGTCTGGTCCGGAATGGAA
CTCGACAATGCGATCGCCCTCG
ATCCAACGCCAATAATGGGCACGTATCCGGTGCCGGCGGGAAAGACGGATCTGATGGT
CGGCATCATGGTTCAGGAGGCA
TACAAGCGCATCGAGTGGTCCGAACGCCTGCGCGAGATGCTCAGGCTGCGCGTCCAGC
CGCCGACGCAGTATGAATACAA
GTTCGACATGTTCTTCACCGTCTGCGAGTCCGTCTACGTCGACAGTTTGGCCAACAAGA
GCGTGCTCGGCTACTACGCCG
AGGCGGCGCGTGACTGGCGTATCGTCAAGACGCTGAAGAGTCTGATCAAGCCGCCCAC
CCTTTCCGAGATGCTGCACCTG
TGGTGGCGCTTGGCTGCCGACCGCAATCCCGAGCTCTACAAGCAGGGCTACAGCGACC
TCACCCTCGGCGGCTTGGTCAT
GCGGGGTAGTCTGGACCAGTACTACAGCAAGCCGTTGCAGACCATGAACAGCATCGTG
CCGGCCTTGCGCCACGACTGCC
CTGAACTCTCGAGCGTCAGCGATCGCTGTGACTTCCGCCTCGATCTCTATGAGAAGCTA
TGGCGCGAGGTGCTCAAACAC
ATCCGCTTCTGGCCCGGCGACCGCAGCGATCGGTTCATGATGCCGGACATGGGCGATG
ACGAAGAATTGGCCCGGGAAGA
GGCGGAGCAAGCAGCCGCAAGGCCACCATCGTCAATTACGCCAACCTGATCGAGGCG
GCGCTGCCGCAGAAGAACCGGG
ACTTCACCGATCAGATCAAGGGCAACGTCGCAAACCTCGAGAACGTCGCCCGGGTCGA
GGGCAACGACATCGTGATGATG
GCCCGCAACCGTGTCGATCGCCACCTCTTGCACAAGCTGGAGCAAGTGGTAAGGAACG
CCACCGACCGCCGGAGCGTTTT
CAACCGCGGGCTGAGTTCAGGGAAGATTCATAGTCGGCGGCTTTACCGCGCCCACACG
ACCGGCGCCGTGTTCCAACAAA
AGAAACACGAATTCGACATGCGAAAGAATGTCGTGCTGCTCGTGGACGCGACCGGGTC
GATGGCGGATCCGACACAATGG
GACCAAGCCGAAATGATCTACCAGACGCTGTTCACGGCGATTCTGGAGTATACGAACA
ACGCGCGACTATTCGCCTACAA
CGAAGTCAGGAACGCCTGCCGCATCACCGAGATCTATCGTGGTGGCCGCATGCTCACA
GTGCTGCCGCACGGAAGGACAG
CTTCCGGTGAGGCCATCATCGCCACGGCGCTAAATACCCGTACACCGGGAAAGAAAC
TCTGCTGGTCCATATCACCGAC
GGCGCCTCAAACTGGGGGTGCGGCGTCGCAGATGCCATCAAGTACTGCAAAGGTAACG
GCATCAGCCTGCTCACCTTGGG
CATCAGCTGCAGTCTGTCCGCCAAACAATCGCTACGCGACGAATACGGCAGTCTCGTG
AAGTTTGTCGACAAGACTGAGC
AATTGCCCAAGTTGTTTGGCGAGTTGATCATCAGCGAAATGCGTGAATCAAGGACAGC
ACAGAAGTGAGCACGTCCTTTC
TCGACCACGTGCTGGAAGCCGAATGGCAGATGTTCGTCCGCGTCCGGAGTGCACGGCA
CGCCCCCTGTCAGAGTGCTCCC
AACAACTTCAAGACGATCCGTTCCAGCCTGTTCGAGACGTGGTCGCAACCAATGCTCG
CTTCCTATCTTGCCGACCTGGA
AGCAGCTGATGCGGTTGGCCGAAACCTGCTCGTGGAGAAGTATGCTCGCATGGACAAC
TTGATTCCACCGCTATCAAACA
ACCCGTTGATCGGCATCATCGTCACCATCGAAAGCAA
```

FIG. 21

MAKNHDTTLRLMSSAGDVKRFVIPGEEGYSDFWRRDKSPIESVELVKLLVAIRKLSTFIG
RNVGEIVWSGMELDNAIALD
PTPIMGTYPVPAGKTDLMVGIMVQEAYKRIEWSERLREMLRLRVQPPTQYEYKFDMFF
TVCESVYVDSLANKSVLGYYAE
AARDWRIVKTLKSLIKPPTLSEMLHLWWRLAADRNPELYKQGYSDLTLGGLVMRGSLD
QYYSKPLQTMNSIVPALRHDCP
ELSSVSDRCDFRLDLYEKLWREVLKHIRFWPGDRSDRFMMPDMGDDEELAREEAEQAA
VKATIVNYANLIEAALPQKNRD
FTDQIKGNVANLENVARVEGNDIVMMARNRVDRHLLHKLEQVVRNATDRRSVFNRGL
SSGKIHSRRLYRAHTTGAVFQQK
KHEFDMRKNVVLLVDATGSMADPTQWDQAEMIYQTLFTAILEYTNNARLFAYNEVRN
ACRITEIYRGGRMLTVLPHGRTA
SGEAIIATALNTRTPGKKTLLVHITDGASNWGCGVADAIKYCKGNGISLLTLGISCSLSA
KQSLRDEYGSLVKFVDKTEQ
LPKLFGELIISEMRESRTAQK

FIG. 22

```
ATGGGAACCACCACATGCAAGCAGTGCGCAAACTTCTTTCCCGTCCCTAAAGAC
GCGGATGACTACGAAGCCGGTAAGGC
AGACTGCGTGCGGGAAAAGGAAGACGAAAAGGGTAAATACTGGCTCTCCAAG
CCCATATTCGAGAACAGCGCGCAATGTG
AAGCCTTTCAAACGAAGCGCTAA
```

FIG. 24

MGTTTCKQCANFFPVPKDADDYEAGKADCVREKEDEKGKYWLSKPIFENSAQCE
AFQTKR

FIG. 25

```
ATGGAGGGCAGCAACATGGAAACAGGACAGAATTTGCAAAACCAGCCGCATAC
CGAGGTGGGTACGGCGAGGCCGTGCCG
GAGTTGCAAATGGCAAACCCCCGACCCCACCGATCCGCACCGTGGGCAATGCA
CCGCCAACCGGCACGCCATGGGTGGCG
TCTGGAAACGCTGGCTTAGGGACGTTGAAAACACGACCTGCTCCAGGCACGAG
GAAGGCAAACTAAGTTTCCGCGACCAC
GTCTGA
```

FIG. 26

MEGSNMETGQNLQNQPHTEVGTARPCRSCKWQTPDPTDPHRGQCTANRHAMGG
VWKRWLRDVENTTCSRHEEGKLSFRDH
V

FIG. 27

```
                         SEQUENCE LISTING

<160> NUMBER OF SEQ ID NOS: 58

<210> SEQ ID NO 1
<211> LENGTH: 5
<212> TYPE: PRT
<213> ORGANISM: Artificial Sequence
<220> FEATURE:
<223> OTHER INFORMATION: Synthetic

<400> SEQUENCE: 1

Arg Val Ser Gly Tyr
1               5

<210> SEQ ID NO 2
<211> LENGTH: 5
<212> TYPE: PRT
<213> ORGANISM: Artificial Sequence
<220> FEATURE:
<223> OTHER INFORMATION: Synthetic

<400> SEQUENCE: 2

Arg Val Ala Gly Tyr
1               5

<210> SEQ ID NO 3
<211> LENGTH: 8
<212> TYPE: PRT
<213> ORGANISM: Artificial Sequence
<220> FEATURE:
<223> OTHER INFORMATION: Synthetic

<400> SEQUENCE: 3

Val Arg Val Ser Gly Tyr Ser Ala
1               5

<210> SEQ ID NO 4
<211> LENGTH: 5
<212> TYPE: PRT
<213> ORGANISM: Artificial Sequence
<220> FEATURE:
<223> OTHER INFORMATION: Synthetic

<400> SEQUENCE: 4

Thr Pro Asp Gly Arg
1               5

<210> SEQ ID NO 5
<211> LENGTH: 6
<212> TYPE: PRT
<213> ORGANISM: Artificial Sequence
<220> FEATURE:
<223> OTHER INFORMATION: Synthetic

<400> SEQUENCE: 5
```

Thr Pro Asp Gly Arg Phe
1               5

<210> SEQ ID NO 6
<211> LENGTH: 6
<212> TYPE: PRT
<213> ORGANISM: Artificial Sequence
<220> FEATURE:
<223> OTHER INFORMATION: Synthetic

<400> SEQUENCE: 6

Gly Pro Thr Ala Val Leu
1               5

<210> SEQ ID NO 7
<211> LENGTH: 5
<212> TYPE: PRT
<213> ORGANISM: Artificial Sequence
<220> FEATURE:
<223> OTHER INFORMATION: Synthetic

<400> SEQUENCE: 7

Gly Asn Asp Asp Asp
1               5

<210> SEQ ID NO 8
<211> LENGTH: 6393
<212> TYPE: DNA
<213> ORGANISM: Thauera aromatica

<400> SEQUENCE: 8

```
ccgcggctca gctaaaatat gcaaataaat atgctgcaac aggtcgctct gggcttgcca      60
gtcgtgcgtg ttggtgcatg atgagtcctt gccttgtcga aggctattag actttggttt     120
agctgcagcg cagcaaaaat agcgtagcga gaaaattcga tgcgatacct gtctttgcat     180
ccacctgaat tcgtgctctc tccagcacgt tttctcatct gctacctcga gcgcatgatt     240
cttcagacct ttgacggcat cttgcgctgt ccgcccgct tgcctgctcg cagctccagg     300
tcgaggatcc agctctcctt gtacagcgcg ggtgcggctt gctcgcctga agttgttca     360
tccgcaggcg agtgcagttc gagtatcgac ttgatcacgt ttggtgtctt caacccttgc     420
gacactggca gtgccctccg atctatcac cgccttcaca tgcaccggct cgcagggtca     480
gcgctgccgc agctacgtac ataacatgct caactggtca gttgcattcc atgggaatag     540
cggcttgcac aaattatgag cagcctgcgg cttctttcga cggggatacg gcttccgcga     600
catgcatcac tggcaatcgg agaatgcggg atgggtaggc gtggcagccc cgctcgcagg     660
gtcgtgcaaa tgagcgccag accggtgtat gtagtcaggt caagccttga gggctgcttg     720
acttcgaagc gctatgtttg attgggccaa ggcaggagag gggcgattgt acaatttcgt     780
caacgtatta cgaggttttc tgcgcggcgc tagcgcaagc tcagggctaa tatcaatgat     840
ggcaaaatca tgacatcgaa caacagttca gtatccgata tttctgcagt gctgcgggtt     900
cgcgatgtga ctttgcgcgc tgtggatgat cttcagacct atcgggaaaa attagcccgt     960
gttgtgcttg atgggcttta tgaatttgta gggcttctcg atgcaaaagg taatactctt    1020
gaaataaatc aagctgcgct ggatggcgcg ggaacccgac ttgaagacat ccgcgacaag    1080
ccgttctggg aggccaggtg gtggcaggtt ccaggaaaa cccaagaaga gcagcgcaaa    1140
cttatcgctc gcgcgagtgc tggcgagttt gttcgatgcg atgttgaaat atatggtcga    1200
gcttccggag aagagacgat tgttgttgat tactcaattc ttccgattcg agattgcaat    1260
```

```
ggaaaagtgg tgttcttgct tcctgaaggc cggaatatca ccgataagaa gctggcggaa    1320
gcagagcttg cgcgaaagaa tgaagagctg cagcatcttc ttgagaagat tcgtcagctg    1380
gatgaggcca agaatgagtt cttcgccaat ctcagtcatg aattgcgtac gcctctttct    1440
ctgattcttg gtccgtaga  atcgctactt gccgattctg gagactattc tggagtgcaa    1500
cgagtcgatc tggatgtcat ccagagaaat gccataacct tgctcaagta tgtgaacgac    1560
cttcttgatc tagcaaaact gcaggcggag aagttgcagc ttcactattc gcgtgtcgac    1620
cttgcagcgg tgacacgaat gatttgcgcg cattttgagg ctctggcaga gtataaatgt    1680 cttttcatatg tcattgacgc tcctgccttt atggaggctg aagtcgatgt cgagaagtat    1740
gagcggatcg ttctgaatct cttatccaat gcctttaagt tctcgccgga cggcgggcgc    1800
attcgctgtt cgttgagtgc gactggtacc ggaagaatct tgctcagtat tcaggacagt    1860
ggtcctggaa ttccagctga tcaacagagt gaaattttcg gccggtttcg gcaaggtggg    1920
gatatcaagt cccggcagtt tggcggtacg ggcttgggtt tgactattgt gaaggatttt    1980
gtctgcctgc atggggggt  tgtggtcgtt tcagacgctc cggagggcgg ggctttattt    2040
cagatcgaat tgcccaggaa tgcgccttct ggggtgtatg taaatgcggt tgcaaaggct    2100
ggtgaattaa gccctacatc ttttgatatc agcgcatggg gcctggaggg gcggagtgaa    2160
tggacaagcg ccgagggagc cagtgatcgt cctcggatcc tgattgtcga agataacgtc    2220
gatatgcgct gttttatagg gagggtgctc attgacgagt atcagatcag tgttgccgct    2280
gatggtgagc aggcactgga gcttattacc tcatcccctc cggatctggt cattacggat    2340
ctgatgatgc ccaaggtcag cggtcagctt ctggtcaaag agatgcgctc gagaggggac    2400
ctagccaatg ttcctatact cgtgctttcg gccaaggcgg atgatgggtt gagaataaaa    2460
ttgctggccg agtcggttca agattatgtt gtcaagccat tctcggctac ggagttgcga    2520
gcgcgagttc gaaatcttgt taccatgaag cgggcccgtg atgctttgca gagagcgctc    2580
gacagtcaga gtgacgattt atcgcaattg actcggcaga tcatcgacaa tcgccaggag    2640
ttgcagcgaa gccatgatgc tttgcaggaa tctgagtccc gctggcgcgc agtctatgag    2700
aattctgctg caggtattgt gttgacaaat ttggacggct tgattttgtc tgcgaatcaa    2760
gcatttcaaa aaatggttgg ctatgccgag gatgagttgc gggtgattga aatatcggat    2820
ctcgtccccg aacatgatcg cgaaaaaatc cggtcgcgcg tttcaaatct gatcagtggc    2880
cgcgtcgacg actatcaagt gcaaaggcaa tgccgacgaa aggacggccg aatgatgtgg    2940
gcaaatgtgc gagcatcgct catacctggg ctggccaatc agtctccgat ggttgtgaga    3000 attttttgatg acattaccga aaagattcag actgaagctg aactggcaag agcaagggaa    3060
aagttgacca gagtcatgcg tgttaccgca atgggagaat tggcggcatc gattgctcat    3120
gagttgaatc aaccgcttgc cgccattgtt accaatggtc atgcatcatt acgctggctt    3180
ggctccgagc cttgtaatct attggaagcc gtcgaagcag tgcgaagaat catccatgat    3240
gctaatcgcg cgagtgaaat aatcaaacgg atccgtggct tcttcagcg  ggggaggggg    3300 aggcgctcgg cagtggatat ttttcaggtt gttgcggatg tggctgcgat tgtcagcgat    3360
atggcgcgca gtcattgcat tgatatgcgt tatcaagcag tcggtcaatt gtcgctagtg    3420
attgcggata aggtccagtt gcaacaggtt attctgaatt tgtgcatcaa tggcatagaa    3480
tccattgttg gcgaaactc  cgaacagggc gaactttcaa ttaccgttac ccagtccgat    3540
aaaagattct tgaccgtcag cgtacatgat tccggcccgg gccttgcacc tggcgaggcg    3600
```

```
gaaaacgtgt tgatgcgtt ctatacgagc aaggtggagg ggcttggcat ggggctcgcc   3660
atcagtcgct ctatcattga ggcgcatggt gggcgccttg atgttctgtc cccttccacg   3720
gagggggat gcacgttctg tttcacgttg cctacgagg agatggctag cccatgtgcc   3780
ccacaataga tgcatcgact gtttatctgg tggacgacga tcgctccatg cgtgacgcaa   3840
tttccagctt ggttcgatcg gtcggcctca atgtggagac atttgcgtct gcaagtgagt   3900
tcttggagca cgctcgttcg gaagcatgtg cctgcttggt tcttgatgtt cggatgccac   3960
gcatgagcgg ttttgatctt cagcatgcgt taagcaaaaa tggtgtcgat attccaatca   4020
tctttattac cggccatggt gatatcccca tggcggttcg cgccatcaag tcgggtgccc   4080
tagaatttct tccaaagcct tttcgtgctg aagaactgct cgaagcaatc aacagggctc   4140
tgaatatcga tcaggaggct cgggagtaca aggcggagct ggataagata ttgaagaaat   4200
atgagggct tacagatcga gaaaggagg tatttcccct tattgcccag ggcttgttga   4260
acaagcagat tgccggatat ctcggaatta ctgaggtcac cataaaggtt catcgtcata   4320
atattacgag aaaaatgggg gtccggacac tggctaatct ggtgcgactt tacgagaagt   4380
taaagaatgc tgggctgatc gaaaaaaaga acggaaatct atcggatga agagccgcga   4440
ctggaaccct tcaggctctt ggcggccacg ctgtaggaac gctatcgcct acctgcgaat   4500
gtctaaactc actgaaacgg catagagttc aaagcaagaa cttagcaaaa tggatttgcc   4560
taacagttga ttgtagaaat aatttttat tgattaatga tcggttgatt gttgctgcag   4620
tcctgggagg gaaagccatt cacaagcact acaatgactg ctgctgcgca tcgcaaaatg   4680
tatcaagtcg ccgtggacc tcagtccaag cttgctcatg atgcgcccgc ggtgagcttc   4740
cacagtctta tggctgatgc ccagcagctt ggcgatttcc ttgctgctgt tgccgcaaac   4800
caccttgtcg agaatctcca tttcgcgctg tgacagggcg gcaagaagat cggcacgctc   4860
ctgcttttcg cgctgcttat tcgtcatctc cttgctgaag gcaagggcgg cgtttacagc   4920
atcaagcaga tcctggttgc gatagggttt ttggagaaag tcgaacgcgc ctttctttac   4980
cgcttgagct cccatctggg catcgccgta ggcggagaga aagatgatcg gcagcttgaa   5040
gcctctgtca cacagcgctt gttgcaactg taggccgctg acattttgca ttcgaacatc   5100
cagaatcaca cagccgtagg tgcatgaaat atcggcatca agaaaatgct ttgcggattc   5160
gtatgccttg acgtttagtg aaatcgagtt gaggagccac gtcagtgagt ccctgaccga   5220
cgcttcgtcg tcgacgacga atacagttgg ggcgttttcca gattttttcga tttgcatgag   5280
gtgctccttt gtgcggtgct atgacaaacg tacggtctat atggcatcgc taatctgaat   5340
atctcttaca ttggcaaggt aaactgaaac ctcgatccgc atccttcggt cttcgaaaat   5400
gaaagttcgc ccccatgtga ttcgatgatc gagcggcaga tcgtcaatcc tattccaagt   5460
ccgtctggct tggttgtgaa atagggttta aagacgcgtt ttgctgttcg gctttcgacg   5520
ccggtcccat agtcttgtac aaacaccttc attgaccttc cctctgcaat gatttcgcta   5580
ccgatcagca gcacgcgaga gtccggttcc atttctgaca tggcctcaat gccattcttg   5640
attagattga ataagacctg ctggatctcg attttgcaga gagggatgag tggagggtcg   5700
ggcattaact gcagattcac cgtagcgtta tgtcgatgga tctcgaaact tagaaatgaa   5760
agagcgtcct ggatgacgtc gttgatgttt tccaatagcc tttctggctt tgtgttgcag   5820
acgaaatcct tgcacgccg caggatctca cccgcttgat ctagatgggt gattgctaac   5880
ccgagtgagt gtgatatctc ctcgactccg ggcacatgtt caagccgtag ccggcagccc   5940
tggagatagt tcacggcgga aaccaggggt tggcccatct ggtgtgcaag cgctgcggcc   6000
```

-continued

```
attccggcca tcgcgttgat gcgtccgagt cgagtgagtt ctgcgtgacg gagcctttcc   6060
aattcctcta tccgcttgcg gtaggtgata tctgcgaagg cggccacaac tattttctca   6120
tccttgatct cgagcaagga tgagctgacg ctgagccatc gcgtcttgtg attttcttcg   6180
tcgcacatgc cgacttcgag gcttctgacc gaacttttct ggaggtcgtg aatccgccaa   6240
ggcaatcgct ttttccagat atttgtcccg tcattgagaa agaaccgttg cggtaattgc   6300
tgccaactca tgggcgtccc ttcctgtgtt cccatcagtt cagaaaactg gcagttttcc   6360
tcgagaatcc tgccgcggct atcagtaatc gat                                6393
```

<210> SEQ ID NO 9
<211> LENGTH: 218
<212> TYPE: PRT
<213> ORGANISM: Thauera aromatica

<400> SEQUENCE: 9

```
Met Cys Pro Thr Ile Asp Ala Ser Thr Val Tyr Leu Val Asp Asp Asp
1               5                   10                  15

Arg Ser Met Arg Asp Ala Ile Ser Ser Leu Val Arg Ser Val Gly Leu
            20                  25                  30

Asn Val Glu Thr Phe Ala Ser Ala Ser Glu Phe Leu Glu His Ala Arg
        35                  40                  45

Ser Glu Ala Cys Ala Cys Leu Val Leu Asp Val Arg Met Pro Arg Met
    50                  55                  60

Ser Gly Phe Asp Leu Gln His Ala Leu Ser Lys Asn Gly Val Asp Ile
65                  70                  75                  80

Pro Ile Ile Phe Ile Thr Gly His Gly Asp Ile Pro Met Ala Val Arg
                85                  90                  95

Ala Ile Lys Ser Gly Ala Leu Glu Phe Leu Pro Lys Pro Phe Arg Ala
            100                 105                 110

Glu Glu Leu Leu Glu Ala Ile Asn Arg Ala Leu Asn Ile Asp Gln Glu
        115                 120                 125

Ala Arg Glu Tyr Lys Ala Glu Leu Asp Lys Ile Leu Lys Lys Tyr Glu
    130                 135                 140

Gly Leu Thr Asp Arg Glu Lys Glu Val Phe Pro Leu Ile Ala Gln Gly
145                 150                 155                 160

Leu Leu Asn Lys Gln Ile Ala Gly Tyr Leu Gly Ile Thr Glu Val Thr
                165                 170                 175

Ile Lys Val His Arg His Asn Ile Thr Arg Lys Met Gly Val Arg Thr
            180                 185                 190

Leu Ala Asn Leu Val Arg Leu Tyr Glu Lys Leu Lys Asn Ala Gly Leu
        195                 200                 205

Ile Glu Lys Lys Asn Gly Asn Leu Ser Gly
    210                 215
```

<210> SEQ ID NO 10
<211> LENGTH: 227
<212> TYPE: PRT
<213> ORGANISM: Bradyrhizobium japonicum

<400> SEQUENCE: 10

```
Met Thr Gly Arg Phe Asp Trp Arg Gly Gln Gly Gly His Thr Glu Ala
1               5                   10                  15

Ser Thr Lys Ala Ile Val Phe Val Glu Asp Asp Ile Ser Met Arg
            20                  25                  30
```

```
Arg Ser Leu Thr Asn Leu Phe Arg Ser Val Gly Leu Glu Val Val Ala
            35                  40                  45

Phe Gly Ser Ala Arg Glu Met Leu Gln Ser Thr Met Pro Asp Val Thr
     50                  55                  60

Ser Cys Leu Val Leu Asp Val Arg Leu Pro Gly Leu Ser Gly Leu Asp
 65                  70                  75                  80

Tyr Gln Thr Glu Leu Ala Arg Leu Asn Ile His Ile Pro Ile Ile Phe
                 85                  90                  95

Ile Thr Gly His Gly Asp Ile Pro Met Thr Val Arg Ala Met Lys Gly
            100                 105                 110

Gly Ala Val Asp Phe Leu Ser Lys Pro Phe Arg Asp Gln Glu Leu Leu
            115                 120                 125

Asp Ala Val Val Ala Ala Thr Glu Arg Asp Arg Lys Arg Arg Glu Ala
    130                 135                 140

Gln Arg Thr Val Ala Asn Leu Lys Ser Leu Phe Glu Thr Leu Ser Pro
145                 150                 155                 160

Arg Glu Gln Ala Val Met Lys Leu Val Ala Thr Gly Leu Met Asn Lys
                165                 170                 175

Gln Val Ala Ala Glu Leu Gly Leu Ala Glu Ile Thr Val Lys Ile Tyr
            180                 185                 190

Arg Gly His Val Met Lys Met Arg Ala Arg Ser Leu Ala Asp Leu
            195                 200                 205

Ile Arg Met Ser Glu Thr Leu Gly Ile Ser Ala Asn His Thr Glu Gln
    210                 215                 220

Thr Gln Val
225

<210> SEQ ID NO 11
<211> LENGTH: 205
<212> TYPE: PRT
<213> ORGANISM: Bradyrhizobium japonicum

<400> SEQUENCE: 11

Met Thr Thr Lys Gly His Ile Tyr Val Ile Asp Asp Ala Ala Met
1               5                  10                  15

Arg Asp Ser Leu Asn Phe Leu Leu Asp Ser Ala Gly Phe Gly Val Thr
            20                  25                  30

Leu Phe Asp Asp Ala Gln Ala Phe Leu Asp Ala Leu Pro Gly Leu Ser
         35                  40                  45

Phe Gly Cys Val Val Ser Asp Val Arg Met Pro Gly Leu Asp Gly Ile
     50                  55                  60

Glu Leu Leu Lys Arg Met Lys Ala Gln Gln Ser Pro Phe Pro Ile Leu
 65                  70                  75                  80

Ile Met Thr Gly His Gly Asp Val Pro Leu Ala Val Glu Ala Met Lys
                 85                  90                  95

Leu Gly Ala Val Asp Phe Leu Glu Lys Pro Phe Glu Asp Asp Arg Leu
            100                 105                 110

Thr Ala Met Ile Glu Ser Ala Ile Arg Gln Ala Glu Pro Ala Ala Lys
            115                 120                 125

Ser Glu Ala Val Ala Gln Asp Ile Ala Ala Arg Val Ala Ser Leu Ser
    130                 135                 140

Pro Arg Glu Arg Gln Val Met Glu Gly Leu Ile Ala Gly Leu Ser Asn
145                 150                 155                 160

Lys Leu Ile Ala Arg Glu Tyr Asp Ile Ser Pro Arg Thr Ile Glu Val
                165                 170                 175
```

```
Tyr Arg Ala Asn Val Met Thr Lys Met Gln Ala Asn Ser Leu Ser Glu
            180                 185                 190

Leu Val Arg Leu Ala Met Arg Ala Gly Met Leu Asn Asp
        195                 200                 205

<210> SEQ ID NO 12
<211> LENGTH: 211
<212> TYPE: PRT
<213> ORGANISM: Azorhizobium caulinodans

<400> SEQUENCE: 12

Met Pro Glu Ser Leu Pro Val His Val Ile Asp Asp Asp Ala Val
 1               5                  10                  15

Arg Glu Ser Leu Ala Phe Leu Leu Glu Ser Ser Gly Leu Ala Val Thr
            20                  25                  30

Gln His Thr Ser Ala Ala Ala Phe Leu Asp Ala Gly Val Pro Leu Asp
        35                  40                  45

Arg Gly Cys Ile Val Thr Asp Val Arg Met Pro Gly Ile Ser Gly Leu
    50                  55                  60

Glu Leu Leu Lys Glu Leu Asn Ala Arg Gly Ala His Met Ala Val Ile
65                  70                  75                  80

Val Met Thr Gly His Gly Asp Val Pro Leu Ala Val Glu Ala Met Lys
                85                  90                  95

Leu Gly Ala Ala Asp Phe Leu Glu Lys Pro Phe Asp Asp Ala Ala Ile
            100                 105                 110

Ile Ala Ala Val Arg Ala Ser Leu Gly Arg Ser Ala Glu Gln Gly Arg
        115                 120                 125

Gln Glu Asp Ala Arg Ser Glu Val Gly Lys Arg Ile Ala Gly Leu Ser
    130                 135                 140

Gln Arg Glu Arg Gln Val Leu Glu Cys Leu Val Asn Gly Leu Ala Asn
145                 150                 155                 160

Lys Thr Ile Ala Tyr Asp Leu Gly Ile Ser Pro Arg Thr Val Glu Val
                165                 170                 175

Tyr Arg Ala Asn Val Met Thr Lys Met Lys Ala Ala Ser Leu Pro Glu
            180                 185                 190

Leu Val Arg Met Ala Leu Leu Ala Gly Val Ala Pro Ala Asp Asp Ala
        195                 200                 205

Thr Pro Thr
    210

<210> SEQ ID NO 13
<211> LENGTH: 204
<212> TYPE: PRT
<213> ORGANISM: Rhizobium meliloti

<400> SEQUENCE: 13

Met Thr Asp Tyr Thr Val His Ile Val Asp Asp Glu Glu Pro Val Arg
 1               5                  10                  15

Lys Ser Leu Ala Phe Met Leu Thr Met Asn Gly Phe Ala Val Lys Met
            20                  25                  30

His Gln Ser Ala Glu Ala Phe Leu Ala Phe Ala Pro Asp Val Arg Asn
        35                  40                  45

Gly Val Leu Val Thr Asp Leu Arg Met Pro Asp Met Ser Gly Val Glu
    50                  55                  60

Leu Leu Arg Asn Leu Gly Asp Leu Lys Ile Asn Ile Pro Ser Ile Val
65                  70                  75                  80
```

```
Ile Thr Gly His Gly Asp Val Pro Met Ala Val Glu Ala Met Lys Ala
                85                  90                  95

Gly Ala Val Asp Phe Ile Glu Lys Pro Phe Glu Asp Thr Val Ile Ile
            100                 105                 110

Glu Ala Ile Glu Arg Ala Ser Glu His Leu Val Ala Ala Glu Ala Asp
        115                 120                 125

Val Asp Asp Ala Asn Asp Ile Arg Ala Arg Leu Gln Thr Leu Ser Glu
130                 135                 140

Arg Glu Arg Gln Val Leu Ser Ala Val Ala Gly Leu Pro Asn Lys
145                 150                 155                 160

Ser Ile Ala Tyr Asp Leu Asp Ile Ser Pro Arg Thr Val Glu Val His
                165                 170                 175

Arg Ala Asn Val Met Ala Lys Met Lys Ala Lys Ser Leu Pro His Leu
            180                 185                 190

Val Arg Met Ala Leu Ala Gly Gly Phe Gly Pro Ser
        195                 200

<210> SEQ ID NO 14
<211> LENGTH: 197
<212> TYPE: PRT
<213> ORGANISM: Rhodobacter capsulatus

<400> SEQUENCE: 14

Met Ser Phe Thr Val His Ile Val Asp Asp Glu Glu Ser Leu Arg Asp
1               5                   10                  15

Ser Leu Gly Phe Leu Phe Ala Ser Arg Gly Ile Ala Thr Arg Thr Trp
            20                  25                  30

Ala Ala Gly Ala Asp Leu Leu Ala Glu Trp Pro Leu Ala Asp Cys Gly
        35                  40                  45

Cys Leu Ile Leu Asp Val Arg Met Glu Gly Met Ser Gly Pro Gln Leu
    50                  55                  60

Leu Asp Ala Leu Gln Ala Arg Pro Glu Gly Leu Val Pro Pro Val Ile
65                  70                  75                  80

Phe Leu Thr Gly His Ala Asp Val Pro Leu Ala Val Gln Ser Leu Lys
                85                  90                  95

Ala Gly Ala Phe Asp Phe Val Glu Lys Pro Phe Asn Asp Asn His Ile
            100                 105                 110

Val Asp Ile Ala Leu Ser Ala Ile Ala Ala His Glu Gly Arg Leu Ala
        115                 120                 125

Glu Ala Gln Ala Arg Glu Ala Val Ala Arg Arg Ala Ser Leu Ser
130                 135                 140

Ala Arg Glu Ala Glu Val Met Ala Leu Met Leu Glu Gly Leu Met Asn
145                 150                 155                 160

Lys Gln Ile Ala Glu Arg Leu Gly Ile Ala Met Arg Thr Val Glu Val
                165                 170                 175

His Arg Ser Arg Val Leu Ala Lys Met Gly Ala Arg Asn Ile Ala Asp
            180                 185                 190

Leu Ala Arg Met Thr
        195

<210> SEQ ID NO 15
<211> LENGTH: 452
<212> TYPE: PRT
<213> ORGANISM: Thauera aromatica

<400> SEQUENCE: 15
```

-continued

```
Val Leu Ser Ala Lys Ala Asp Asp Gly Leu Arg Ile Lys Leu Leu Ala
  1               5                  10                  15
Glu Ser Val Gln Asp Tyr Val Val Lys Pro Phe Ser Ala Thr Glu Leu
                 20                  25                  30
Arg Ala Arg Val Arg Asn Leu Val Thr Met Lys Arg Ala Arg Asp Ala
             35                  40                  45
Leu Gln Arg Ala Leu Asp Ser Gln Ser Asp Asp Leu Ser Gln Leu Thr
         50                  55                  60
Arg Gln Ile Ile Asp Asn Arg Gln Glu Leu Gln Arg Ser His Asp Ala
 65                  70                  75                  80
Leu Gln Glu Ser Glu Ser Arg Trp Arg Ala Val Tyr Glu Asn Ser Ala
                 85                  90                  95
Ala Gly Ile Val Leu Thr Asn Leu Asp Gly Leu Ile Leu Ser Ala Asn
             100                 105                 110
Gln Ala Phe Gln Lys Met Val Gly Tyr Ala Glu Asp Glu Leu Arg Val
         115                 120                 125
Ile Glu Ile Ser Asp Leu Val Pro Glu His Asp Arg Glu Lys Ile Arg
     130                 135                 140
Ser Arg Val Ser Asn Leu Ile Ser Gly Arg Val Asp Asp Tyr Gln Val
145                 150                 155                 160
Gln Arg Gln Cys Arg Arg Lys Asp Gly Arg Met Met Trp Ala Asn Val
                 165                 170                 175
Arg Ala Ser Leu Ile Pro Gly Leu Ala Asn Gln Ser Pro Met Val Val
             180                 185                 190
Arg Ile Phe Asp Asp Ile Thr Glu Lys Ile Gln Thr Glu Ala Glu Leu
         195                 200                 205
Ala Arg Ala Arg Glu Lys Leu Thr Arg Val Met Arg Val Thr Ala Met
     210                 215                 220
Gly Glu Leu Ala Ala Ser Ile Ala His Glu Leu Asn Gln Pro Leu Ala
225                 230                 235                 240
Ala Ile Val Thr Asn Gly His Ala Ser Leu Arg Trp Leu Gly Ser Glu
                 245                 250                 255
Pro Cys Asn Leu Leu Glu Ala Val Glu Ala Val Arg Arg Ile Ile His
             260                 265                 270
Asp Ala Asn Arg Ala Ser Glu Ile Ile Lys Arg Ile Arg Gly Phe Leu
         275                 280                 285
Gln Arg Gly Glu Gly Arg Arg Ser Ala Val Asp Ile Phe Gln Val Val
     290                 295                 300
Ala Asp Val Ala Ala Ile Val Ser Asp Met Ala Arg Ser His Cys Ile
305                 310                 315                 320
Asp Met Arg Tyr Gln Ala Val Gly Gln Leu Ser Leu Val Ile Ala Asp
                 325                 330                 335
Lys Val Gln Leu Gln Gln Val Ile Leu Asn Leu Cys Ile Asn Gly Ile
             340                 345                 350
Glu Ser Ile Val Gly Gly Asn Ser Glu Arg Gly Glu Leu Ser Ile Thr
         355                 360                 365
Val Thr Gln Ser Asp Lys Arg Phe Leu Thr Val Ser Val His Asp Ser
     370                 375                 380
Gly Pro Gly Leu Ala Pro Gly Glu Ala Glu Asn Val Phe Asp Ala Phe
385                 390                 395                 400
Tyr Thr Ser Lys Val Glu Gly Leu Gly Met Gly Leu Ala Ile Ser Arg
                 405                 410                 415
```

Ser Ile Ile Glu Ala His Gly Gly Arg Leu Asp Val Leu Ser Pro Ser
            420                 425                 430

Thr Glu Gly Gly Cys Thr Phe Cys Phe Thr Leu Pro Thr Glu Glu Met
            435                 440                 445

Ala Ser Pro Cys
    450

<210> SEQ ID NO 16
<211> LENGTH: 376
<212> TYPE: PRT
<213> ORGANISM: Bradyrhizobium japonicum

<400> SEQUENCE: 16

Arg Glu Arg Leu Glu Asn Thr Leu Val Ala Leu Arg Glu Ser Glu Gln
1               5                  10                  15

Arg Phe Arg Asp Tyr Ala Glu Thr Ala Ser Asp Trp Leu Trp Glu Thr
            20                  25                  30

Gly Pro Asp His Arg Val Thr His Leu Ser Glu His Thr Ser Ala Ala
            35                  40                  45

Gly Ile Leu Ala Thr Gly Leu Thr Gly Leu Leu Arg Trp Asp Ile Ala
    50                  55                  60

Cys Asp Met Glu Glu Glu Pro Glu Lys Trp Arg Gln His Arg Ala Thr
65                  70                  75                  80

Leu Gln Ala His Leu Pro Phe Arg Asp Leu Ile Tyr Arg Thr Val Asn
                85                  90                  95

Arg Met Gly Ser Pro Ile Tyr Val Arg Thr Ser Gly Lys Pro Phe Phe
            100                 105                 110

Asp Gly Asn Gly Asn Phe Leu Gly Tyr Arg Gly Val Ser Thr Asp Ile
            115                 120                 125

Thr Ala Thr Ile Arg Ala Asp Gln Ala Glu Gln Glu Leu Arg Lys Ala
    130                 135                 140

Gln Ala Glu Leu Ala His Val Thr Arg Val Thr Thr Leu Gly Glu Met
145                 150                 155                 160

Thr Thr Ser Ile Ala His Glu Ile Thr Gln Pro Leu Ala Ala Ile Leu
                165                 170                 175

Ser Asn Ala Asp Ala Cys Leu Gly Trp Met Ala Arg Asp Val Pro Asn
            180                 185                 190

Leu Ala Ala Ala Arg Ser Ser Val Glu Trp Ile Ile Glu Asp Ala Ile
            195                 200                 205

Arg Ala Ser Glu Val Ile Arg Ser Ile Arg Ala Leu Ala Lys Lys Gly
    210                 215                 220

Glu Ile Glu Met Val Pro Leu Asp Ile Asn Gln Val Val Arg Asp Val
225                 230                 235                 240

Ser Ala Leu Val Thr Arg Glu Leu Val Ser His Gln Val Thr Leu Arg
                245                 250                 255

Ser Glu Leu Ala Ser Ala Leu Pro Arg Val Leu Gly Asp Arg Ile Gln
            260                 265                 270

Leu Gln Gln Val Ile Ile Asn Leu Val Met Asn Gly Ile Glu Ala Met
            275                 280                 285

Asp Ala Val Thr Asp Arg Pro Arg Glu Leu Leu Ile Gln Ser Ser Thr
    290                 295                 300

Asp Asp Leu Gly Tyr Val Gln Leu Ser Val Thr Asp Cys Gly Val Gly
305                 310                 315                 320

Ile Ala Glu Asn Asp Ala Asp Arg Val Leu Asp Pro Phe Phe Thr Thr
                325                 330                 335

```
Lys Ser Ser Gly Leu Gly Met Gly Leu Ser Ile Cys Arg Ser Ile Val
            340                 345                 350

Glu Val His Gly Gly Arg Ile Ser Val Val Gln Lys Asn Gly Pro Gly
            355                 360                 365

Ala Thr Phe Gln Phe Ala Leu Pro
        370                 375

<210> SEQ ID NO 17
<211> LENGTH: 399
<212> TYPE: PRT
<213> ORGANISM: Bradyrhizobium japonicum

<400> SEQUENCE: 17

Arg Ala Arg Ala Gly Leu Ile Arg Asp Glu Ala Gly Thr Ala Arg His
1               5                   10                  15

Leu Ser Gly Ile Phe Leu Asp Ile Asp Glu Glu Lys Gln Val Glu Gly
            20                  25                  30

Ala Leu Arg Thr Arg Glu Thr His Leu Arg Ser Ile Leu His Thr Ile
            35                  40                  45

Pro Asp Ala Met Ile Val Ile Asp Gly His Gly Ile Ile Gln Leu Phe
        50                  55                  60

Ser Thr Ala Ala Glu Arg Leu Phe Gly Trp Ser Glu Leu Glu Ala Ile
65              70                  75                  80

Gly Gln Asn Val Asn Ile Leu Met Pro Glu Pro Asp Arg Ser Arg His
            85                  90                  95

Asp Ser Tyr Ile Ser Arg Tyr Arg Thr Thr Ser Asp Pro His Ile Ile
            100                 105                 110

Gly Ile Gly Arg Ile Val Thr Gly Lys Arg Arg Asp Gly Thr Thr Phe
            115                 120                 125

Pro Met His Leu Ser Ile Gly Glu Met Gln Ser Gly Gly Glu Pro Tyr
        130                 135                 140

Phe Thr Gly Phe Val Arg Asp Leu Thr Glu His Gln Gln Thr Gln Ala
145                 150                 155                 160

Arg Leu Gln Glu Leu Gln Ser Glu Leu Val His Val Ser Arg Leu Ser
            165                 170                 175

Ala Met Gly Glu Met Ala Ser Ala Leu Ala His Glu Leu Asn Gln Pro
            180                 185                 190

Leu Ala Ala Ile Ser Asn Tyr Met Lys Gly Ser Arg Arg Leu Leu Ala
            195                 200                 205

Gly Ser Ser Asp Pro Asn Thr Pro Lys Val Glu Ser Ala Leu Asp Arg
        210                 215                 220

Ala Ala Glu Gln Ala Leu Arg Ala Gly Gln Ile Ile Arg Arg Leu Arg
225                 230                 235                 240

Asp Phe Val Ala Arg Gly Glu Ser Glu Lys Arg Val Glu Ser Leu Ser
            245                 250                 255

Lys Leu Ile Glu Glu Ala Gly Ala Leu Gly Leu Ala Gly Ala Arg Glu
            260                 265                 270

Gln Asn Val Gln Leu Arg Phe Ser Leu Asp Pro Gly Ala Asp Leu Val
            275                 280                 285

Leu Ala Asp Arg Val Gln Ile Gln Gln Val Leu Val Asn Leu Phe Arg
        290                 295                 300

Asn Ala Leu Glu Ala Met Ala Gln Ser Gln Arg Arg Glu Leu Val Val
305                 310                 315                 320

Thr Asn Thr Pro Ala Ala Asp Asp Met Ile Glu Val Glu Val Ser Asp
```

-continued 325                 330                 335
Thr Gly Ser Gly Phe Gln Asp Asp Val Ile Pro Asn Leu Phe Gln Thr
                340                 345                 350
Phe Phe Thr Thr Lys Asp Thr Gly Met Gly Val Gly Leu Ser Ile Ser
        355                 360                 365
Arg Ser Ile Ile Glu Ala His Gly Gly Arg Met Trp Ala Glu Ser Asn
370                 375                 380
Ala Ser Gly Gly Ala Thr Phe Arg Phe Thr Leu Pro Ala Ala Asp
385                 390                 395

<210> SEQ ID NO 18
<211> LENGTH: 440
<212> TYPE: PRT
<213> ORGANISM: Azorhizobium caulinodans

<400> SEQUENCE: 18

Leu Val Ile Val Val Leu Ala Ser Ser Gly Gly Leu Phe Ala Gly Leu
1               5                   10                  15
Ala Ala Thr Ala Val Ser Ala Leu Gly Leu Ala Leu Arg Gly Leu Leu
                20                  25                  30
Ser Gly Asp Thr Val Val Ala Asp Trp Gln Ser Leu Gly Leu Leu Thr
            35                  40                  45
Ile Ala Gly Ala Gly Ile Ala Val Leu Gly Glu Arg Leu Arg Arg Thr
        50                  55                  60
Arg Leu Asp Ala Val Ala Arg Asp Arg Ala Leu Leu Ala Arg Glu Ala
65                  70                  75                  80
His Leu Ser Ser Ile Leu Asp Thr Val Pro Asp Ala Met Ile Val Ile
                85                  90                  95
Asp Glu Arg Gly Ile Met Gln Ser Phe Ser Ile Thr Ala Glu Arg Leu
                100                 105                 110
Phe Gly Tyr Ser Pro Ser Glu Val Ile Gly Arg Asn Val Ser Met Leu
            115                 120                 125
Met Pro Asn Pro His Arg Asp Gln His Asp Leu Tyr Leu Ser Arg Tyr
        130                 135                 140
Leu Thr Thr Gly Glu Arg Arg Ile Ile Gly Ile Gly Arg Val Val Thr
145                 150                 155                 160
Gly Glu Arg Lys Asp Gly Ala Thr Phe Pro Met Glu Leu Ala Val Gly
                165                 170                 175
Glu Met His Ser Val Ser Gly Arg Phe Phe Thr Gly Phe Ile Arg Asp
                180                 185                 190
Leu Thr Glu Arg Gln Asn Thr Glu Ala Arg Leu Gln Glu Leu Gln Ala
            195                 200                 205
Glu Leu Val His Ile Ser Arg Leu Thr Ala Leu Gly Glu Met Ala Ser
        210                 215                 220
Thr Leu Ala His Glu Leu Asn Gln Pro Leu Ser Ala Ile Ala Asn Tyr
225                 230                 235                 240
Ile Lys Gly Ser Arg Arg Leu Leu Asp Asp Gly Asp Pro Lys Arg Ile
                245                 250                 255
Pro Met Leu Gln Gly Ala Leu Asp Lys Ala Ala Glu Gln Ala Leu Arg
            260                 265                 270
Ala Gly Gln Ile Ile Arg Arg Leu Arg Asp Phe Val Ser Arg Gly Glu
        275                 280                 285
Thr Glu Arg Arg Val Glu Ser Leu Ser Lys Leu Ile Glu Glu Ala Ser
    290                 295                 300

```
Ala Leu Ala Leu Val Gly Ala Lys Glu His Gly Ile Gln Val Arg Tyr
305                 310                 315                 320

Gln Ile Asp Thr Ser Cys Asp Leu Val Leu Ala Asp Lys Val Gln Val
            325                 330                 335

Gln Gln Val Leu Leu Asn Leu Met Arg Asn Ala Leu Glu Ala Met Met
            340                 345                 350

Asp Ala Ser Arg Arg Gln Leu Leu Val Gln Thr Thr Pro Ala Glu Asp
            355                 360                 365

Asp Met Val Thr Val Ser Val Cys Asp Thr Gly His Gly Ile Ser Asp
370                 375                 380

Glu Met Arg Ala Gln Leu Phe Thr Pro Phe Val Thr Thr Lys Ala Gln
385                 390                 395                 400

Gly Met Gly Val Gly Leu Ser Ile Ser Arg Thr Ile Ile Glu Ala His
                405                 410                 415

Gly Gly Arg Ile Trp Ala Glu Pro Asn Ala Gly Gly Thr Ile Phe
            420                 425                 430

Arg Phe Thr Leu Arg Thr Val Asp
            435                 440

<210> SEQ ID NO 19
<211> LENGTH: 385
<212> TYPE: PRT
<213> ORGANISM: Rhizobium meliloti

<400> SEQUENCE: 19

Ile Val Ala Leu Gly Glu Val Leu Glu Ala Ala Arg Arg Ala Ile Asp
1               5                   10                  15

Arg Thr Glu Asp Val Val Arg Ala Arg Asp Ala His Leu Arg Ser Ile
            20                  25                  30

Leu Asp Thr Val Pro Asp Ala Thr Val Val Ser Ala Thr Asp Gly Thr
            35                  40                  45

Ile Val Ser Phe Asn Ala Ala Val Arg Gln Phe Gly Tyr Ala Glu
        50                  55                  60

Glu Glu Val Ile Gly Gln Asn Leu Arg Ile Leu Met Pro Glu Pro Tyr
65                  70                  75                  80

Arg His Glu His Asp Gly Tyr Leu Gln Arg Tyr Met Ala Thr Gly Glu
                85                  90                  95

Lys Arg Ile Ile Gly Ile Asp Arg Val Val Ser Gly Gln Arg Lys Asp
            100                 105                 110

Gly Ser Thr Phe Pro Met Lys Leu Ala Val Gly Glu Met Arg Ser Gly
            115                 120                 125

Gly Glu Arg Phe Phe Thr Gly Phe Ile Arg Asp Leu Thr Glu Arg Glu
            130                 135                 140

Glu Ser Ala Ala Arg Leu Glu Gln Ile Gln Ala Glu Leu Ala Arg Leu
145                 150                 155                 160

Ala Arg Leu Asn Glu Met Gly Glu Met Ala Ser Thr Leu Ala His Glu
                165                 170                 175

Leu Asn Gln Pro Leu Ser Ala Ile Ala Asn Tyr Ser His Gly Cys Thr
            180                 185                 190

Arg Leu Leu Arg Asp Met Asp Asp Ala Val Ala Thr Arg Ile Arg Glu
            195                 200                 205

Ala Leu Glu Glu Val Ala Ser Gln Ser Leu Arg Ala Gly Gln Ile Ile
            210                 215                 220

Lys His Leu Arg Glu Phe Val Thr Lys Gly Glu Thr Glu Lys Ala Pro
225                 230                 235                 240
```

-continued

```
Glu Asp Ile Arg Lys Leu Val Glu Glu Ser Ala Ala Leu Ala Leu Val
                245                 250                 255

Gly Ser Arg Glu Gln Gly Val Arg Thr Val Phe Glu Tyr Leu Pro Gly
            260                 265                 270

Ala Glu Met Val Leu Val Asp Arg Ile Gln Val Gln Gln Val Leu Ile
            275                 280                 285

Asn Leu Met Arg Asn Ala Ile Glu Ala Met Arg His Val Asp Arg Arg
        290                 295                 300

Glu Leu Thr Ile Arg Thr Met Pro Ala Asp Pro Gly Glu Val Ala Val
305                 310                 315                 320

Val Val Glu Asp Thr Gly Gly Ile Pro Glu Glu Val Ala Gly Gln
                325                 330                 335

Leu Phe Lys Pro Phe Val Thr Thr Lys Ala Ser Gly Met Gly Ile Gly
                340                 345                 350

Leu Ser Ile Ser Lys Arg Ile Val Glu Ala His Gly Gly Glu Met Thr
            355                 360                 365

Val Ser Lys Asn Glu Ala Gly Gly Ala Thr Phe Arg Phe Thr Leu Pro
        370                 375                 380

Ala
385

<210> SEQ ID NO 20
<211> LENGTH: 387
<212> TYPE: PRT
<213> ORGANISM: Rhodobacter capsulatus

<400> SEQUENCE: 20

Val Val Leu His Arg Asn Ala Leu Arg Arg Met Ala Glu Asp Arg
1               5                   10                  15

Leu Arg Ala Glu Met Ala Phe Arg Ala Met Glu Glu Ser Leu Thr
                20                  25                  30

Val Gly Met Arg Ala Lys Asp Leu Ser Gly Arg Ile Leu Tyr Val Asn
            35                  40                  45

Gly Ala Phe Cys Lys Leu Val Gly Leu Ala Ala Glu Asp Leu Val Gly
        50                  55                  60

Arg Ala Gln Pro Met Pro Tyr Trp Ala Pro Asp Phe Leu Glu Glu Thr
65                  70                  75                  80

Leu Ala Arg Gln Arg Gln Leu Ile Glu Gly Gln Pro Val Pro Gln Ala
                85                  90                  95

Phe Glu Thr Arg Phe Arg Arg Ser Asp Gly Ser Glu Ile Glu Val Gln
            100                 105                 110

Val Phe Glu Ala Pro Leu Ile Asp Ala Gly Gly Arg His Arg Gly Trp
        115                 120                 125

Met Gly Ser Val Ile Asp Ile Thr Gln Ala Lys Gln Ala Ala Arg Leu
    130                 135                 140

Ala Arg Ala Gln Asp Glu Ser Leu Ala Arg Thr Gly Arg Leu Val Thr
145                 150                 155                 160

Leu Gly Glu Met Ala Ser Thr Leu Ala His Glu Leu Asn Gln Pro Leu
                165                 170                 175

Ala Ala Ile Ala Ser Tyr Ala Ala Gly Gly Leu Asn Leu Phe Asp Gln
            180                 185                 190

Pro Glu Pro Asn Leu Thr Met Leu Arg Gln Ala Phe Glu Lys Met Gly
        195                 200                 205

Ala Gln Ala Arg Arg Ala Gly Leu Val Ile Arg Arg Val Gln Asp Phe
```

```
                    210              215                 220
Val Lys Lys Arg Thr Pro Gln Leu Ala Ala Leu Asp Leu Ser Glu Val
225                 230                 235                 240

Leu Ala Glu Ala Leu Ser Ile Thr Ala Pro Val Ala Arg Glu His Arg
                245                 250                 255

Val Lys Leu Ala Ser Leu Ile Glu Gly Arg Ile Pro Gly Val Gln Ala
                260                 265                 270

Asp Arg Ile Leu Ile Glu Gln Val Leu Val Asn Leu Ile Arg Asn Gly
                275                 280                 285

Val Glu Ala Met Ala Glu Gly Pro Arg Thr Gly Asp Asp Leu Thr Val
                290                 295                 300

Arg Leu Ala Arg Ala Gly Ala Val Thr Ile Glu Val Met Asp Arg
305                 310                 315                 320

Gly Pro Gly Ile Ser Asp Ala Val Ala Ala Ser Leu Phe Asp Pro Phe
                325                 330                 335

Thr Ser Thr Lys Ser Glu Gly Met Gly Met Gly Leu Asn Ile Cys Arg
                340                 345                 350

Ser Ile Val Glu Met His His Gly Ser Leu Ser His Gly Pro Arg Ala
                355                 360                 365

Gly Gly Gly Thr Val Phe Thr Val Thr Leu Pro Val Pro Gln Glu Gly
                370                 375                 380

Ala Pro Ala
385

<210> SEQ ID NO 21
<211> LENGTH: 3106
<212> TYPE: DNA
<213> ORGANISM: Thauera aromatica

<400> SEQUENCE: 21
gaattcatcg tcggctacca cgccgaagat cccaacatgt tcccgctgta tcccgaactg      60
tcccacatgg ccgtgcagga ctacctgcgg agcgactact cgccgcagcc ggccgacgag     120
gcggcggcga tcaatgaata ctggaagccg catagcctgc agagcaagtg tcagccctat     180
ttcgatccgg cagacctcgg ccgcatgtat caggtcagca gcatggaggc gccgtccttc     240
gcttccggtt acaacagcat cgtgccgccc tacgaaaccg tcctggaaga cgggctgctg     300
gcgcgcatca gctcgccga aaagcatatc gccgaagccc aggccgacat gtcgaccttc     360
ccctggaacg gcacgaaggg tctcgacaac atcgccaaga tcgacaactg gaaggcgatg     420
gtcatcgcct gcaaggcggt gatcagctgg gcgcgccggc agggccggct gtgcaagatc     480
gtcgcggaaa acttcgagac cgatccgaag cgccaggccg agctgctcga atcgccgac     540 atctgtcagc gcattccgc cgagccctgc aagggcctca aggacgcgat gcaggcgaaa     600
ttctttacct tcctgatctg tcacgcgatc gagcgctacg cgagcggcta cgcccagaag     660
gaagacaccc tgctgtggcc gtactacaag gcctccgtcg tcgacaagaa attccagccg     720
atgagccaca tggatgcggt ggaactcgtc gagatggaac gtttgaagat ttccgagcat     780
ggcgccggca gtcgcgcgc ctaccgcgaa atcttcccgg ggtcgaacga tctgttcatc     840
ctcaccgtcg gcggcaccaa cgccaagggc gaggacgcct gcaacgacat gaccgacgcc     900
atcctcgagg cagccaagcg gatccgcacg gccgagccct ccatcgtctt ccgctattcc     960
aagaagaacc gcgagaagac gctgcgctgg gttttcgagt gcatccgcga cggactcggc    1020
tatccgtcga tcaagcacga cgagatcggc acggagcaga tgaaggaata cgccaagttc    1080
```

```
agcctcaacg gcaacggcgc caccgacgag gaagcccaca actgggtcaa cgtgctgtgc    1140
atgtcgcccg gcatccacgg tcgccgcaag acgcaaaaaa cccgttcgga aggtggcggc    1200
tcaatcttcc cggccaagct gctggaaatc tcgctcaatg acggctacga ctggtcgtac    1260
gccgacatgc aactcggccc gaagaccggt gatctctcgt cgctgaagtc cttcgaggat    1320
gtttgggagg ctttccgcaa gcagtatcaa tatgcgatca acctctgtat cagcaccaag    1380
gacgtgtcgc gctacttcga gcagcgcttc ctgcagatgc ctttcgtgtc cgcaatcgac    1440
gacggctgca tggaactcgg gatggacgcc tgcgccctgt ccgagcagcc caatggctgg    1500
cacaacccga tcacgacgat cgtcgcggcg aactccctcg tggccatcaa gaaactggta    1560
ttcgaggaga agaaatacac cctcgagcaa ctcagccaag cgttgaaggc gaactgggaa    1620
ggtttcgagg aaatgcgcgt cgacttcaag cgggcgccga agtggggcaa cgacgatgat    1680
tacgccgacg gtatcatcac ccgcttctac gaggaaatca tcggcggcga aatgcgcaag    1740
atcaccaact actctggtgg tccggtcatg ccgactggtc aggctgtcgg cctgtacatg    1800
gaagtcggtt cgcgcacggg ccccacgccg gacgggcgct cgggggtgta agcggcagac    1860
gacggcggca tttctcccta catgggaacc gacaagaagg ggccgacggc ggtgttgcgc    1920
tcggtgtcca aggtgcagaa gaaccagaag ggcaacctgc tgaaccagcg cttgtcggtg    1980
ccgatcatgc gctccaagca tggcttcgaa atctggaact cgtacatgaa gacttggcac    2040
gatctgaata tcgatcatgt tcagttcaat gtcgtcagca cggatgaaat gcgcgctgcg    2100
cagcgcgaac ccgagaagca ccatgatctt atcgtgcgcg tttccggcta cagcgctcgg    2160
ttcgtagaca ttccgaccta tgggcagaac accatcatcg cccgtcagga acaggatttc    2220
agcgcatccg atctcgagtt cctaaacgtc gaaatctagg acaagccact caaggggggc    2280
agcatcccgt cccccttttac cttacggttg cacgaaaaaa catggagggc agcaacatgg    2340
aaacaggaca gaatttgcaa aaccagccgc ataccgaggt gggtacggcg aggccgtgcc    2400
ggagttgcaa atggcaaacc cccgacccca ccgatccgca ccgtgggcaa tgcaccgcca    2460
accggcacgc catgggtggc gtctggaaac gctggcttag ggacgttgaa acacgacct    2520 gctccaggca cgaggaaggc aaactaagtt tccgcgacca cgtctgaaca ccggacagac    2580
gtggttcacc tccagaccac tgtagtgata gatcatgaaa acctactcca gcgcaaatgg    2640
cctgttcgtc ccggaagtcg atccctacta ctatgtaagt acggaaaacc agagcttcct    2700
cgataaattt gcaaagatat cgaaaaagca tcccgtcaat gtactggtgg tcggcaaaca    2760
aggctgcggc aagtcttccc tagtgcggca atacgccgcc gtcaacaggc tacccttggc    2820
gaccttccag atcggcatcc tgtcggagcc gggggcaactg tttggtgaat acgcgctgga    2880
gaacggggag acccgttaca agcagttcct cttcccccag gccatccaga cacccaattg    2940
cgtcatccac cttgaagaga tcaatcgccc cgagcatccg aaggcgttga acatgttgtt    3000
ctccattctc tccgatgacc gtcaggtatg gatggacgag ctcggactgc tgcaagtagc    3060
gcccggagtc gttttcttcg caacgctcaa cgaagggtcc gaattc              3106
```

<210> SEQ ID NO 22
<211> LENGTH: 557
<212> TYPE: DNA
<213> ORGANISM: Thauera aromatica
<220> FEATURE:
<221> NAME/KEY: misc_feature
<222> LOCATION: (235)..(235)
<223> OTHER INFORMATION: N at this position can be A, C, T, or G.

<400> SEQUENCE: 22

-continued

```
atacggcgac gcagcgcatg caattgatgc acttgctgcg gtcgagctta agcacctgct    60
tgcgcccggt ccatcaagaa gctgcgatgc accggttggg cagaccgttg cacaccgtcc   120
gcagctcacg caacgatcac ggttgtaata gtattccttg cccaccttt gggtttcagg    180
gttgtggcac cacggacatc tcaatgggca acccttcaag aacaccgtcg tccgnaatcc   240
aggaccgtct tgcaggctaa aacgctgtat ttcggtgact aatggaattt tcacgtcagc   300
cccagaatcg catgttggaa acgtcatccg tccggtatca atcggctcgc tgtgcgagca   360
ttcatttcga acgattacgc ctccgcccaa atccggcggc ggaggccgat ccaccacgac   420
catagaagtg aatcttgtaa gggttcattg aacttccgcc ctgctggcgg cgtcaataag   480
tgcgatcacc agtcggtgtg gtgatttccc tcatgtattc gtttgtcacc gcggctcagc   540
taaaatatgc aaataaa                                                   557
```

<210> SEQ ID NO 23
<211> LENGTH: 740
<212> TYPE: PRT
<213> ORGANISM: Thauera aromatica

<400> SEQUENCE: 23

```
Met Phe Pro Leu Tyr Pro Glu Leu Ser His Met Ala Val Gln Asp Tyr
  1               5                  10                  15

Leu Arg Ser Asp Tyr Ser Pro Gln Pro Ala Asp Glu Ala Ala Ala Ile
                 20                  25                  30

Asn Glu Tyr Trp Lys Pro His Ser Leu Gln Ser Lys Cys Gln Pro Tyr
             35                  40                  45

Phe Asp Pro Ala Asp Leu Gly Arg Met Tyr Gln Val Ser Ser Met Glu
         50                  55                  60

Ala Pro Ser Phe Ala Ser Gly Tyr Asn Ser Ile Val Pro Pro Tyr Glu
 65                  70                  75                  80

Thr Val Leu Glu Asp Gly Leu Leu Ala Arg Ile Lys Leu Ala Glu Lys
                 85                  90                  95

His Ile Ala Glu Ala Gln Ala Asp Met Ser Thr Phe Pro Trp Asn Gly
            100                 105                 110

Thr Lys Gly Leu Asp Asn Ile Ala Lys Ile Asp Asn Trp Lys Ala Met
        115                 120                 125

Val Ile Ala Cys Lys Ala Val Ile Ser Trp Ala Arg Arg Gln Gly Arg
    130                 135                 140

Leu Cys Lys Ile Val Ala Glu Asn Phe Glu Thr Asp Pro Lys Arg Gln
145                 150                 155                 160

Ala Glu Leu Leu Glu Ile Ala Asp Ile Cys Gln Arg Ile Pro Ala Glu
                165                 170                 175

Pro Cys Lys Gly Leu Lys Asp Ala Met Gln Ala Lys Phe Phe Thr Phe
            180                 185                 190

Leu Ile Cys His Ala Ile Glu Arg Tyr Ala Ser Gly Tyr Ala Gln Lys
        195                 200                 205

Glu Asp Thr Leu Leu Trp Pro Tyr Tyr Lys Ala Ser Val Val Asp Lys
    210                 215                 220

Lys Phe Gln Pro Met Ser His Met Asp Ala Val Glu Leu Val Glu Met
225                 230                 235                 240

Glu Arg Leu Lys Ile Ser Glu His Gly Ala Gly Lys Ser Arg Ala Tyr
                245                 250                 255

Arg Glu Ile Phe Pro Gly Ser Asn Asp Leu Phe Ile Leu Thr Val Gly
            260                 265                 270
```

-continued

```
Gly Thr Asn Ala Lys Gly Glu Asp Ala Cys Asn Asp Met Thr Asp Ala
        275                 280                 285
Ile Leu Glu Ala Ala Lys Arg Ile Arg Thr Ala Glu Pro Ser Ile Val
290                 295                 300
Phe Arg Tyr Ser Lys Lys Asn Arg Glu Lys Thr Leu Arg Trp Val Phe
305                 310                 315                 320
Glu Cys Ile Arg Asp Gly Leu Gly Tyr Pro Ser Ile Lys His Asp Glu
                325                 330                 335
Ile Gly Thr Glu Gln Met Lys Gly Tyr Ala Lys Phe Ser Leu Asn Gly
                340                 345                 350
Asn Gly Ala Thr Asp Glu Glu Ala His Asn Trp Val Asn Val Leu Cys
        355                 360                 365
Met Ser Pro Gly Ile His Gly Arg Arg Lys Thr Gln Lys Thr Arg Ser
    370                 375                 380
Glu Gly Gly Gly Ser Ile Phe Pro Ala Lys Leu Leu Glu Ile Ser Leu
385                 390                 395                 400
Asn Asp Gly Tyr Asp Trp Ser Tyr Ala Asp Met Gln Leu Gly Pro Lys
                405                 410                 415
Thr Gly Asp Leu Ser Ser Leu Lys Ser Phe Glu Asp Val Trp Glu Ala
                420                 425                 430
Phe Arg Lys Gln Tyr Gln Tyr Ala Ile Asn Leu Cys Ile Ser Thr Lys
        435                 440                 445
Asp Val Ser Arg Tyr Phe Glu Gln Arg Phe Leu Gln Met Pro Phe Val
    450                 455                 460
Ser Ala Ile Asp Asp Gly Cys Met Glu Leu Gly Met Asp Ala Cys Ala
465                 470                 475                 480
Leu Ser Glu Gln Pro Asn Gly Trp His Asn Pro Ile Thr Thr Ile Val
                485                 490                 495
Ala Ala Asn Ser Leu Val Ala Ile Lys Lys Leu Val Phe Glu Glu Lys
        500                 505                 510
Lys Tyr Thr Leu Glu Gln Leu Ser Gln Ala Leu Lys Ala Asn Trp Glu
    515                 520                 525
Gly Phe Glu Glu Met Arg Val Asp Phe Lys Arg Ala Pro Lys Trp Gly
530                 535                 540
Asn Asp Asp Asp Tyr Ala Asp Gly Ile Ile Thr Arg Phe Tyr Glu Glu
545                 550                 555                 560
Ile Ile Gly Gly Glu Met Arg Lys Ile Thr Asn Tyr Ser Gly Gly Pro
                565                 570                 575
Val Met Pro Thr Gly Gln Ala Val Gly Leu Tyr Met Glu Val Gly Ser
                580                 585                 590
Arg Thr Gly Pro Thr Pro Asp Gly Arg Phe Gly Gly Glu Ala Ala Asp
        595                 600                 605
Asp Gly Gly Ile Ser Pro Tyr Met Gly Thr Asp Lys Lys Gly Pro Thr
    610                 615                 620
Ala Val Leu Arg Ser Val Ser Lys Val Gln Lys Asn Gln Lys Gly Asn
625                 630                 635                 640
Leu Leu Asn Gln Arg Leu Ser Val Pro Ile Met Arg Ser Lys His Gly
                645                 650                 655
Phe Glu Ile Trp Asn Ser Tyr Met Lys Thr Trp His Asp Leu Asn Ile
                660                 665                 670
Asp His Val Gln Phe Asn Val Val Ser Thr Asp Glu Met Arg Ala Ala
        675                 680                 685
```

```
Gln Arg Glu Pro Glu Lys His His Asp Leu Ile Val Arg Val Ser Gly
    690             695                 700
Tyr Ser Ala Arg Phe Val Asp Ile Pro Thr Tyr Gly Gln Asn Thr Ile
705             710                 715                 720
Ile Ala Arg Gln Glu Gln Asp Phe Ser Ala Ser Asp Leu Glu Phe Leu
                725                 730                 735
Asn Val Glu Ile
            740

<210> SEQ ID NO 24
<211> LENGTH: 765
<212> TYPE: PRT
<213> ORGANISM: Escherichia coli

<400> SEQUENCE: 24

Met Thr Asn Arg Ile Ser Arg Leu Lys Thr Ala Leu Phe Ala Asn Thr
1               5                   10                  15
Arg Glu Ile Ser Leu Glu Arg Ala Leu Leu Tyr Thr Ala Ser His Arg
                20                  25                  30
Gln Thr Glu Gly Glu Pro Val Ile Leu Arg Arg Ala Lys Ala Thr Ala
            35                  40                  45
Tyr Ile Leu Glu His Val Glu Ile Ser Ile Arg Asp Glu Glu Leu Ile
50                  55                  60
Ala Gly Asn Arg Thr Val Lys Pro Arg Ala Gly Ile Met Ser Pro Glu
65                  70                  75                  80
Met Asp Pro Tyr Trp Leu Leu Lys Glu Leu Asp Gln Phe Pro Thr Arg
                85                  90                  95
Pro Gln Asp Arg Phe Ala Ile Ser Glu Glu Asp Lys Arg Ile Tyr Arg
            100                 105                 110
Glu Glu Leu Phe Pro Tyr Trp Glu Lys Arg Ser Met Lys Asp Phe Ile
        115                 120                 125
Asn Gly Gln Met Thr Asp Glu Val Lys Ala Ala Thr Asn Thr Gln Ile
130                 135                 140
Phe Ser Ile Asn Gln Thr Asp Lys Gly Gln Gly His Ile Ile Ile Asp
145                 150                 155                 160
Tyr Pro Arg Leu Leu Asn His Gly Leu Gly Glu Leu Val Ala Gln Met
                165                 170                 175
Gln Gln His Cys Gln Gln Gln Pro Glu Asn His Phe Tyr Gln Ala Ala
            180                 185                 190
Leu Leu Leu Leu Glu Ala Ser Gln Lys His Ile Leu Arg Tyr Ala Glu
        195                 200                 205
Leu Ala Glu Thr Met Ala Ala Asn Cys Thr Asp Ala Gln Arg Arg Glu
    210                 215                 220
Glu Leu Leu Thr Ile Ala Glu Ile Ser Arg His Asn Ala Gln His Lys
225                 230                 235                 240
Pro Gln Thr Phe Trp Gln Ala Cys Gln Leu Phe Trp Tyr Met Asn Ile
                245                 250                 255
Ile Leu Gln Tyr Glu Ser Asn Ala Ser Ser Leu Ser Leu Gly Arg Phe
            260                 265                 270
Asp Gln Tyr Met Leu Pro Phe Tyr Gln Thr Ser Leu Thr Gln Gly Glu
        275                 280                 285
Asp Ala Ala Phe Leu Lys Glu Leu Leu Glu Ser Leu Trp Val Lys Cys
    290                 295                 300
Asn Asp Ile Val Leu Leu Arg Ser Thr Ser Ser Ala Arg Tyr Phe Ala
305                 310                 315                 320
```

-continued

```
Gly Phe Pro Thr Gly Tyr Thr Ala Leu Leu Gly Leu Thr Glu Asn
            325                 330                 335

Gly Arg Ser Ala Val Asn Val Leu Ser Phe Leu Cys Leu Asp Ala Tyr
            340                 345                 350

Gln Ser Val Gln Leu Pro Gln Pro Asn Leu Gly Val Arg Thr Asn Ala
            355                 360                 365

Leu Ile Asp Thr Pro Phe Leu Met Lys Thr Ala Glu Thr Ile Arg Phe
            370                 375                 380

Gly Thr Gly Ile Pro Gln Ile Phe Asn Asp Glu Val Val Val Pro Ala
385                 390                 395                 400

Phe Leu Asn Arg Gly Val Ser Leu Glu Asp Ala Arg Asp Tyr Ser Val
            405                 410                 415

Val Gly Cys Val Glu Leu Ser Ile Pro Gly Arg Thr Tyr Gly Leu His
            420                 425                 430

Asp Ile Ala Met Phe Asn Leu Leu Lys Val Met Glu Ile Cys Leu His
            435                 440                 445

Glu Asn Glu Gly Asn Ala Ala Leu Thr Tyr Glu Gly Leu Leu Glu Gln
450                 455                 460

Ile Arg Ala Lys Ile Ser His Tyr Ile Thr Leu Met Val Glu Gly Ser
465                 470                 475                 480

Asn Ile Cys Asp Ile Gly His Arg Asp Trp Ala Pro Val Pro Leu Leu
            485                 490                 495

Ser Ser Phe Ile Ser Asp Cys Leu Glu Lys Gly Arg Asp Ile Thr Asp
            500                 505                 510

Gly Gly Ala Arg Tyr Asn Phe Ser Gly Val Gln Gly Ile Gly Ile Ala
            515                 520                 525

Asn Leu Ser Asp Ser Leu His Ala Leu Lys Gly Met Val Phe Glu Gln
            530                 535                 540

Gln Arg Leu Ser Phe Asp Glu Leu Leu Ser Val Leu Lys Ala Asn Phe
545                 550                 555                 560

Ala Thr Pro Glu Gly Glu Lys Val Arg Ala Arg Leu Ile Asn Arg Phe
            565                 570                 575

Glu Lys Tyr Gly Asn Asp Ile Asp Glu Val Asp Asn Ile Ser Ala Glu
            580                 585                 590

Leu Leu Arg His Tyr Cys Lys Glu Val Glu Lys Tyr Gln Asn Pro Arg
            595                 600                 605

Gly Gly Tyr Phe Thr Pro Gly Ser Tyr Thr Val Ser Ala His Val Pro
            610                 615                 620

Leu Gly Ser Val Val Gly Ala Thr Pro Asp Gly Arg Phe Ala Gly Glu
625                 630                 635                 640

Gln Leu Ala Asp Gly Gly Leu Ser Pro Met Leu Gly Gln Asp Ala Gln
            645                 650                 655

Gly Pro Thr Ala Val Leu Lys Ser Val Ser Lys Leu Asp Asn Thr Leu
            660                 665                 670

Leu Ser Asn Gly Thr Leu Leu Asn Val Lys Phe Thr Pro Ala Thr Leu
            675                 680                 685

Glu Gly Glu Ala Gly Leu Arg Lys Leu Ala Asp Phe Leu Arg Ala Phe
            690                 695                 700

Thr Gln Leu Lys Leu Gln His Ile Gln Phe Asn Val Val Asn Ala Asp
705                 710                 715                 720

Thr Leu Arg Glu Ala Gln Gln Arg Pro Gln Asp Tyr Ala Gly Leu Val
            725                 730                 735
```

```
Val Arg Val Ala Gly Tyr Ser Ala Phe Phe Val Glu Leu Ser Lys Glu
            740                 745                 750

Ile Gln Asp Asp Ile Ile Arg Arg Thr Ala His Gln Leu
            755                 760             765
```

<210> SEQ ID NO 25
<211> LENGTH: 740
<212> TYPE: PRT
<213> ORGANISM: Clostridium pasteurianum

<400> SEQUENCE: 25

```
Met Phe Lys Gln Trp Glu Gly Phe Gln Asp Gly Glu Trp Thr Asn Asp
1               5                   10                  15

Val Asn Val Arg Asp Phe Ile Gln Lys Asn Tyr Lys Glu Tyr Thr Gly
            20                  25                  30

Asp Lys Ser Phe Leu Lys Gly Pro Thr Glu Lys Thr Lys Lys Val Trp
        35                  40                  45

Asp Lys Ala Val Ser Leu Ile Leu Glu Glu Leu Lys Lys Gly Ile Leu
    50                  55                  60

Asp Val Asp Thr Glu Thr Ile Ser Gly Ile Asn Ser Phe Lys Pro Gly
65                  70                  75                  80

Tyr Leu Asp Lys Asp Asn Glu Val Ile Val Gly Phe Gln Thr Asp Ala
            85                  90                  95

Pro Leu Lys Arg Ile Thr Asn Pro Phe Gly Gly Ile Arg Met Ala Glu
            100                 105                 110

Gln Ser Leu Lys Glu Tyr Gly Phe Lys Ile Ser Asp Glu Met His Asn
        115                 120                 125

Ile Phe Thr Asn Tyr Arg Lys Thr His Asn Gln Gly Val Phe Asp Ala
    130                 135                 140

Tyr Ser Glu Glu Thr Arg Ile Ala Arg Ser Ala Gly Val Leu Thr Gly
145                 150                 155                 160

Leu Pro Asp Ala Tyr Gly Arg Gly Arg Ile Ile Gly Asp Tyr Arg Arg
            165                 170                 175

Val Ala Leu Tyr Gly Ile Asp Phe Leu Ile Gln Glu Lys Lys Lys Asp
            180                 185                 190

Leu Ser Asn Leu Lys Gly Asp Met Leu Asp Glu Leu Ile Arg Leu Arg
        195                 200                 205

Glu Glu Val Ser Glu Gln Ile Arg Ala Leu Asp Glu Ile Lys Lys Met
    210                 215                 220

Ala Leu Ser Tyr Gly Val Asp Ile Ser Arg Pro Ala Val Asn Ala Lys
225                 230                 235                 240

Glu Ala Ala Gln Phe Leu Tyr Phe Gly Tyr Leu Ala Gly Val Lys Glu
            245                 250                 255

Asn Asn Gly Ala Ala Met Ser Leu Gly Arg Thr Ser Thr Phe Leu Asp
            260                 265                 270

Ile Tyr Ile Glu Arg Asp Leu Glu Gln Gly Leu Ile Thr Glu Asp Glu
        275                 280                 285

Ala Gln Glu Val Ile Asp Gln Phe Ile Ile Lys Leu Arg Leu Val Arg
    290                 295                 300

His Leu Arg Thr Pro Glu Tyr Asn Glu Leu Phe Ala Gly Asp Pro Thr
305                 310                 315                 320

Trp Val Thr Glu Ser Ile Ala Gly Val Gly Ile Asp Gly Arg Ser Leu
            325                 330                 335

Val Thr Lys Asn Ser Phe Arg Tyr Leu His Thr Leu Ile Asn Leu Gly
            340                 345                 350
```

-continued

```
Ser Ala Pro Glu Pro Asn Met Thr Val Leu Trp Ser Glu Asn Leu Pro
        355                 360                 365
Glu Ser Phe Lys Lys Phe Cys Ala Glu Met Ser Ile Leu Thr Asp Ser
    370                 375                 380
Ile Gln Tyr Glu Asn Asp Asp Ile Met Arg Pro Ile Tyr Gly Asp Asp
385                 390                 395                 400
Tyr Ala Ile Ala Cys Cys Val Ser Ala Met Arg Val Gly Lys Asp Met
                405                 410                 415
Gln Phe Phe Gly Ala Arg Cys Asn Leu Ala Lys Cys Leu Leu Leu Ala
            420                 425                 430
Ile Asn Gly Gly Val Asp Glu Lys Lys Gly Ile Lys Val Val Pro Asp
        435                 440                 445
Ile Glu Pro Ile Thr Asp Glu Val Leu Asp Tyr Glu Lys Val Lys Glu
    450                 455                 460
Asn Tyr Phe Lys Val Leu Glu Tyr Met Ala Gly Leu Tyr Val Asn Thr
465                 470                 475                 480
Met Asn Ile Ile His Phe Met His Asp Lys Tyr Ala Tyr Glu Ala Ser
                485                 490                 495
Gln Met Ala Leu His Asp Thr Lys Val Gly Arg Leu Met Ala Phe Gly
            500                 505                 510
Ile Ala Gly Phe Ser Val Ala Ala Asp Ser Leu Ser Ala Ile Arg Tyr
        515                 520                 525
Ala Lys Val Lys Pro Ile Arg Glu Asn Gly Ile Thr Val Asp Phe Val
    530                 535                 540
Lys Glu Gly Asp Phe Pro Lys Tyr Gly Asn Asp Asp Arg Val Asp
545                 550                 555                 560
Ser Ile Ala Val Glu Ile Val Glu Lys Phe Ser Asp Glu Leu Lys Lys
                565                 570                 575
His Pro Thr Tyr Arg Asn Ala Lys His Thr Leu Ser Val Leu Thr Ile
            580                 585                 590
Thr Ser Asn Val Met Tyr Gly Lys Lys Thr Gly Thr Thr Pro Asp Gly
        595                 600                 605
Arg Lys Val Gly Glu Pro Leu Ala Pro Gly Ala Asn Pro Met His Gly
    610                 615                 620
Arg Asp Met Glu Gly Ala Leu Ala Ser Leu Asn Ser Val Ala Lys Val
625                 630                 635                 640
Pro Tyr Val Cys Cys Glu Asp Gly Val Ser Asn Thr Phe Ser Ile Val
                645                 650                 655
Pro Asp Ala Leu Gly Asn Asp His Asp Val Arg Ile Asn Asn Leu Val
            660                 665                 670
Ser Ile Met Gly Gly Tyr Phe Gly Gln Gly Ala His His Leu Asn Val
        675                 680                 685
Asn Val Leu Asn Arg Glu Thr Leu Ile Asp Ala Met Asn Asn Pro Asp
    690                 695                 700
Lys Tyr Pro Thr Leu Thr Ile Arg Val Ser Gly Tyr Ala Val Asn Phe
705                 710                 715                 720
Asn Arg Leu Ser Lys Asp His Gln Lys Glu Val Ile Ser Arg Thr Phe
                725                 730                 735
His Glu Lys Leu
            740

<210> SEQ ID NO 26
<211> LENGTH: 147
```

-continued

```
<212> TYPE: DNA
<213> ORGANISM: Escherichia coli
<220> FEATURE:
<221> NAME/KEY: CDS
<222> LOCATION: (1)..(147)

<400> SEQUENCE: 26 atg acc atg att acg cca agc ttg cat gca tcg gta ccg ggc ccc ccc      48
Met Thr Met Ile Thr Pro Ser Leu His Ala Ser Val Pro Gly Pro Pro
1               5                   10                  15 tcg agg tcg acg gta tcg ata agc ttg ata tcg aat tcc tgc agc ccg      96
Ser Arg Ser Thr Val Ser Ile Ser Leu Ile Ser Asn Ser Cys Ser Pro
                20                  25                  30 ggg gat cca cta gtt cta gag cgg ccg cca ccg cgg tgg agc tcg aat     144
Gly Asp Pro Leu Val Leu Glu Arg Pro Pro Pro Arg Trp Ser Ser Asn
            35                  40                  45 tca                                                                  147
Ser

<210> SEQ ID NO 27
<211> LENGTH: 49
<212> TYPE: PRT
<213> ORGANISM: Escherichia coli

<400> SEQUENCE: 27

Met Thr Met Ile Thr Pro Ser Leu His Ala Ser Val Pro Gly Pro Pro
1               5                   10                  15

Ser Arg Ser Thr Val Ser Ile Ser Leu Ile Ser Asn Ser Cys Ser Pro
                20                  25                  30

Gly Asp Pro Leu Val Leu Glu Arg Pro Pro Pro Arg Trp Ser Ser Asn
            35                  40                  45

Ser

<210> SEQ ID NO 28
<211> LENGTH: 864
<212> TYPE: PRT
<213> ORGANISM: Thauera aromatica

<400> SEQUENCE: 28

Met Asn Asp Ile Val Ser Ala Lys Val Leu Glu Tyr Lys Gly Lys Lys
1               5                   10                  15

Leu Asn Phe Thr Pro Glu Asp Pro Ala Glu Glu Thr Ile Pro Ala Asp
                20                  25                  30

Glu Leu His Glu His Leu Gln Lys Pro Ser Thr Ala Arg Thr Lys Arg
            35                  40                  45

Leu Lys Glu Arg Cys Arg Trp Lys His Ala Ser Ala Gly Glu Phe Ile
        50                  55                  60

Glu Lys Ser Val Thr Ala Gly Ile Glu Arg Met Arg Tyr Leu Thr Glu
65                  70                  75                  80

Ala His Lys Ala Ser Glu Gly Lys Pro Glu Ala Ile Arg Arg Ala Leu
                85                  90                  95

Gly Leu Ala Asn Val Leu Asn Lys Ser Thr Leu Val Leu Gln Glu Asp
            100                 105                 110

Glu Phe Ile Val Gly Tyr His Ala Glu Asp Pro Asn Met Phe Pro Leu
        115                 120                 125

Tyr Pro Glu Leu Ser His Met Ala Val Gln Asp Tyr Leu Arg Ser Asp
    130                 135                 140

Tyr Ser Pro Gln Pro Ala Asp Glu Ala Ala Ile Asn Glu Tyr Trp
145                 150                 155                 160
```

-continued

```
Lys Pro His Ser Leu Gln Ser Lys Cys Gln Pro Tyr Phe Asp Pro Ala
            165                 170                 175
Asp Leu Gly Arg Met Tyr Gln Val Ser Ser Met Glu Ala Pro Ser Phe
        180                 185                 190
Ala Ser Gly Tyr Asn Ser Ile Val Pro Pro Tyr Glu Thr Val Leu Glu
    195                 200                 205
Asp Gly Leu Leu Ala Arg Ile Lys Leu Ala Glu Lys His Ile Ala Glu
210                 215                 220
Ala Gln Ala Asp Met Ser Thr Phe Pro Trp Asn Gly Thr Lys Gly Leu
225                 230                 235                 240
Asp Asn Ile Ala Lys Ile Asp Asn Trp Lys Ala Met Val Ile Ala Cys
            245                 250                 255
Lys Ala Val Ile Ser Trp Ala Arg Arg Gln Gly Arg Leu Cys Lys Ile
            260                 265                 270
Val Ala Glu Asn Phe Glu Thr Asp Pro Lys Arg Gln Ala Glu Leu Leu
        275                 280                 285
Glu Ile Ala Asp Ile Cys Gln Arg Ile Pro Ala Glu Pro Cys Lys Gly
    290                 295                 300
Leu Lys Asp Ala Met Gln Ala Lys Phe Phe Thr Phe Leu Ile Cys His
305                 310                 315                 320
Ala Ile Glu Arg Tyr Ala Ser Gly Tyr Ala Gln Lys Glu Asp Thr Leu
            325                 330                 335
Leu Trp Pro Tyr Tyr Lys Ala Ser Val Val Asp Lys Lys Phe Gln Pro
            340                 345                 350
Met Ser His Met Asp Ala Val Glu Leu Val Glu Met Glu Arg Leu Lys
        355                 360                 365
Ile Ser Glu His Gly Ala Gly Lys Ser Arg Ala Tyr Arg Glu Ile Phe
    370                 375                 380
Pro Gly Ser Asn Asp Leu Phe Ile Leu Thr Val Gly Gly Thr Asn Ala
385                 390                 395                 400
Lys Gly Glu Asp Ala Cys Asn Asp Met Thr Asp Ala Ile Leu Glu Ala
            405                 410                 415
Ala Lys Arg Ile Arg Thr Ala Glu Pro Ser Ile Val Phe Arg Tyr Ser
            420                 425                 430
Lys Lys Asn Arg Glu Lys Thr Leu Arg Trp Val Phe Glu Cys Ile Arg
        435                 440                 445
Asp Gly Leu Gly Tyr Pro Ser Ile Lys His Asp Glu Ile Gly Thr Glu
    450                 455                 460
Gln Met Lys Glu Tyr Ala Lys Phe Ser Leu Asn Gly Asn Gly Ala Thr
465                 470                 475                 480
Asp Glu Glu Ala His Asn Trp Val Asn Val Leu Cys Met Ser Pro Gly
            485                 490                 495
Ile His Gly Arg Arg Lys Thr Gln Lys Thr Arg Ser Glu Gly Gly Gly
            500                 505                 510
Ser Ile Phe Pro Ala Lys Leu Leu Glu Ile Ser Leu Asn Asp Gly Tyr
        515                 520                 525
Asp Trp Ser Tyr Ala Asp Met Gln Leu Gly Pro Lys Thr Gly Asp Leu
    530                 535                 540
Ser Ser Leu Lys Ser Phe Glu Asp Val Trp Glu Ala Phe Arg Lys Gln
545                 550                 555                 560
Tyr Gln Tyr Ala Ile Asn Leu Cys Ile Ser Thr Lys Asp Val Ser Arg
            565                 570                 575
```

-continued

Tyr Phe Glu Gln Arg Phe Leu Gln Met Pro Phe Val Ser Ala Ile Asp
            580                 585                 590

Asp Gly Cys Met Glu Leu Gly Met Asp Ala Cys Ala Leu Ser Glu Gln
            595                 600                 605

Pro Asn Gly Trp His Asn Pro Ile Thr Thr Ile Val Ala Ala Asn Ser
    610                 615                 620

Leu Val Ala Ile Lys Lys Leu Val Phe Glu Glu Lys Lys Tyr Thr Leu
625                 630                 635                 640

Glu Gln Leu Ser Gln Ala Leu Lys Ala Asn Trp Glu Gly Phe Glu Glu
                645                 650                 655

Met Arg Val Asp Phe Lys Arg Ala Pro Lys Trp Gly Asn Asp Asp Asp
            660                 665                 670

Tyr Ala Asp Gly Ile Ile Thr Arg Phe Tyr Glu Glu Ile Ile Gly Gly
            675                 680                 685

Glu Met Arg Lys Ile Thr Asn Tyr Ser Gly Gly Pro Val Met Pro Thr
            690                 695                 700

Gly Gln Ala Val Gly Leu Tyr Met Glu Val Gly Ser Arg Thr Gly Pro
705                 710                 715                 720

Thr Pro Asp Gly Arg Phe Gly Gly Glu Ala Ala Asp Asp Gly Gly Ile
            725                 730                 735

Ser Pro Tyr Met Gly Thr Asp Lys Lys Gly Pro Thr Ala Val Leu Arg
            740                 745                 750

Ser Val Ser Lys Val Gln Lys Asn Gln Lys Gly Asn Leu Leu Asn Gln
            755                 760                 765

Arg Leu Ser Val Pro Ile Met Arg Ser Lys His Gly Phe Glu Ile Trp
    770                 775                 780

Asn Ser Tyr Met Lys Thr Trp His Asp Leu Asn Ile Asp His Val Gln
785                 790                 795                 800

Phe Asn Val Val Ser Thr Asp Glu Met Arg Ala Ala Gln Arg Glu Pro
                805                 810                 815

Glu Lys His His Asp Leu Ile Val Arg Val Ser Gly Tyr Ser Ala Arg
            820                 825                 830

Phe Val Asp Ile Pro Thr Tyr Gly Gln Asn Thr Ile Ile Ala Arg Gln
            835                 840                 845

Glu Gln Asp Phe Ser Ala Ser Asp Leu Glu Phe Leu Asn Val Glu Ile
            850                 855                 860

<210> SEQ ID NO 29
<211> LENGTH: 810
<212> TYPE: PRT
<213> ORGANISM: Escherichia coli

<400> SEQUENCE: 29

Met Thr Thr Leu Lys Leu Asp Thr Leu Ser Asp Arg Ile Lys Ala His
1               5                   10                  15

Lys Asn Ala Leu Val His Ile Val Lys Pro Pro Val Cys Thr Glu Arg
            20                  25                  30

Ala Gln His Tyr Thr Glu Met Tyr Gln Gln His Leu Asp Lys Pro Ile
        35                  40                  45

Pro Val Arg Arg Ala Leu Ala Leu Ala His His Leu Ala Asn Arg Thr
    50                  55                  60

Ile Trp Ile Lys His Asp Glu Leu Ile Ile Gly Asn Gln Ala Ser Glu
65                  70                  75                  80

Val Arg Ala Ala Pro Ile Phe Pro Glu Tyr Thr Val Ser Trp Ile Glu
                85                  90                  95

```
Lys Glu Ile Asp Asp Leu Ala Asp Arg Pro Gly Ala Gly Phe Ala Val
            100                 105                 110
Ser Glu Glu Asn Lys Arg Val Leu His Glu Val Cys Pro Trp Trp Arg
        115                 120                 125
Gly Gln Thr Val Gln Asp Arg Cys Tyr Gly Met Phe Thr Asp Glu Gln
    130                 135                 140
Lys Gly Leu Leu Ala Thr Gly Ile Ile Lys Ala Glu Gly Asn Met Thr
145                 150                 155                 160
Ser Gly Asp Ala His Leu Ala Val Asn Phe Pro Leu Leu Glu Lys
                165                 170                 175
Gly Leu Asp Gly Leu Arg Glu Glu Val Ala Glu Arg Arg Ser Arg Ile
            180                 185                 190
Asn Leu Thr Val Leu Glu Asp Leu His Gly Glu Gln Phe Leu Lys Ala
        195                 200                 205
Ile Asp Ile Val Leu Val Ala Val Ser Glu His Ile Glu Arg Phe Ala
    210                 215                 220
Ala Leu Ala Arg Glu Met Ala Ala Thr Glu Thr Arg Glu Ser Arg Arg
225                 230                 235                 240
Asp Glu Leu Leu Ala Met Ala Glu Asn Cys Asp Leu Ile Ala His Gln
                245                 250                 255
Pro Pro Gln Thr Phe Trp Gln Ala Leu Gln Leu Cys Tyr Phe Ile Gln
            260                 265                 270
Leu Ile Leu Gln Ile Glu Ser Asn Gly His Ser Val Ser Phe Gly Arg
        275                 280                 285
Met Asp Gln Tyr Leu Tyr Pro Tyr Tyr Arg Arg Asp Val Glu Leu Asn
    290                 295                 300
Gln Thr Leu Asp Arg Glu His Ala Ile Glu Met Leu His Ser Cys Trp
305                 310                 315                 320
Leu Lys Leu Leu Glu Val Asn Lys Ile Arg Ser Gly Ser His Ser Lys
                325                 330                 335
Ala Ser Ala Gly Ser Pro Leu Tyr Gln Asn Val Thr Ile Gly Gly Gln
            340                 345                 350
Asn Leu Val Asp Gly Gln Pro Met Asp Ala Val Asn Pro Leu Ser Tyr
        355                 360                 365
Ala Ile Leu Glu Ser Cys Gly Arg Leu Arg Ser Thr Gln Pro Asn Leu
    370                 375                 380
Ser Val Arg Tyr His Ala Gly Met Ser Asn Asp Phe Leu Asp Ala Cys
385                 390                 395                 400
Val Gln Val Ile Arg Cys Gly Phe Gly Met Pro Ala Phe Asn Asn Asp
            405                 410                 415
Glu Ile Val Ile Pro Glu Phe Ile Lys Leu Gly Ile Glu Pro Gln Asp
        420                 425                 430
Ala Tyr Asp Tyr Ala Ala Ile Gly Cys Ile Glu Thr Ala Val Gly Gly
    435                 440                 445
Lys Trp Gly Tyr Arg Cys Thr Gly Met Ser Phe Ile Asn Phe Ala Arg
450                 455                 460
Val Met Leu Ala Ala Leu Glu Gly Gly His Asp Ala Thr Ser Gly Lys
465                 470                 475                 480
Val Phe Leu Pro Gln Glu Lys Ala Leu Ser Ala Gly Asn Phe Asn Asn
            485                 490                 495
Phe Asp Glu Val Met Asp Ala Trp Asp Thr Gln Ile Arg Tyr Tyr Thr
        500                 505                 510
```

-continued

Arg Lys Ser Ile Glu Ile Glu Tyr Val Val Asp Thr Met Leu Glu Glu
            515                 520                 525

Asn Val His Asp Ile Leu Cys Ser Ala Leu Val Asp Asp Cys Ile Glu
        530                 535                 540

Arg Ala Lys Ser Ile Lys Gln Gly Ala Lys Tyr Asp Trp Val Ser
545                 550                 555                 560

Gly Leu Gln Val Gly Ile Ala Asn Leu Gly Asn Ser Leu Ala Ala Val
                565                 570                 575

Lys Lys Leu Val Phe Glu Gln Gly Ala Ile Gly Gln Gln Leu Ala
            580                 585                 590

Ala Ala Leu Ala Asp Asp Phe Asp Gly Leu Thr His Glu Gln Leu Arg
            595                 600                 605

Gln Arg Leu Ile Asn Gly Ala Pro Lys Tyr Gly Asn Asp Asp Thr
    610                 615                 620

Val Asp Thr Leu Leu Ala Arg Ala Tyr Gln Thr Tyr Ile Asp Glu Leu
625                 630                 635                 640

Lys Gln Tyr His Asn Pro Arg Tyr Gly Arg Gly Pro Val Gly Gly Asn
                645                 650                 655

Tyr Tyr Ala Gly Thr Ser Ser Ile Ser Ala Asn Val Pro Phe Gly Ala
                660                 665                 670

Gln Thr Met Ala Thr Pro Asp Gly Arg Lys Ala His Thr Pro Leu Ala
            675                 680                 685

Glu Gly Ala Ser Pro Ala Ser Gly Thr Asp His Leu Gly Pro Thr Ala
            690                 695                 700

Val Ile Gly Ser Val Gly Lys Leu Pro Thr Ala Ala Ile Leu Gly Gly
705                 710                 715                 720

Val Leu Leu Asn Gln Lys Leu Asn Pro Ala Thr Leu Glu Asn Glu Ser
                725                 730                 735

Asp Lys Gln Lys Leu Met Ile Leu Leu Arg Thr Phe Phe Glu Val His
            740                 745                 750

Lys Gly Trp His Ile Gln Tyr Asn Ile Val Ser Arg Glu Thr Leu Leu
            755                 760                 765

Asp Ala Lys Lys His Pro Asp Gln Tyr Arg Asp Leu Val Val Arg Val
        770                 775                 780

Ala Gly Tyr Ser Ala Phe Phe Thr Ala Leu Ser Pro Asp Ala Gln Asp
785                 790                 795                 800

Asp Ile Ile Ala Arg Thr Glu His Met Leu
                805                 810

<210> SEQ ID NO 30
<211> LENGTH: 765
<212> TYPE: PRT
<213> ORGANISM: Escherichia coli

<400> SEQUENCE: 30

Met Thr Asn Arg Ile Ser Arg Leu Lys Thr Ala Leu Phe Ala Asn Thr
1               5                   10                  15

Arg Glu Ile Ser Leu Glu Arg Ala Leu Leu Tyr Thr Ala Ser His Arg
                20                  25                  30

Gln Thr Glu Gly Glu Pro Val Ile Leu Arg Arg Ala Lys Ala Thr Ala
            35                  40                  45

Tyr Ile Leu Glu His Val Glu Ile Ser Ile Arg Asp Glu Glu Leu Ile
        50                  55                  60

Ala Gly Asn Arg Thr Val Lys Pro Arg Ala Gly Ile Met Ser Pro Glu
65                  70                  75                  80

```
Met Asp Pro Tyr Trp Leu Leu Lys Glu Leu Asp Gln Phe Pro Thr Arg
                85                  90                  95
Pro Gln Asp Arg Phe Ala Ile Ser Glu Asp Lys Arg Ile Tyr Arg
            100                 105                 110
Glu Glu Leu Phe Pro Tyr Trp Glu Lys Arg Ser Met Lys Asp Phe Ile
            115                 120                 125
Asn Gly Gln Met Thr Asp Glu Val Lys Ala Ala Thr Asn Thr Gln Ile
        130                 135                 140
Phe Ser Ile Asn Gln Thr Asp Lys Gly Gln Gly His Ile Ile Ile Asp
145                 150                 155                 160
Tyr Pro Arg Leu Leu Asn His Gly Leu Gly Glu Leu Val Ala Gln Met
                165                 170                 175
Gln Gln His Cys Gln Gln Gln Pro Glu Asn His Phe Tyr Gln Ala Ala
            180                 185                 190
Leu Leu Leu Leu Glu Ala Ser Gln Lys His Ile Leu Arg Tyr Ala Glu
            195                 200                 205
Leu Ala Glu Thr Met Ala Ala Asn Cys Thr Asp Ala Gln Arg Arg Glu
        210                 215                 220
Glu Leu Leu Thr Ile Ala Glu Ile Ser Arg His Asn Ala Gln His Lys
225                 230                 235                 240
Pro Gln Thr Phe Trp Gln Ala Cys Gln Leu Phe Trp Tyr Met Asn Ile
                245                 250                 255
Ile Leu Gln Tyr Glu Ser Asn Ala Ser Ser Leu Ser Leu Gly Arg Phe
            260                 265                 270
Asp Gln Tyr Met Leu Pro Phe Tyr Gln Thr Ser Leu Thr Gln Gly Glu
            275                 280                 285
Asp Ala Ala Phe Leu Lys Glu Leu Leu Glu Ser Leu Trp Val Lys Cys
        290                 295                 300
Asn Asp Ile Val Leu Leu Arg Ser Thr Ser Ser Ala Arg Tyr Phe Ala
305                 310                 315                 320
Gly Phe Pro Thr Gly Tyr Thr Ala Leu Leu Gly Gly Leu Thr Glu Asn
                325                 330                 335
Gly Arg Ser Ala Val Asn Val Leu Ser Phe Leu Cys Leu Asp Ala Tyr
            340                 345                 350
Gln Ser Val Gln Leu Pro Gln Pro Asn Leu Gly Val Arg Thr Asn Ala
            355                 360                 365
Leu Ile Asp Thr Pro Phe Leu Met Lys Thr Ala Glu Thr Ile Arg Phe
        370                 375                 380
Gly Thr Gly Ile Pro Gln Ile Phe Asn Asp Glu Val Val Pro Ala
385                 390                 395                 400
Phe Leu Asn Arg Gly Val Ser Leu Glu Asp Ala Arg Asp Tyr Ser Val
                405                 410                 415
Val Gly Cys Val Glu Leu Ser Ile Pro Gly Arg Thr Tyr Gly Leu His
            420                 425                 430
Asp Ile Ala Met Phe Asn Leu Leu Lys Val Met Glu Ile Cys Leu His
            435                 440                 445
Glu Asn Glu Gly Asn Ala Ala Leu Thr Tyr Glu Gly Leu Leu Glu Gln
        450                 455                 460
Ile Arg Ala Lys Ile Ser His Tyr Ile Thr Leu Met Val Glu Gly Ser
465                 470                 475                 480
Asn Ile Cys Asp Ile Gly His Arg Asp Trp Ala Pro Val Pro Leu Leu
                485                 490                 495
```

-continued

```
Ser Ser Phe Ile Ser Asp Cys Leu Glu Lys Gly Arg Asp Ile Thr Asp
            500                 505                 510

Gly Gly Ala Arg Tyr Asn Phe Ser Gly Val Gln Gly Ile Gly Ile Ala
            515                 520                 525

Asn Leu Ser Asp Ser Leu His Ala Leu Lys Gly Met Val Phe Glu Gln
            530                 535                 540

Gln Arg Leu Ser Phe Asp Glu Leu Leu Ser Val Leu Lys Ala Asn Phe
545                 550                 555                 560

Ala Thr Pro Glu Gly Glu Lys Val Arg Ala Arg Leu Ile Asn Arg Phe
            565                 570                 575

Glu Lys Tyr Gly Asn Asp Ile Asp Glu Val Asp Asn Ile Ser Ala Glu
            580                 585                 590

Leu Leu Arg His Tyr Cys Lys Glu Val Glu Lys Tyr Gln Asn Pro Arg
            595                 600                 605

Gly Gly Tyr Phe Thr Pro Gly Ser Tyr Thr Val Ser Ala His Val Pro
            610                 615                 620

Leu Gly Ser Val Val Gly Ala Thr Pro Asp Gly Arg Phe Ala Gly Glu
625                 630                 635                 640

Gln Leu Ala Asp Gly Gly Leu Ser Pro Met Leu Gly Gln Asp Ala Gln
            645                 650                 655

Gly Pro Thr Ala Val Leu Lys Ser Val Ser Lys Leu Asp Asn Thr Leu
            660                 665                 670

Leu Ser Asn Gly Thr Leu Leu Asn Val Lys Phe Thr Pro Ala Thr Leu
            675                 680                 685

Glu Gly Glu Ala Gly Leu Arg Lys Leu Ala Asp Phe Leu Arg Ala Phe
            690                 695                 700

Thr Gln Leu Lys Leu Gln His Ile Gln Phe Asn Val Val Asn Ala Asp
705                 710                 715                 720

Thr Leu Arg Glu Ala Gln Gln Arg Pro Gln Asp Tyr Ala Gly Leu Val
            725                 730                 735

Val Arg Val Ala Gly Tyr Ser Ala Phe Phe Val Glu Leu Ser Lys Glu
            740                 745                 750

Ile Gln Asp Asp Ile Ile Arg Arg Thr Ala His Gln Leu
            755                 760                 765

<210> SEQ ID NO 31
<211> LENGTH: 760
<212> TYPE: PRT
<213> ORGANISM: Escherichia coli

<400> SEQUENCE: 31

Met Ser Glu Leu Asn Glu Lys Leu Ala Thr Ala Trp Glu Gly Phe Thr
1               5                   10                  15

Lys Gly Asp Trp Gln Asn Glu Val Asn Val Arg Asp Phe Ile Gln Lys
            20                  25                  30

Asn Tyr Thr Pro Tyr Glu Gly Asp Glu Ser Phe Leu Ala Gly Ala Thr
            35                  40                  45

Glu Ala Thr Thr Thr Leu Trp Asp Lys Val Met Glu Gly Val Lys Leu
        50                  55                  60

Glu Asn Arg Thr His Ala Pro Val Asp Phe Asp Thr Ala Val Ala Ser
65                  70                  75                  80

Thr Ile Thr Ser His Asp Ala Gly Tyr Ile Asn Lys Gln Leu Glu Lys
                85                  90                  95

Ile Val Gly Leu Gln Thr Glu Ala Pro Leu Lys Arg Ala Leu Ile Pro
            100                 105                 110
```

```
Phe Gly Gly Ile Lys Met Ile Glu Gly Ser Cys Lys Ala Tyr Asn Arg
            115                 120                 125
Glu Leu Asp Pro Met Ile Lys Lys Ile Phe Thr Glu Tyr Arg Lys Thr
    130                 135                 140
His Asn Gln Gly Val Phe Asp Val Tyr Thr Pro Asp Ile Leu Arg Cys
145                 150                 155                 160
Arg Lys Ser Gly Val Leu Thr Gly Leu Pro Asp Ala Tyr Gly Arg Gly
                165                 170                 175
Arg Ile Ile Gly Asp Tyr Arg Arg Val Ala Leu Tyr Gly Ile Asp Tyr
            180                 185                 190
Leu Met Lys Asp Lys Leu Ala Gln Phe Thr Ser Leu Gln Ala Asp Leu
        195                 200                 205
Glu Asn Gly Val Asn Leu Glu Gln Thr Ile Arg Leu Arg Glu Glu Ile
    210                 215                 220
Ala Glu Gln His Arg Ala Leu Gly Gln Met Lys Glu Met Ala Ala Lys
225                 230                 235                 240
Tyr Gly Tyr Asp Ile Ser Gly Pro Ala Thr Asn Ala Gln Glu Ala Ile
                245                 250                 255
Gln Trp Thr Tyr Phe Gly Tyr Leu Ala Ala Val Lys Ser Gln Asn Gly
            260                 265                 270
Ala Ala Met Ser Phe Gly Arg Thr Ser Thr Phe Leu Asp Val Tyr Ile
        275                 280                 285
Glu Arg Asp Leu Lys Ala Gly Lys Ile Thr Glu Gln Glu Ala Gln Glu
    290                 295                 300
Met Val Asp His Leu Val Met Lys Leu Arg Met Val Arg Phe Leu Arg
305                 310                 315                 320
Thr Pro Glu Tyr Asp Glu Leu Phe Ser Gly Asp Pro Ile Trp Ala Thr
                325                 330                 335
Glu Ser Ile Gly Gly Met Gly Leu Asp Gly Arg Thr Leu Val Thr Lys
            340                 345                 350
Asn Ser Phe Arg Phe Leu Asn Thr Leu Tyr Thr Met Gly Pro Ser Pro
        355                 360                 365
Glu Pro Asn Met Thr Ile Leu Trp Ser Glu Lys Leu Pro Leu Asn Phe
    370                 375                 380
Lys Lys Phe Ala Ala Lys Val Ser Ile Asp Thr Ser Ser Leu Gln Tyr
385                 390                 395                 400
Glu Asn Asp Asp Leu Met Arg Pro Asp Phe Asn Asn Asp Asp Tyr Ala
                405                 410                 415
Ile Ala Cys Cys Val Ser Pro Met Ile Val Gly Lys Gln Met Gln Phe
            420                 425                 430
Phe Gly Ala Arg Ala Asn Leu Ala Lys Thr Met Leu Tyr Ala Ile Asn
        435                 440                 445
Gly Gly Val Asp Glu Lys Leu Lys Met Gln Val Gly Pro Lys Ser Glu
    450                 455                 460
Pro Ile Lys Gly Asp Val Leu Asn Tyr Asp Glu Val Met Glu Arg Met
465                 470                 475                 480
Asp His Phe Met Asp Trp Leu Ala Lys Gln Tyr Ile Thr Ala Leu Asn
                485                 490                 495
Ile Ile His Tyr Met His Asp Lys Tyr Ser Tyr Glu Ala Ser Leu Met
            500                 505                 510
Ala Leu His Asp Arg Asp Val Ile Arg Thr Met Ala Cys Gly Ile Ala
        515                 520                 525
```

Gly Leu Ser Val Ala Ala Asp Ser Leu Ser Ala Ile Lys Tyr Ala Lys
          530                 535                 540

Val Lys Pro Ile Arg Asp Glu Asp Gly Leu Ala Ile Asp Phe Glu Ile
545                 550                 555                 560

Glu Gly Glu Tyr Pro Gln Phe Gly Asn Asn Asp Pro Arg Val Asp Asp
                565                 570                 575

Leu Ala Val Asp Leu Val Glu Arg Phe Met Lys Ile Gln Lys Leu
            580                 585                 590

His Thr Tyr Arg Asp Ala Ile Pro Thr Gln Ser Val Leu Thr Ile Thr
        595                 600                 605

Ser Asn Val Val Tyr Gly Lys Lys Thr Gly Asn Thr Pro Asp Gly Arg
        610                 615                 620

Arg Ala Gly Ala Pro Phe Gly Pro Gly Ala Asn Pro Met His Gly Arg
625                 630                 635                 640

Asp Gln Lys Gly Ala Val Ala Ser Leu Thr Ser Val Ala Lys Leu Pro
                645                 650                 655

Phe Ala Tyr Ala Lys Asp Gly Ile Ser Tyr Thr Phe Ser Ile Val Pro
                660                 665                 670

Asn Ala Leu Gly Lys Asp Asp Glu Val Arg Lys Thr Asn Leu Ala Gly
            675                 680                 685

Leu Met Asp Gly Tyr Phe His His Glu Ala Ser Ile Glu Gly Gly Gln
    690                 695                 700

His Leu Asn Val Asn Val Met Asn Arg Glu Met Leu Leu Asp Ala Met
705                 710                 715                 720

Glu Asn Pro Glu Lys Tyr Pro Gln Leu Thr Ile Arg Val Ser Gly Tyr
                725                 730                 735

Ala Val Arg Phe Asn Ser Leu Thr Lys Glu Gln Gln Gln Asp Val Ile
            740                 745                 750

Thr Arg Thr Phe Thr Gln Ser Met
        755                 760

<210> SEQ ID NO 32
<211> LENGTH: 4928
<212> TYPE: DNA
<213> ORGANISM: Thauera aromatica

<400> SEQUENCE: 32
tttatttgca tattttagct gagccgcggt gacaaacgaa tacatgaggg aaatcaccac      60
accgactggt gatcgcactt attgacgccg ccagcagggc ggaagttcaa tgaaccctta     120
caagattcac ttctatggtc gtggtggatc ggcctccgcc gccggatttg ggcggaggcg     180
taatcgttcg aaatgaatgc tcgcacacgc agccgattga taccggacgg atgacgtttc     240
caacatgcga ttctggggct gacgtgaaaa ttccattagt caccgaaata cagcgtttta     300
gcctgcaaga cggtcctgga ttccggacga cggtgttctt gaagggttgc ccattgagat     360
gtccgtggtg ccacaaccct gaaacccaaa aggtgggcaa ggaatactat tacaaccgtg     420
atcgttgcgt gagctgcgga cggtgtgcaa cggtctgccc aaccggtgca tcgcagcttc     480
ttgatggacc gggcgcaagc caggtgctta agctcgaccg cagcaagtgc atcaattgca     540
tgcgctgcgt cgccgtatgc ctcaccggta gccgcgactc tgtcgggatg gaaatgacac     600
tcgacgagat tttgcgcgag gtcttgtccg atgagccttt ctaccgcaat agcgggggcg     660
gagtgacgat cagcggaggc gatcctctct tccaccctgc attcacattg gaactagcgc     720
gcaagatcaa ggaacgcggc gtccatgtcg cgatcgagac ttcctgcttc ccaaaaaaat     780

-continued

```
gggcgactat ccagccgcta cttaaactcg tcgatctttt catcgtcgac ctgaaatcgc    840
tgaatcggaa aaagcatgag gaaactgttg gctggccact gcaacccata ctcgacaata    900
tcgagcatct catacaagcc aaggccaata tccgcataca cattcctgta atccctggat    960
tcaacgactc accaatggat ttcgaggatt acatcgctta cttgggtcgc catgccgcgc   1020
agctggatgg cgtagacatt ctaaattatc acgtctatgg agaaggcaag taccgctcct   1080
tgggccggga aaatgaatac cagtattttg gcgtggaaga gaacccaccc gaaaaggtag   1140
tgccactcgc gaaaggtttg aaactcgccg gcatacgagc cgtaacgatc ggcgggttgg   1200
tcgggatcac agcggacaga cacaagagta gtcgcgacgc tgggactggg tgtattgcat   1260
aaatcaaagg agactcatcc atgggaacca ccacatgcaa gcagtgcgca aacttctttc   1320
ccgtccctaa agacgcggat gactacgaag ccggtaaggc agactgcgtg cgggaaaagg   1380
aagacgaaaa gggtaaatac tggctctcca agcccatatt cgagaacagc gcgcaatgtg   1440
aagcctttca acgaagcgc taaaactaca gatcaaggag accgccatga acgacatcgt   1500
aagcgccaag gttctggaat ataaaggaaa gaagctcaat ttcacgccgg aagatccggc   1560
tgaagagaca attccggccg acgagttgca cgagcatctg caaaagcctt cgacggcgag   1620
gaccaagcgc ctgaaggagc gttgccgctg gaaacacgca tctgccggcg aattcattga   1680
aaagagcgtc acgccggca tcgagcgcat gcgctatctg accgaagcac acaaggccag   1740
cgaaggcaaa cccgaagcca tccgtcgcgc gctgggcctg cgaacgtcc tgaacaagtc   1800
gaccctggtg ctccaggagg acgaattcat cgtcggctac cacgccgaag atcccaacat   1860
gttcccgctg tatccgaac tgtcccacat ggccgtgcag gactacctgc ggagcgacta   1920
ctcgccgcag ccgccgacg aggcggcggc gatcaatgaa tactggaagc cgcatagcct   1980
gcagagcaag tgtcagccct atttcgatcc ggcagacctc ggccgcatgt atcaggtcag   2040
cagcatggag gcgccgtcct tcgcttccgg ttacaacagc atcgtgccgc cctacgaaac   2100
cgtcctggaa gacgggctgc tggcgcgcat caagctcgcc gaaaagcata tcgccgaagc   2160
ccaggccgac atgtcgacct tccctggaa cggcacgaag gtctcgaca acatcgccaa   2220
gatcgacaac tggaaggcga tggtcatcgc ctgcaaggcg gtgatcagct gggcgcgccg   2280
gcagggccgg ctgtgcaaga tcgtcgcgga aaacttcgag accgatccga agcgccaggc   2340
cgagctgctc gaaatcgccg acatctgtca gcgcattccc ccgagccct gcaagggcct   2400
caaggacgcg atgcaggcga aattctttac cttcctgatc tgtcacgcga tcgagcgcta   2460
cgcgagcggc tacgcccaga aggaagacac cctgctgtgg ccgtactaca aggcctccgt   2520
cgtcgacaag aaattccagc cgatgagcca catggatgcg gtggaactcg tcgagatgga   2580
acgtttgaag atttccgagc atggcgccgg caagtcgcgc gcctaccgcg aaatcttccc   2640
ggggtcgaac gatctgttca tcctcaccgt cggcggcacc aacgccaagg gcgaggacgc   2700
ctgcaacgac atgaccgacg ccatcctcga ggcagccaag cggatccgca cggccgagcc   2760
ctccatcgtc ttccgctatt ccaagaagaa ccgcgagaag acgctgcgct gggttttcga   2820
gtgcatccgc gacggactcg gctatccgtc gatcaagcac gacgagatcg gcacggagca   2880
gatgaaggaa tacgccaagt tcagcctcaa cggcaacggc gccaccgacg aggaagccca   2940
caactgggtc aacgtgctgt gcatgtcgcc cggcatccac ggtcgccgca agacgcaaaa   3000
aacccgttcg gaaggtggcg gctcaatctt cccggccaag ctgctggaaa tctcgctcaa   3060
tgacggctac gactggtcgt acgccgacat gcaactcggc ccgaagaccg gtgatctctc   3120
gtcgctgaag tccttcgagg atgtttggga ggctttccgc aagcagtatc aatatgcgat   3180
```

-continued

```
caacctctgt atcagcacca aggacgtgtc gcgctacttc gagcagcgct tcctgcagat    3240
gcctttcgtg tccgcaatcg acgacggctg catggaactc gggatggacg cctgcgccct    3300
gtccgagcag cccaatggct ggcacaaccc gatcacgacg atcgtcgcgg cgaactcccc    3360
cgtggccatc aagaaactgg tattcgagga agaaaatac accctcgagc aactcagcca    3420
agcgttgaag gcgaactggg aaggtttcga ggaaatgcgc gtcgacttca gcgggcgcc    3480
gaagtggggc aacgacgatg attacgccga cggtatcatc acccgcttct acgaggaaat    3540
catcggcggc gaaatgcgca agatcaccaa ctactctggt ggtccggtca tgccgactgg    3600
tcaggctgtc ggcctgtaca tggaagtcgg ttcgcgcacg ggcccacgc cggacgggcg    3660
cttcgggggt gaagcggcag acgacggcgg catttctccc tacatgggaa ccgacaagaa    3720
ggggccgacg gcggtgttgc gctcggtgtc caaggtgcag aagaaccaga agggcaacct    3780
gctgaaccag cgcttgtcgg tgccgatcat gcgctccaag catggcttcg aaatctggaa    3840
ctcgtacatg aagacttggc acgatctgaa tatcgatcat gttcagttca atgtcgtcag    3900
cacggatgaa atgcgcgctg cgcagcgcga acccgagaag caccatgatc ttatcgtgcg    3960
cgtttccggc tacagcgctc ggttcgtaga cattccgacc tatgggcaga acaccatcat    4020
cgcccgtcag gaacaggatt tcagcgcatc cgatctcgag ttcctaaacg tcgaaatcta    4080
ggacaagcca ctcaaggggg gcagcatccc gtcccccttt accttacggt tgcacgaaaa    4140
aacatggagg gcagcaacat ggaaacagga cagaatttgc aaaaccagcc gcataccgag    4200
gtgggtacgg cgaggccgtg ccggagttgc aaatggcaaa cccccgaccc caccgatccg    4260
caccgtgggc aatgcaccgc caaccggcac gccatgggtg gcgtctggaa acgctggctt    4320
agggacgttg aaaacacgac ctgctccagg cacgaggaag gcaaactaag tttccgcgac    4380
cacgtctgaa caccggacag acgtggttca cctccagacc actgtagtga tagatcatga    4440
aaacctactc cagcgcaaat ggcctgttcg tcccggaagt cgatccctac tactatgtaa    4500
gtacggaaaa ccagagcttc ctcgataaat ttgcaaagat atcgaaaaag catcccgtca    4560
atgtactggt ggtcggcaaa caaggctgcg gcaagtcttc cctagtgcgg caatacgccg    4620
ccgtcaacag gctaccttg gcgaccttcc agatcggcat cctgtcggag ccggggcaac    4680
tgtttggtga atacgcgctg gagaacgggg agacccgtta caagcagttc ctcttccccc    4740
aggccatcca gacacccaat tgcgtcatcc accttgaaga gatcaatcgc cccgagcatc    4800
cgaaggcgtt gaacatgttg ttctccattc tctccgatga ccgtcaggta tggatggacg    4860
agctcggact gctgcaagta gcgcccggag tcgttttctt cgcaacgctc aacgaagggt    4920
ccgaattc                                                              4928
```

<210> SEQ ID NO 33
<211> LENGTH: 375
<212> TYPE: PRT
<213> ORGANISM: Thauera aromatica

<400> SEQUENCE: 33

```
Met Val Val Val Asp Arg Pro Pro Pro Asp Leu Gly Gly Gly Val
1               5                  10                 15

Ile Val Arg Asn Glu Cys Ser His Ser Glu Pro Ile Asp Thr Gly Arg
                20                  25                  30

Met Thr Phe Pro Thr Cys Asp Ser Gly Ala Asp Val Lys Ile Pro Leu
        35                  40                  45

Val Thr Glu Ile Gln Arg Phe Ser Leu Gln Asp Gly Pro Gly Phe Arg
```

```
                    50                  55                  60
Thr Thr Val Phe Leu Lys Gly Cys Pro Leu Arg Cys Pro Trp Cys His
65                  70                  75                  80

Asn Pro Glu Thr Gln Lys Val Gly Lys Glu Tyr Tyr Tyr Asn Arg Asp
                    85                  90                  95

Arg Cys Val Ser Cys Gly Arg Cys Ala Thr Val Cys Pro Thr Gly Ala
                    100                 105                 110

Ser Gln Leu Leu Asp Gly Pro Gly Ala Ser Gln Val Leu Lys Leu Asp
                    115                 120                 125

Arg Ser Lys Cys Ile Asn Cys Met Arg Cys Val Ala Val Cys Leu Thr
130                 135                 140

Gly Ser Arg Asp Ser Val Gly Met Glu Met Thr Leu Asp Glu Ile Leu
145                 150                 155                 160

Arg Glu Val Leu Ser Asp Glu Pro Phe Tyr Arg Asn Ser Gly Gly Gly
                    165                 170                 175

Val Thr Ile Ser Gly Gly Asp Pro Leu Phe His Pro Ala Phe Thr Leu
                    180                 185                 190

Glu Leu Ala Arg Lys Ile Lys Glu Arg Gly Val His Val Ala Ile Glu
                    195                 200                 205

Thr Ser Cys Phe Pro Lys Lys Trp Ala Thr Ile Gln Pro Leu Leu Lys
210                 215                 220

Leu Val Asp Leu Phe Ile Val Asp Leu Lys Ser Leu Asn Arg Lys Lys
225                 230                 235                 240

His Glu Glu Thr Val Gly Trp Pro Leu Gln Pro Ile Leu Asp Asn Ile
                    245                 250                 255

Glu His Leu Ile Gln Ala Lys Ala Asn Ile Arg Ile His Ile Pro Val
                    260                 265                 270

Ile Pro Gly Phe Asn Asp Ser Pro Met Asp Phe Glu Asp Tyr Ile Ala
                    275                 280                 285

Tyr Leu Gly Arg His Ala Ala Gln Leu Asp Gly Val Asp Ile Leu Asn
                    290                 295                 300

Tyr His Val Tyr Gly Glu Gly Lys Tyr Arg Ser Leu Gly Arg Glu Asn
305                 310                 315                 320

Glu Tyr Gln Tyr Phe Gly Val Glu Glu Asn Pro Pro Glu Lys Val Val
                    325                 330                 335

Pro Leu Ala Lys Gly Leu Lys Leu Ala Gly Ile Thr Ser Val Thr Ile
                    340                 345                 350

Gly Gly Leu Val Gly Ile Thr Ala Asp Arg His Lys Ser Ser Arg Asp
                    355                 360                 365

Ala Gly Thr Gly Cys Ile Ala
                    370                 375

<210> SEQ ID NO 34
<211> LENGTH: 308
<212> TYPE: PRT
<213> ORGANISM: Escherichia coli

<400> SEQUENCE: 34

Met Leu Glu Arg Asn Arg Glu Ala Thr Met Ile Phe Asn Ile Gln Arg
1                   5                   10                  15

Tyr Ser Thr His Asp Gly Pro Gly Ile Arg Thr Val Val Phe Leu Lys
                    20                  25                  30

Gly Cys Ser Leu Gly Cys Arg Trp Cys Gln Asn Pro Glu Ser Arg Ala
                    35                  40                  45
```

-continued

```
Arg Thr Gln Asp Leu Leu Tyr Asp Ala Arg Leu Cys Leu Glu Gly Cys
     50                  55                  60

Glu Leu Cys Ala Lys Ala Pro Glu Val Ile Glu Arg Ala Leu Asn
 65                  70                  75                  80

Gly Leu Leu Ile His Arg Glu Lys Leu Thr Pro Glu His Leu Thr Ala
                 85                  90                  95

Leu Thr Asp Cys Cys Pro Thr Gln Ala Leu Thr Val Cys Gly Glu Val
            100                 105                 110

Lys Ser Val Glu Glu Ile Met Thr Thr Val Leu Arg Asp Lys Pro Phe
        115                 120                 125

Tyr Asp Arg Ser Gly Gly Leu Thr Leu Ser Gly Gly Glu Pro Phe
    130                 135                 140

Met Gln Pro Glu Met Ala Met Ala Leu Leu Gln Ala Ser His Glu Ala
145                 150                 155                 160

Gly Ile His Thr Ala Val Glu Thr Cys Leu His Val Pro Trp Lys Tyr
                165                 170                 175

Ile Ala Pro Ser Leu Pro Tyr Ile Asp Leu Phe Leu Ala Asp Leu Lys
            180                 185                 190

His Val Ala Asp Ala Pro Phe Lys Gln Trp Thr Asp Gly Asn Ala Ala
        195                 200                 205

Arg Val Leu Asp Asn Leu Lys Lys Leu Ala Ala Gly Lys Lys Ile
    210                 215                 220

Ile Ile Arg Val Pro Leu Ile Gln Gly Phe Asn Ala Asp Glu Thr Ser
225                 230                 235                 240

Val Lys Ala Ile Thr Asp Phe Ala Ala Asp Glu Leu His Val Gly Glu
                245                 250                 255

Ile His Phe Leu Pro Tyr His Thr Leu Gly Ile Asn Lys Tyr His Leu
            260                 265                 270

Leu Asn Leu Pro Tyr Asp Ala Pro Glu Lys Pro Leu Asp Ala Pro Glu
        275                 280                 285

Leu Leu Asp Phe Ala Gln Gln Tyr Ala Cys Gln Lys Gly Leu Thr Ala
    290                 295                 300

Thr Leu Arg Gly
305
```

<210> SEQ ID NO 35
<211> LENGTH: 292
<212> TYPE: PRT
<213> ORGANISM: Escherichia coli

<400> SEQUENCE: 35

```
Met Thr Ser Ser Ala Gly Gln Arg Ile Ser Cys Asn Val Glu Thr
 1                   5                  10                  15

Arg Arg Asp Asp Val Ala Arg Ile Phe Asn Ile Gln Arg Tyr Ser Leu
                 20                  25                  30

Asn Asp Gly Glu Gly Ile Arg Thr Val Val Phe Phe Lys Gly Cys Pro
            35                  40                  45

His Leu Cys Pro Trp Cys Ala Asn Pro Glu Ser Ile Ser Gly Lys Ile
        50                  55                  60

Gln Thr Val Arg Arg Glu Ala Lys Cys Leu His Cys Ala Lys Cys Leu
 65                  70                  75                  80

Arg Asp Ala Asp Glu Cys Pro Ser Gly Ala Phe Glu Arg Ile Gly Arg
                 85                  90                  95

Asp Ile Ser Leu Asp Ala Leu Glu Arg Glu Val Met Lys Asp Asp Ile
            100                 105                 110
```

```
Phe Phe Arg Thr Ser Gly Gly Val Thr Leu Ser Gly Gly Glu Val
        115                 120                 125

Leu Met Gln Ala Glu Phe Ala Thr Arg Phe Leu Gln Arg Leu Arg Leu
    130                 135                 140

Trp Gly Val Ser Cys Ala Ile Glu Thr Ala Gly Asp Ala Pro Ala Ser
145                 150                 155                 160

Lys Leu Leu Pro Leu Ala Lys Leu Cys Asp Glu Val Leu Phe Asp Leu
                165                 170                 175

Lys Ile Met Asp Ala Thr Gln Ala Arg Asp Val Val Lys Met Asn Leu
            180                 185                 190

Pro Arg Val Leu Glu Asn Leu Arg Leu Leu Val Ser Glu Gly Val Asn
        195                 200                 205

Val Ile Pro Arg Leu Pro Leu Ile Pro Gly Phe Thr Leu Ser Arg Glu
    210                 215                 220

Asn Met Gln Gln Ala Leu Asp Val Leu Ile Pro Leu Asn Ile Arg Gln
225                 230                 235                 240

Ile His Leu Leu Pro Phe His Gln Tyr Gly Glu Pro Lys Tyr Arg Leu
                245                 250                 255

Leu Gly Lys Thr Trp Ser Met Lys Glu Val Pro Ala Pro Ser Ser Ala
            260                 265                 270

Asp Val Ala Thr Met Arg Glu Met Ala Glu Arg Ala Gly Leu Gln Val
        275                 280                 285

Thr Val Gly Gly
        290

<210> SEQ ID NO 36
<211> LENGTH: 246
<212> TYPE: PRT
<213> ORGANISM: Escherichia coli

<400> SEQUENCE: 36

Met Ser Val Ile Gly Arg Ile His Ser Phe Glu Ser Cys Gly Thr Val
1               5                   10                  15

Asp Gly Pro Gly Ile Arg Phe Ile Thr Phe Phe Gln Gly Cys Leu Met
            20                  25                  30

Arg Cys Leu Tyr Cys His Asn Arg Asp Thr Trp Asp Thr His Gly Gly
        35                  40                  45

Lys Glu Val Thr Val Glu Asp Leu Met Lys Glu Val Val Thr Tyr Arg
    50                  55                  60

His Phe Met Asn Ala Ser Gly Gly Val Thr Ala Ser Gly Gly Glu
65                  70                  75                  80

Ala Ile Leu Gln Ala Glu Phe Val Arg Asp Trp Phe Arg Ala Cys Lys
                85                  90                  95

Lys Glu Gly Ile His Thr Cys Leu Asp Thr Asn Gly Phe Val Arg Arg
            100                 105                 110

Tyr Asp Pro Val Ile Asp Glu Leu Leu Glu Val Thr Asp Leu Val Met
        115                 120                 125

Leu Asp Leu Lys Gln Met Asn Asp Glu Ile His Gln Asn Leu Val Gly
    130                 135                 140

Val Ser Asn His Arg Thr Leu Glu Phe Ala Lys Tyr Leu Ala Asn Lys
145                 150                 155                 160

Asn Val Lys Val Trp Ile Arg Tyr Val Val Pro Gly Trp Ser Asp
                165                 170                 175

Asp Asp Asp Ser Ala His Arg Leu Gly Glu Phe Thr Arg Asp Met Gly
```

```
                    180              185              190
Asn Val Glu Lys Ile Glu Leu Leu Pro Tyr His Glu Leu Gly Lys His
                195              200              205
Lys Trp Val Ala Met Gly Glu Glu Tyr Lys Leu Asp Gly Val Lys Pro
    210              215              220
Pro Lys Lys Glu Thr Met Glu Arg Val Lys Gly Ile Leu Glu Gln Tyr
225              230              235              240
Gly His Lys Val Met Phe
                245

<210> SEQ ID NO 37
<211> LENGTH: 270
<212> TYPE: PRT
<213> ORGANISM: Paracoccus halodenitrificans

<400> SEQUENCE: 37

Met Thr Leu Ser Thr Val Ala Ala Gln Ser Ala Asp Gln Glu Ile Pro
1               5                  10                  15
Tyr Tyr Asp Ser Val Gly Asn Glu Cys Ala Met Phe Glu His Ala Tyr
                20                  25                  30
Ala Gln Arg Leu Pro Leu Leu Leu Lys Gly Pro Thr Gly Cys Gly Lys
            35                  40                  45
Thr Arg Phe Val Ser His Met Ala Ala Lys Leu Gly Lys Pro Leu Phe
    50                  55                  60
Thr Val Ser Cys His Asp Asp Leu Thr Ala Ala Asp Leu Thr Gly Arg
65                  70                  75                  80
Tyr Leu Leu Gln Gly Gly Glu Thr Arg Trp Val Asp Gly Pro Leu Thr
                85                  90                  95
Arg Ala Val Arg Glu Gly Gly Ile Cys Tyr Leu Asp Glu Val Val Glu
                100                 105                 110
Ala Arg Lys Asp Val Thr Val Leu His Pro Leu Thr Asp Asp Arg
            115                 120                 125
Arg Leu Leu Pro Leu Glu Arg Thr Gly Glu Leu Leu Glu Ala Pro Asp
    130                 135                 140
Asp Phe Met Leu Val Ala Ser Tyr Asn Pro Gly Tyr Gln His Ile Leu
145                 150                 155                 160
Lys Ser Leu Lys Pro Ser Thr Arg Gln Arg Phe Val Ala Met Thr Phe
                165                 170                 175
Asp Phe Pro Pro Pro Lys Val Glu Arg Asp Ile Val Ala Arg Glu Ser
                180                 185                 190
Gly Leu Glu Ser Glu Arg Cys Ala Ala Leu Val Asn Leu Ala Ala Ser
            195                 200                 205
Leu Arg Ala Met Lys Gly Gln Asp Leu Glu Glu Gly Ile Ser Thr Arg
    210                 215                 220
Leu Leu Val Tyr Cys Ala Thr Leu Ile Gln Ala Gly Met Pro Ile Arg
225                 230                 235                 240
Asp Ala Ala Arg Ala Thr Leu Val Glu Pro Leu Ser Asp Asp Ala Asp
                245                 250                 255
Val Gln Glu Gly Leu Met Glu Ala Val Gln Ala Thr Phe Gly
            260                 265                 270

<210> SEQ ID NO 38
<211> LENGTH: 270
<212> TYPE: PRT
<213> ORGANISM: Paracoccus denitrificans
```

-continued

```
<400> SEQUENCE: 38

Met Asn Ala His Val Lys Thr Gln Gly Asn Gly Ala Val Asp Ala Pro
1               5                   10                  15

Leu Leu Pro Ala Ala Gly Asp Glu Val Ala Val Phe Glu Ala Ala Ala
            20                  25                  30

Ala Asn Asp Leu Pro Val Leu Leu Lys Gly Pro Thr Gly Cys Gly Lys
        35                  40                  45

Thr Arg Phe Val Ala His Met Ala Ala Arg Leu Gly Arg Pro Leu Tyr
    50                  55                  60

Thr Val Ala Cys His Asp Asp Leu Ser Ala Ala Asp Leu Ile Gly Arg
65                  70                  75                  80

Tyr Leu Lys Gly Gly Glu Thr Val Trp Thr Asp Gly Pro Leu Thr
                85                  90                  95

Arg Ala Val Arg Glu Gly Ala Ile Cys Tyr Leu Asp Glu Val Val Glu
            100                 105                 110

Ala Arg Lys Asp Val Thr Val Val Leu His Pro Leu Thr Asp Asp Arg
        115                 120                 125

Arg Ile Leu Pro Ile Asp Arg Thr Gly Glu Glu Ile Glu Ala Ala Pro
    130                 135                 140

Gly Phe Met Leu Val Ala Ser Tyr Asn Pro Gly Tyr Gln Asn Ile Leu
145                 150                 155                 160

Lys Thr Leu Lys Pro Ser Thr Arg Gln Arg Phe Val Ala Met Glu Phe
                165                 170                 175

Asp Phe Pro Glu Pro Ala Arg Glu Val Glu Ile Val Ala Arg Glu Ser
            180                 185                 190

Gly Leu Asp Arg Asp Arg Thr Leu Gly Leu Val Arg Leu Ala Gly Lys
        195                 200                 205

Ile Arg Gly Leu Lys Gly Gln Asp Leu Glu Glu Gly Val Ser Thr Arg
    210                 215                 220

Leu Val Val Tyr Ala Ala Ser Leu Thr Arg Arg Gly Met Asn Leu Asp
225                 230                 235                 240

Arg Ala Ile Glu Ala Ala Met Ile Glu Pro Leu Thr Asp Asp Ala Glu
                245                 250                 255

Val Lys Arg Gly Leu Arg Asp Leu Ala Ala Ala Ile Phe Gly
            260                 265                 270

<210> SEQ ID NO 39
<211> LENGTH: 275
<212> TYPE: PRT
<213> ORGANISM: Pseudomonas stutzeri

<400> SEQUENCE: 39

Met Arg Tyr Leu Pro Val Asn Ala Ile Glu Ile Pro Thr Thr Ala Gly
1               5                   10                  15

Thr Pro Asp Ala Pro Phe Tyr Gln Pro Leu Gly Asn Glu Glu Gln Leu
            20                  25                  30

Phe Gln Gln Ala Trp Gln His Gly Met Pro Val Leu Ile Lys Gly Pro
        35                  40                  45

Thr Gly Cys Gly Lys Thr Arg Phe Val Gln His Met Ala His Arg Leu
    50                  55                  60

Asn Leu Pro Leu Tyr Thr Val Ala Cys His Asp Asp Leu Ser Ala Ala
65                  70                  75                  80

Asp Leu Val Gly Arg His Leu Ile Gly Ala Gln Gly Thr Trp Trp Gln
                85                  90                  95
```

-continued

```
Asp Gly Pro Leu Thr Arg Ala Val Arg Glu Gly Ile Cys Tyr Leu
            100                 105                 110

Asp Glu Val Val Glu Ala Arg Gln Asp Thr Ala Val Val Leu His Pro
        115                 120                 125

Leu Ala Asp Asp Arg Arg Glu Leu Phe Ile Glu Arg Thr Gly Glu Ala
    130                 135                 140

Leu Lys Ala Pro Pro Gly Phe Met Leu Val Val Ser Tyr Asn Pro Gly
145                 150                 155                 160

Tyr Gln Asn Leu Leu Lys Gly Met Lys Pro Ser Thr Arg Gln Arg Phe
                165                 170                 175

Val Ala Met Arg Phe Asp Tyr Pro Pro Thr Ala Glu Glu Arg Ile
            180                 185                 190

Val Ala Asn Glu Ala Gln Val Asp Ala Ala Leu Ala Ala Gln Val Val
        195                 200                 205

Lys Leu Gly Gln Ala Leu Arg Arg Leu Glu Gln His Asp Leu Glu Glu
    210                 215                 220

Val Ala Ser Thr Arg Leu Leu Ile Phe Thr Ala Arg Met Ile Arg Ser
225                 230                 235                 240

Gly Met Thr Pro Arg Gln Ala Cys Leu Ala Cys Leu Ala Glu Pro Leu
                245                 250                 255

Ser Asp Asp Pro Gln Thr Val Ala Ala Leu Met Asp Val Val Tyr Val
            260                 265                 270

His Phe Gly
        275

<210> SEQ ID NO 40
<211> LENGTH: 262
<212> TYPE: PRT
<213> ORGANISM: Rhodobacter sphaeroides

<400> SEQUENCE: 40

Met Asn Ala Ile Leu Arg Asp Ala Thr Val Pro Phe Tyr Lys Pro Val
1               5                   10                  15

Gly Asn Glu Cys Glu Leu Phe Glu Ala Ala Ser Ala Asn Gly Leu Pro
            20                  25                  30

Leu Leu Lys Gly Ala Thr Gly Cys Gly Lys Thr Arg Asn Val Glu His
        35                  40                  45

Met Ala Ala Arg Met Gly Arg Lys Leu His Thr Val Ala Cys His Thr
    50                  55                  60

Leu Ser Ala Ala Asp Leu Ile Gly Arg Phe Leu Leu Lys Gly Gly Ala
65                  70                  75                  80

Thr Glu Trp Val Asp Gly Pro Leu Thr Arg Ala Val Arg Glu Gly Ala
                85                  90                  95

Ile Cys Tyr Leu Asp Glu Val Val Glu Ala Arg Lys Asp Val Thr Val
            100                 105                 110

Val Leu His Pro Leu Thr Asp Asn Arg Arg Thr Leu Met Ile Asp Arg
        115                 120                 125

Thr Gly Glu Glu Leu Val Ala Pro Pro Gly Phe Met Leu Val Ala Ser
    130                 135                 140

Tyr Asn Pro Gly Tyr Gln Asn Ile Leu Lys Arg Leu Lys Pro Ser Thr
145                 150                 155                 160

Arg Gln Arg Phe Leu Ser Ile Ser Phe Thr Phe Pro Asp Pro Val Thr
                165                 170                 175

Glu Thr Ala Val Val Arg Glu Ser Gly Leu Ser Glu Ala Arg Val Ala
            180                 185                 190
```

```
Pro Leu Val Arg Leu Ala Gly His Val Arg Ala Leu Ser Gly Met Asp
        195                 200                 205

Leu Glu Glu Gly Val Ser Thr Arg Leu Leu Val Tyr Ala Ala Ser Leu
    210                 215                 220

Met Ala Gly Gly Met Thr Val Glu Gln Ala Leu Glu Ala Ala Val Ile
225                 230                 235                 240

Glu Pro Leu Thr Asp Glu Pro Asp Val Ala Gln Ala Leu Arg Asp Leu
                245                 250                 255

Ile Ala Thr Val Tyr Gly
            260

<210> SEQ ID NO 41
<211> LENGTH: 25
<212> TYPE: DNA
<213> ORGANISM: Artificial Sequence
<220> FEATURE:
<223> OTHER INFORMATION: Synthetic

<400> SEQUENCE: 41
gtgcgcgttt ccgcctacag cgctc                                          25

<210> SEQ ID NO 42
<211> LENGTH: 25
<212> TYPE: DNA
<213> ORGANISM: Artificial Sequence
<220> FEATURE:
<223> OTHER INFORMATION: Synthetic

<400> SEQUENCE: 42
gagcgctgta ggcggaaacg cgcac                                          25

<210> SEQ ID NO 43
<211> LENGTH: 1018
<212> TYPE: DNA
<213> ORGANISM: Thauera aromatica

<400> SEQUENCE: 43
ccatgggtgg cgtctggaaa cgctggctta gggacgttga aaacacgacc tgctccaggc    60
acgaggaagg caaactaagt ttccgcgacc acgtctgaac accggacaga cgtggttcac   120
ctccagacca ctgtagtgat agatcatgaa aacctactcc agcgcaaatg gcctgttcgt   180
cccggaagtc gatccctact actatgtaag tacgaaaaac cagagcttcc tcgataaatt   240
tgcaaagata tcgaaaaagc atcccgtcaa tgtactggtg gtcggcaaac aaggctgcgg   300
caagtcttcc ctagtgcggc aatacgccgc cgtcaacagg ctacccttgg cgaccttcca   360
gatcggcatc ctgtcggagc cggggcaact gtttggtgaa tacgcgctgg agaacgggga   420
gacccgttac aagcagttcc tcttccccca ggccatccag acacccaatt gcgtcatcca   480
ccttgaagag atcaatcgcc ccgagcatcc gaaggcgttg aacatgttgt tctccattct   540
ctccgatgac cgtcaggtat ggatggacga gctcggactg ctgcaagtag cgcccggagt   600
cgttttcttc gcaacgctca acgaagggtc cgaattcgtc ggtaccgagt tactcgaccc   660
ggccctgcgc gaccgttttt atgtcactac catggatttc ctgccgaatg aagtggaagt   720
cgaggtgctg gaaaagaaga ccggcgtgaa aaatgagcag gcgagggaaa tcatcgcggt   780
agcaaacagc atccgcgcca atgccgacct cggcatcgat gtttccacac gcaagatcct   840
gatgctcggc gagatgattg ccgccggcgg aacgttgcgc gaagccatcg tgacgagtct   900
ccaaaccgac aagaagacgc ttgaatcggt tttgctgtcc ctgcacgtca atctggggaa   960
```
ggtggaaaaa agcaagacag aatacgtcca atacatcgcc gcctaaggtc ttccatgg  1018

<210> SEQ ID NO 44
<211> LENGTH: 286
<212> TYPE: PRT
<213> ORGANISM: Thauera aromatica

<400> SEQUENCE: 44

```
Met Lys Thr Tyr Ser Ser Ala Asn Gly Leu Phe Val Pro Glu Val Asp
1               5                   10                  15

Pro Tyr Tyr Tyr Val Ser Thr Glu Asn Gln Ser Phe Leu Asp Lys Phe
            20                  25                  30

Ala Lys Ile Ser Lys Lys His Pro Val Asn Val Leu Val Val Gly Lys
        35                  40                  45

Gln Gly Cys Gly Lys Ser Ser Leu Val Arg Gln Tyr Ala Ala Val Asn
    50                  55                  60

Arg Leu Pro Leu Ala Thr Phe Gln Ile Gly Ile Leu Ser Glu Pro Gly
65                  70                  75                  80

Gln Leu Phe Gly Glu Tyr Ala Leu Glu Asn Gly Glu Thr Arg Tyr Lys
                85                  90                  95

Gln Phe Leu Phe Pro Gln Ala Ile Gln Thr Pro Asn Cys Val Ile His
            100                 105                 110

Leu Glu Glu Ile Asn Arg Pro Glu His Pro Lys Ala Leu Asn Met Leu
        115                 120                 125

Phe Ser Ile Leu Ser Asp Asp Arg Gln Val Trp Met Asp Glu Leu Gly
    130                 135                 140

Leu Leu Gln Val Ala Pro Gly Val Val Phe Phe Ala Thr Leu Asn Glu
145                 150                 155                 160

Gly Ser Glu Phe Val Gly Thr Glu Leu Leu Asp Pro Ala Leu Arg Asp
                165                 170                 175

Arg Phe Tyr Val Thr Thr Met Asp Phe Leu Pro Asn Glu Val Glu Val
            180                 185                 190

Glu Val Leu Glu Lys Lys Thr Gly Val Lys Asn Glu Gln Ala Arg Glu
        195                 200                 205

Ile Ile Ala Val Ala Asn Ser Ile Arg Ala Asn Ala Asp Leu Gly Ile
    210                 215                 220

Asp Val Ser Thr Arg Lys Ile Leu Met Leu Gly Glu Met Ile Ala Ala
225                 230                 235                 240

Gly Gly Thr Leu Arg Glu Ala Ile Val Thr Ser Leu Gln Thr Asp Lys
                245                 250                 255

Lys Thr Leu Glu Ser Val Leu Leu Ser Leu His Val Asn Leu Gly Lys
            260                 265                 270

Val Glu Lys Ser Lys Thr Glu Tyr Val Gln Tyr Ile Ala Ala
        275                 280                 285
```

<210> SEQ ID NO 45
<211> LENGTH: 2038
<212> TYPE: DNA
<213> ORGANISM: Thauera aromatica

<400> SEQUENCE: 45
ccatggccaa gaaccacgac accacacttc ggctgatgag ccagcgctgg agacgtcaag  60
cgtttcgtca ttcccggcga ggagggctat tccgatttct ggcgtcgaga caagtcgccg  120
atcgaatccg tcgagttggt gaagctattg gtcgccattg gtaaactctc gactttcatc  180

| | |
|---|---|
| ggacgcaacg tcggcgaaat cgtctggtcc ggaatggaac tcgacaatgc gatcgccctc | 240 |
| gatccaacgc caataatggg cacgtatccg gtgccggcgg aaagacgga tctgatggtc | 300 |
| ggcatcatgg ttcaggaggc atacaagcgc atcgagtggt ccgaacgcct gcgcgagatg | 360 |
| ctcaggctgc gcgtccagcc gccgacgcag tatgaataca agttcgacat gttcttcacc | 420 |
| gtctgcgagt ccgtctacgt cgacagtttg gccaacaaga gcgtgctcgg ctactacgcc | 480 |
| gaggcggcgc gtgactggcg tatcgtcaag acgctgaaga gtctgatcaa gccgcccacc | 540 |
| ctttccgaga tgctgcacct gtggtggcgc ttggctgccg accgcaatcc cgagctctac | 600 |
| aagcagggct acagcgacct caccctcggc ggcttggtca tgcggggtag tctggaccag | 660 |
| tactacagca agccgttgca gaccatgaac agcatcgtgc cggccttgcg ccacgactgc | 720 |
| cctgaactct cgagcgtcag cgatcgctgt gacttccgcc tcgatctcta tgagaagcta | 780 |
| tggcgcgagg tgctcaaaca catccgcttc tggcccggcg accgcagcga tcggttcatg | 840 |
| atgccggaca tgggcgatga cgaagaattg gcccgggaag aggcggagca agcagccgtc | 900 |
| aaggccacca tcgtcaatta cgccaacctg atcgaggcgg cgctgccgca gaagaaccgg | 960 |
| gacttcaccg atcagatcaa gggcaacgtc gcaaacctcg agaacgtcgc ccgggtcgag | 1020 |
| ggcaacgaca tcgtgatgat ggcccgcaac cgtgtcgatc gccacctctt gcacaagctg | 1080 |
| gagcaagtgg taaggaacgc caccgaccgc cggagcgttt tcaaccgcgg gctgagttca | 1140 |
| gggaagattc atagtcggcg gctttaccgc gcccacacga ccggcgccgt gttccaacaa | 1200 |
| aagaaacacg aattcgacat gcgaaagaat gtcgtgctgc tcgtggacgc gaccgggtcg | 1260 |
| atggcggatc cgacacaatg ggaccaagcc gaaatgatct accagacgct gttcacggcg | 1320 |
| attctggagt atacgaacaa cgcgcgacta ttcgcctaca cgaagtcag gaacgcctgc | 1380 |
| cgcatcaccg agatctatcg tggtggccgc atgctcacag tgctgccgca cggaaggaca | 1440 |
| gcttccggtg aggccatcat cgccacggcg ctaaatacc gtacaccggg aaagaaaact | 1500 |
| ctgctggtcc atatcaccga cggcgcctca aactgggggt gcggcgtcgc agatgccatc | 1560 |
| aagtactgca aagtaacgg catcagcctg ctcaccttgg gcatcagctg cagtctgtcc | 1620 |
| gccaaacaat cgctacgcga cgaatacggc agtctcgtga gtttgtcga caagactgag | 1680 |
| caattgccca gttgtttgg cgagttgatc atcagcgaaa tgcgtgaatc aaggacagca | 1740 |
| cagaagtgag cacgtccttt ctcgaccacg tgctggaagc cgaatggcag atgttcgtcc | 1800 |
| gcgtccggag tgcacggcac gccccctgtc agagtgctcc caacaacttc aagacgatcc | 1860 |
| gttccagcct gttcgagacg tggtcgcaac caatgctcgc ttcctatctt gccgacctgg | 1920 |
| aagcagctga tgcggttggc cgaaacctgc tcgtggagaa gtatgctcgc atggacaact | 1980 |
| tgattccacc gctatcaaac aacccgttga tcggcatcat cgtcaccatc gaaagcaa | 2038 |

<210> SEQ ID NO 46
<211> LENGTH: 581
<212> TYPE: PRT
<213> ORGANISM: Thauera aromatica

<400> SEQUENCE: 46

Met Ala Lys Asn His Asp Thr Thr Leu Arg Leu Met Ser Ser Ala Gly
1               5                   10                  15

Asp Val Lys Arg Phe Val Ile Pro Gly Glu Gly Tyr Ser Asp Phe
            20                  25                  30

Trp Arg Arg Asp Lys Ser Pro Ile Glu Ser Val Glu Leu Val Lys Leu
        35                  40                  45

-continued

```
Leu Val Ala Ile Arg Lys Leu Ser Thr Phe Ile Gly Arg Asn Val Gly
         50                  55                  60

Glu Ile Val Trp Ser Gly Met Glu Leu Asp Asn Ala Ile Ala Leu Asp
 65                  70                  75                  80

Pro Thr Pro Ile Met Gly Thr Tyr Pro Val Pro Ala Gly Lys Thr Asp
                     85                  90                  95

Leu Met Val Gly Ile Met Val Gln Glu Ala Tyr Lys Arg Ile Glu Trp
                100                 105                 110

Ser Glu Arg Leu Arg Glu Met Leu Arg Leu Arg Val Gln Pro Pro Thr
            115                 120                 125

Gln Tyr Glu Tyr Lys Phe Asp Met Phe Phe Thr Val Cys Glu Ser Val
        130                 135                 140

Tyr Val Asp Ser Leu Ala Asn Lys Ser Val Leu Gly Tyr Tyr Ala Glu
145                 150                 155                 160

Ala Ala Arg Asp Trp Arg Ile Val Lys Thr Leu Lys Ser Leu Ile Lys
                165                 170                 175

Pro Pro Thr Leu Ser Glu Met Leu His Leu Trp Trp Arg Leu Ala Ala
                180                 185                 190

Asp Arg Asn Pro Glu Leu Tyr Lys Gln Gly Tyr Ser Asp Leu Thr Leu
            195                 200                 205

Gly Gly Leu Val Met Arg Gly Ser Leu Asp Gln Tyr Tyr Ser Lys Pro
        210                 215                 220

Leu Gln Thr Met Asn Ser Ile Val Pro Ala Leu Arg His Asp Cys Pro
225                 230                 235                 240

Glu Leu Ser Ser Val Ser Asp Arg Cys Asp Phe Arg Leu Asp Leu Tyr
                245                 250                 255

Glu Lys Leu Trp Arg Glu Val Leu Lys His Ile Arg Phe Trp Pro Gly
                260                 265                 270

Asp Arg Ser Asp Arg Phe Met Met Pro Asp Met Gly Asp Asp Glu Glu
            275                 280                 285

Leu Ala Arg Glu Glu Ala Glu Gln Ala Ala Val Lys Ala Thr Ile Val
        290                 295                 300

Asn Tyr Ala Asn Leu Ile Glu Ala Ala Leu Pro Gln Lys Asn Arg Asp
305                 310                 315                 320

Phe Thr Asp Gln Ile Lys Gly Asn Val Ala Asn Leu Glu Asn Val Ala
                325                 330                 335

Arg Val Glu Gly Asn Asp Ile Val Met Met Ala Arg Asn Arg Val Asp
                340                 345                 350

Arg His Leu Leu His Lys Leu Glu Gln Val Val Arg Asn Ala Thr Asp
            355                 360                 365

Arg Arg Ser Val Phe Asn Arg Gly Leu Ser Ser Gly Lys Ile His Ser
        370                 375                 380

Arg Arg Leu Tyr Arg Ala His Thr Thr Gly Ala Val Phe Gln Gln Lys
385                 390                 395                 400

Lys His Glu Phe Asp Met Arg Lys Asn Val Val Leu Val Asp Ala
                405                 410                 415

Thr Gly Ser Met Ala Asp Pro Thr Gln Trp Asp Gln Ala Glu Met Ile
                420                 425                 430

Tyr Gln Thr Leu Phe Thr Ala Ile Leu Glu Tyr Thr Asn Asn Ala Arg
            435                 440                 445

Leu Phe Ala Tyr Asn Glu Val Arg Asn Ala Cys Arg Ile Thr Glu Ile
        450                 455                 460

Tyr Arg Gly Gly Arg Met Leu Thr Val Leu Pro His Gly Arg Thr Ala
```

```
465                 470                 475                 480
Ser Gly Glu Ala Ile Ile Ala Thr Ala Leu Asn Thr Arg Thr Pro Gly
                485                 490                 495

Lys Lys Thr Leu Leu Val His Ile Thr Asp Gly Ala Ser Asn Trp Gly
                500                 505                 510

Cys Gly Val Ala Asp Ala Ile Lys Tyr Cys Lys Gly Asn Gly Ile Ser
                515                 520                 525

Leu Leu Thr Leu Gly Ile Ser Cys Ser Leu Ser Ala Lys Gln Ser Leu
                530                 535                 540

Arg Asp Glu Tyr Gly Ser Leu Val Lys Phe Val Asp Lys Thr Glu Gln
545                 550                 555                 560

Leu Pro Lys Leu Phe Gly Glu Leu Ile Ile Ser Glu Met Arg Glu Ser
                565                 570                 575

Arg Thr Ala Gln Lys
                580
```

<210> SEQ ID NO 47
<211> LENGTH: 183
<212> TYPE: DNA
<213> ORGANISM: Thauera aromatica

<400> SEQUENCE: 47

```
atgggaacca ccacatgcaa gcagtgcgca aacttctttc ccgtccctaa agacgcggat    60
gactacgaag ccggtaaggc agactgcgtg cgggaaaagg aagacgaaaa gggtaaatac   120
tggctctcca agcccatatt cgagaacagc gcgcaatgtg aagcctttca acgaagcgc   180
taa                                                                183
```

<210> SEQ ID NO 48
<211> LENGTH: 60
<212> TYPE: PRT
<213> ORGANISM: Thauera aromatica

<400> SEQUENCE: 48

```
Met Gly Thr Thr Thr Cys Lys Gln Cys Ala Asn Phe Phe Pro Val Pro
1               5                  10                  15

Lys Asp Ala Asp Asp Tyr Glu Ala Gly Lys Ala Asp Cys Val Arg Glu
                20                  25                  30

Lys Glu Asp Glu Lys Gly Lys Tyr Trp Leu Ser Lys Pro Ile Phe Glu
            35                  40                  45

Asn Ser Ala Gln Cys Glu Ala Phe Gln Thr Lys Arg
        50                  55                  60
```

<210> SEQ ID NO 49
<211> LENGTH: 246
<212> TYPE: DNA
<213> ORGANISM: Thauera aromatica

<400> SEQUENCE: 49

```
atggagggca gcaacatgga aacaggacag aatttgcaaa accagccgca taccgaggtg    60
ggtacggcga ggccgtgccg gagttgcaaa tggcaaaccc ccgaccccac cgatccgcac   120
cgtgggcaat gcaccgccaa ccggcacgcc atgggtggcg tctggaaacg ctggcttagg   180
gacgttgaaa acacgacctg ctccaggcac gaggaaggca aactaagttt ccgcgaccac   240
gtctga                                                             246
```

<210> SEQ ID NO 50

<211> LENGTH: 81
<212> TYPE: PRT
<213> ORGANISM: Thauera aromatica

<400> SEQUENCE: 50

Met Glu Gly Ser Asn Met Glu Thr Gly Gln Asn Leu Gln Asn Gln Pro
1               5                   10                  15

His Thr Glu Val Gly Thr Ala Arg Pro Cys Arg Ser Cys Lys Trp Gln
            20                  25                  30

Thr Pro Asp Pro Thr Asp Pro His Arg Gly Gln Cys Thr Ala Asn Arg
        35                  40                  45

His Ala Met Gly Gly Val Trp Lys Arg Trp Leu Arg Asp Val Glu Asn
    50                  55                  60

Thr Thr Cys Ser Arg His Glu Glu Gly Lys Leu Ser Phe Arg Asp His
65                  70                  75                  80

Val

<210> SEQ ID NO 51
<211> LENGTH: 20
<212> TYPE: DNA
<213> ORGANISM: Artificial Sequence
<220> FEATURE:
<223> OTHER INFORMATION: Synthetic

<400> SEQUENCE: 51
ctgcttgcat gtggtggttc                                              20

<210> SEQ ID NO 52
<211> LENGTH: 21
<212> TYPE: DNA
<213> ORGANISM: Artificial Sequence
<220> FEATURE:
<223> OTHER INFORMATION: Synthetic

<400> SEQUENCE: 52
gatccaccac gaccatagaa g                                            21

<210> SEQ ID NO 53
<211> LENGTH: 29
<212> TYPE: DNA
<213> ORGANISM: Artificial Sequence
<220> FEATURE:
<223> OTHER INFORMATION: Synthetic

<400> SEQUENCE: 53
caacgtgctg gccatgtcgc ccggcatcc                                    29

<210> SEQ ID NO 54
<211> LENGTH: 29
<212> TYPE: DNA
<213> ORGANISM: Artificial Sequence
<220> FEATURE:
<223> OTHER INFORMATION: Synthetic

<400> SEQUENCE: 54
ggatgccggg cgacatgccc agcacgttg                                    29

<210> SEQ ID NO 55
<211> LENGTH: 979
<212> TYPE: PRT
<213> ORGANISM: Thauera aromatica

<400> SEQUENCE: 55

-continued

```
Met Thr Ser Asn Asn Ser Ser Val Ser Asp Ile Ser Ala Val Leu Arg
1               5                   10                  15

Val Arg Asp Val Thr Leu Arg Ala Val Asp Asp Leu Gln Thr Tyr Arg
            20                  25                  30

Glu Lys Leu Ala Arg Val Val Leu Asp Gly Leu Tyr Glu Phe Val Gly
        35                  40                  45

Leu Leu Asp Ala Lys Gly Asn Thr Leu Glu Ile Asn Gln Ala Ala Leu
    50                  55                  60

Asp Gly Ala Gly Thr Arg Leu Glu Asp Ile Arg Asp Lys Pro Phe Trp
65                  70                  75                  80

Glu Ala Arg Trp Trp Gln Val Ser Arg Glu Thr Gln Glu Gln Arg
                85                  90                  95

Lys Leu Ile Ala Arg Ala Ser Ala Gly Glu Phe Val Arg Cys Asp Val
            100                 105                 110

Glu Ile Tyr Gly Arg Ala Ser Gly Glu Thr Ile Val Val Asp Tyr
            115                 120                 125

Ser Ile Leu Pro Ile Arg Asp Cys Asn Gly Lys Val Val Phe Leu Leu
    130                 135                 140

Pro Glu Gly Arg Asn Ile Thr Asp Lys Lys Leu Ala Glu Ala Glu Leu
145                 150                 155                 160

Ala Arg Lys Asn Glu Glu Leu Gln His Leu Leu Glu Lys Ile Arg Gln
            165                 170                 175

Leu Asp Glu Ala Lys Asn Glu Phe Phe Ala Asn Leu Ser His Glu Leu
            180                 185                 190

Arg Thr Pro Leu Ser Leu Ile Leu Gly Ser Val Glu Ser Leu Leu Ala
            195                 200                 205

Asp Ser Gly Asp Tyr Ser Gly Val Gln Arg Val Asp Leu Asp Val Ile
    210                 215                 220

Gln Arg Asn Ala Ile Thr Leu Leu Lys Tyr Val Asn Asp Leu Leu Asp
225                 230                 235                 240

Leu Ala Lys Leu Gln Ala Glu Lys Leu Gln Leu His Tyr Ser Arg Val
            245                 250                 255

Asp Leu Ala Ala Val Thr Arg Met Ile Cys Ala His Phe Glu Ala Leu
            260                 265                 270

Ala Glu Tyr Lys Cys Leu Ser Tyr Val Ile Asp Ala Pro Ala Phe Met
            275                 280                 285

Glu Ala Glu Val Asp Val Glu Lys Tyr Glu Arg Ile Val Leu Asn Leu
        290                 295                 300

Leu Ser Asn Ala Phe Lys Phe Ser Pro Asp Gly Gly Arg Ile Arg Cys
305                 310                 315                 320

Ser Leu Ser Ala Thr Gly Thr Gly Arg Ile Leu Leu Ser Ile Gln Asp
            325                 330                 335

Ser Gly Pro Gly Ile Pro Ala Asp Gln Gln Ser Glu Ile Phe Gly Arg
            340                 345                 350

Phe Arg Gln Gly Gly Asp Ile Lys Ser Arg Gln Phe Gly Gly Thr Gly
            355                 360                 365

Leu Gly Leu Thr Ile Val Lys Asp Phe Val Cys Leu His Gly Gly Val
        370                 375                 380

Val Val Val Ser Asp Ala Pro Gly Gly Ala Leu Phe Gln Ile Glu
385                 390                 395                 400

Leu Pro Arg Asn Ala Pro Ser Gly Val Tyr Val Asn Ala Val Ala Lys
            405                 410                 415

Ala Gly Glu Leu Ser Pro Thr Ser Phe Asp Ile Ser Ala Trp Gly Leu
```

-continued

```
              420                 425                 430
Glu Gly Arg Ser Glu Trp Thr Ser Ala Glu Gly Ala Ser Asp Arg Pro
              435                 440                 445
Arg Ile Leu Ile Val Glu Asp Asn Val Asp Met Arg Cys Phe Ile Gly
450                 455                 460
Arg Val Leu Ile Asp Glu Tyr Gln Ile Ser Val Ala Ala Asp Gly Glu
465                 470                 475                 480
Gln Ala Leu Glu Leu Ile Thr Ser Ser Pro Pro Asp Leu Val Ile Thr
              485                 490                 495
Asp Leu Met Met Pro Lys Val Ser Gly Gln Leu Leu Val Lys Glu Met
              500                 505                 510
Arg Ser Arg Gly Asp Leu Ala Asn Val Pro Ile Leu Val Leu Ser Ala
              515                 520                 525
Lys Ala Asp Asp Gly Leu Arg Ile Lys Leu Leu Ala Glu Ser Val Gln
530                 535                 540
Asp Tyr Val Val Lys Pro Phe Ser Ala Thr Glu Leu Arg Ala Arg Val
545                 550                 555                 560
Arg Asn Leu Val Thr Met Lys Arg Ala Arg Asp Ala Leu Gln Arg Ala
              565                 570                 575
Leu Asp Ser Gln Ser Asp Asp Leu Ser Gln Leu Thr Arg Gln Ile Ile
              580                 585                 590
Asp Asn Arg Gln Glu Leu Gln Arg Ser His Asp Ala Leu Gln Glu Ser
              595                 600                 605
Glu Ser Arg Trp Arg Ala Val Tyr Glu Asn Ser Ala Ala Gly Ile Val
              610                 615                 620
Leu Thr Asn Leu Asp Gly Leu Ile Leu Ser Ala Asn Gln Ala Phe Gln
625                 630                 635                 640
Lys Met Val Gly Tyr Ala Glu Asp Glu Leu Arg Val Ile Glu Ile Ser
              645                 650                 655
Asp Leu Val Pro Glu His Asp Arg Glu Lys Ile Arg Ser Arg Val Ser
              660                 665                 670
Asn Leu Ile Ser Gly Arg Val Asp Asp Tyr Gln Val Gln Arg Gln Cys
              675                 680                 685
Arg Arg Lys Asp Gly Arg Met Met Trp Ala Asn Val Arg Ala Ser Leu
690                 695                 700
Ile Pro Gly Leu Ala Asn Gln Ser Pro Met Val Val Arg Ile Phe Asp
705                 710                 715                 720
Asp Ile Thr Glu Lys Ile Gln Thr Glu Ala Glu Leu Ala Arg Ala Arg
                  725                 730                 735
Glu Lys Leu Thr Arg Val Met Arg Val Thr Ala Met Gly Glu Leu Ala
              740                 745                 750
Ala Ser Ile Ala His Glu Leu Asn Gln Pro Leu Ala Ala Ile Val Thr
              755                 760                 765
Asn Gly His Ala Ser Leu Arg Trp Leu Gly Ser Glu Pro Cys Asn Leu
770                 775                 780
Leu Glu Ala Val Glu Ala Val Arg Arg Ile His Asp Ala Asn Arg
785                 790                 795                 800
Ala Ser Glu Ile Ile Lys Arg Ile Arg Gly Phe Leu Gln Arg Gly Glu
              805                 810                 815
Gly Arg Arg Ser Ala Val Asp Ile Phe Gln Val Val Ala Asp Val Ala
              820                 825                 830
Ala Ile Val Ser Asp Met Ala Arg Ser His Cys Ile Asp Met Arg Tyr
              835                 840                 845
```

-continued

```
Gln Ala Val Gly Gln Leu Ser Leu Val Ile Ala Asp Lys Val Gln Leu
        850                 855                 860

Gln Gln Val Ile Leu Asn Leu Cys Ile Asn Gly Ile Glu Ser Ile Val
865                 870                 875                 880

Gly Gly Asn Ser Glu Arg Gly Glu Leu Ser Ile Thr Val Thr Gln Ser
                885                 890                 895

Asp Lys Arg Phe Leu Thr Val Ser Val His Asp Ser Gly Pro Gly Leu
                900                 905                 910

Ala Pro Gly Glu Ala Glu Asn Val Phe Asp Ala Phe Tyr Thr Ser Lys
            915                 920                 925

Val Glu Gly Leu Gly Met Gly Leu Ala Ile Ser Arg Ser Ile Ile Glu
930                 935                 940

Ala His Gly Gly Arg Leu Asp Val Leu Ser Pro Ser Thr Glu Gly Gly
945                 950                 955                 960

Cys Thr Phe Cys Phe Thr Leu Pro Thr Glu Glu Met Ala Ser Pro Cys
                965                 970                 975

Ala Pro Gln

<210> SEQ ID NO 56
<211> LENGTH: 218
<212> TYPE: PRT
<213> ORGANISM: Thauera aromatica

<400> SEQUENCE: 56

Met Cys Pro Thr Ile Asp Ala Ser Thr Val Tyr Leu Val Asp Asp Asp
1               5                  10                  15

Arg Ser Met Arg Asp Ala Ile Ser Ser Leu Val Arg Ser Val Gly Leu
            20                  25                  30

Asn Val Glu Thr Phe Ala Ser Ala Ser Glu Phe Leu Glu His Ala Arg
        35                  40                  45

Ser Glu Ala Cys Ala Cys Leu Val Leu Asp Val Arg Met Pro Arg Met
    50                  55                  60

Ser Gly Phe Asp Leu Gln His Ala Leu Ser Lys Asn Gly Val Asp Ile
65                  70                  75                  80

Pro Ile Ile Phe Ile Thr Gly His Gly Asp Ile Pro Met Ala Val Arg
                85                  90                  95

Ala Ile Lys Ser Gly Ala Leu Glu Phe Leu Pro Lys Pro Phe Arg Ala
            100                 105                 110

Glu Glu Leu Leu Glu Ala Ile Asn Arg Ala Leu Asn Ile Asp Gln Glu
        115                 120                 125

Ala Arg Glu Tyr Lys Ala Glu Leu Asp Lys Ile Leu Lys Lys Tyr Glu
    130                 135                 140

Gly Leu Thr Asp Arg Glu Lys Glu Val Phe Pro Leu Ile Ala Gln Gly
145                 150                 155                 160

Leu Leu Asn Lys Gln Ile Ala Gly Tyr Leu Gly Ile Thr Glu Val Thr
                165                 170                 175

Ile Lys Val His Arg His Asn Ile Thr Arg Lys Met Gly Val Arg Thr
            180                 185                 190

Leu Ala Asn Leu Val Arg Leu Tyr Glu Lys Leu Lys Asn Ala Gly Leu
        195                 200                 205

Ile Glu Lys Lys Asn Gly Asn Leu Ser Gly
    210                 215

<210> SEQ ID NO 57
```

```
<211> LENGTH: 13
<212> TYPE: DNA
<213> ORGANISM: Artificial Sequence
<220> FEATURE:
<223> OTHER INFORMATION: Synthetic

<400> SEQUENCE: 57
acgtggttgt gcg                                                          13

<210> SEQ ID NO 58
<211> LENGTH: 13
<212> TYPE: DNA
<213> ORGANISM: Artificial Sequence
<220> FEATURE:
<223> OTHER INFORMATION: Synthetic

<400> SEQUENCE: 58
ccagccctag tgt                                                          13
```

COMPOSITION AND METHODS FOR BIOREMEDIATION

This application is a Continuation-In-Part of application Ser. No. 09/072,433 filed May 4, 1998 and claims priority from Provisional Application 60/046,845 filed May 5, 1997.

This invention was made with government support under NSF grant MCB9733210. The government had certain rights in the invention.

FIELD OF THE INVENTION

This invention relates to biological treatment of organic compounds, and particularly to the degradation of toluene and toluene analogues.

BACKGROUND

Industrial processes that use or generate toxic organic compounds (e.g., toluene, benzene, xylenes) has lead to the contamination of nearby water and land. Such compounds are among the most water soluble of all gasoline components and can also enter aquatic environments from many sources such as gasoline underground storage tanks, leaks, and spills.

Most approaches to decontamination or "remediation" involve stopping the local dumping of such compounds and transport of the waste to another area for containment. This is costly and does not eliminate the hazard.

As a remediation technology, bioremediation is considerably more attractive. Rather than merely transporting wastes, it offers the possibility of degrading toxic compounds to harmless reaction products by the use of biologicals.

Bioremediation field trials have involved both in-situ and ex-situ treatment methods. Typically, ex-situ treatment involves the transfer of contaminated waste from the site into a treatment tank designed to support microbial growth, i.e., a "bioreactor". The reactor provides for effective mixing of nutrients and control over temperature, pH and aeration to allow optimum microbial growth.

In-situ treatment involves adding biologicals directly to the waste. This avoids the problems associated with handling (e.g., pumping) toxic compounds. However, in-situ treatment has its own problems. Unlike bioreactors, where microbial growth can be monitored and adjusted, in-situ environmental conditions are difficult to measure and control.

Fries el al., "Isolation, characterization and distribution of denitrifying toluene degraders from a variety of habitats," *Appl. Environ. Microbiol.* 60:2802 (1994) generally indicates that biodegradation of benzene, toluene, ethylbenzene and xylenes under aerobic conditions is well known, although the availability of oxygen due to its low solubility in water and low rate of transport in soils and sediments is rate limiting. Fries et al. describes anaerobic respiration of toluene by microorganisms isolated from nature. The microorganisms could grow on 25 ppm toluene and could be fed 50 ppm toluene.

Rates have been determined at 28–30° C. with intact cells from a variety of strains. The rates vary from between 8 to 80 nmoles toluene $min^{-1}$ $mg^{-1}$ protein. A. Frazer et al., "Toluene Metabolism Under Anaerobic Conditions: A Review," *Anaerobe* 1:293 (1995).

There remains a need to develop a bioremediation procedure that can be operated economically on a commercial scale. Such a procedure must be able to degrade organic compounds with high efficiency.

SUMMARY OF THE INVENTION

This invention relates to biological treatment of organic compounds, and particularly to the degradation of toluene and toluene analogues. In one embodiment, the present invention contemplates a method of degrading compounds contained in a liquid or solid waste source, comprising the steps of: a) providing, i) a waste source comprising toluene (and/or a toluene analogue), ii) a reaction containing means, and iii) a compound selected from the group consisting of a functional, cell-free pyruvate formate lyase homologue of a toluene-degrading bacterium and a functional, cell-free pyruvate formate lyase activating homologue of a toluene-degrading bacterium; and b) reacting said homologue and said waste source in said containing means under conditions such that toluene (and/or the toluene analogue) is degraded.

It is not intended that the present invention be limited by the specific toluene-degrading bacterium. In one embodiment, said homologue is derived from an organism of the genus Thauera. In one embodiment, the organism is *Thauera aromatica*.

In another embodiment, said homologue is derived from an organism of the genus Xanthomonas. In one embodiment, the organism is *Xanthomonas maltophilia*.

In yet another embodiment, said homologue is derived from an organism of the genus Geobacter. In one embodiment, the organism is *Geobacter metallireducens*.

In still another embodiment, said homologue is derived from members of the genus Azoarcus. In one embodiment, the organism is *Azoarcus tolulyticus*.

The present invention contemplates nucleic acid sequences (and constructs comprising said sequences) and amino acid sequences of toluene degrading enzymes as compositions of matter (as well as antibodies to such amino acid sequences). In one embodiment, the present invention contemplates a purified nucleic acid comprising DNA having the sequence as set forth in FIGS. 12A–Y. In one embodiment, said DNA is in a vector. In another embodiment, said vector is a bacterial plasmid. In a particular embodiment, said bacterial plasmid is in a host cell. In one embodiment, said host cell expresses a toluene-degrading enzyme.

The present invention contemplates a functional, cell-free product of the tutD gene having the amino acid sequence as set forth in FIGS. 11A–D. In one embodiment, said product is contained within a reaction containing means. In a preferred embodiment, said reaction containing means is a bioreactor.

It is also not intended that the present invention be limited by the precise amino acid sequence of the homologue. In one embodiment, it is encoded by the tutD gene, a nucleic acid sequence for which is shown in FIGS. 5A–O, and has the amino acid sequence shown in FIGS. 7A–C. In another embodiment, the homologue is an expanded TutD protein having the amino acid shown in FIGS. 11A–D and the corresponding nucleic acid sequence shown in FIGS. 12A–Y. In another embodiment, the homologue is encoded by the tutE gene having a nucleic acid sequence shown in FIGS. 12A–Y, and a corresponding amino acid sequence shown in FIGS. 13A–B.

Additionally, the present invention contemplates a reporter gene fusion product constructed by fusing the tutD gene in frame to a reporter such as lacZ, luxA, or green fluorescence protein. Such constructs can be used to demonstrate regulated expression in response to toluene.

In another embodiment, the present invention contemplates a reporter gene fusion product constructed by fusing the tutE gene in frame to a reporter such as lacZ, luxA, or green fluorescence protein. Such constructs can be used to demonstrate regulated expression in response to toluene.

The present invention contemplates a functional, cell-free product of the tutH gene having the nucleic acid sequence as set forth in FIG. 18 and the amino acid sequence shown in FIG. 19. In one embodiment, said product is contained within a reaction containing means. In a preferred embodiment, said reaction containing means is a bioreactor.

Additionally, the present invention contemplates a reporter gene fusion product constructed by fusing the tutH gene in frame to a reporter such as lacZ, luxA, or green fluorescence protein. Such constructs can be used to demonstrate regulated expression in response to toluene.

The present invention contemplates a functional, cell-free product of the tutI gene having the nucleic acid sequence as set forth in FIG. 21 and the amino acid sequence shown in FIG. 22. In one embodiment, said product is contained within a reaction containing means. In a preferred embodiment, said reaction containing means is a bioreactor.

Additionally, the present invention contemplates a reporter gene fusion product constructed by fusing the tutI gene in frame to a reporter such as lacZ, luxA, or green fluorescence protein. Such constructs can be used to demonstrate regulated expression in response to toluene.

The present invention contemplates a functional, cell-free product of the tutF gene having the nucleic acid sequence as set forth in FIG. 24 and the amino acid sequence shown in FIG. 25. In one embodiment, said product is contained within a reaction containing means. In a preferred embodiment, said reaction containing means is a bioreactor.

Additionally, the present invention contemplates a reporter gene fusion product constructed by fusing the tutF gene in frame to a reporter such as lacZ, luxA, or green fluorescence protein. Such constructs can be used to demonstrate regulated expression in response to toluene.

The present invention contemplates a functional, cell-free product of the tutG gene having the nucleic acid sequence as set forth in FIG. 26 and the amino acid sequence shown in FIG. 27. In one embodiment, said product is contained within a reaction containing means. In a preferred embodiment, said reaction containing means is a bioreactor.

Additionally, the present invention contemplates a reporter gene fusion product constructed by fusing the tutG gene in frame to a reporter such as lacZ, luxA, or green fluorescence protein. Such constructs can be used to demonstrate regulated expression in response to toluene.

Additionally, the present invention contemplates a composition comprising isolated and purified DNA having an oligonucleotide sequence selected form the group consisting of, SEQ ID NO: 43, SEQ ID NO: 45, SEQ ID NO: 47, and SEQ ID NO: 49.

Additionally, the present invention contemplates a composition comprising isolated and purified polypeptide selected form the group consisting of, SEQ ID NO: 44, SEQ ID NO: 46, SEQ ID NO: 48, and SEQ ID NO: 50.

Definitions

To facilitate understanding of the invention, a number of terms are defined below.

The term "reaction" or "chemical reaction" means reactions involving chemical reactants, such as organic compounds. A "reaction containing means" refers to anything that can contain a reaction, including but not limited to, tubes, microtiter plates, vessels, and bioreactors. It is not intended that the present invention be limited by a particular reaction containing means. U.S. Pat. Nos. 5,610,061, 5,585, 272, 5,571,705, 5,560,737, 5,057,221 and 5,037,551 all describe various reaction containing means (including bioreactors) and are hereby incorporated by reference.

"Initiating a reaction" means causing a reaction to take place. Reactions can be initiated by any means (e.g., mixing, heat, wavelengths of light, addition of a catalyst, etc.)

A "solvent" is a liquid substance capable of dissolving or dispersing one or more other substances. It is not intended that the present invention be limited by the nature of the solvent used.

A "waste source" can be a solid or liquid waste source (e.g., paper pulp, pulp mill effluent, sludge, wastewater, petroleum spill, etc.).

"Toluene analogues" are structural analogues of toluene. While it is not intended that the present invention be limited to particular analogues, examples include the o-, m-, and p-isomers of chlorotoluene, fluorotoluene and xylene.

A "pyruvate formate lyase homologue" is defined as a gene product from a toluene-degrading organism, said gene product comprising i) regions of identity with the pyruvate formate lyase from *E. coli* (the PflD gene Genebank G418519) and/or from *Clostridium pasteurianum* (Genebank G1072361) such that the gene product contains the motif RVSGY (SEQ ID NO:1), RVAGY (SEQ ID NO:2), or VRVSGYSA (SEQ ID NO:3) at the essential glycine (shown in bold and discussed below), and ii) regions of non-identity. The gene product may contain other regions of identity with pyruvate formate lyase from *E. coli* (the PflD gene Genebank G418519) and from *Clostridium pasteurianum* (Genebank G1072361), including but not limited to, the motif TPDGR (SEQ ID NO:4), TPDGRF (SEQ ID NO:5), GPTAVL (SEQ ID NO:6), and GNDDD (SEQ ID NO:7). As noted below, the present invention also identifies other conserved regions, including but not limited to those associated with an essential conserved cysteine.

A "functional" homologue is one where transfer of the gene or expression of the gene product confers the ability to degrade toluene. Functional homologues need not comprise the entire gene product, i.e. functional peptide fragments (portions that are less than the entire gene product) are specifically contemplated.

The term "purified" means separated from some components that are normally present in the native state. Thus, a spectrum of purity is contemplated. At the very basic level, a cell-free preparation is "purified." Similarly, nucleic acid that is even substantially protein-free is "purified." At a more extreme level, the present invention contemplates a particular toluene degrading protein that is substantially free of all other proteins (usually less than 10% and preferably less than 5% of other proteins are present).

The term "gene" refers to a DNA sequence that comprises control and coding sequences necessary for the production of a polypeptide or precursor thereof. The polypeptide can be encoded by a full length coding sequence or by any portion of the coding sequence so long as the desired enzymatic activity is retained.

The term "wild-type" refers to a gene or gene product which has the characteristics of that gene or gene product when isolated from a naturally occurring source. A wild-type gene is that which is most frequently observed in a population and is thus arbitrarily designated the "normal" or "wild-type" form of the gene. In contrast, the term "modified" or "mutant" refers to a gene or gene product which displays modifications in sequence and or functional properties (i.e., altered characteristics) when compared to the wild-type gene or gene product. It is noted that naturally-occurring mutants can be isolated; these are identified by the fact that they have altered characteristics when compared to the wild-type gene or gene product.

The term "oligonucleotide" as used herein is defined as a molecule comprised of two or more deoxyribonucleotides or ribonucleotides, usually more than three (3), and typically more than ten (10) and up to one hundred (100) or more (although preferably between twenty and thirty). The exact size will depend on many factors, which in turn depends on the ultimate function or use of the oligonucleotide. The oligonucleotide may be generated in any manner, including chemical synthesis, DNA replication, reverse transcription, or a combination thereof.

Because mononucleotides are reacted to make oligonucleotides in a manner such that the 5' phosphate of one mononucleotide pentose ring is attached to the 3' oxygen of its neighbor in one direction via a phosphodiester linkage, an end of an oligonucleotide is referred to as the "5' end" if its 5' phosphate is not linked to the 3' oxygen of a mononucleotide pentose ring and as the "3' end" if its 3' oxygen is not linked to a 5' phosphate of a subsequent mononucleotide pentose ring. As used herein, a nucleic acid sequence, even if internal to a larger oligonucleotide, also may be said to have 5' and 3' ends.

When two different, non-overlapping oligonucleotides anneal to different regions of the same linear complementary nucleic acid sequence, and the 3' end of one oligonucleotide points towards the 5' end of the other, the former may be called the "upstream" oligonucleotide and the latter the "downstream" oligonucleotide.

The term "primer" refers to an oligonucleotide which is capable of acting as a point of initiation of synthesis when placed under conditions in which primer extension is initiated. An oligonucleotide "primer" may occur naturally, as in a purified restriction digest or may be produced synthetically.

A primer or oligonucleotide is selected to be "substantially" complementary to a strand of specific sequence of the template. A primer must be sufficiently complementary to hybridize with a template strand for primer elongation to occur. A primer sequence need not reflect the exact sequence of the template. For example, a non-complementary nucleotide fragment may be attached to the 5' end of the primer, with the remainder of the primer sequence being substantially complementary to the strand. Non-complementary bases or longer sequences can be interspersed into the primer, provided that the primer sequence has sufficient complementarily with the sequence of the template to hybridize and thereby form a template primer complex for synthesis of the extension product of the primer.

"Hybridization" methods involve the annealing of a complementary sequence to the target nucleic acid (the sequence to be detected). The ability of two polymers of nucleic acid containing complementary sequences to find each other and anneal through base pairing interaction is a well-recognized phenomenon. The initial observations of the "hybridization" process by Marmur and Lane, *Proc. Natl. Acad. Sci. USA* 46:453 (1960) and Doty et al., *Proc. Natl. Acad. Sci. USA* 46:461 (1960) have been followed by the refinement of this process into an essential tool of modern biology.

Even where the sequence of a probe or oligonucleotide is completely complementary to the sequence of the target, i.e., the target's primary structure, the target sequence must be made accessible to the probe via rearrangements of higher-order structure. These higher-order structural rearrangements may concern either the secondary structure or tertiary structure of the molecule. Secondary structure is determined by intramolecular bonding. In the case of DNA or RNA targets this consists of hybridization within a single, continuous strand of bases (as opposed to hybridization between two different strands). Depending on the extent and position of intramolecular bonding, the probe can be displaced from the target sequence preventing hybridization.

Solution hybridization of oligonucleotide probes to denatured double-stranded DNA is further complicated by the fact that the longer complementary target strands can renature or reanneal. Again, hybridized probe is displaced by this process. This results in a low yield of hybridization (low "coverage") relative to the starting concentrations of probe and target.

Hybridization, regardless of the method used, requires some degree of complementarily between the sequence being assayed (the target sequence) and the fragment of DNA used to perform the test (the probe). (Of course, one can obtain binding without any complementarily but this binding is nonspecific and to be avoided.)

The complement of a nucleic acid sequence as used herein refers to an oligonucleotide which, when aligned with the nucleic acid sequence such that the 5' end of one sequence is paired with the 3' end of the other, is in "antiparallel association." Certain bases not commonly found in natural nucleic acids may be included in the nucleic acids of the present invention and include, for example, inosine and 7-deazaguanine. Complementarily need not be perfect; stable duplexes may contain mismatched base pairs or unmatched bases. Those skilled in the art of nucleic acid technology can determine duplex stability empirically considering a number of variables including, for example, the length of the oligonucleotide, base composition and sequence of the oligonucleotide, ionic strength and incidence of mismatched base pairs.

Stability of a nucleic acid duplex is measured by the melting temperature, or "$T_m$." The $T_m$ of a particular nucleic acid duplex under specified conditions is the temperature at which on average half of the base pairs have disassociated. The equation for calculating the $T_m$ of nucleic acids is well known in the art. As indicated by standard references, an estimate of the $T_m$ value may be calculated by the equation:

$$T_m = 81.5° \text{ C.} + 16.6 \log M + 0.41(\%GC) - 0.61(\% \text{form}) - 500/L$$

where M is the molarity of monovalent cations, %GC is the percentage of guanosine and cytosine nucleotides in the DNA, %form is the percentage of formamide in the hybridization solution, and L=length of the hybrid in base pairs. [See e.g., Guide to Molecular Cloning Techniques, Ed. S. L. Berger and A. R. Kimmel, in Methods in Enzymology Vol. 152, 401 (1987)]. Other references include more sophisticated computations which take structural as well as sequence characteristics into account for the calculation of $T_m$.

The present invention contemplates utilizing the nucleic acid sequence of the tutD gene to isolate other genes encoding pyruvate formate lyase homologues by hybridizing portions of the tutD gene to total DNA of various toluene-degrading organisms. Preferably, hybridization is carried out at high stringency (i.e., carried out at or near the $T_m$ of the particular duplex). Hybridization can be used to capture other genes. Alternatively, hybridization can be followed by primer extension or PCR.

The present invention also contemplates utilizing the nucleic acid sequence of the tutE gene to isolate other genes encoding pyruvate formate lyase homologues by hybridizing portions of the tutE gene to total DNA of various toluene-degrading organisms. Preferably, hybridization is carried out at high stringency (i.e., carried out at or near the $T_m$ of the particular duplex). Hybridization can be used to capture other genes. Alternatively, hybridization can be followed by primer extension or PCR.

Mullis, et al., U.S. Pat. Nos. 4,683,195 and 4,683,202 (both of which are hereby incorporated by reference), describe a methods for increasing the concentration of a segment of target sequence in a mixture of genomic DNA without cloning or purification. This process for amplifying the target sequence consists of introducing a molar excess of two oligonucleotide primers to the DNA mixture containing the desired target sequence. The two primers are complementary to their respective strands of the double-stranded sequence. The mixture is denatured and then allowed to hybridize. Following hybridization, the primers are extended with polymerase so as to form complementary strands. The steps of denaturation, hybridization, and polymerase extension can be repeated as often as needed to obtain are relatively high concentration of a segment of the desired target sequence. The length of the segment of the desired target sequence is determined by the relative positions of the primers with respect to each other, and therefore, this length is a controllable parameter. By virtue of the repeating aspect of the process, the method is referred to by the inventors as the "Polymerase Chain Reaction" (hereinafter PCR). Because the desired segment of the target sequence become the dominant sequences (in terms of concentration) in the mixture, they are said to be "PCR-amplified."

It is not intended that the present invention be limited to a particular toluene-degrading organism. The present invention contemplates identifying homologues in both known and yet undiscovered toluene-degrading organisms. Known organisms are set forth in the Table 1.

TABLE 1

| Strain Designations | Energy Metabolism |
| --- | --- |
| T | Denitrifying |
| T1 | Denitrifying |
| Thauera aromatica, K172 | Denitrifying |
| S100 and S2 | Denitrifying |
| Azoarcus tolulyticus, Tol 4 (type strain); others include Td-1, Td-2, Td-3, Td-15, Td-17, Td-19, Td-21 | Denitrifying |
| ToN1, mXyN1, and EbN1 | Denitrifying |
| Xanthomonas maltophilia, Sul | Denitrifying |
| Geobacter metallireducens, Gs-15 | Denitrifying |
| Desulfobacula toluolica, Tol2 | Denitrifying |
| PRTOL1 | Denitrifying |

The term "probe" as used herein refers to a labeled oligonucleotide which forms a duplex structure with a sequence in another nucleic acid, due to complementarily of at least one sequence in the probe with a sequence in the other nucleic acid.

The term "label" as used herein refers to any atom or molecule which can be used to provide a detectable (preferably quantifiable) signal, and which can be attached to a nucleic acid or protein. Labels may provide signals detectable by fluorescence, radioactivity, colorimetry, gravimetry, X-ray diffraction or absorption, magnetism, enzymatic activity, and the like.

The terms "nucleic acid substrate" and nucleic acid template" are used herein interchangeably and refer to a nucleic acid molecule which may comprise single- or double-stranded DNA or RNA.

The term "substantially single-stranded" when used in reference to a nucleic acid substrate means that the substrate molecule exists primarily as a single strand of nucleic acid in contrast to a double-stranded substrate which exists as two strands of nucleic acid which are held together by inter-strand base pairing interactions.

The term "sequence variation" as used herein refers to differences in nucleic acid sequence between two nucleic acid templates. For example, a wild-type structural gene and a mutant form of this wild-type structural gene may vary in sequence by the presence of single base substitutions and/or deletions or insertions of one or more nucleotides. These two forms of the structural gene are said to vary in sequence from one another. A second mutant form of the structural gene may exist. This second mutant form is said to vary in sequence from both the wild-type gene and the first mutant form of the gene. It is noted, however, that the invention does not require that a comparison be made between one or more forms of a gene to detect sequence variations.

The term "$K_m$" as used herein refers to the Michaelis-Menten constant for an enzyme and is defined as the concentration of the specific substrate at which a given enzyme yields one-half its maximum velocity in an enzyme catalyzed reaction.

The term "nucleotide analog" as used herein refers to modified or non-naturally occurring nucleotides such as 7-deaza purines (i.e., 7-deaza-dATP and 7-deaza-dGTP). Nucleotide analogs include base analogs and comprise modified forms of deoxyribonucleotides as well as ribonucleotides. As used herein the term "nucleotide analog" when used in reference to substrates present in a PCR mixture refers to the use of nucleotides other than dATP, dGTP, dCTP and dTTP; thus, the use of dump (a naturally occurring dNTP) in a PCR would comprise the use of a nucleotide analog in the PCR. A PCR product generated using dump, 7-deaza-dATP, 7-deaza-dGTP or any other nucleotide analog in the reaction mixture is said to contain nucleotide analogs.

"Oligonucleotide primers matching or complementary to a gene sequence" refers to oligonucleotide primers capable of facilitating the template-dependent synthesis of single or double-stranded nucleic acids. Oligonucleotide primers matching or complementary to a gene sequence may be used in PCRs, RT-PCRs and the like.

A "consensus gene sequence" refers to a gene sequence which is derived by comparison of two or more gene sequences and which describes the nucleotides most often present in a given segment of the genes; the consensus sequence is the canonical sequence. A "motif" refers to the corresponding amino acid sequence defining a region of identity following a comparison of two or more amino acid sequences.

The term "polymorphic locus" is a locus present in a population which shows variation between members of the population (i.e., the most common allele has a frequency of less than 0.95). In contrast, a "monomorphic locus" is a genetic locus at little or no variations seen between members of the population (generally taken to be a locus at which the most common allele exceeds a frequency of 0.95 in the gene pool of the population).

The term "microorganism" as used herein means an organism too small to be observed with the unaided eye and includes, but is not limited to bacteria, viruses, protozoans, fungi, and ciliates.

The term "microbial gene sequences" refers to gene sequences derived from a microorganism.

The term "bacteria" refers to any bacterial species including abacterial and archaebacterial species.

The term "recombinant DNA molecule" as used herein refers to a DNA molecule which is comprised of segments of DNA joined together by means of molecular biological techniques.

The terms "in operable combination" or "operably linked" as used herein refers to the linkage of nucleic acid sequences in such a manner that a nucleic acid molecule capable of directing the synthesis of a desired protein molecule is produced. When a promoter sequence is operably linked to sequences encoding a protein, the promoter directs the expression of mRNA which can be translated to produce a functional form of the encoded protein. The term also refers to the linkage of amino acid sequences in such a manner that a functional protein is produced.

The term "an oligonucleotide having a nucleotide sequence encoding a gene" means a DNA sequence comprising the coding region of a gene or, in other words, the DNA sequence which encodes a gene product. The coding region may be present in either a cDNA or genomic DNA form. Suitable control elements such as enhancers/promoters, splice junctions, polyadenylation signals, etc. may be placed in close proximity to the coding region of the gene if needed to permit proper initiation of transcription and/or correct processing of the primary RNA transcript. Alternatively, the coding region utilized in the expression vectors of the present invention may contain endogenous enhancers/promoters, splice junctions, intervening sequences, polyadenylation signals, etc. or a combination of both endogenous and exogenous control elements.

The term "recombinant oligonucleotide" refers to an oligonucleotide created using molecular biological manipulations, including but not limited to, the ligation of two or more oligonucleotide sequences generated by restriction enzyme digestion of a polynucleotide sequence, the synthesis of oligonucleotides (e.g., the synthesis of primers or oligonucleotides) and the like.

The term "recombinant oligonucleotide having a sequence encoding a protein operably linked to a heterologous promoter" or grammatical equivalents indicates that the coding region encoding the protein (e.g., an enzyme) has been joined to a promoter which is not the promoter naturally associated with the coding region in the genome of an organism (i.e., it is linked to an exogenous promoter). The promoter which is naturally associated or linked to a coding region in the genome is referred to as the "endogenous promoter" for that coding region.

The term "transcription unit" as used herein refers to the segment of DNA between the sites of initiation and termination of transcription and the regulatory elements necessary for the efficient initiation and termination. For example, a segment of DNA comprising an enhancer/promoter, a coding region, and a termination and polyadenylation sequence comprises a transcription unit.

The term "regulatory element" as used herein refers to a genetic element which controls some aspect of the expression of nucleic acid sequences. For example, a promoter is a regulatory element which facilitates the initiation of transcription of an operably linked coding region.

The term "expression vector" or "vector" as used herein refers to a recombinant DNA molecule containing a desired coding sequence and appropriate nucleic acid sequences necessary for the expression of the operably linked coding sequence in a particular host organism. Nucleic acid sequences necessary for expression in prokaryotes include a promoter, optionally an operator sequence, a ribosome binding site and possibly other sequences. Eukaryotic cells are known to utilize promoters, enhancers, and termination and polyadenylation signals.

Transcriptional control signals in eucaryotes comprise "promoter" and "enhancer" elements. Promoters and enhancers consist of short arrays of DNA sequences that interact specifically with cellular proteins involved in transcription [Maniatis et al., Science 236:1237 (1987)]. Promoter and enhancer elements have been isolated from a variety of eukaryotic sources including genes in yeast, insect and mammalian cells and viruses (analogous control elements, i.e., promoters, are also found in prokaryotes). The selection of a particular promoter and enhancer depends on what cell type is to be used to express the protein of interest. Some eukaryotic promoters and enhancers have a broad host range while others are functional in a limited subset of cell types [for review see Voss et al., *Trends Biochem. Sci.* 11:287 (1986) and Maniatis et al., supra (1987)]. For example, the SV40 early gene enhancer is very active in a wide variety of cell types from many mammalian species and has been widely used for the expression of proteins in mammalian cells [Dijkema et al., *EMBO J.* 4:761 (1985)]. Two other examples of promoter/enhancer elements active in a broad range of mammalian cell types are those from the human elongation factor 1α gene [Uetsuki et al., *J. Biol. Chem.*, 264:5791 (1989); Kim et al., *Gene* 91:217 (1990); and Mizushima and Nagata, Nuc. Acids. Res., 18:5322 (1990)] and the long terminal repeats of the Rous sarcoma virus [Gorman et al., *Proc. Natl. Acad. Sci. USA* 79:6777 (1982)] and the human cytomegalovirus [Boshart et al., *Cell* 41:521 (1985)].

The term "promoter/enhancer" denotes a segment of DNA which contains sequences capable of providing both promoter and enhancer functions (for example, the long terminal repeats of retroviruses contain both promoter and enhancer functions). The enhancer/promoter may be "endogenous" or "exogenous" or "heterologous." An endogenous enhancer/promoter is one which is naturally linked with a given gene in the genome. An exogenous (heterologous) enhancer/promoter is one which is placed in juxtaposition to a gene by means of genetic manipulation (i.e., molecular biological techniques).

As used herein "tutF" denotes a segment of DNA (presented in FIG. 24) substantially similar to the open reading frame designated as "open reading frame 2" which consists of a 60 amino acid sequence which would code for a protein with a calculated molecular mass of 6,900 Da and a predicted pI of 5.2. The translational start begins at the NcoI restriction site and hence no upstream transcriptional regulatory sites or ribosome binding sites for this open reading frame are included on this fragment.

As used herein "tutG" denotes a segment of DNA (presented in FIG. 26) substantially similar to the open reading frame designated as "open reading frame 4" identified in the SacII/EcoRI fragment consisting essentially of an 81 amino acids sequence with a calculated molecular mass of 9,300 Da and a predicted pI of 7.8.

DESCRIPTION OF THE DRAWINGS

Figure 2A:
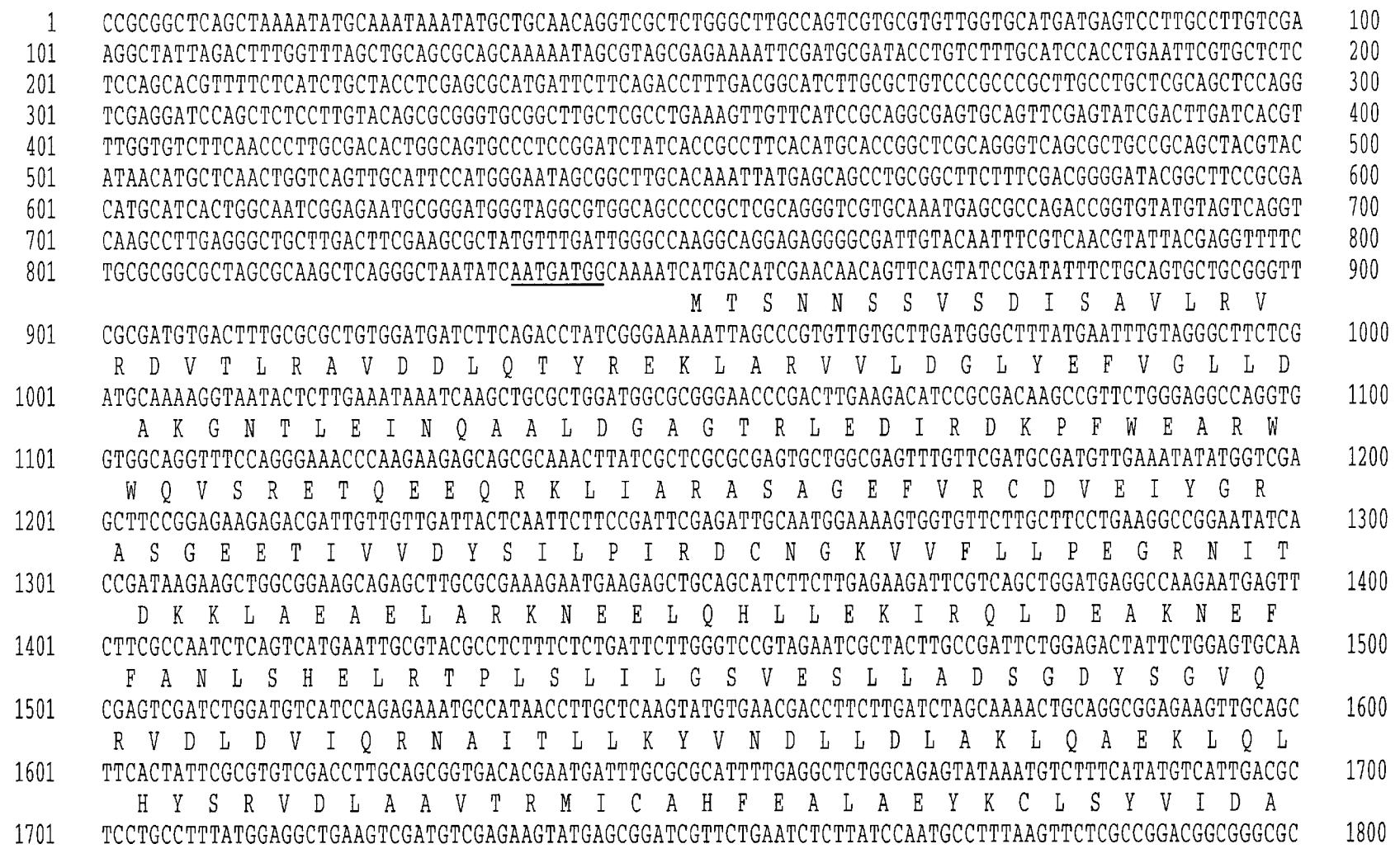

FIGS. 2A–D shows the nucleic acid sequence (SEQ ID NO: 8) of the tutB gene and tutC gene (submitted to the GenBank data base and assigned accession number U57900).

FIG. 3 shows the amino acid sequence of the tutB gene product (SEQ ID NO: 9), and gene products from *Bradyrhizobium japonicum* Bra ja NodW (SEQ ID NO:10), *Bradyrhizobium japonicum* Bra ja FixJ (SEQ ID NO:11), *Azorhizobium caulinodans* Azo ca FixJ (SEQ ID NO:12), *Rhizobium meliloti* Rhi me FixJ (SEQ ID NO:13), and *Rhodobacter capsulatus* Rho ca DctR (SEQ ID NO:14).

FIGS. 4A–B shows the amino acid sequence of the tutC gene product (SEQ ID NO: 10).

FIGS. 6A–C shows part of the nucleic acid sequence of the tutE gene (SEQ ID NO: 12).

FIGS. 7A–C shows the amino acid sequence of the tutD gene product (SEQ ID NO: 13).

FIG. 9 shows the polylinker (SEQ ID NO: 26) contained in pRK415 and the encoded amino acid sequence (SEQ ID NO: 27).

Figure 11A:
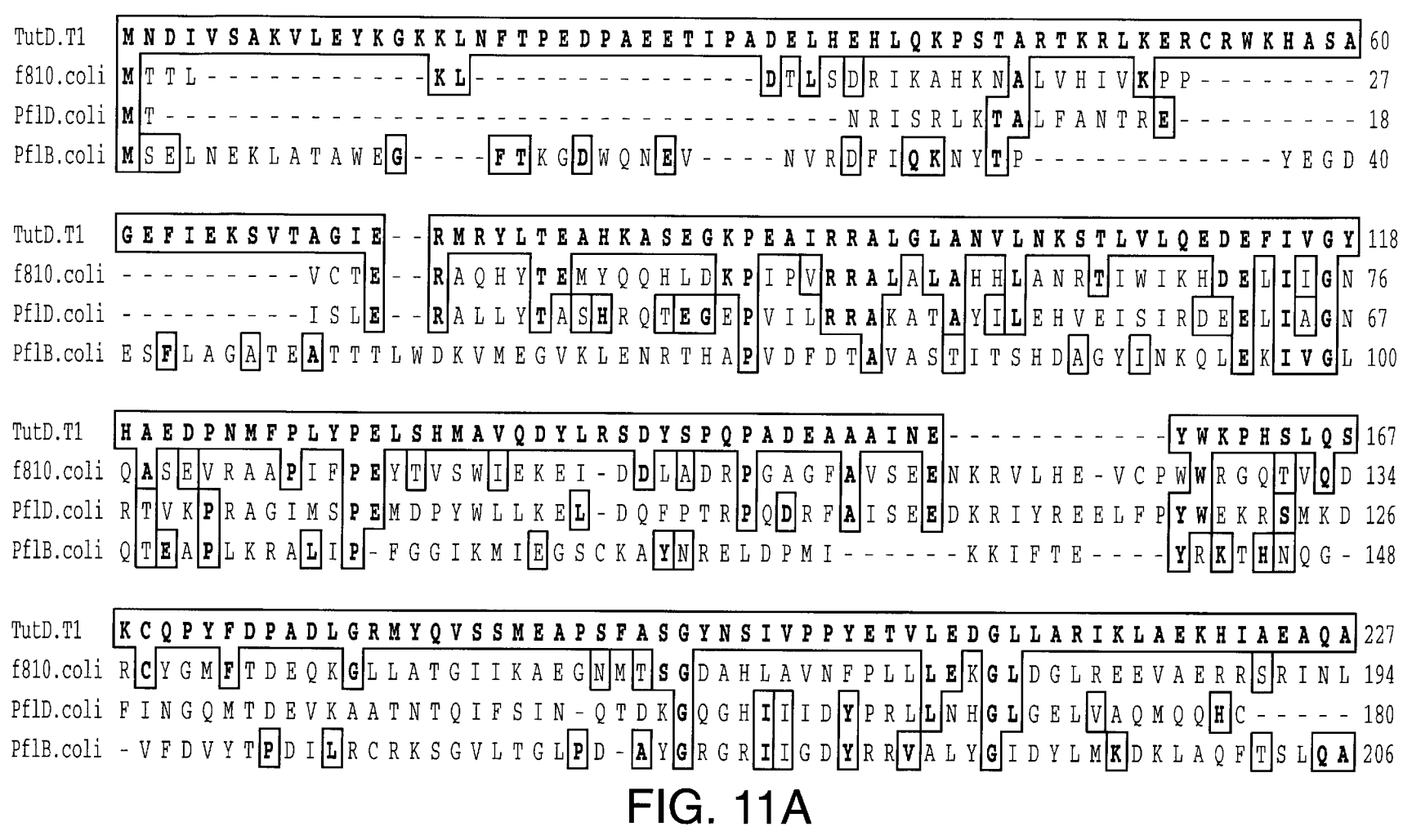
Figure 11B:
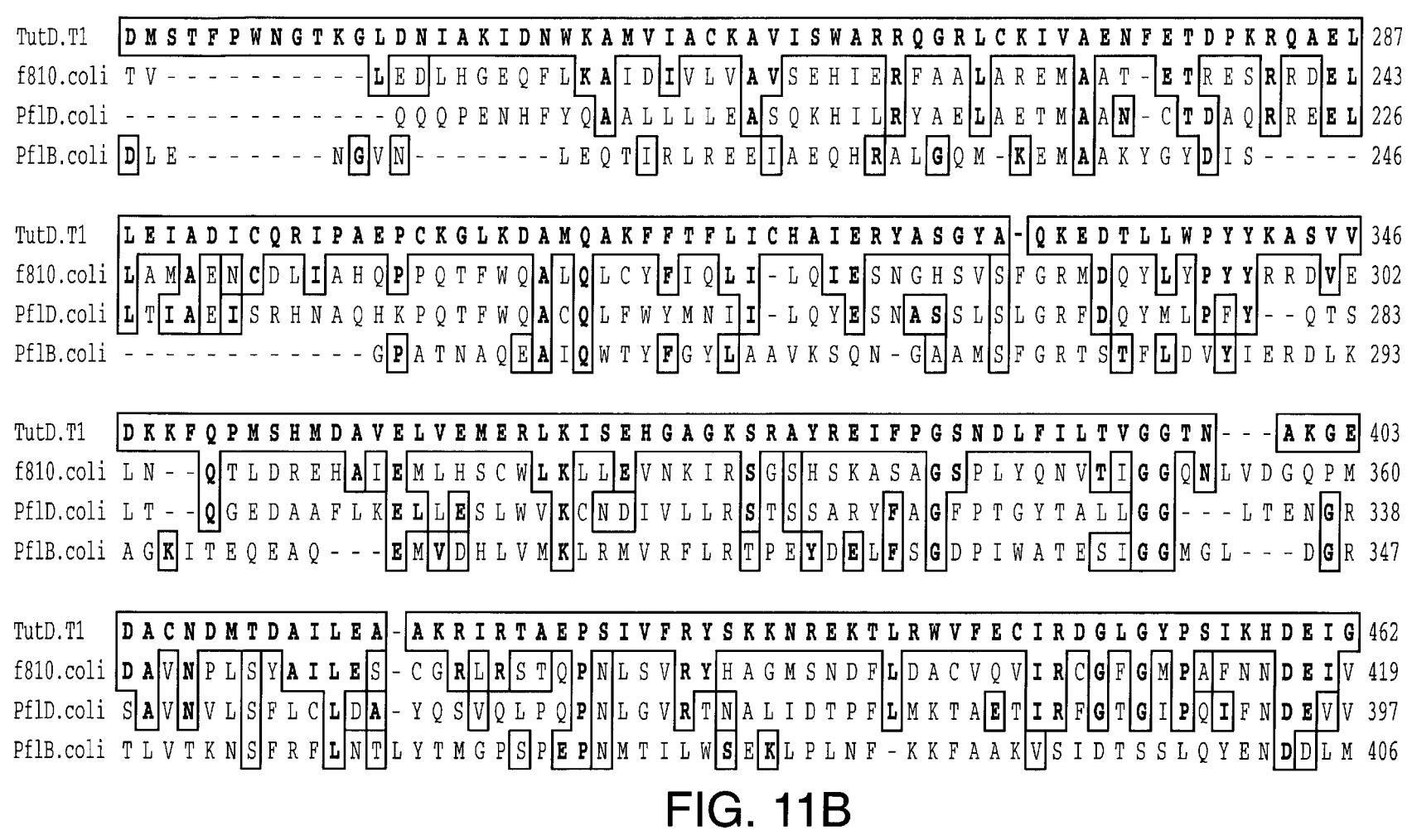
Figure 11C:
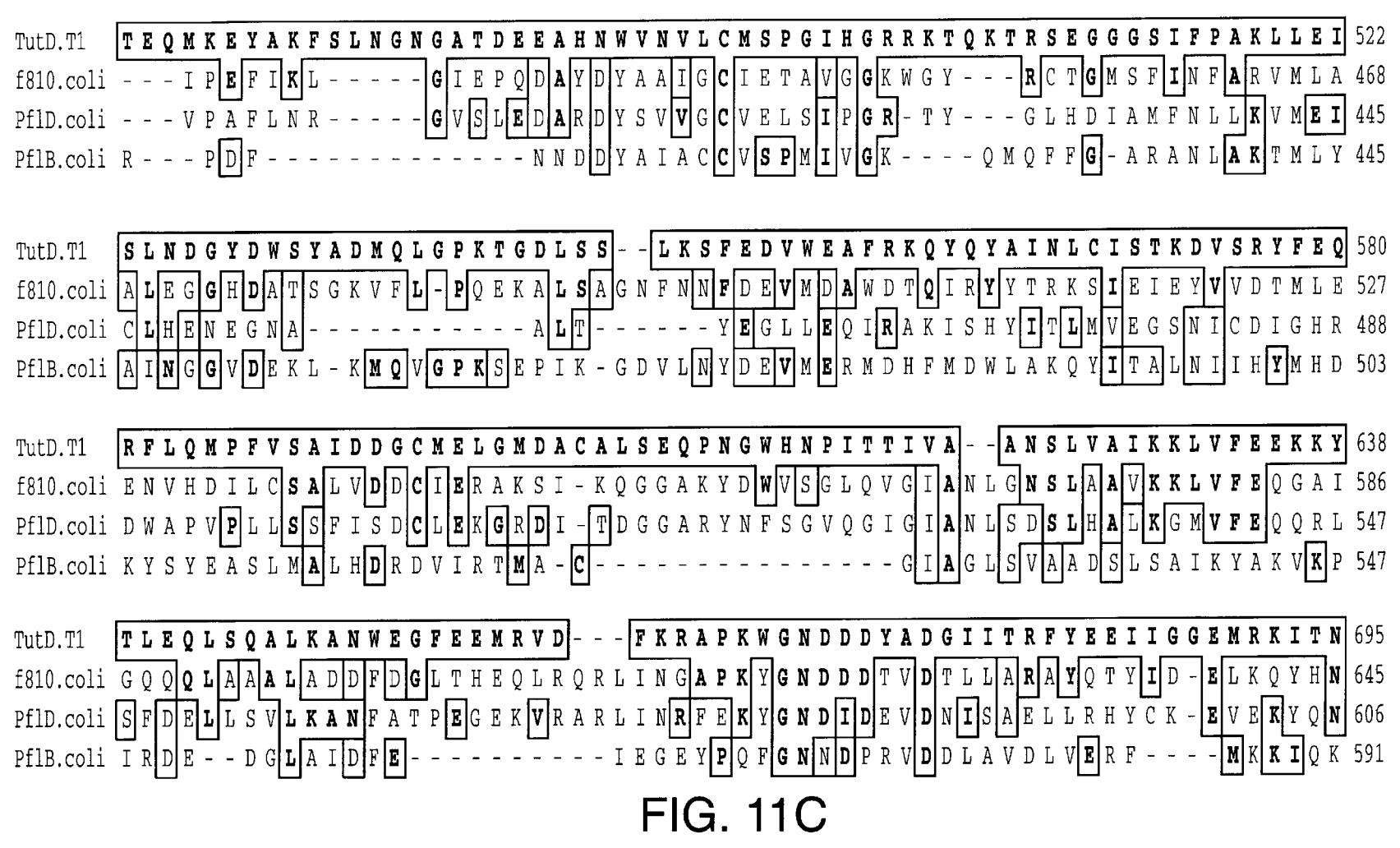
Figure 11D:
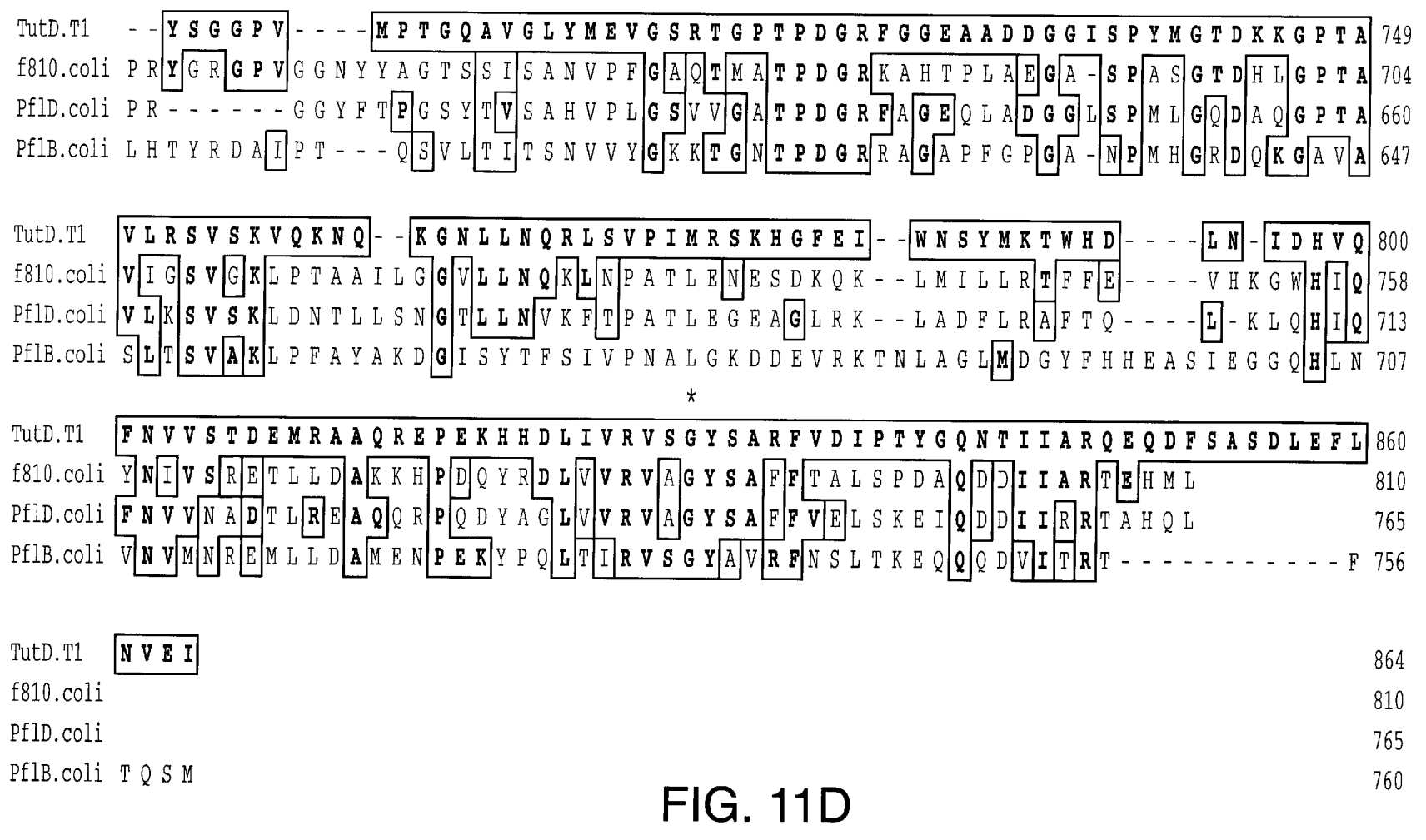

FIGS. 11A–D shows an expanded amino acid sequence of the tutD gene product (SEQ ID NO: 14).

FIGS. 13A–B shows the amino acid sequence of the tutE gene product (SEQ ID NO: 16).

FIG. 18 shows the nucleic acid sequence of the tutH gene (SEQ ID NO: 43).

FIG. 19 shows the amino acid sequence of the tutH gene product (SEQ ID NO: 44).

FIG. 20 presents a comparison of the predicted amino acid sequence of the TutH protein (SEQ ID NO: 44) to the predicted sequences of the NorQ proteins from *P. halodenitrificans* NorQ.Phalo (SEQ ID NO: 37), *P. denitrificans* NorQ.Pdeni (SEQ ID NO: 38), and *R. sphaeroides* NorQ.Rsph (SEQ ID NO: 40), and the NirQ protein from *P. stutzeri* NirQ.Psst (SEQ ID NO: 39). The region defined as a putative ATP/GTP binding domain is shown with a line above it (position 47 to 54 of TutH). Amino acids identical to the tutH translation are shaded and conserved amino acids are boxed. Dashes indicate gaps introduced by the computer program to maximize the alignment score.

FIG. 21 shows the nucleic acid sequence of the tutI gene (SEQ ID NO: 45).

FIG. 22 shows the amino acid sequence of the tutI gene product (SEQ ID NO: 46).

FIG. 24 shows the nucleic acid sequence of the tutF gene (SEQ ID NO: 47).

FIG. 25 shows the amino acid sequence of the tutF gene product (SEQ ID NO: 48).

FIG. 26 shows the nucleic acid sequence of the tutG gene (SEQ ID NO: 49).

FIG. 27 shows the amino acid sequence of the tutG gene product (SEQ ID NO: 50).

DESCRIPTION OF THE INVENTION

This invention relates to biological treatment of organic compounds, and particularly to the degradation of toluene. Toluene, along with benzene and xylenes, is a common contaminant of ground and surface water. Toluene has been classified by the U.S. Environmental Protection Agency as a priority pollutant due to its ability to depress the central nervous system and to enhance the effect of known carcinogens.

Anaerobic toluene degrading bacterial strains have been isolated. Most importantly, mutants have been obtained. These mutants fall into two classes, one class that fails to metabolize toluene, and another class that metabolizes toluene but fails to use it as a growth substrate.

Figure 1:
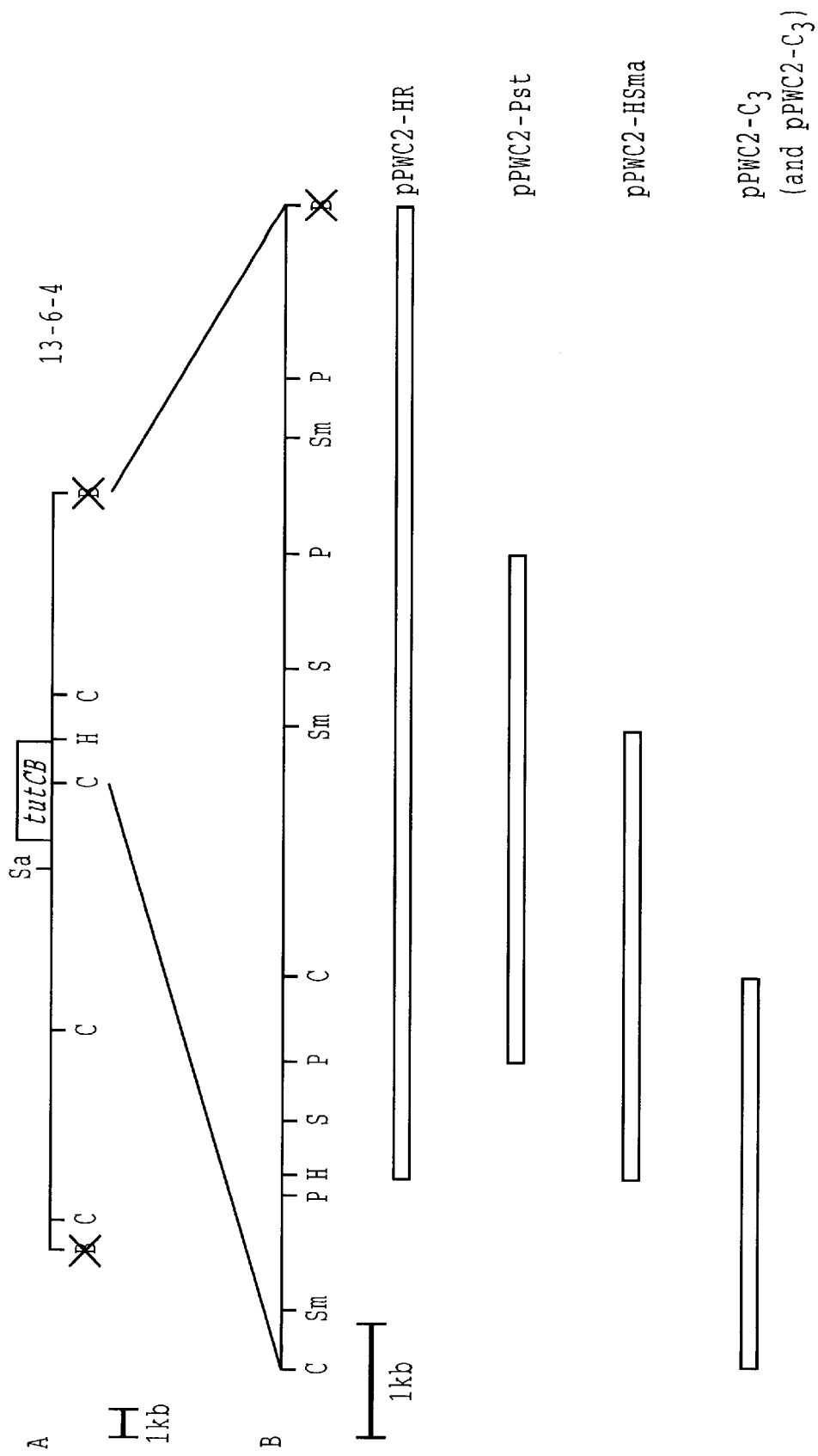
FIG. 1 shows the restriction map of a cosmid clone capable of restoring the ability to grow on toluene in toluene-nondegrading mutants.

A cosmid library was generated from total DNA isolated from the toluene-degrading bacterium strain T1. Triparental matings were used to identify a clone that restored the ability of mutants to grow on toluene and utilize it as a carbon source. This clone has now been characterized (FIG. 1 shows the restriction map). The DNA of this clone has now been sequenced and the genes identified are believed to be both regulatory and structural.

Regulatory Genes

The sequence of the cloned SacII-ClaI-ClaI fragment (approximately 6.4 kb containing the tutB gene and the tutC gene), that fully complements the tutB-16 mutation and carries all the information necessary to restore the ability to utilize toluene, is shown in FIGS. 2A–D (the restriction sites for SacII and ClaI are indicated in FIG. 1 as "Sa" and C" respectively, although not all SacII sites are shown; BamHI, HindII, PstI, SmaI and SalI sites are indicated as "B", "H", "P", "Sm" and "S", respectively). The subclone complements the mutation when inserted into the pRK415 vector (described below) in either orientation. This strongly suggests that the subclone provides all the cis acting factors necessary for gene expression and the vector does not provide any elements essential for expression of the insert.

Figure 3:
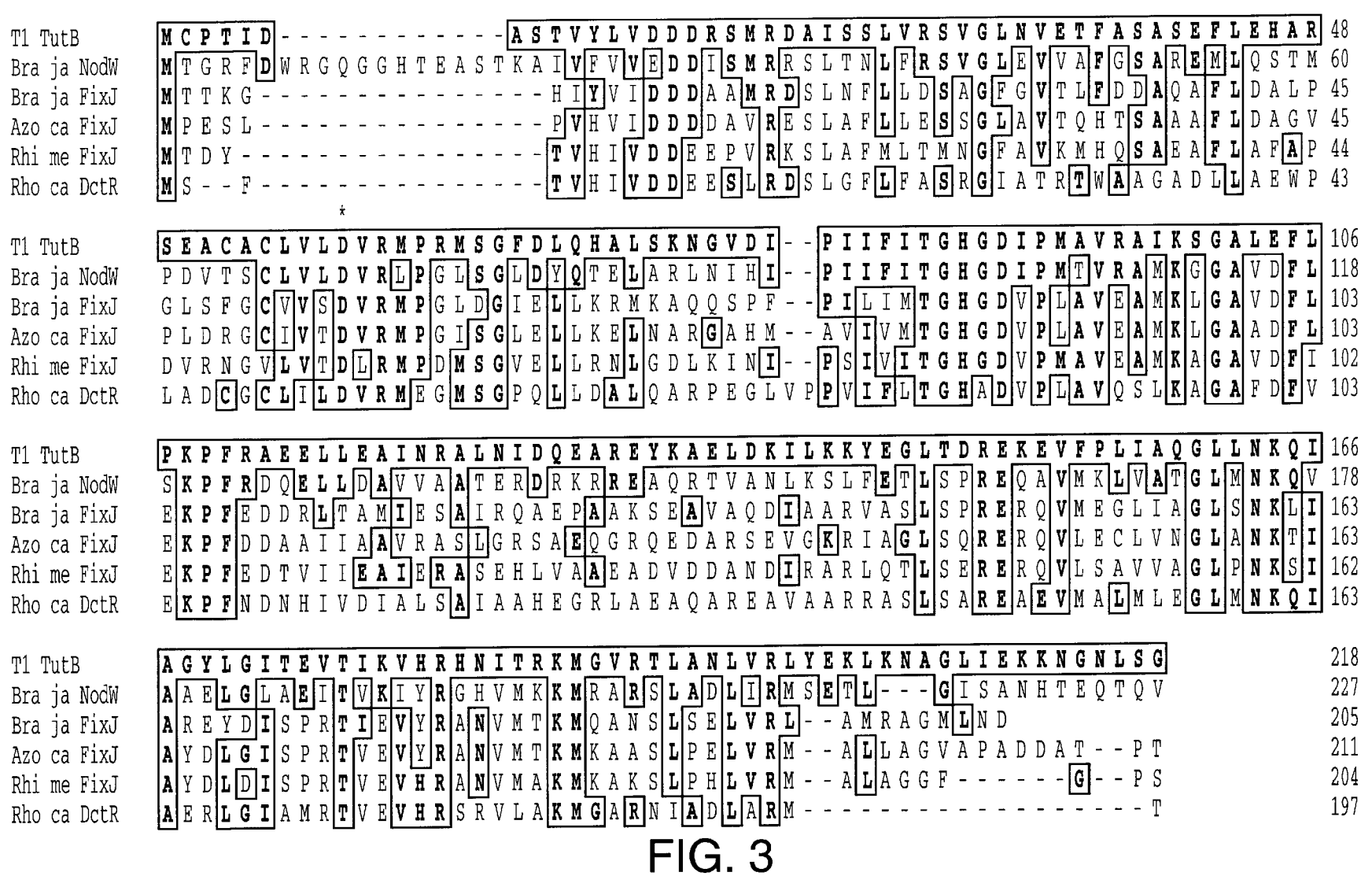

DNA sequence analysis of the fragment has identified an open reading frame that has homology to the nodW gene product of *B. japonicum* and other proteins presented in FIG. 3. All of these proteins have been identified as DNA binding regulatory proteins and members of the two component family of signal transduction proteins. All have phosphorylation sites at a conserved aspartic acid residue. The tutB gene product also has an aspartic acid residue in the analogous location, at amino acid 58.

Figure 4A:
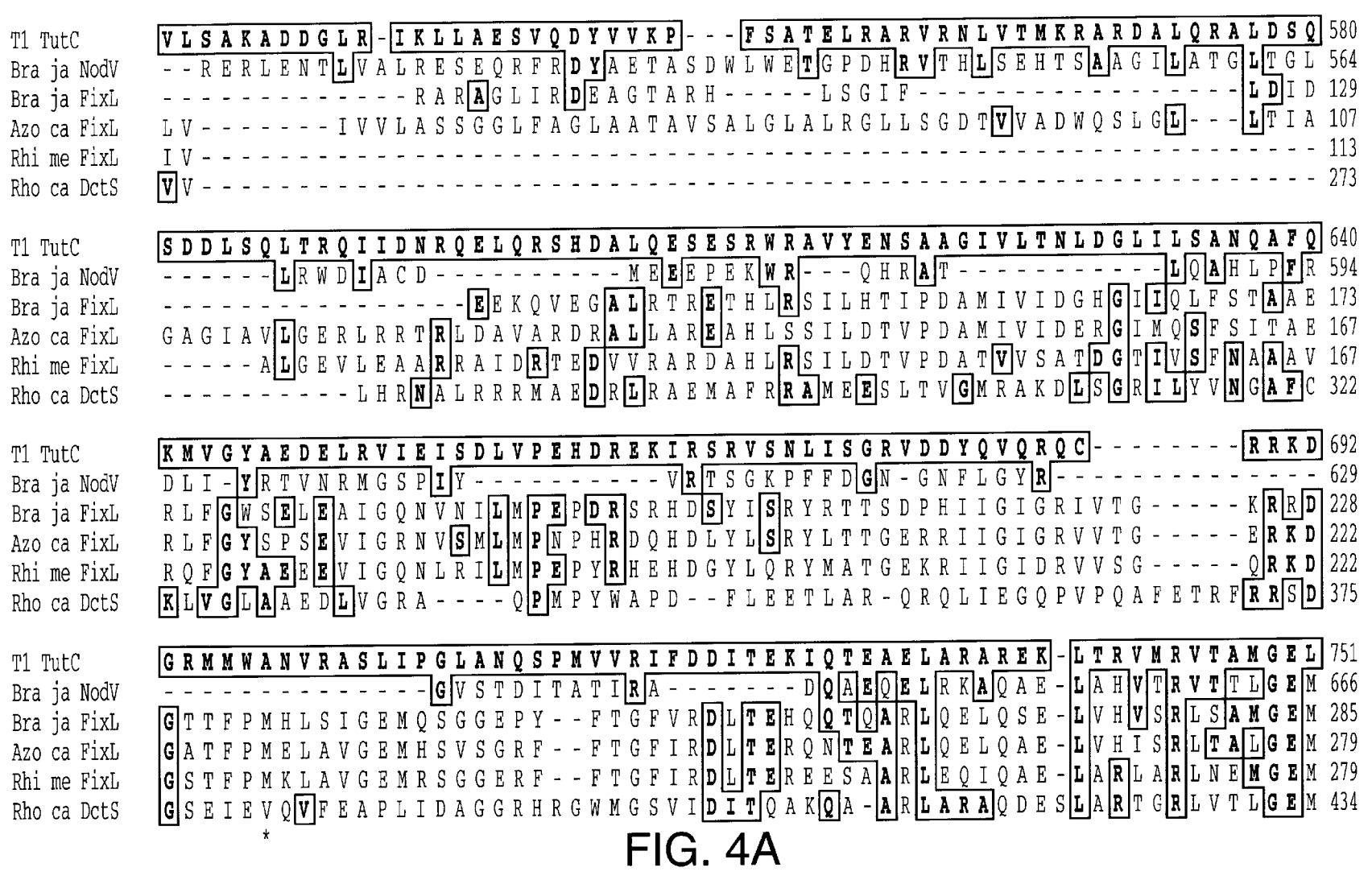
Figure 4B:
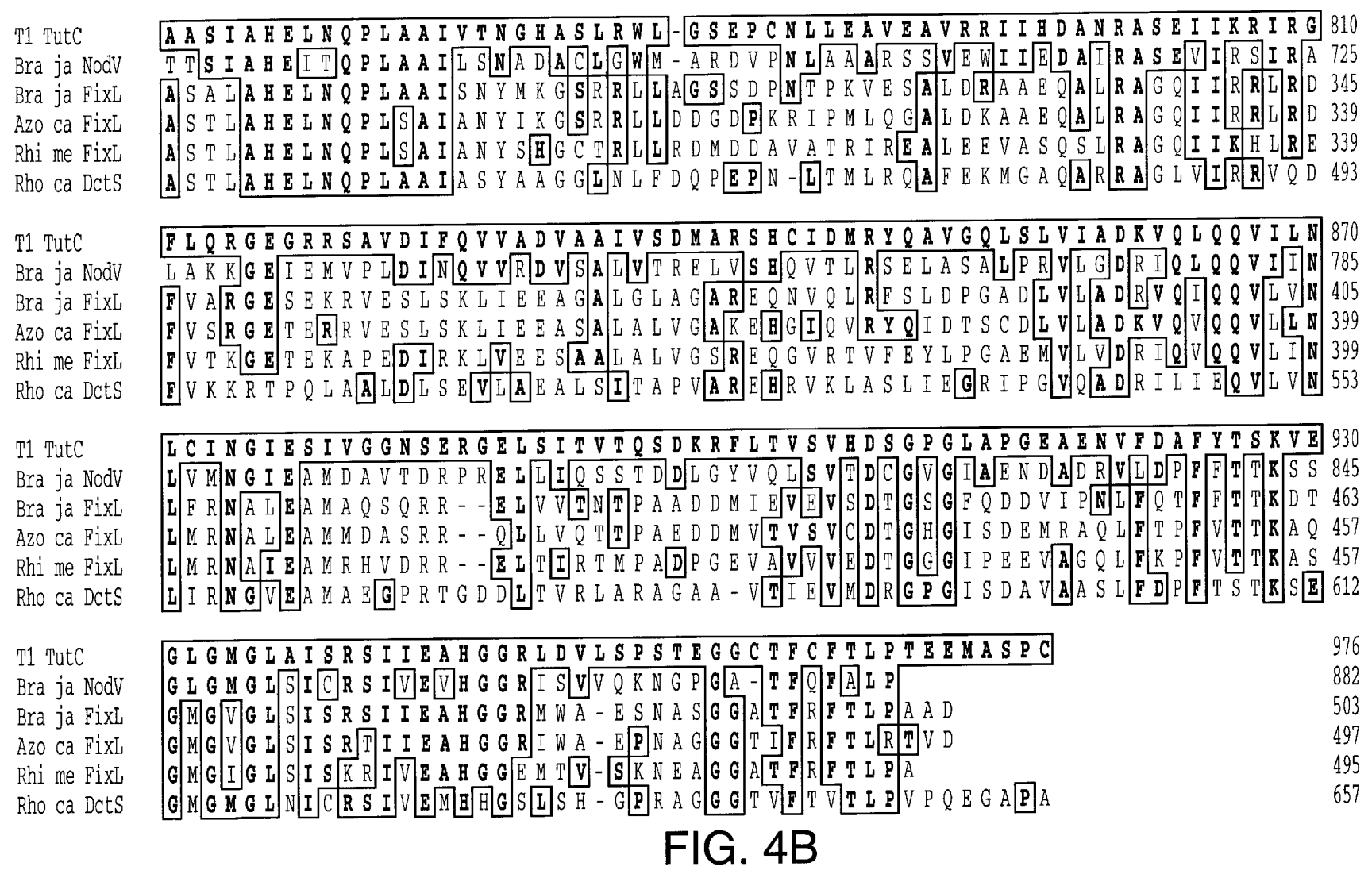

Additional DNA sequence analysis has identified a second open reading frame upstream of the tutB gene. This open reading frame, named tutC, has homology to the nodV gene product of *B. japonicum* and other proteins presented in FIGS. 4A–B. These gene products are proposed to serve as the sensor protein in the two component regulatory system). In their role as sensor proteins, they must autophosphorylate and then transfer the phosphate to the DNA binding protein. The site of autophosphorylation is a histidine residue that is conserved in all the systems. The tutC gene product has a histidine residue in the analogous location at amino acid 757. As can also be seen in FIGS. 4A–B, the homology of the sensor proteins extends only about 400 amino acids. This region is proposed to be the transmitter domain, the part of the protein that sends the regulatory signal to the DNA binding protein. The remainder of the protein presumably serves to detect the signal from the environment and would not be expected to be conserved across the different systems.

The proteins that have the greatest similarity to the tutCB gene products appear to regulate a diverse set of genes. Both FixL/FixJ from *R. meliloti* and from *A. caulinodans* regulate genes involved in nitrogen fixation, while FixL/FixJ from *B. japonicum* are proposed to regulate anaerobic respiratory genes. The nodVW gene products of *B. japonicum* play a role in the nodulation process, while the dctSR gene products of *R. capsulatus* serve as regulators of C4-dicarboxylate transport. It is apparent that these genes function in a similar manner but the classes of genes they regulate have little in common.

Structural Genes

Figure 5B:
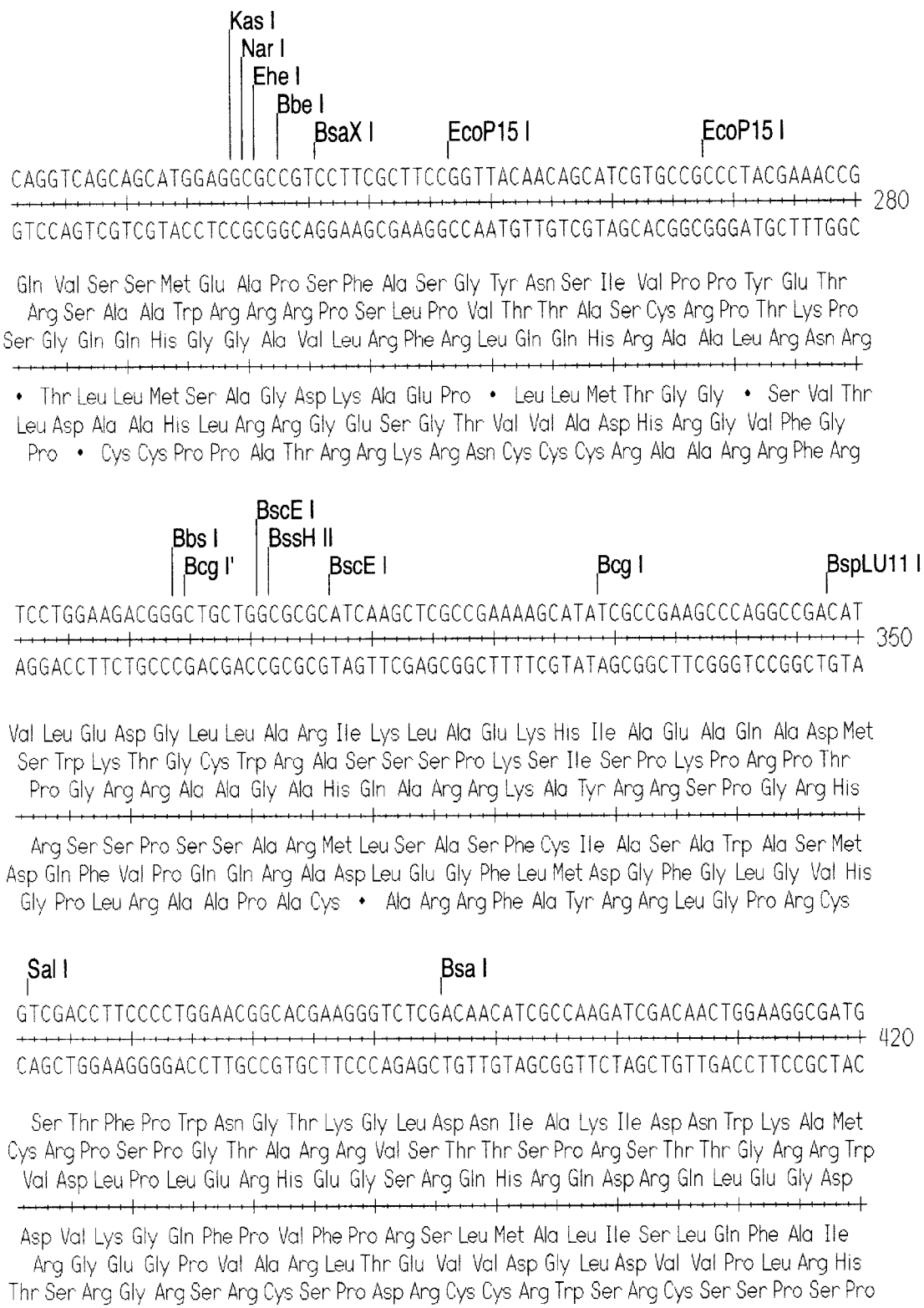
FIGS. 5A–P shows the nucleic acid sequence of the tutD gene (SEQ ID NO: 11).
Figure 5E:
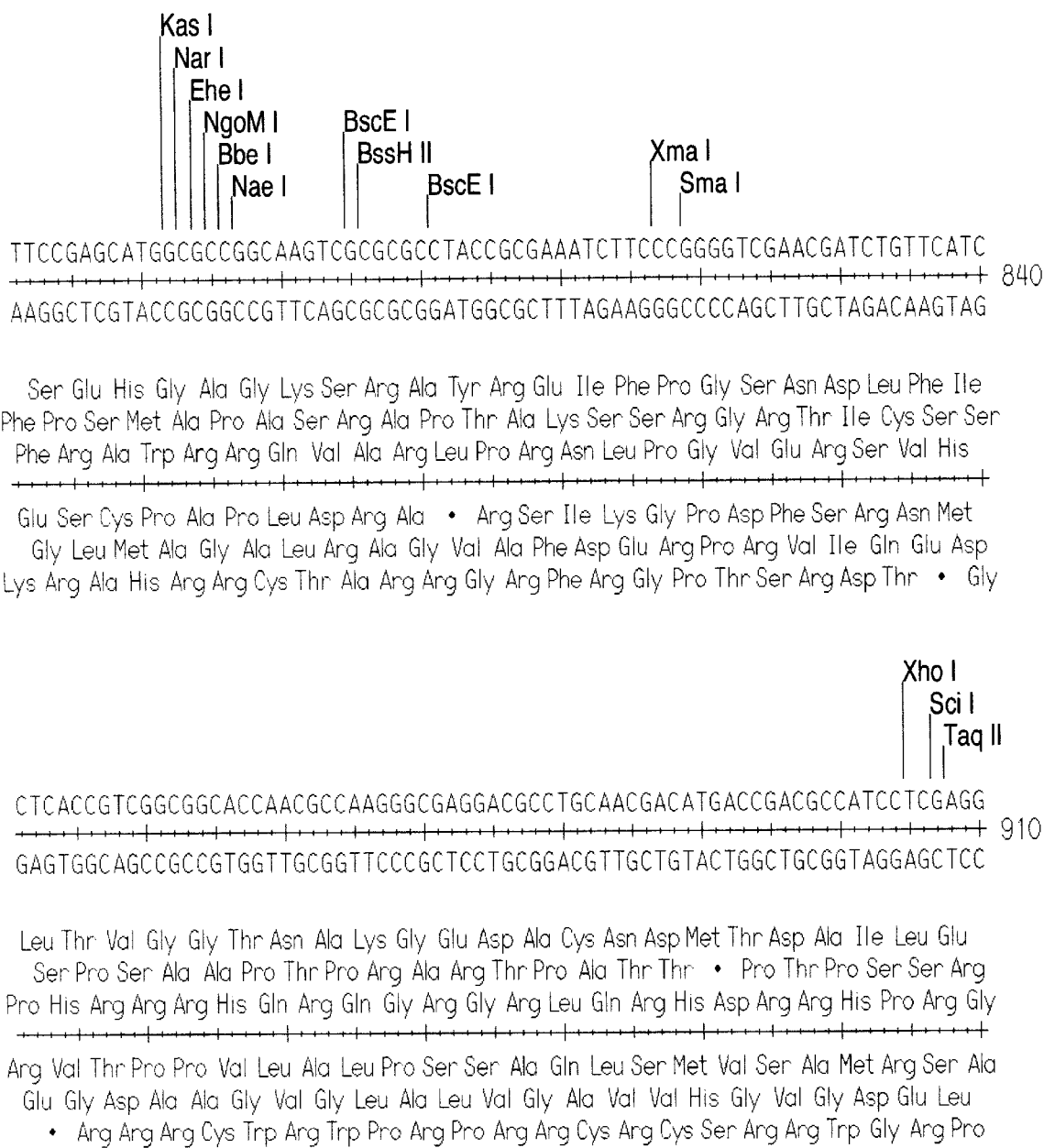
Figure 12G:
FIGS. 12A–Y shows an expanded nucleic acid sequence encompassing both the tutD and tutE gene (SEQ ID NO: 15).
Figure 12J:
Figure 12P:
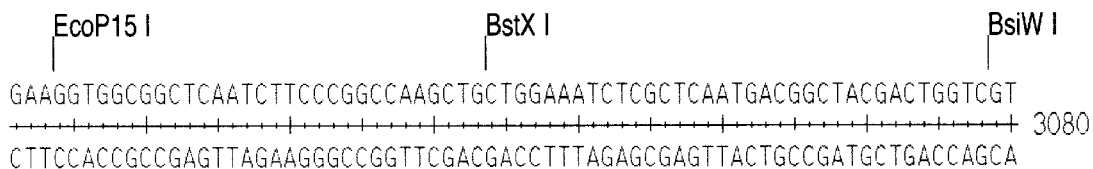
Figure 12R:
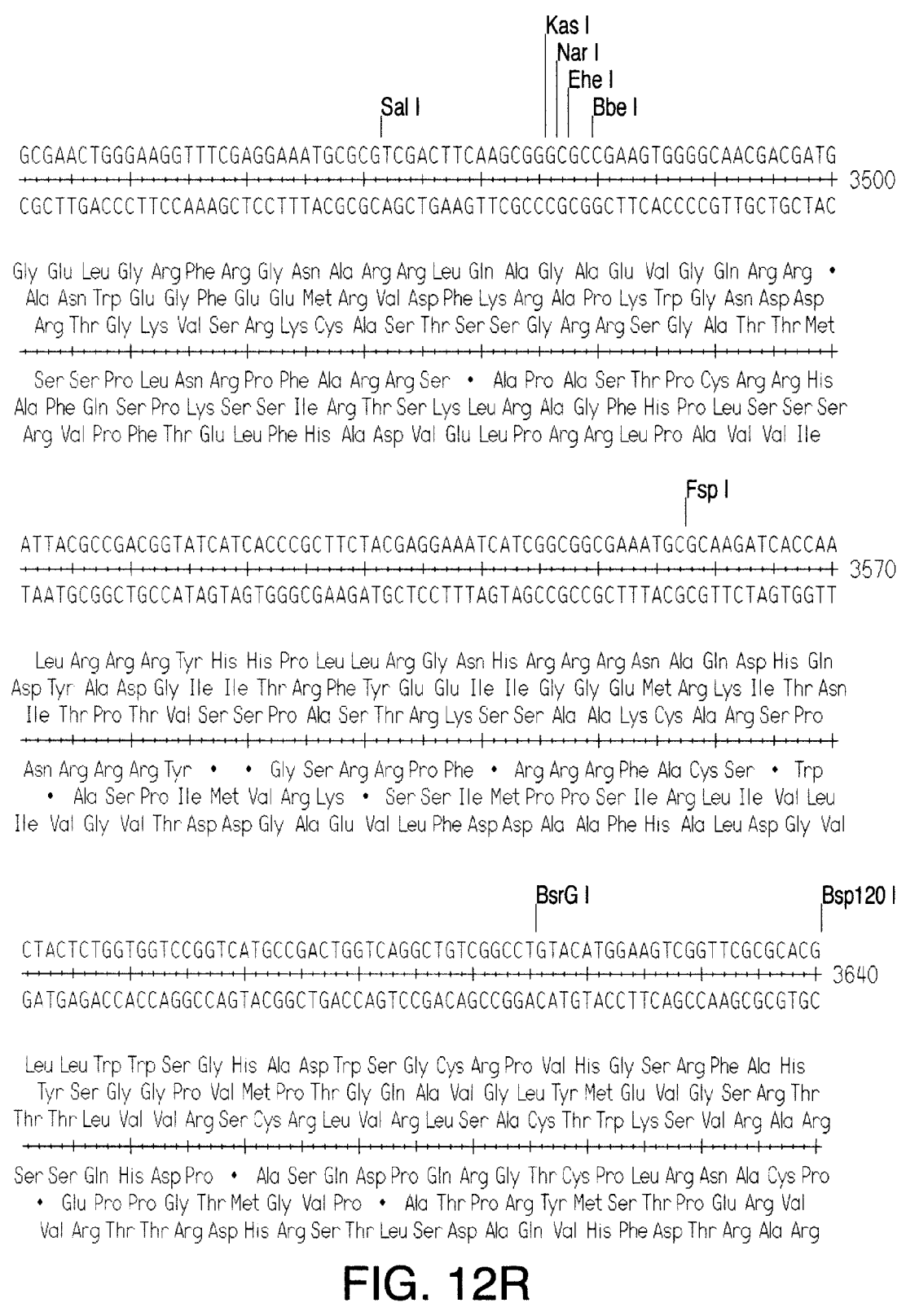

Sequencing of another region of the cosmid clone has revealed the tutD gene (FIGS. 5A–O shows the sequence of an approximately 3.1 kb fragment) and part of the tutE gene (FIGS. 6A–C). An expanded tutD gene is presented in FIGS. 12A–Y (FIGS. 12A–Y shows the sequence of approximately 5 kb fragment) with a corresponding amino acid sequence presented in FIGS. 11A–D (shown aligned with other pyruvate formate lyases). An analysis of this sequence shows that tutD encodes a protein having homologies with the pyruvate formate lyase from *E. coli* (the PflD gene Genebank G418519) and from *Clostridium pasteurianum* (Genebank G1072361) (FIGS. 7A–C). Other pyruvate formate lyases also show homologies (not shown).

Pyruvate formate lyase catalyzes the conversion of pyruvate and CoA to acetyl-CoA and formate, which is the key step of the glucose fermentation route in anaerobically grown *E. coli* cells. See generally, Knappe and Wagner, *Methods Enzymol.* 258:343 (1995). The active form of pyruvate formate-lyase (PFL) from *Escherichia coli* contains a glycyl radical in position 734 of the polypeptide chain which is produced post-translationally by pyruvate formate-lyase-activating enzyme (PFL activase) using S-adenosylmethionine (AdoMet) and dihydroflavodoxin as co-substrates. A. F. Wagner et al., "The free radical in pyruvate formate-lyase is located on glycine-734," *Proc. Natl Acad. Sci. U.S.A.* 89, 996–1000 (1992). The glycyl radical has been shown to participate in catalysis by guiding the carbon-carbon bond cleavage step along a radical-chemical route. The radical is thought to interact with a cystein residue; indeed, a reversible hydrogen transfer, induced by substrate binding, has been proposed between the Gly-734 resting-state spin localization and Cys-418, whose thiyl radical will function as the "working radical" for substrate processing.

It is not known how the homologue of the present invention functions. However, the comparison shown in FIGS. 7A–C reveals the essential glycine (marked in the Figure with a '*'). While an understanding of the precise mechanism is not necessary to the successful practice of the invention, it is now known that a cysteine of the tutD gene product is also involved in the transfer that is ultimately directed to the methyl group of toluene (see discussion below). Again, while it is not necessary to the successful practice of the invention, the lack of homology at the 5' end of the tutD gene suggests that this portion of the gene product involves the unique substrate recognition.

Transcriptional Organization and Regulation

Data presented herein is consistent with the toluene regulated tutE and tutFDGH genes of *T. aromatica* T1 being organized into two operons. Additionally, these data are consistent with the tutF, tutD, tutG, tutH, and tutI genes being organized in a single operon and use the same transcriptional start site The tutEtutFDG genes of *T. aromatica* T1 are similar to the bssDCAB genes of *T. aromatica* K172. Specifically, the bssDCAB genes are regulated in response to toluene. However, the bssDCAB are organized into only one transcriptional unit. Since genes encoding subunits of the benzylsuccinate synthase enzyme (bssCAB) are included in the bssDCAB gene cluster, it is not surprising that they would be located together in a single operon. In contrast, since both the tutE and bssD gene products likely function as activators that enzymatically form a glycine free radical in the proteins encoded by the tutD and bssA genes respectively, it would not be completely unexpected that the activator proteins and the activated proteins are located on separate transcriptional units. Indeed, in the case of the pyruvate formate-lyase systems of *E. coli, Haemophilus influenzae,* and *Clostridium pasteurianum,* which show sequence similarities to the tutD/tutE genes and the bssA/bssD genes, the pyruvate formate-lyase activating protein is located on a different transcriptional unit from the pyruvate formate-lyase. See, Rödel, W., et al., Primary structure of *Escherichia coli* pyruvate formate-lyase and pyruvate formate-lyase activating enzyme deduced from the DNA nucleotide sequences., Eur. J. Biochem., 177:153–158 (1988).

Northern analysis of toluene grown *T. aromatica* T1 using probes derived from the tutF, tutD, and tutG genes all identified a mRNA transcript with a maximum size of about 5.0 kb.

Experimental

The following examples serve to illustrate certain preferred embodiments and aspects of the present invention and are not to be construed as limiting the scope thereof.

In the experimental disclosure which follows, the following abbreviations apply: eq (equivalents); M (Molar); $\mu$M (micromolar); N (Normal); mol (moles); mmol (millimoles); $\mu$mol (micromoles); nmol (nanomoles); gm (grams); mg (milligrams); $\mu$g (micrograms); L (liters); ml (milliliters); $\mu$l (microliters); cm (centimeters); mm (millimeters); $\mu$m (micrometers); nm (nanometers); ° C. (degrees Centigrade).

Strains And Plasmids

The *Escherichia coil* strains HB101, XL-1 Kan Blue (Stratagene, LaJolla, Calif.), and XL-1 Blue (Stratagene), used to propagate and transfer DNA, were transformed by the calcium chloride technique or were purchased from the company as competent cells. Strain HB101(pRK2013) (Kan$^R$) contains a helper plasmid that permitted mobilization of cosmids and plasmids into the T1 strain background.

Plasmids used in this study include pLAFR3 for construction of the genomic cosmid library, pRK415 (FIG. 8) for construction of subclones and matings, and the pBluescript vector (Stratagene) for subcloning and preparation of DNA fragments.

Ditta et al. [Plasmid 13(1985) 149–153] constructed the moderately-sized cloning vector pRK404 from pRK290. In order to increase the cloning usefulness of this plasmid, the EcoRI site outside the polylinker was deleted and the polylinker, derived from pUC9, was replaced by the pUC19 polylinker (FIG. 9). The resulting construct, pRK415 (FIG. 8), permits cloning into all of the polylinker restriction sites of pRK404 as well as the additional unique EcoRI, XbaI, KpnI and SstI sites. The SphI site of the pUC19 polylinker is not generally useful because an SphI site occurs elsewhere in the plasmid. The unique DraI, ApaI, SmaI and Eco RV sites are convenient for mapping the orientation of inserted DNA fragments into the polylinker sites. Since pRK415 retains the lac promoter of pRK404, bacterial genes inserted in the proper orientation into the polylinker should be expressed in E. coli. XGal color screening can also be used for plasmid constructions in E. coli. pRK415 has proven useful for subcloning and maintaining small DNA fragments in field isolates of P. syringae pv. glycinea and other P. syringae pathovars. If fragments larger than approx. 5 kb are cloned, however, from a few to more that 50% of the P. syringae exconjugants have been observed to suffer deletions in the inserted DNA.

Figure 8:
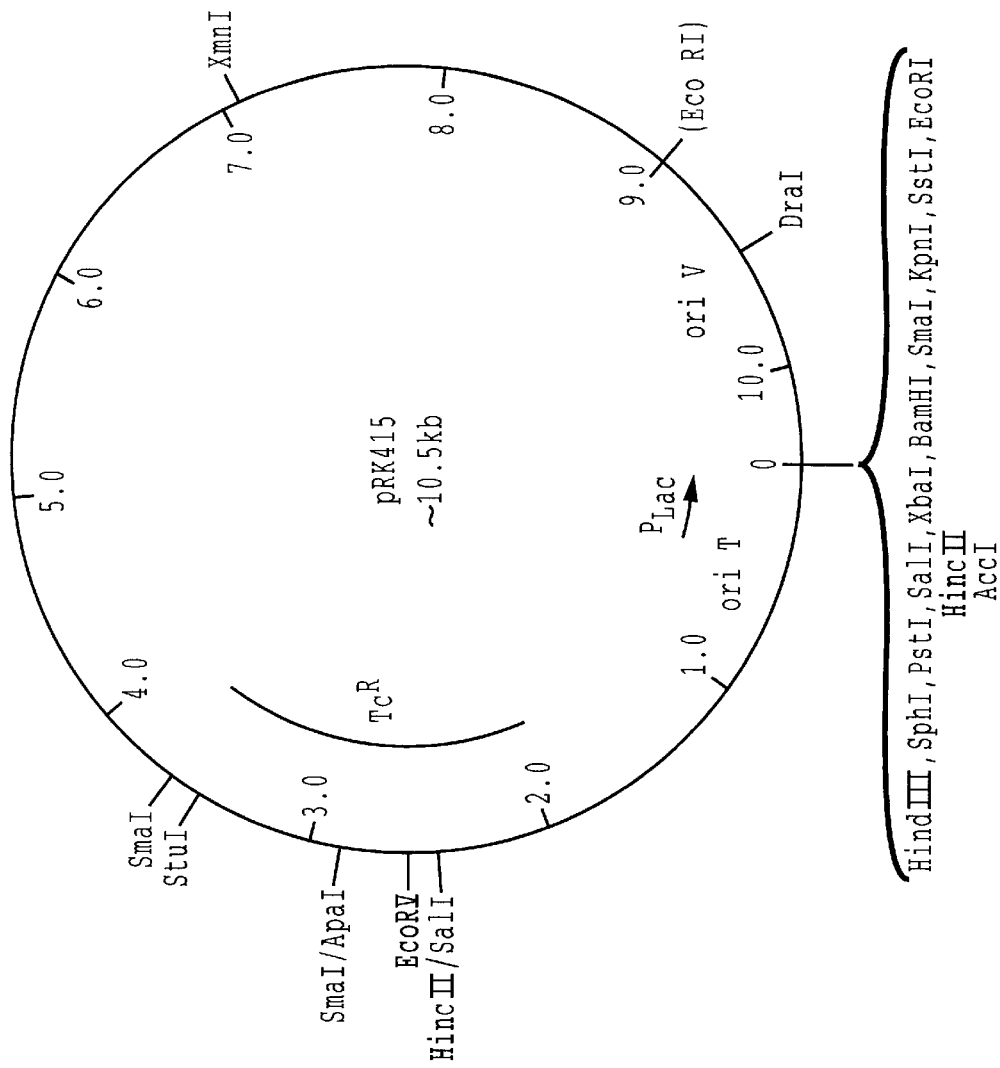
FIG. 8 shows the restriction map for pRK415.

The restriction map for pRK415 is shown in FIG. 8. This DNA was transformed into strain JM-101, a blue colony on XGal medium was retained and the resultant plasmid designated pRK415. The deleted EcoRI site is shown in brackets. Restriction sites separated by a slash occur close together.

Media

Strain T1 and all strains derived from T1 were grown on either Brain Heart Infusion (BHI, Difco Laboratories, Detroit, Mich.) medium or a mineral salts medium (vitamins and yeast extract omitted). Unless otherwise specified, toluene (0.3–0.5 mM) or pyruvic acid (5 mM) were used as the carbon source to supplement the minimal medium. Nitrate was supplied to a concentration of 10 to 20 mM unless otherwise specified. Plates always contained 2% Agar Noble (Difco Laboratories). Liquid media was prepared and placed in serum bottles which were then tightly stoppered with teflon coated butyl rubber and aluminum crimp seals. Anaerobic conditions were generated by evacuation and subsequent filling of the bottles with argon. This process was performed a total of four times. E. coli was grown in Luria-Bertani agar or broth (LB) or on BHI agar plates.

The antibiotics kanamycin (used at 50 mg/ml) and tetracycline (used at 25 mg/ml) were supplied where indicated. A 12.5 mg/ml stock of tetracycline was made in ethanol. Upon addition to minimal media the tetracycline served to select for the cosmid while the ethanol (final concentration of approximately 17 mM) served as the carbon source for the transconjugant strains.

Mutagenesis

Mutagenesis was carried out on strain T1 under aerobic conditions. Strain T1 was grown in a rich medium (BHI+nitrate), washed, and resuspended in 100 mM sodium citrate buffer (pH 5.5) to a cell density of about $3.5 \times 10^8$ cells/ml. The cell suspensions were treated with nitrosoguanidine (final concentration of 50 $\mu$g/ml) and aliquots were removed at various times. The mutagenized cells were harvested by centrifugation and washed with 100 mM potassium phosphate buffer (pH 7.0) to remove the nitrosoguanidine and then resuspended in the phosphate buffer. The treated cells were tittered on BHI plates to establish a killing curve. The treatment group that resulted in about 50% killing was used for the isolation of mutants. Treated cells were diluted in phosphate buffer to yield 100–200 colonies per plate and spread onto minimal medium plates supplemented with nitrate and pyruvic acid. After 5 days of incubation (30° C. anoxic) colonies were replica plated to rich medium and minimal medium with nitrate and toluene supplied in the vapor phase. The plates were placed in an anaerobic incubation jar which was then sealed and filled with hydrogen gas (to 12 psi). In the presence of a palladium catalyst oxygen is removed by reaction with the hydrogen producing water and resulting in an anoxic atmosphere. After 5 days of anaerobic incubation (30° C.) colonies that grew on the rich medium but not on the minimal medium with nitrate and toluene were picked and streaked onto rich plates. The strains were retested for the ability to grow with toluene serving as the sole carbon source in both liquid and solid media. The strains were later tested for the ability to utilize toluene and produce the dead-end products benzylfumaric acid and benzylsuccinic acid in liquid culture.

Chemicals

Tetracycline was purchased from Fluka (Ronkonkoma, N.Y.). Kanamycin and N-methyl-N'-nitro-N-nitrosoguanidine (nitrosoguanidine) were obtained from Sigma (St. Louis, Mo.).

Construction Of Cosmid Library

Strain T1 was grown in 500 ml of minimal+nitrate+ethanol medium under anaerobic conditions and genomic DNA was isolated. The DNA was purified by two successive CsCl gradient centrifugations. A partial digest of the DNA with Sau3AI enzyme was carried out and fragments of 15–25 kb were isolated on a 10–40% glycerol gradient. These fragments were ligated into the BamHI site of pLAFR3. The resulting ligation mix was packaged into phage heads using a Packagene kit from Promega (Madison, Wis.). E. coli strain HB101 was infected with the phage and plated onto LB+tetracycline plates. The resulting 750 colonies were streaked on plates of the same medium and the isolates served as the genomic library for obtaining the cosmid clone.

Triparental Mating

Triparental matings were carried out. Mutants of strain T1 were grown for 3 days in minimal+nitrate+pyruvic acid media. HB101 (or XL-1 Kan Blue) carrying the donor cosmid or plasmid was grown in LB+tetracycline overnight. HB101(pRK2013) was grown in LB+kanamycin overnight. One ml of each culture was centrifuged and resuspended in an equal volume of 100 mM phosphate buffer (pH 7). Ten $\mu$l of each culture was spotted (one on top of the other) onto a BHI+nitrate plate. After a three day incubation at 30° C. in an anoxic environment, the resulting growth was scraped off the plate, resuspended in phosphate buffer, and spotted onto a minimal agar plate containing pyruvic acid, nitrate, ethanol, and tetracycline to select for transconjugants. After another three day incubation, cells from the resultant growth were streaked onto the same media and grown in a sealed jar in the absence of oxygen. After three days of incubation, single transconjugant colonies were isolated from these plates and tested for complementation.

Restriction Mapping And Subcloning

DNA manipulations were carried out as described by Maniatis et al. All enzymes were obtained from New England Biolabs (Beverely, Mass.). Cosmid 13-6-4 was the original clone isolated. Plasmid pPWC1-HSma was constructed in two steps. The first step entailed deleting the HindIII fragment of 13-6-4 (from the HindIII site internal to the insert to the HindIII site (not shown in FIG. 1) in the pLAFR vector just beyond (to the right) the BamHI site) by digestion of 13-6-4 with HindIII and subsequent religation. The resulting cosmid (13-6-4-ΔH) was digested with the enzymes HindIII and SmaI and the 3.8 kb DNA fragment was isolated and inserted into HindIII-SmaI digested pBluescript. The HindIII-SmaI fragment was transferred to pRK415 by cutting both plasmids with the enzymes XbaI and KpnI and then isolating and ligating the fragments. The resulting plasmid was designated pPWC2-HSma (see FIG. 1). Plasmid pPWC1-$C_s$ was constructed by cutting 13-6-4 with ClaI enzyme, isolating the small (3.3 kb) DNA fragment and inserting it into ClaI digested, calf intestinal alkaline phosphatase treated pBluescript. The ClaI fragment was transferred into pRK415 by cutting PPWC1-$C_s$ and the vector with XbaI and KpnI enzymes (to generate pPWC2-$C_s$) or with KpnI and EcoRI enzymes (to generate pPWC2-$C_s'$, the reverse orientation of pPWC2-$C_s$) and ligating.

Restriction mapping was carried out with fragments inserted into the pBluescript vector to facilitate identification of restriction sites and to help place the sites on a restriction map. Digests were run on varying percentages of agarose gels with size standards to estimate the size of the fragments and to locate restriction sites.

Testing For Complementation

Cosmid clones and subclones constructed in pLAFR3 or plasmid subclones constructed in pRK415 were mated into the tutB-16 mutant background via the triparental mating technique. The resultant transconjugant strain was tested to determine if the subclone complements the mutation. First, the transconjugants were streaked onto minimal+nitrate plates in which toluene was supplied in the vapor phase. After 5–7 days of anaerobic incubation (30° C.), the subclones were scored for the ability to restore growth on toluene to the mutants. The transconjugants were also grown in sealed 50 ml serum bottles of minimal+nitrate (10 mM)+pyruvic acid (1 mM)+toluene (0.4 mM) liquid media with an argon headspace. After 3–4 days of incubation (30° C.) samples were withdrawn for toluene and dead-end product analysis (see below). The clones were scored for the ability to restore toluene utilization (in the presence of pyruvate) in liquid culture and for the ability to restore production of the dead-end metabolites under the same conditions to the mutants. If the transconjugate was positive for all three of these tests, the subclone was considered to complement the mutation.

Toluene Analysis

One ml samples of the culture to be tested were withdrawn anaerobically and added to 400 ml of pentane containing 1 mM fluorobenzene as an internal standard in a sample vial. One ml of the organic phase (into which toluene had been extracted) was injected using a CTC A200S autosampler (LEAP Technologies, Chapel Hill, N.C.) into an HP5890 gas chromatograph (Hewlett Packard, Palo Alto, Calif.) equipped with a Flame Ionization Detector, a DB-WAX column (J&W Scientific, Folsom, Calif.) and helium as the carrier gas. The injector temperature was set at 250° C., the detector at 300° C., and the column at 35° C. The amount of toluene present in each sample was quantified by comparison to external standards using the Chemstation software (Hewlett Packard).

Analysis Of Dead-End Products

Samples of the culture were withdrawn anaerobically with a sterile syringe flushed with argon. The samples were centrifuged (5 min., microfuge) and the supernatant was filtered through a 0.45 mm filter (Millipore, Bedford, Mass.) into a sample vial. Samples were analyzed by high pressure liquid chromatography using a Beckman System Gold HPLC (Fullerton, Calif.) equipped with a Gilson (Middleton, Wis.) autosampler and a C18 column (250 mm by 4.6 mm, particle size 5 mm, Beckman) with UV detection at 260 nm. The mobile phase was 30:68:2 methanol:water::acetic acid (vol/vol) at a flow rate of 1 ml/min. Peaks were identified by comparison to the external standards benzylmaleic acid and benzylsuccinic acid.

Plasmid DNA Preparation

In general DNA plasmid minipreps were performed. When larger scale preps were needed, Qiagen maxi-preps were carried out (Qiagen, Chatsworth, Calif.) according to the manufacturer's instructions.

DNA Sequence Analysis

DNA was sequenced (both strands) by the dideoxy method of Sanger et al. with (a-$^{35}$S)dATP serving as the label. Sequenase enzyme (modified T7 polymerase) and reagents were obtained in a Sequenase kit from U.S. Biochemicals (Cleveland, Ohio). The Bluescript vector and the T3, T7, -20, and M13 reverse primers used for sequence analysis were obtained from Stratagene. An Erase-a-Base System (Promega, Madison, Wis.) was used to generate deletions of the cloned DNA inserted in the Bluescript vector for sequence analysis. Synthetic oligonucleotide primers were also purchased so that sequence data could be obtained to fill in gaps not covered by the deletions. Searches for protein sequence similarity were carried out against the Swissprot data base (release 32.0) of protein sequences using the FASTA and BLAST programs in the GCG software package (version 7.2) (GCG software, Madison, Wis.). Multiple sequence alignment was performed with the Lasergene software package from DNASTAR (Madison, Wis.).

RNA Preparation

In some embodiments of the present invention, wild type *T. aromatica* T1 cells were grown under denitrifying conditions on a mineral salts medium (vitamins and yeast extract omitted) with either pyruvate or toluene serving as the carbon source. When the density of the culture reached about $4 \times 10^7$ cells/ml, 35 ml of the culture was processed using the RNeasy mini kit from Qiagen according to the manufacturer's instructions. Samples were run on a gel to confirm that there was no RNA degradation.

Northern Blot Analysis

In some examples recited wherein, between 0.25 and 1 $\mu$g of total RNA was run on a agarose gel containing formaldehyde. Ethidium bromide was added to each RNA sample to a final concentration of 31 $\mu$g/ml before denaturation and loading to allow visualization of the RNA without affecting the efficiency of RNA transfer to the membrane. After electrophoresis, the gels were treated with 0.05 N NaOH for 30 min; 0.1 M Tris pH 7.5 for 30 min; and 10×SSC (1×SSC is 0.15 M NaCl and 0.015 M sodium citrate) for 30 min. RNA was transferred to a Hybond-N Membrane (Boehringer Mannheim, Indianapolis, Ind.) by capillary blotting over night. The RNA was cross-linked to the membrane by baking at 80° C. for at least 1 hr in a vacuum oven. Antisense, digoxigenen-labeled, gene specific DNA probes spanning nucleotides 97 to 398 of the predicted tutD coding region (302 nuclcotides), 106 to 792 of the predicted tutE coding region (687 nucleotides), 14 to 152 of the predicted tutF coding region (139 nucleotides), 36 to 241 of the predicted tutG coding region (206 nucleotides), and 59 to 470 of the predicted tutH coding region (412 nucleotides) and 234–555 of the predicted tutI coding region (322 nucleotide) were made by PCR. Prehybridization was performed at 42° C. for at least 1 hr in DIG Easy Hyb solution (Boehringer Mannheim). The probe was heated to 95° C. and then added to the prehybridization mix at a final concentration of about 50 ng/ml. Hybridization was continued overnight at 42° C. The blots were washed twice with 2×SSC, 0.1% SDS (5 min, room temperature) and twice with 0.5×SSC, 0.1% SDS (15 min, 65° C.). The probes were visualized on BioMax ML film (Eastman Kodak, Rochester, N.Y.) using the DIG High Prime DNA Labeling and Detection Starter Kit II (Boehringer Mannheim) according to the manufacturer's instructions with the chemiluminescence substrate CSPD. Digoxigenin-labeled RNA (Boehringer Mannheim) was also loaded on the gel to serve as a size marker.

Primer Extension Analysis

The Primer Extension System-AMV Reverse Transcriptase kit (Promega, Madison, Wis.) was used according to the manufacturer's instructions. About 2.5 µg of total RNA was used for each reaction. Primers F-PE1 (CTG CTT GCA TGT GGT GGT TC) (SEQ ID NO:51) binding from 4 to 23 bp downstream of the translational start and E-PE3 (GAT CCA CCA CGA CCA TAG AAG) (SEQ ID NO:52) binding 5 bp upstream to 15 bp downstream of the translational start were labeled with T4 polynucleotide kinase (New England Biolabs, Beverly, Mass.) and ($\gamma$-$^{32}$P)ATP (New England Nuclear, Boston, Mass.). The labeled primers were used for both the primer extension reaction and for the sequencing ladder. The primer extension reaction products and the sequencing ladder were run on a standard 8M urea 5% polyacrylamide sequencing gel.

Nuclease Protection Assay

The Multi-NPA RNA/DNA/Oligo Probe Protection Assay Kit (Ambion, Austin, Tex.) was used according to the standard protocols recommended by the manufacturer. About 5 µg of total RNA was used for each reaction. Antisense gene specific DNA probes of 354 bases (for tutE) or 623 bases (for tutF) spanning both the predicted transcriptional and translational start sites were synthesized by PCR (17) and labeled with T4 polynucleotide kinase (New England Biolabs) and (g-$^{32}$P)ATP (New England Nuclear). About 3×10$^5$ cpm of the probe was added to assay mix. After completion of the reaction, the products were run on a 8M urea 5% polyacrylamide gel.

Site-Directed Mutagenesis

The QuickChange site directed mutagenesis kit (Stratagene) is used to make mutations in the tutD gene. To change the a glycine to an alanine, primers G828AF (GTGCGCGTTTCCGCCTACAGCGCTC) (SEQ ID NO: 41) and G828AR (GAGCGCTGTAGGCGGAAACGCGCAC) (SEQ ID NO: 42) are synthesized and used as directed. Plasmid pPWC3-C$_L$-SacII serve as the target for the mutagenesis. The resulting plasmids are sequenced to identify those containing the desired mutation. The 4.9 kb SacI/SacII fragment of three plasmids with the correct change are subcloned into plasmid pRK415 and used to test for complementation of the tutD17 mutation. To change the cysteine at position 492 to an alanine primers C492AF (CAACGTGCTGGCCATGTCGCCCGGCATCC) (SEQ ID NO: 53) and C492AR (GGATGCCGGGCGACATGCCCAGCACGTTG) (SEQ ID NO: 54) are synthesized and used in the same manner described above.

EXAMPLE 1

This example describes the isolation and characterization of tut mutants. Cells of strain T1 were grown and mutagenized with nitrosoguanidine as described above. Mutants were isolated from the treatment group that resulted in about 50% killing. Cells were diluted and plated onto minimal medium supplemented with nitrate and pyruvic acid to a density of about 100–200 colonies per plate. After about 5 days of incubation at 30° C. in the absence of oxygen the colonies were replica plated to both rich medium and minimal medium with nitrate and with toluene supplied in the vapor phase. After incubation, colonies that grew on the rich medium but failed to grow on the minimal medium with nitrate and toluene were chosen for further study. Of about 10,000 colonies screened, 32 candidates were isolated in this manner. These 32 mutant candidates were again tested for their ability to grow on minimal medium supplemented with nitrate and toluene both in liquid and on plates. Retesting the candidates identified seven mutants which were truly defective for toluene utilization. These seven were designated tut mutants for their defect in toluene utilization.

The seven tut mutants were tested for their ability to grow on various carbon sources. Four of the mutants are able to use benzoic acid and phenylpropionic acid as a sole carbon source while three are not able to use either substrate. Based on this observation, the first group is predicted to be blocked early in the toluene utilization pathway and were designated tutB mutants. The second group is blocked later in the pathway, probably in benzoic acid utilization. This group was designated tutA. These designations are not meant to imply that all mutants in a particular group are defective in the same gene or in the same step of the pathway, only that they utilize the same range of substrates.

The tut mutants were also tested for their ability to metabolize toluene when provided with both toluene and pyruvic acid in liquid media. Pyruvic acid was added to insure that the transconjugants grew and that there was no selective pressure for reversion of the mutation to occur. Although the tutB-16 mutant metabolized toluene slightly, none of the tutB mutants tested were able to metabolize toluene to the same extent as the wild type control. Similarly, the tutB mutants did not produce significant amounts of the dead-end products benzylsuccinic acid and benzylfumaric acid. Members of the tutA class of mutants were able to both metabolize toluene and produce the dead-end products. This result indicates that the tutB mutants are blocked in a step (or steps) that is common to both the metabolic degradation of toluene and the side reaction that produces the dead-end compounds or in the regulation of such a step (or steps).

EXAMPLE 2

Figure 23:
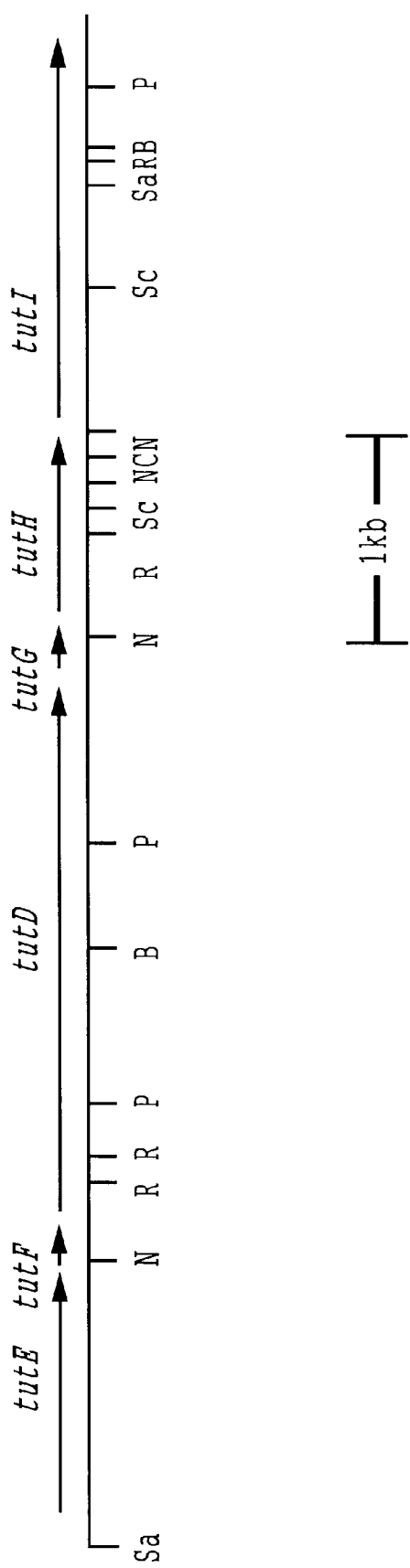
FIG. 23 presents a restriction map of the region of cosmid clone 13-6-4 containing the tutEtutFDGHI genes. The five identified open reading frames are indicated with arrows. Abbreviations are: B=BamHI, C=ClaI, N=NcoI, P=PstI, R=EcoRI, Sa=Sac II, Sc=SacI. Sites blocked by methylation are omitted from the figure.

This example describes the generation of T1 DNA library and the isolation of a clone that complements the tutB-16 mutant. It has previously been shown that pLAFR3 derived cosmids can be transferred into and stably maintained in the strain T1 background. Consequently, this vector was chosen for the construction of a genomic DNA library of strain T1. Genomic DNA was isolated from strain T1 as described above. A partial digest of the genomic DNA was carried out with the restriction enzyme Sau3AI and fragments of between 15 and 25 kb were isolated. These fragments were ligated into the BamHI site of pLAFR3. The resulting ligation mix was packaged into lambda phage heads and used to infect E. coli strain HB101. About 750 tetracycline resistant E. coli colonies were picked and formed the genomic library used to isolate clones that complement the tut mutations. The genomic T1 library constructed in pLAFR3 was introduced into a T1 derived strain carrying the tutB-16 mutation via a triparental mating. The donors for all the cosmids were E. coli strain HB101 derived strains, while E. coli HB101 carrying plasmid pRK2013 served as the helper to mobilize the cosmids. Transconjugants were selected on minimal medium supplemented with nitrate, pyruvic acid, and tetracycline and then screened for the ability to grow with toluene serving as the sole carbon source. One cosmid, designated 13-6-4, restored the ability of the tutB-16 carrying T1 strain to grow on toluene. This cosmid also restored the ability of the mutant strain to metabolize toluene in the presence of pyruvic acid in liquid culture and produce the dead-end products benzylsuccinic acid and benzylfumaric acid in this culture. This cosmid was used for further subcloning and restriction mapping to specifically identify the region containing the complementing gene. In an effort to determine where on the cosmid the fragment that complements the tutB-16 mutation lies, deletions and subclones were constructed. All subclones were made in plasmid pRK415, a broad host range tetracycline resistance vector that can be conjugatively transferred into the T1 background in the same manner as pLAFR3 and is stably maintained in this background. FIG. 1 shows a restriction map of cosmid 13-6-4. The relevant region of the cosmid is shown in more detail. The figure includes a number of subclones that were constructed in an effort to identify the region of the cosmid that contains the complementing gene. Additionally, FIG. 23 presents a restriction map of the region of cosmid clone 13-6-4 that contains the tutEtutFDGHI genes.

Complementation tests were performed for the various subclones shown in FIG. 1 when mated into a T1 strain carrying the tutB-16 mutation. Complementation was assayed in three ways: (1) the ability to grow with toluene serving as the sole carbon source on solid media, (2) the ability to metabolize toluene in the presence of pyruvic acid in liquid media, and (3) the ability to produce the dead-end products benzylsuccinic acid and benzylfumaric acid from toluene in liquid media. The original clone and all complementing subclones were positive (i.e., behaved just as the wild type strain) in all three assays.

The small 3.3 kb ClaI fragment of 13-6-4 when inserted into pRK415 in either orientation is able to complement the tutB-16 mutation. Subclones constructed that do not contain this entire region do not complement this mutation. These results indicate that this 3.3 kb fragment is sufficient to replace the missing activity in the tutB-16 mutant strain.

EXAMPLE 3

This example describes the sequence analysis of the tutCB region. The complete nucleotide sequence of the 3.3 ClaI fragment of 13-6-4 (containing the tutB gene) was determined in both orientations. Analysis of this sequence revealed the presence of a second open reading frame (designated tutC) upstream of the tutB gene. As a result, the sequence was extended to a SacII site about 3 kb upstream of the ClaI site. FIGS. 2A–D presents the complete 6393 bp nucleotide sequence of the tutCB region. The protein translation of the two genes are presented below the DNA sequence in the figure. The TutC protein is 979 amino acids long with a calculated molecular mass of 108.0 da and a calculated pI of 5.2, while the TutB protein is 218 amino acids long with a calculated molecular mass of 24.3 da and a calculated pI of 7.9.

Goldman-Engleman-Steitz hydropathicity analysis failed to detect any membrane spanning regions in either protein but Kyte-Doolittle analysis suggested two possible membrane spanning regions in the TutC protein, amino acids 367–399 and 489–508 (data not shown). The translation of the tutB gene is shown as over-lapping the sequence of the tutC gene by 13 nucleotides. This methinone was chosen as likely to be the first amino acid in the sequence based on the location of a potential Shine-Dalgarno sequence and protein similarity analysis.

The protein sequence of the tutC gene product was compared to the Swissprot protein data base in an effort to identify other proteins with homologous sequences. The results of this analysis are presented in FIGS. 4A–B. The TutC protein shows significant sequence similarity to sensor members of the two component family of signal transduction proteins, a set of bacterial regulatory proteins in which one member senses the environmental conditions of the microorganism and transmits a signal (via phosphorylation) to the other member (a DNA binding protein). The five proteins, all sensor proteins, with the greatest sequence similarity to the tutC gene product are included in FIGS. 4A–B. These proteins (and their percent identity to the tutC gene product) are the products of the nodV gene of *Bradyrhizobium japonicum* (36%), fixL gene of *B. japonicum* (33%), *Azorhizobium caulinodans* (30%), and *Rhizobium meliloti* (30%), and dctS gene of *Rhodobacter capsulatus* (33%).

In a similar manner, the sequence of the tutB gene product was compared to the Swissprot protein data base in an effort to identify other proteins with homologous sequences. The results of this analysis are presented in FIG. 3. The TutB protein shows significant sequence similarity to DNA binding protein members of two component sensor/regulator families. These proteins (and their percent identity to the tutB gene product) are the products of the nodW gene of *B. japonicum* (48%), the fixJ gene of *B. japonicum* (38%), *A. caulinodans* (37%), and *R. meliloti* (39%), and the dctR gene of *R. capsulatus* (38%). Because the similarity between these proteins and TutB extends nearly to the methionine that over-laps the tutC gene product, it is believed that translation begins at this over-lapping methionine. Based on the results of the sequence similarity analysis and the previous result that the toluene utilization pathway of strain T1 is inducible, the tutB and tutC gene products are likely involved in the regulation of gene expression (specifically toluene metabolic genes) in response to toluene.

EXAMPLE 4

This example describes the identification and cloning of the tutD and tutE genes. One class of mutants, the tutB class, are unable to grow with toluene serving as the sole carbon source but was able to grow when provided with benzoate. These mutants are also unable to metabolize (at wild type levels) toluene when provided with pyruvate and were unable to produce (at wild type levels) benzylsuccinic acid and a monounsaturated derivative from toluene in liquid media. P. J. Evans, et al., Metabolites formed during anaerobic transformation of toluene and o-xylene and their proposed relationship to the initial steps of toluene mineralization. *Appl. Environ. Microbiol.* 58:496(1992). Hence, it is determined this class of mutants is blocked early in the toluene utilization pathway. A cosmid with a genomic insert of approximately 20 kb (cosmid 13-6-4) is isolated for its ability to complement the tutB16 mutation. P. W. Coschigano et al., Identification and sequence analysis of two regulatory genes involved in anaerobic toluene metabolism by strain T1. *Appl. Environ. Microbiol.* 63:652(1997). This original cosmid clone, along with a number of subclones generated in the characterization of the tutB gene, are tested for their ability to complement the mutations referred to as tut and tutB21, which have phenotypes similar to the tutB16 mutation. These mutations are placed in new complementation groups and are designated tutD17 and tutE21.

Figure 10:
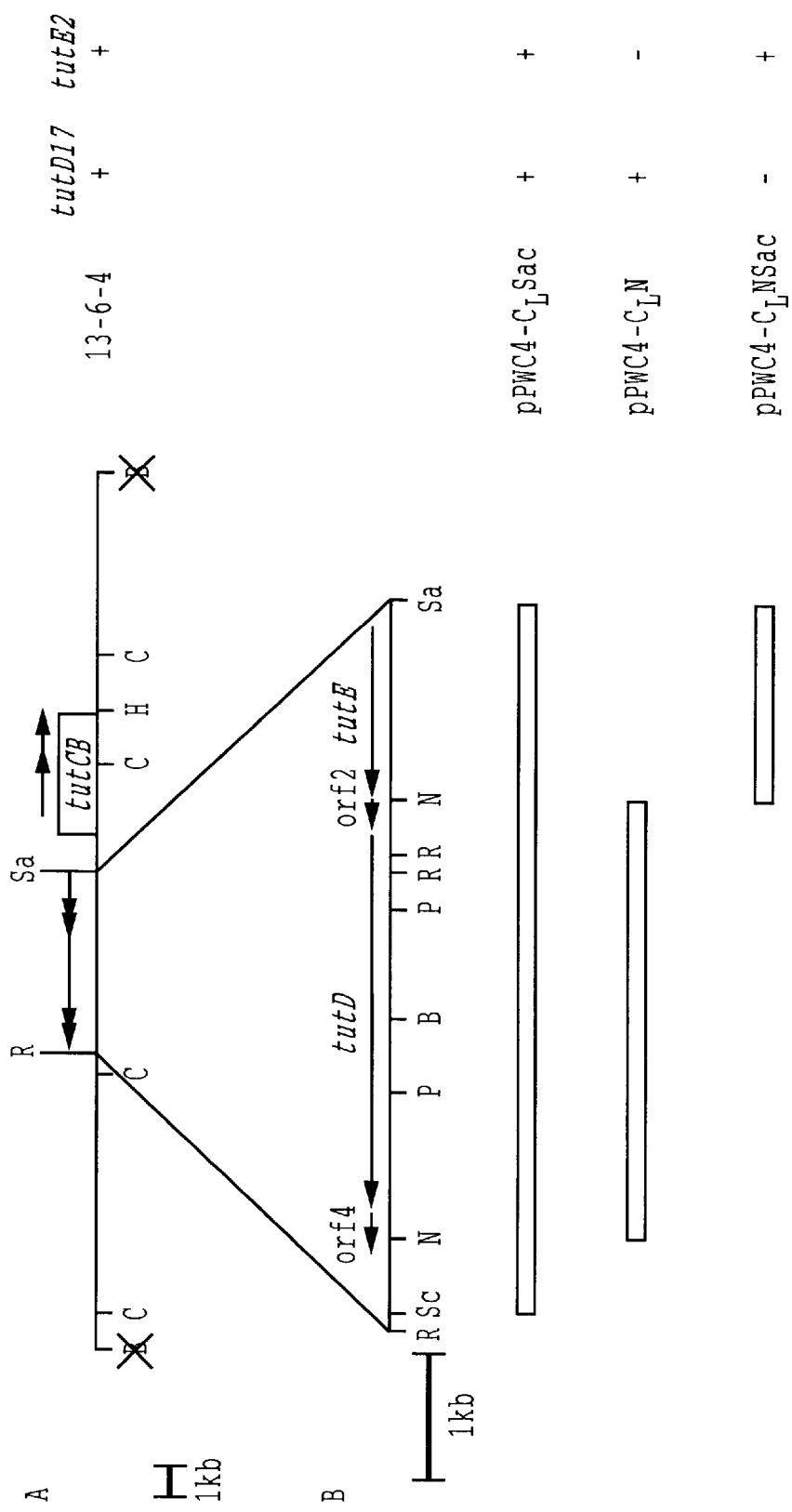
FIG. 10 shows the restriction map of a cosmid clone containing the tutD and tutE genes.

Determining where on the cosmid the fragments that complement the tutD17 and tutE21 mutations are located, a series of subclones are constructed. Subclones are made in plasmid pRK415, a broad host range tetracycline resistant vector that can be conjugatively transferred into the T1 background. FIG. 10 shows a restriction map of cosmid 13-6-4 and a schematic representation of three of the subclones. Each subclone is tested for its ability to complement the tutD17 and tutE21 mutations. Complementation was assayed in three ways: (1) the ability to grow with toluene serving as the sole carbon source on solid media, (2) the ability to metabolize toluene in the presence of pyruvic acid in liquid media, and (3) the ability to produce benzylsuccinic acid and a monounsaturated derivative from toluene in liquid media. P. J. Evans, et al. Metabolites formed during anaerobic transformation of toluene and o-xylene and their proposed relationship to the initial steps of toluene mineralization. *Appl. Environ. Microbiol.* 58:496(1997). Restoration of the wild type phenotype in all three assays is required in order for the subclones to be considered as complementing the mutation.

As shown in FIG. 10, the tutD17 mutation and the tutE21 mutation are complemented by mutually exclusive subclones. The 3.0 kb NcoI fragment of 13-6-4 (pPWC4-$C_L$N) is able to complement the tutD17 mutation but not the tutE21 mutation. Conversely, the adjacent 1.3 kb NcoI/SacII fragment (pPWC4-$C_L$NSac) is able to complement the tutE21 mutation but not the tutD17 mutation. These data suggest the 3.0 kb NcoI fragment is sufficient to replace the missing activity in the tutD17 mutant strain and the 1.3 kb NcoI/SacII fragment is sufficient to replace the missing activity in the tutE21 mutant strain; thereby confirming the mutations belong to distinct complementation groups.

EXAMPLE 5

This example describes the complete nucleotide sequence of the 4905 bp SacII/EcoRI fragment of cosmid 13-6-4 (containing the tutD and tutE genes), as determined for both strands. This nucleotide sequence has been deposited in the GenBank (accession number AF036765). Analysis of this sequence reveals the presence of four open reading frames on the same strand of DNA. The first open reading frame, present between the SacII and NcoI sites (subclone pPWC4-$C_L$NSac) and corresponding to the tutE gene, is a sequence of 375 amino acids. The TutE protein has a calculated molecular mass of 41,300 Da and a predicted pI of 6.8.

Two open reading frames are identified on the 3.0 kb NcoI fragment immediately downstream of the tutE gene (subclone pPWC4-$C_L$N). The first of these two open reading frames (designated open reading frame 2) consists of a 60 amino acid sequence which would code for a protein with a calculated molecular mass of 6,900 Da and a predicted pI of 5.2. The translational start begins at the NcoI restriction site and hence no upstream transcriptional regulatory sites or ribosome binding sites for this open reading frame are included on this fragment. Therefore, it is highly unlikely that this open reading frame is responsible for the complementation of the tutD17 mutation observed with this subclone. This observation, along with evidence from the site-directed mutagenesis experiments indicates that ORF2 is not the tutD gene.

The second open reading frame in this fragment is 864 amino acids in length with a calculated molecular mass of 97,600 Da. The predicted pI of this protein is 6.0. Results from the site-directed mutagenesis clearly show that this open reading frame corresponds to the tutD gene.

The fourth open reading frame (designated open reading frame 4) identified in the SacII/EcoRI fragment consists of a sequence of 81 amino acids with a calculated molecular mass of 9,300 Da and a predicted pI of 7.8. The pPWC4-$C_L$N subclone removes approximately 50% of the C-terminal end of this protein. This result, in conjunction with the evidence presented regarding the third open reading frame, indicates that this 81 amino acid protein is not the tutD gene product.

EXAMPLE 6

This example describes homologies between the protein sequence of the tutD and tutE gene product and proteins in the Genbank protein database. The BLAST program identified a number of similar proteins, all of which are identified as either pyruvate formate-lyases (formate acetyl transferases) or pyruvate formate-lyase homologues. Interestingly, the sequences showing the highest degree of similarity with TutD are the *E. coli* proteins f810 (27% identical to TutD as calculated by the BLAST program) and PflD (26% identical to TutD), both pyruvate formate-lyase homologues. F. R. Blattner, et al. Analysis of the *Escherichia coli* genome. IV. DNA sequence of the region from 89.2 to 92.8 minutes. *Nucleic Acids Res.* 21:5408(1993). F. Blattner, et al, The complete genome sequence of *Escherichia coli* K-12. *Science* (Wash. D.C.). 277:1453(1997).

The sequence similarities between TutD and these two proteins plus PflB (22% identical to TutD), a pyruvate formate-lyase from *E. coli,* are shown in FIGS. 11A–D. R. Rabus, et al., Complete oxidation of toluene under strictly anoxic conditions by a new sulfate-reducing bacterium. *Appl. Environ. Microbiol.* 59:1444( 1993). A. F. Wagner, et al. The free radical in pyruvate formate-lyase is located on glycine-734. *Proc.Natl. Acad. Sci. USA.* 89:996(1992). As can be seen in FIGS. 11A–D, the most conserved region is in the carboxyl end of these proteins. There is a highly conserved region around the glycine residue at position 828 of TutD (marked with an asterisk). In the *E. coli* pyruvate formate-lyase, this glycine has been shown to form a free radical which is essential for enzymatic function. Additionally, in a less conserved region there is a cysteine residue at position 492 of TutD (marked with a dagger) that has been shown to transiently form a covalent bond with the acetyl group that is being transferred, an action which is also essential to enzyme function. A. Ogiwara, et al. Construction and analysis of a profile library characterizing groups of structurally known proteins. *Protein Sci.* 5:1991( 1996). W. Rödel, et al. Primary structure of *Escherichia coli* pyruvate formate-lyase and pyruvate formate-lyase activating enzyme deduced from the DNA nucleotide sequences. *Eur. J. Biochem.* 177:153(1988). While it is not intended that the instant invention be limited to any one mechanism, the results of this protein sequence similarity analysis suggest a mechanism for TutD where glycine-828 forms a free radical which is necessary for the transient formation of a covalent bond between cysteine-492 and the compound (possibly acetate or fumarate) that is being transferred to the methyl group of toluene (or a toluene metabolite). This mechanism may involve a transient cysteine radical at an undetermined location, as proposed in the *E. coli* pyruvate formate-lyase system. A. F. Wagner, et al. The free radical in pyruvate formate-lyase is located on glycine-734. *Proc.Natl. Acad. Sci. USA.* 89:996(1992).

A similar search was performed with the protein sequence of the tutE gene product. The proteins with the highest homology are identified as pyruvate formate-lyase activating enzymes or pyruvate formate-lyase activating enzyme homologues. The sequence similarities between TutE and f308 (34% identical to TutE as calculated by the BLAST program), PflC (32% identical to TutE), and PflA (28% identical to TutE) (all from *E. coli*) are shown in FIGS. 13A–B. Subsequent subjection of the TutE protein sequence to a Motif analysis identified a radical activating region from amino acids 60 to 81 (labeled with a line over it in FIGS. 13A–B). This region which contains potential Fe binding sites (as identified by the Motif analysis) is conserved in the pyruvate formate-lyase activating enzymes. Additionally, the analysis revealed a 4Fe-4S binding domain typically found in ferredoxins (amino acids 98 to 109, labeled with a box over it in FIGS. 13A–B). This region is not very well conserved in the E. coli pyruvate formate-lyase activating enzyme and homologues. PflA is missing this region and both f308 and PflC have alterations to the spacing or sequence. The results of this protein sequence similarity analysis are consistent with the predicted role of TutE serving as the activator for TutD and suggest that the activation may involve iron and/or iron-sulfur binding.

EXAMPLE 7

Figure 14:
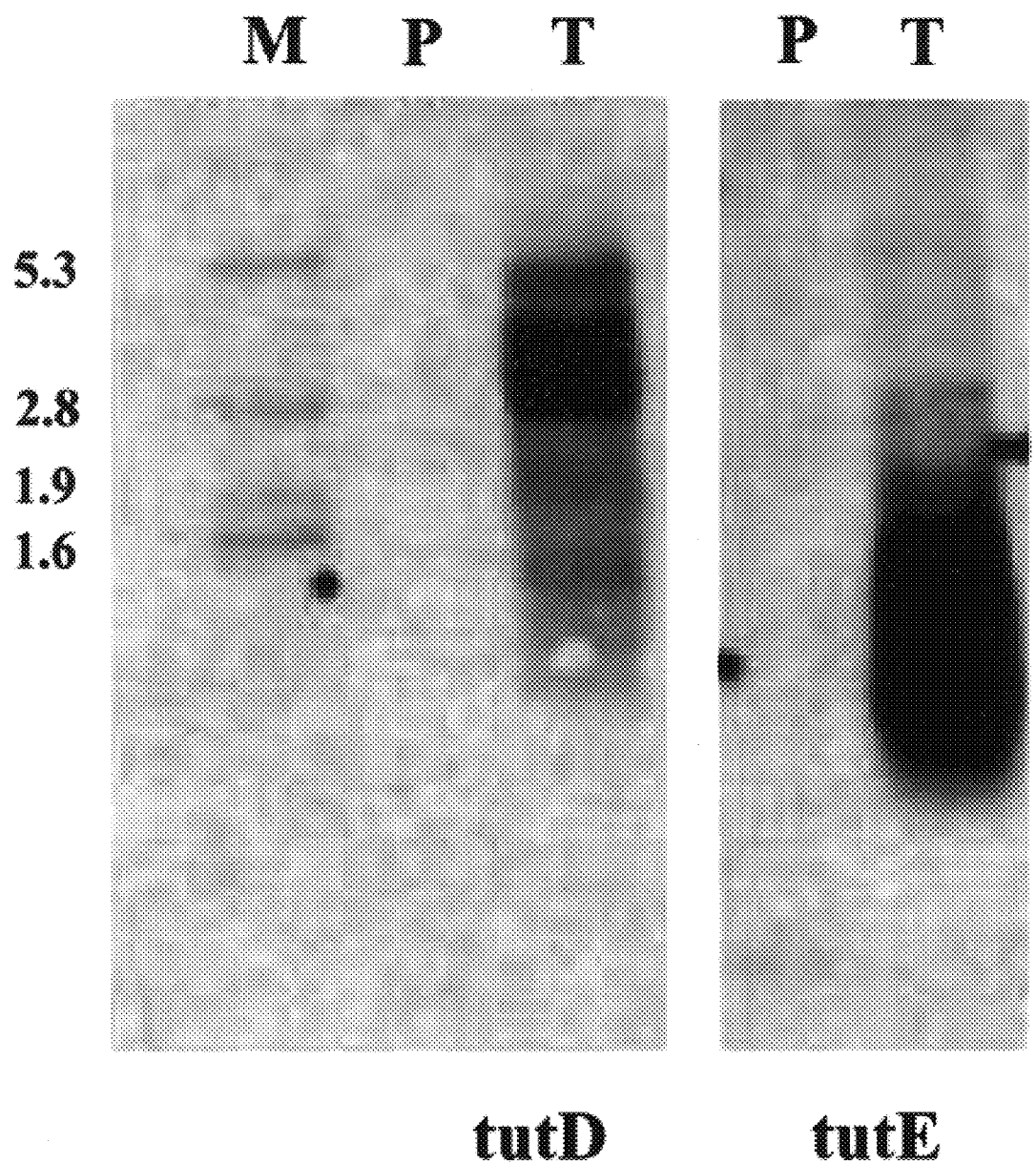
FIG. 14 shows Northern gel results indicating that both tutD and tutE are regulated by toluene.

This example describes various protocols to examine the regulation of the tutD and tutE genes. To confirm that tutD and tutE genes are regulated in response to toluene, a Northern blot analysis is performed. Wild type cells of strain T1 are grown in liquid media containing either pyruvate or toluene as the carbon source. RNA is isolated from both of these cultures and subjected to Northern analysis. About 1 micro gram of total RNA from each culture is loaded in each of two lanes on a 1% gel. After electrophoresis the RNA is transferred to a nylon membrane and cut in two. One set of RNA is hybridized to a tutD probe while the other was hybridized to tutE probe. FIG. 14 shows that only cells grown with toluene as the carbon source have tutD and tutE mRNA. It can also be seen that the size of the two messages differ, indicating that the two genes are not contained in one polycistronic mRNA. The fact that both genes are regulated by toluene suggests that common regulatory protein binding sites is upstream of these and possibly other toluene metabolic genes.

EXAMPLE 8

This example describes the site-directed mutagenesis of TutE protein. Specifically, two cysteine arc individually changed to an alanine in an effort to determine if the conserved potential Fe binding site (as identified by the Motif analysis) of TutE plays a role in the enzymatic function of the protein. Three independent isolates of the resulting plasmids (pPWC-$C_L$NSac-C72A, pPWC4-$C_L$NSac-C79A, and pPWC4-$C_L$NSac-C101A) are mated into the strain carrying the tutE21 mutation and the resulting transconjugants are then tested for their ability to complement the mutation. The plasmid carrying the unaltered clone (pPWC-$C_L$NSac) fully complements the tutE21 mutation (utilizing 100% of the toluene provided in the presence in of pyruvate and produces wild type levels of benzylsuccinic acid and a monounsaturated derivative). Neither of the altered plasmids pPWC4-$C_L$NSac-C72A and pPWC4-$C_L$NSac-C79A are able to complement the tutE21 mutation (see Table 2). both of these strains utilize about the same amount of toluene as is utilized by the mutant carrying plasmid pRK415, the vector alone. Likewise, they produce significantly less benzylsuccinic acid and a monounsaturated derivative than the tutE21 mutant strain carrying the unaltered plasmid pPWC4-$C_{Sac}$. In fact, they produce about the same amount of these compounds as the mutant carrying plasmid pRK415. Therefore. the results in Table 2 clearly demonstrate that cystcine 72 and cysteine 79 are essential for function of the TutE protein. Thus, while it is not intended that the present invention be limited to any one mechanism, the role of iron binding appears to be a mechanistic feature of the TutE protein in its role in toluene metabolism by strain T1.

TABLE 2

| Plasmid | Percent toluene utilized | Percent benzylsuccininic acid like compound produced |
|---|---|---|
| PPWC4-$C_L$NSac[a] | 100 | 100 |
| pRK415[b] | 31.3 ± 5.4 | 8.6 ± 1.2 |
| PPWC4-$C_L$NSac-C72A | 19.5 ± 7.4 | 8.3 ± 0.8 |
| PPWC4-$C_L$NSac-C79A | 31.3 ± 13.8 | 7.8 ± 1.9 |
| PPWC4-$C_L$NSac-C101A | 88.8 ± 13.8 | 55.7 ± 6.1 |

[a]the plasmid carrying the unaltered clone, serving as a postive control.
[b]the vector alone, serving as a negative control.
[c]normalized to 100% for PPWC4-$C_L$NSac, the positive control.

EXAMPLE 9

This example describes the site-directed mutagenesis of TutD protein. To determine if the conserved glycine and cysteine residues of TutD play an essential role in the enzymatic function of the protein has been shown for PflB, both amino acids arc individually changed to an alanine as described in materials and methods. W. Plana, et al. Catalytic-site mapping of pyruvate formate lyase. Eur. J. Biochem. 178:445(1988), W. Rödel, et al. Primary structure of Escherichia coli pyruvate formate-lyase and pyruvate formate-lyasc activating enzyme deduced from the DNA nucleotide sequences. Eur. J. Biochem. 177:153(1988). Three independent isolates of the resulting plasmids (pPWC4-$C_{Sac}$-G828A and pPWC4-$C_{Sac}$-C492A) are mated into the strain carrying the tutD17 mutation and the resulting transconjugants arc then tested for their ability to complement the mutation. The plasmid carrying the unaltered clone (pPWC4-$C_{Sac}$) fully complements the tutD17 mutation (utilizes 100% of the toluene provided in the presence of pyruvate and produces wild type levels of benzylsuccinic acid and a monounsaturated derivative). Neither of the altered plasmids pPWC4-$C_{Sac}$-G828A nor pPWC4-$C_{Sac}$-C492A are able to fully complement the tutD17 mutation (see Table 3).

Both of these strains utilized about the same amount of toluene as was utilized by the mutant carrying plasmid pRK415, the vector alone. Likewise, they produce significantly less benzylsuccinic acid and a monounsaturated derivative than the tutD17 mutant strain carrying the unaltered plasmid pPWC4-$C_{Sac}$. The mutant carrying plasmid pPWC4-$C_{Sac}$-C492A produced about the same amount of these compounds as the mutant carrying plasmid pRK415, while the strain carrying plasmid pPWC4-$C_{Sac}$-G828A show higher levels of these compounds than the vector alone but levels much lower than observed with the unaltered plasmid. Since the E. coli pyruvate formate-lyase is known to be a homodimer which requires the formation of only one glycine free radical, the small amount of activity observed in the mutant carrying plasmid pPWC4-$C_{Sac}$-G828A may be due to mixed dimers where the free radical forms on the defective chromosomally encoded TutD protein. A. F. Wagner, et al., The free radical in pyruvate formate-lyase is located on glycine-734. Proc. Natl. Acad. Sci. USA. 89:996 (1992). The results in Table 3 clearly demonstrate that glycine 828 and cysteine 492 are essential for function of the TutD protein. While it is not intended the present invention be limited to any one mechanism, the role of a glycine free radical and a covalent substrate-cysteine bond appear to be important mechanistic features of the TutD protein in its role in toluene metabolism by strain T1.

From the above, it should be clear that the present invention provides genes encoding toluene degrading enzymes useful for bioremediation. The genes can be used with an expression vector to over-express the enzymes in a host. In addition, the genes can be used to confer the ability of toluene degradation in an host organism that was not otherwise able to degrade toluene. In this manner, an organism that is native to a waste source (and therefore adapted for competition in the waste source) can be modified to have toluene degrading capabilities. In addition, an organism that is adapted to the laboratory that can overexpress the enzyme in large amounts can be made and used to provide a more efficient system of bioremediation (both in situ and ex-situ).

TABLE 3

| Plasmid | Percent toluene utilized | Percent monounsaturated benzylsuccinic acid derived compound produced[c] |
|---|---|---|
| pPWC4-C$_{Sac}$[a] | 100 | 100 |
| pRK415[b] | 23.5 ± 6.4 | 1.3 ± 0.1 |
| pPWC4-C$_{Sac}$-G828A | 34.2 ± 9.7 | 13.0 ± 3.8 |
| pPWC4-C$_{Sac}$-G492A | 17.7 ± 5.4 | 1.8 ± 0.1 |

[a]The plasmid carrying the unaltered clone, serving as a positive control.
[b]The vector alone, serving as a negative control.
[c]Normalized to 100% for pPWC4-C$_{Sac}$, the positive control.

EXAMPLE 10

In this example, Northern analysis was used to examine the regulation of the toluene utilization genes of *T. aromatica* T1. Intense bands were detected when tutD, tutE, tutG and tutF gene probes were hybridized to RNA isolated from toluene grown cells (lanes marked T in FIG. 15). In contrast, no bands were detected by any of the tut gene probes using RNA isolated from pyruvate grown cells (lanes marked P in FIG. 15). These results indicate that the tut genes are induced by toluene.

Figure 15:
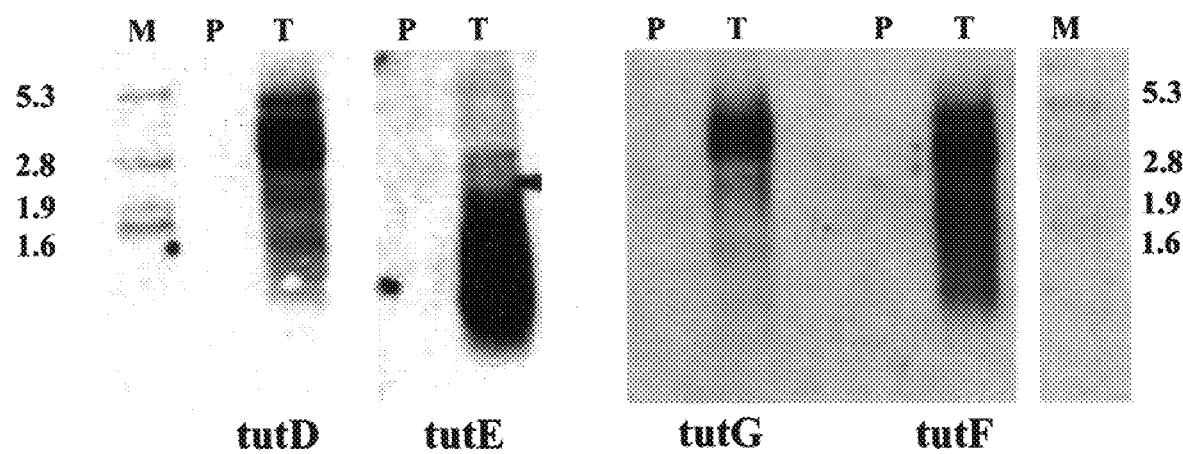
FIG. 15 shows Northern analysis of total RNA isolated from cells grown under denitrifying conditions with either pyruvate (P) or toluene (T) as the carbon source and visualized with probes derived from tutD, tutE, tutG, or tutF. Samples of digoxigenin-labeled RNA were included to serve as size markers (M).

It can also be seen from FIG. 15 that the banding pattern observed with the tutE probe is distinct from the patterns observed with the tutD, tutG, and tutF probes. Multiple sizes of MRNA transcripts are observed using the tutE probe, with the predominant transcripts being approximately 1.6 kb and smaller. Multiple sizes of mRNA transcripts are also observed with the other three probes, but the predominant transcripts are approximately 5.0 to 2.8 kb in size. While it is not intended that the present invention be limited by any specific mechanism or the genes and gene products claimed herein be limited by any motif of the transcriptional units, the banding patterns suggest that tutF, tutD, and tutG are part of the same transcriptional unit and that tutE is a separate transcriptional unit.

EXAMPLE 11

Figure 16:
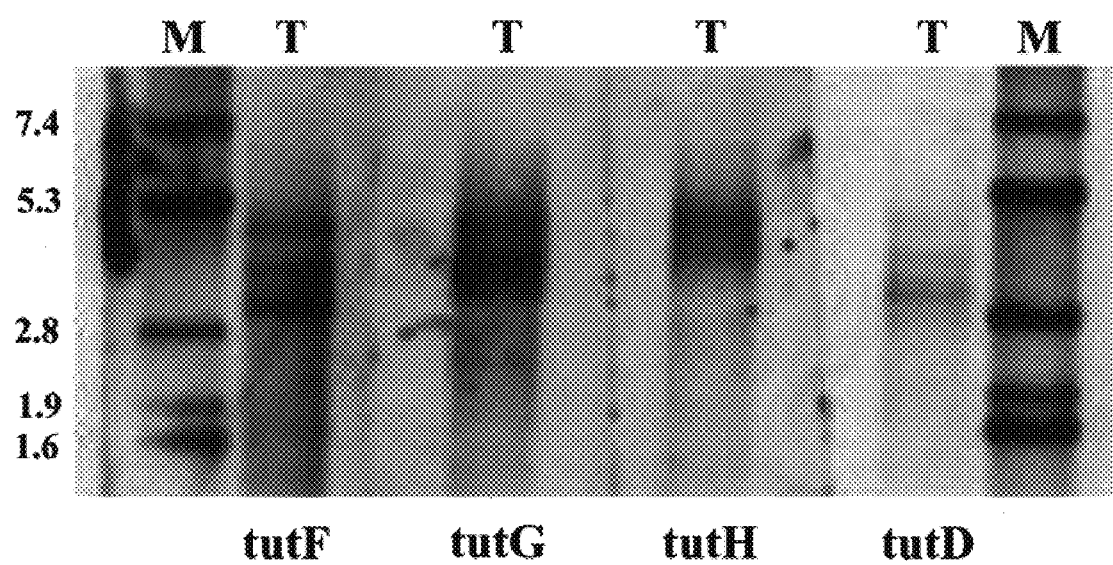
FIG. 16 shows Northern analysis of total RNA isolated from cells grown under denitrifying conditions with toluene (T) as the carbon source. Samples of digoxigenin-labeled RNA were included to serve as size markers (M).

In this example, an additional open reading frame was identified and designated tutH. FIG. 16 includes the results of a Northern analysis in which tutH was used as the probe to identify transcripts from toluene grown cells. While it is not intended that genes claimed through the present invention be limited by a particular level of expression, a similar range of RNA transcript sizes that was observed with the tutF, tutD, and tutG probes was also seen with the tutH probe (FIG. 16). In addition, the tutH probe did not identify any transcripts in RNA isolated from pyruvate grown cells, indicating that it is also induced by toluene (data not shown).

EXAMPLE 12

Figure 17:
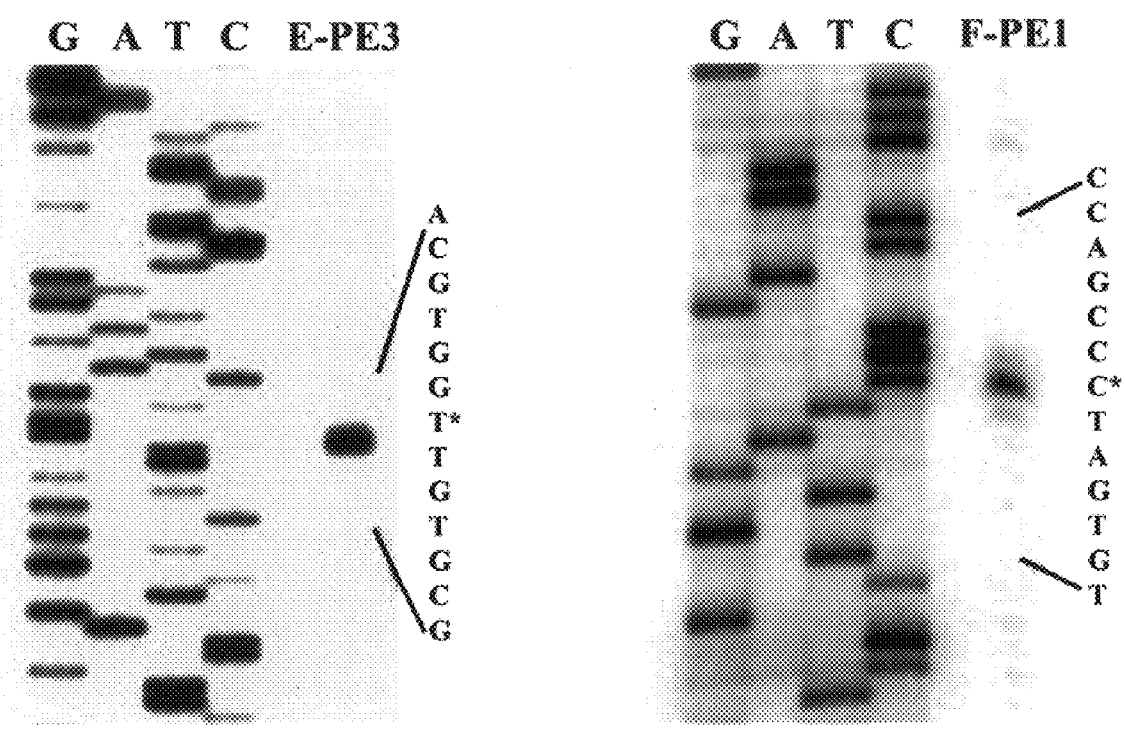
FIG. 17 presents primer extension analysis to map the transcriptional start sites of the tutE and tutF genes. End-labeled primer E-PE3 was used to identify the tutE start of transcription and end-labeled primer F-PE1 was used to identify the tutF start of transcription. The same primers were used to generate the sequencing ladder by the dideoxy method (lanes marked G A T C). The sequence (SEQ ID NOs: 57 and 58) encompassing the transcriptional start (marked with an asterisk) is enlarged.

This example presents data on primer extension and nuclease protection analysis to identify the start sites(s) present in genes described in the instant application. FIG. 17 shows the results of a primer extension reaction using the E-PE3 primer which contains the predicted tutE translational start. The major transcriptional start site is located 177 bp upstream of the tutE translational start. This same start site was also observed when a nuclease protection assay was carried out with a DNA probe spanning the tutE translational start (data not shown). Minor start sites were also observed 178 bp upstream (FIG. 17) and in the region 119–124 bp upstream of the tutE translational start (data not shown).

As can also be seen in FIG. 17, results of a primer extension reaction using the F-PE1 primer (located just downstream of the predicted tutF translational start site) identifies a major transcriptional start site 76 bp upstream of the tutF translational start. This site is located within the tutE coding region. This start site was also observed when a nuclease protection assay was carried out with a DNA probe spanning this region of the tutF translational start (data not shown). Minor transcriptional start sites were observed 75 and 77 bp upstream (FIG. 17) and in the region 125–129 bp upstream of the tutF translational start site (data not shown). These results are consistent with the results of the Northern analysis indicating that the tutE transcript is separate from the tutFDGH transcript.

A primer extension reaction carried out with a primer located downstream of the predicted tutD translational start and a nuclease protection assay carried out with a DNA probe spanning the tutD translational start did not identify a transcriptional start immediately upstream of tutD. Instead, these reactions did identify the same start site located upstream of tutF(data not shown). Primer extension reactions carried out with primers located downstream of the predicted tutG and tutH translational starts and nuclease protection assays carried out with DNA probes spanning these translational start sites failed to identify transcriptional start sites immediately upstream of these genes (data not shown). The start site identified preceding tutf could not be verified for tuIG and tutH due to its considerable distance from these genes (about 2.9 kb and 3.2 kb respectively). While it is not intended that the present invention be limited by any mechanism or trasncriptional motif, the RNA analyses suggest that the tutF, tutD, tutG, and tutH genes are transcribed as a single unit from one start site.

EXAMPLE 13

This example presents DNA and protein analysis of tutH. Specifically, given that the 4905 bp SacII/EcoRI fragment of cosmid 13-6-4 (GenBank accession number AF036765) did not contain the complete sequence of the tutH gene, an additional 381 base pair of this cosmid were sequenced on both strands. The 1018 bp NcoI fragment (part of which is contained in the SacII/EcoRI fragment previously reported) containing the tutH sequence has been deposited in GenBank (accession number AF113168). Analysis of this sequence identified the complete tutH coding region whose predicted protein product is 286 amino acids. The nucleic acid sequence corresponding to tutH is presented in FIG. 18. The TutH protein has a calculated molecular mass of about 31,800 Da and a predicted pI of 5.4. The amino acid sequence corresponding to TutH is presented in FIG. 19.

Figure 20:
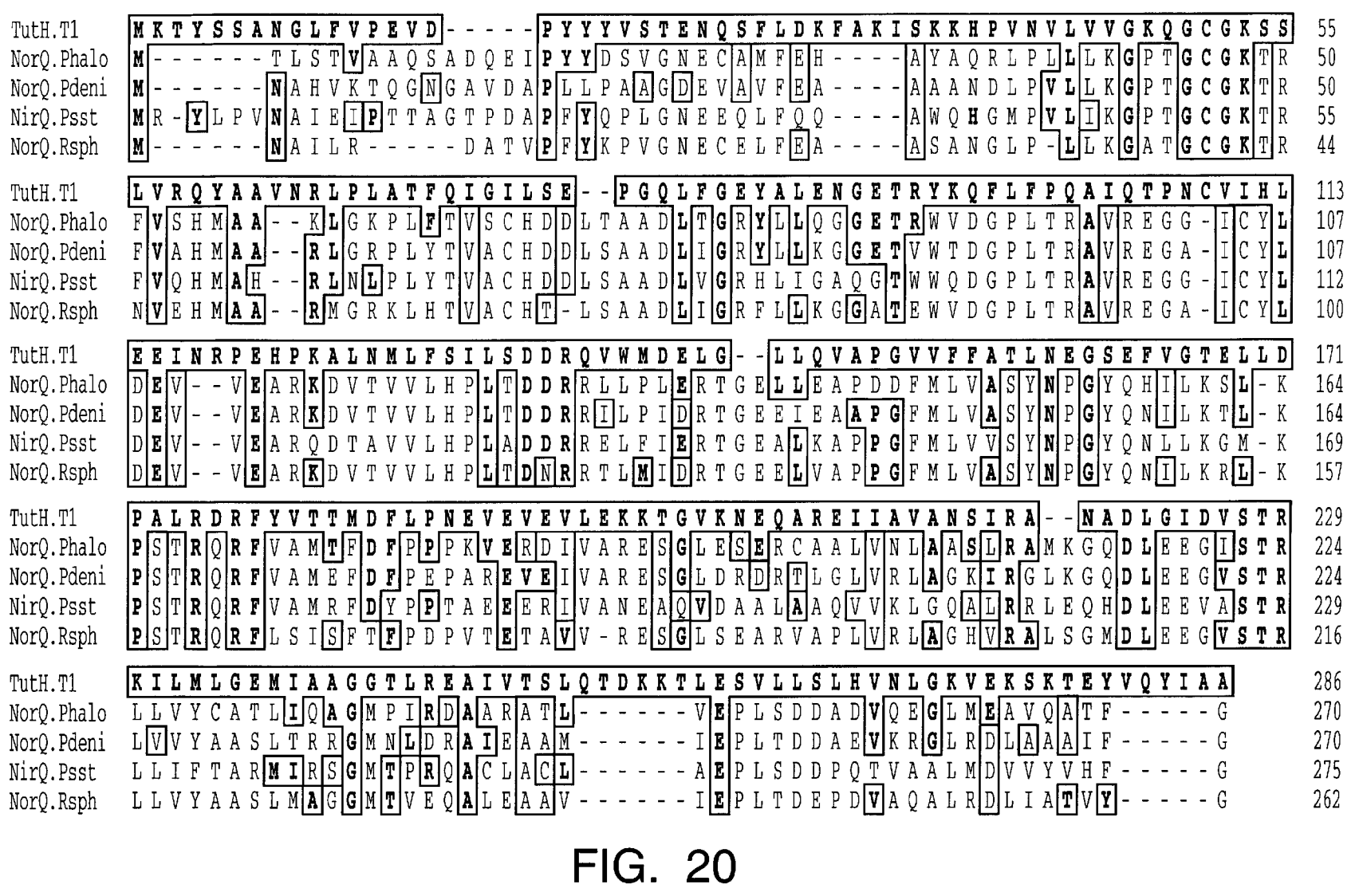

The BLAST program was used to identify proteins similar to the predicted TutH protein. The four proteins with the highest degree of similarity were NorQ from *Paracoccus halodenitrificans, Paracoccus denitrificans,* and *Rhodobacter sphaeroides,* and NirQ from *Pseudomonas stutzeri.* The BLAST program calculated that these proteins are 27%, 28%, 27%, and 22% identical (over nearly their entire sequence) to TutH, respectively. A protein alignment of these proteins is presented in FIG. 20.

The TutH protein sequence was also subjected to a Motif analysis. Amino acids 47 to 54 (labeled with a line in FIG. 20) were identified as a putative ATP/GTP binding domain. This region is conserved in the NorQ/NirQ proteins included in FIG. 20. While it is not intended that the present invention be limited by any specific operative mechanism, this observation suggests that the NorQ/NirQ family of proteins and the TutH protein may use a similar mechanism involving ATP/GTP binding.

EXAMPLE 14

This example presents DNA and protein analysis of tutI. The DNA sequence, presented in FIG. 21, starts with an Nco site near the end of the tutH sequence. The protein sequence, presented in FIG. 22, is the translation of the open reading frame. Additionally, Northern blot data has demonstrated tutI is regulated in response to toluene (data not shown).

What is claimed is:

1. A composition comprising isolated and purified DNA as set forth in SEQ ID NO: 47.

2. RNA transcribed from the DNA of claim 1.

3. Expression constructs comprising DNA of claim 1.

* * * * *